US007968088B2

(12) United States Patent
Honmou et al.

(10) Patent No.: US 7,968,088 B2
(45) Date of Patent: Jun. 28, 2011

(54) INTERNALLY ADMINISTERED THERAPEUTIC AGENTS FOR CRANIAL NERVE DISEASES COMPRISING MESENCHYMAL CELLS AS AN ACTIVE INGREDIENT

(76) Inventors: Osamu Honmou, Hokkaido (JP); Hirofumi Hamada, Hokkaido (JP)

( * ) Notice: Subject to any disclaimer, the term of this patent is extended or adjusted under 35 U.S.C. 154(b) by 205 days.

(21) Appl. No.: 12/149,646

(22) Filed: May 6, 2008

(65) Prior Publication Data

US 2008/0286246 A1    Nov. 20, 2008

Related U.S. Application Data

(63) Continuation of application No. 11/377,610, filed on Mar. 17, 2006, which is a continuation-in-part of application No. 10/562,202, filed as application No. PCT/JP2004/009386 on Jun. 25, 2004.

(30) Foreign Application Priority Data

Jun. 27, 2003  (JP) ................................ 2003-185260
Dec. 26, 2003  (JP) ................................ 2003-432329

(51) Int. Cl.
    *A61K 35/12*  (2006.01)
    *A61P 7/00*   (2006.01)
(52) U.S. Cl. ..................................................... 424/93.7
(58) Field of Classification Search .................... None
    See application file for complete search history.

(56) References Cited

U.S. PATENT DOCUMENTS

| 6,673,606 B1 | 1/2004 | Tennekoon et al. |
| 2002/0123465 A1 | 9/2002 | Twardzik et al. |
| 2002/0132343 A1 | 9/2002 | Lum |
| 2002/0168766 A1 | 11/2002 | Gold et al. |
| 2003/0161818 A1 | 8/2003 | Weiss et al. |

FOREIGN PATENT DOCUMENTS

| JP | 2002-027983 A | 1/2002 |
| JP | 2002-544234 A | 12/2002 |
| JP | 2004-544234 A | 12/2002 |
| WO | WO 99/01145 | 1/1999 |
| WO | WO 01/05944 A1 | 1/2001 |
| WO | WO 01/66698 A1 | 9/2001 |
| WO | WO 02/00849 A1 | 1/2002 |
| WO | WO 03/025167 A2 | 3/2003 |
| WO | WO 03/038075 A1 | 5/2003 |

OTHER PUBLICATIONS

Chen et al (Stroke. 2001; 32:1005-1011).*
Tocci et al. (Hematol-J. Feb. 2003. 4(2): 92-96).*
Reyes et al. (Blood. Nov. 1, 2001; 98(9): 2615-2625).*
Fernandez et al. Bone Marrow Transplantation. 1997; 20: 265-271).*
Ukai et al., "Mesenchymal Stem Cells Derived from Peripheral Blood Protects against Ischemia," Journal of Neurotrauma, 2007, 24(3):508-520.
Kennea et al., "Perinatal applications of neural stem cells," Best Practice & Research Clinical Obstetrics and Gynaecology, 2004, 18(6), 977-994.
Tocci et al., "Mesenchymal stem cell: use and perspectives," The Hematology Journal, 2003, 4, 92-96.
The Hokkaido Shimbun, "Treatment of cerebral infarction with the patient's own bone-marrow stem cells collected in advance," Sapporo Medical University, Jul. 7, 2003, one page (and English Translation, two pages).
"Gene therapy for rat glioma based on mesenchymal stem cell transplantation," Cancer Science, Sep. 25-27, 2003, Proceedings of the 62$^{nd}$ Annual Meeting of the Japanese Cancer Association, five pages including cover, table of contents, p. 325 and last page of publication (and English translation of p. 325, one page).
Database Biosis on STN, (Last Updated on Stn: Jun. 19, 2003) abstract No. 200300283245 & S. Ilhoshi et al., "Intravenous administration of autologous bone marrow cells repairs the ischemic lesions in the rat middle cerebral artery occlusion model", Society for Neuroscience Abstract Viewer & Itinerary Planner, (2002), vol. 2002, abstract No. 237.8., http://sfn.scholarone.com.
D. Lu et al., "Adult bone marrow stromal cells administered intravenously to rats after traumatic brain injury migratein to brain and improve neurological outcome", Neuroreport, 2001, vol. 12, No. 3, pp. 559-563.
J. Chen et al., "Therapeutic benefit of intravenous administ ratino of bone marrow stromal cells after cerebral ischemia in rats", Stroke, 2001, vol. 32, No. 4, pp. 1005-1011.
K. Chu et al., "Human neural stem cells can migrate, differentiate and integrate after intravenous transplantation in adult rats with transient forebrain ischemia", Nurosci. Lett., Jun. 5, 2003, vol. 343, No. 2, pp. 129-133.
Y. Akiyama et al., "Remyelination of the spinal cord following intravenous delivery of bone marrow cells", Glia., (2002), vol. 39, pp. 229-236.
A. Mahmood et al., "Treatment of traumatic brain injury in female rats with intravenous administration of bone marrow stromal cells", Neurosurgery, 2002, vol. 49, No. 5, pp. 1196-1203.
Database Medline on STN, (2002), abstract No. 2002333228 & D. Lu et al., "Intravenous administration of human unbilical cord blood reduces neurological deficit in the rat after traumatic brain injury", Cell Transplant. (2002), vol. 11, No. 3, pp. 275-281.
Database Biosis on STN, (2001), abstract No. 200100547979 & Y. Akiyama et al., "Remyelination of spinal cord axons by intravenous delivery of bone marrow cells", Society for Neuroscience Abstracts, 2001, vol. 27. No. 2, p. 1562.
Database Biosis in STN, (2003), abstract No. 200300315449 & P. Lu et al., "Transplantation of bone marrow stromal cells (MSCS) and BDNF-transducer MSCS promotoes robust axonal growth after spinal cord injury", Society for Neuroscience Abstract Viewer & Itinerary Planner, 2002, vol. 202, abstract No. 634.11 http://sfn.scholarone.com.

(Continued)

*Primary Examiner* — Scott Long
(74) *Attorney, Agent, or Firm* — Foley & Lardner LLP; Stephen B. Maebius; Sunit Talapatra

(57) ABSTRACT

Intravenous administration of bone marrow cells collected from rat bone marrow or peripheral blood to a rat cerebral infarction model was found to be effective in treating cerebral infarction. Human and murine bone marrow stem cells showed similar effects. Mesenchymal cells such as bone marrow cells, cord blood cells, or peripheral blood cells can be used as agents for in vivo administration against cranial nerve diseases.

3 Claims, 69 Drawing Sheets

OTHER PUBLICATIONS

Ma Keane-Moore et al., "Human mesenchylmal stem cells can be genetically modified to function as antigen presenting cells", Blood, (1998), vol. 92, No. 10, suppl. 1, part 1 to 2, p. 338A, Abstract #1388.

Aggarwal, et al., "Human mesenchymal stem cells modulate allogeneic immune cell responses", Blood, vol. 105, No. 4,. pp. 1815-1822, (2005).

Akiyama, et al., "Transplantation of Clonal Neural Precursor Cells Derived from Adult Human Brain Establishes Functional Peripheral Myelin in the Rat Spinal Cord", Experimental Neurology, vol. 167, pp. 27-39 (2001).

Archer, et al., "Myelination by Cryopreserved Xenografts and Allografts in the Myelin-Deficient Rat", Experimental Neurology, vol. 125, pp. 268-277 (1994).

Auner, et al., "Evaluation of potential risk factors for early infectious complications after autologous peripheral blood stem cell transplantation in patients with lymphoproliferative diseases", Ann Hematol, vol. 84, pp. 532-537 (2005).

Bang, et al., "Autologous Mesenchymal Stem Cell Transplantation in Stroke Patients", Ann Neurol, vol. 57, pp. 874-882 (2005).

Barker, et al., "Acute Stroke: Evaluation with Serial Proton MR Spectroscopic Imaging", Radiology, vol. 192, pp. 723-732 (1994).

Bederson, et al., "Evaluation of 2, 3, 5-Triphenyltetrazolium Chloride as a Stain for Detection and Quantification of Experimental Cerebral Infarction in Rats", Stroke, vol. 17, No. 6, pp. 1304-1308 (1986).

Bender, et al., "Identification and Comparison of CD34-Positive Cells and Their Subpopulations From Normal Peripheral Blood and Bone Marrow Using Multicolor Flow Cytometry", Blood, vol. 77, No. 12, pp. 2591-2596 (1991).

Bernstein, et al., "Suppression of Human Cytotoxic T Lymphocyte Responses by Adherent Peripheral Blood Leukocytes", Annals New York Academy of Science, vol. 532, pp. 206-213 (1988).

Bjornson, et al., "Turning Brain into Blood: A Hematopoietic Fate Adopted by Adult Neural Stem Cells in Vivo", Science, vol. 283, pp. 534-537 (1999).

Blakemore, et al., "Extensive Oligodendrocyte Remyelination following Injection of Cultured Central Nervous System Cells into Demyelinating Lesions in Adult Central Nervous System", Dev. Neurosci., vol. 10, pp. 1-11 (1988).

Wiesel, et al., "Remyelination of CNS axons by Schwann cells transplanted from the sciatic nerve", Nature, vol. 266, p. 68-69, (1977).

Brown, et al., "Factors That Influence the Collection and Enraftment of Allogeneic Peripheral-Blood Stem Cells in Patients With Hematologic Malignancies", Journal of Clinical Oncology, vol. 15, No. 9, pp. 3067-3074 (1997).

Chalmers-Redman, et al., "In Vitro Propagation And Inducible Differentiation of Multipotential Progenitor Cells From Human Fetal Brain", Neuroscience, vol. 76, No. 4, pp. 1121-1128 (1997).

Chen, et al., "Therapeutic benefit of intracerebral transplantation of bone marrow stromal cells after cerebral ischemia in rats", Journal of the Neurological Sciences, vol. 189, pp. 49-57 (2001).

Chopp, et al., "Spinal cord injury in rat: treatment with bone marrow stromal cell transplantation", NeuronReport, vol. 11, No. 13, pp. 3001-3005 (2000).

Deshari, et al., "Enhanced antitumor effect of RGD fiber-modified adenovirus for gene therapy of oral cancer", Cancer Gene Therapy, vol. 10, pp. 75-85 (2003).

Escolar, et al., "Transplantation of Umbilical-Cord Blood in Babies with Infantile Krabbe's Disease", The New England Journal of Medicine, pp. 2069-2081 (2005).

Flax, et al., "Engraftable human neural stem cells respond to developmental cues, replace neurons, and express foreign genes", Nature Biotechnology, vol. 16, pp. 1033-1039 (1988).

Franklin, et al., "Schwann Cell-Like Myelination Following Transplantation of an Olfactory Bulb-Ensheathing Cell Line Into Areas of Demyelination in the Adult CNS", GLIA, vol. 17, pp. 217-224 (1996).

Friedenstein, A.J., "Precursor Cells of Mechanocytes", International Review of Cytology, 1976, vol. 47, pp. 327-359.

Gage, et al., Survival and differentiation of adult neuronal progenitor cells transplanted to the adult brain, Proc. Natl. Acad. Sci., vol. 92, pp. 11879-11883 (1995).

Gavrieli, et al., "Identification of Programmed Cell Death In Situ via Specific Labeling of Nuclear DNA Fragmentation", The Journal of Cell Biology, vol. 119, No. 3, pp. 493-501 (1992).

Goto, et al., "GABA Receptor Agonist Promotes Reformation of the Striatonigral Pathway by Transplant Derived from Fetal Striatal Primordia in the Lesioned Striatum", Experimental Neurology, vol. 147, pp. 503-509 (1997).

Gumpel, et al., "Transplantation of Human Embryonic Oligodendrocytes into Shiverer Brain", Annals New York Academy of Sciences, vol. 495, pp. 70-85 (1987).

Hamano, et al., "Angiogenesis Induced by the Implantation of Self-Bone Marrow Cells: A New Material for Therapeutic Angiogenesis", Cell Transplantation, vol. 9, pp. 439-443 (2000).

Hayashi, et al., "Reduction of Ischemic Damage by Application of Vascular Endothelial Growth Factor in Rat Brain After Transient Ischemia", Journal of Cerebral Blood Flow and Metabolism, vol. 18, pp. 887-895 (1998).

Hirouchi et al., "Current state on development of neuroprotective agents for cerebral ishemia," Folia Pharmacol. Jpn., vol. 120, pp. 107-113 (2002).

Honma, et al., Intravenous infusion of immortalized human mesenchymal stem cells protects against injury in a cerebral ischemia model in adult rat,. Experimental Neurology, pp. 1-11 (2005).

Honmou, et al., "Restoration of Normal Conduction Properties in Demyelinated Spinal Cord Axons in the Adult Rat by Transplantation of Exogenous Schwann Cells", The Journal of Neuroscience, vol. 16, pp. 3199-3208 (1996).

Huss, et al., "Evidence of Peripheral Blood-Derived, Plastic-Adherent $CD34^{-/low}$ Hematopoietic Stem Cell Clones with Mesenchymal Stem Cell Characteristics", Stem Cells, vol. 18, pp. 252-260 (2000).

Iihoshi, et al., "A therapeutic window for intravenous administration of autologous bone marrow after cerebral ischemia in adult rats", Brain Research, vol. 1007, pp. 1-9 (2004).

Imaizumi, et al., "Transplanted Olfactory Ensheathing Cells Remyelinate and Enhance Axonal Conduction in the Demyelinated Dorsal Columns of the Rat Spinal Cord", The Journal of Neuroscience, vol. 18, pp. 6176-6185 (1998).

Inoue et al., "Comparative Analysis of Remyelinating Potential of Focal and Intravenous Administration of Autologous Bone Marrow Cells Into the Rat Demyelinated Spinal Cord," GLIA, 2003, pp. 111-118, vol. 44.

Iwadate et al., "Induction of Immunity in Peripheral Tissues Combined with Intracerebral Transplantation of Interleukin-2-producing Cells Eliminates Established Brain Tumors," Cancer Research, Dec. 15, 2001, pp. 8769-8774, vol. 61.

Kanegae et al., "Efficient gene activation in mammalian cells by using recombinant adenovirus expressing site-specific Cre recombinase," Nucleic Acids Research, 1995, pp. 3816-3821, vol. 23, No. 19.

Kato et al., "Transplantation of Human Olfactory Ensheathing Cells Elicits Remyelination of Demyelinated Rat Spinal Cord," GLIA, 2000, pp. 209-218, vol. 30.

Kawano et al., "Ex vivo expansion of human umbilical cord hematopoietic progenitor cells using a coculture system with human telomerase catalytic subunit (hTERT)—transfected human stromal cells," Blood, Jan. 15, 2003, pp. 532-540, vol. 101, No. 2.

Keirstead et al., "Polysialylated Neural Cell Adhesion Molecule-Positive CNS Precursors Generate Both Oligodenodrocytes and Schwann Cells to Remyelinate the CNS after Transplantation," J. Neurosci., Sep. 1, 1999, pp. 7529-7536, vol. 19, No. 17.

Kobune et al., "Telomerized human multipotent mesenchymal cells can differentiate into hematopoietic and cobblestone area-supporting cells," Experimental Hematology, 2003, pp. 715-722, vol. 31, Elsevier Inc.

Koç et al., Allogeneic mesenchymal stem cell infusion for treatment of metachromatic leukodystrophy (MLD) and hurler syndrome (MPS-IH), Bone Marrow Transplantation, 2002, pp. 215-222, vol. 30.

Koç et al., "Rapid Hematopoietic Recovery After Coinfusion of Autologous-Blood Stem Cells and Culture-Expanded Marrow Mesenchymal Stem Cells in Advanced Breast Cancer Patients Receiving High-dose Chemotherapy," J. Clin. Oncol., 2000, pp. 307-316, vol. 18, No. 2.

Kopen et al., "Marrow stromal cells migrate throughout forebrain and cerebellum, and they differentiate into astrocytes after injection into neonatal mouse brains," Proc. Natl. Acad. Sci., Sep. 1999, pp. 10711-10716, vol. 96, USA.

Kurozumi et al., "BDNF Gene-Modified Mesenchymal Stem Cells Promote Functional Recovery and Reduce Infarct Size in the Rat Middle Cerebral Artery Occlusion Model," Molecular Therapy, Feb. 2004, pp. 189-197, vol. 9, No. 2.

Lois et al., "Proliferating subventricular zone cells in the adult mammalian forebrain can differentiate into neurons and glia," Proc. Natl. Acad. Sci., Mar. 1993, pp. 2074-2077, vol. 90, USA.

Longa et al., "Reversible Middle Cerebral Artery Occlusion Without Craniectomy in Rats," Stroke, Jan. 1989, vol. 20, No. 1, pp. 84-91.

Majumdar et al., "Phenotypic and Functional Comparison of Cultures of Marrow-Derived Mesenchymal Stem Cells (MSCs) and Stromal Cells," J. Cell. Physiol., 1998, pp. 57-66, vol. 176.

J. Mokrý, "Experimental Models and Behavioural Tests Used in the Study of Parkinson's Disease," Physiol. Res., 1995, pp. 143-150, vol. 44, No. 3.

R. Morris, "Spatial Localization Does Not Require the Presence of Local Cues," Learning and Motivation, 1981, pp. 239-260, vol. 12.

Morshead et al., "Neural Stem Cells in the Adult Mammalian Forebrain: A Relatively Quiescent Subpopulation of Subependymal Cells," Neuron, Nov. 1994, pp. 1071-1082, vol. 13.

Moyer et al., "Culture, Expansion, and Transplantation of Human Fetal Neural Progenitor Cells," Transplantation Proceedings, 1997, pp. 2040-2041, vol. 29, Elsevier.

Nakagawa et al., "Persistent and Secondary Adenovirus-Mediated Hepatic Gene Expression Using Adenovirus Vector Containing CTLA4IgG," Hum.Gene Ther., Aug. 10, 1998, pp. 1739-1745, vol. 9, No. 12, Mary Ann Liebert, Inc.

Nakamura et al., "Effective Gene Transfer to Human Melanomas via Integrin-Targeted Adenoviral Vectors," Hum.Gene Ther., Mar. 20, 2002, pp. 613-626, vol. 13.

Nakamura et al., "Adoptive Immunotherapy with Murine Tumor-specific T Lymphocytes Engineered to Secrete Interleukin 2," Cancer Research, Nov. 15, 1994, pp. 5757-5760, vol. 54, No. 22.

Namba et al., "Evaluation of the Bystander Effect in Experimental Brain Tumors Bearing Herpes Simplex Virus-Thymidine Kinase Gene by Serial Magnetic Resonance Imaging," Hum. Gene Ther., Oct. 1, 1996, pp. 1847-1852, vol. 7, No. 15, Mary Ann Liebert, Inc.

Neumann-Haefelin et al., "Serial MRI After Transient Focal Cerebral Ischemia in Rats," Stroke, Aug. 2000, pp. 1965-1973.

Niwa et al., "Efficient selection for high-expression transfectants with a novel eukaryotic vector," Gene, 1991, pp. 193-199, vol. 108.

Nomura et al., "I.V. Infusion of Brain-Derived Neurotrophic Factor Gene-Modified Human Mesenchymal Stem Cells Protects Against Injury in a Cerebral Ischemia Model in Adult Rat," Neuroscience, 2005, pp. 161-169, vol. 136.

Nyberg-Hoffman et al., "Sensitivity and reproducibility in adenoviral infectious titer determination," Nature Medicine, Jul. 1997, pp. 808-811, vol. 3, No. 7.

Ohlsson et al., "Environment Influences Functional Outcome of Cerebral Infarction in Rats," Stroke, Apr. 1995, pp. 644-649, vol. 26, No. 4.

Paxinos et al., "Bregma, lambda and the interaural midpoint in stereotaxic surgery with rats of different sex, strain and weight," J. Neurosci. Methods, 1985, pp. 139-143, vol. 13, Elsevier.

Pluchino et al., "Neurosphere-derived multipotent precursors promote neuroprotection by an immunomodulatory mechanism," Nature, Jul. 14, 2005, pp. 266-271, vol. 436.

Pluchino et al., "Injection of adult neurospheres induces recovery in a chronic model of multiple sclerosis," Nature, Apr. 17, 2003, pp. 688-694, vol. 422.

Prockop et al., "One strategy for cell and gene therapy: Harnessing the power of adult stem cells to repair tissues," PNAS, Sep. 30, 2003, pp. 11917-11923, vol. 100, Suppl. 1.

D. Prockop, "Marrow Stromal Cells as Stem Cells for Nonhematopoietic Tissues," Science, Apr. 4, 1997, pp. 71-74, vol. 276.

Reynolds et al., "Generation of Neurons and Astrocytes from Isolated Cells of the Adult Mammalian Central Nervous System," Science, Mar. 27, 1992, pp. 1707-1710, vol. 255.

Rhines et al., "Local Immunotherapy with Interleukin-2 Delivered from Biodegradable Polymer Microspheres Combined with Interstitial Chemotherapy: A Novel Treatment for Experimental Malignant. Glioma," Neurosurgery, Apr. 2003, pp. 872-880, vol. 52, No. 4.

Rochefort et al., "Influence of hypoxia on the domiciliation of Mesenchymal Stem Cells after infusion into rats: possibilities of targeting pulmonary artery remodeling via cells therapies?" Respiratory Research, 2005, pp. 1-13, vol. 6, No. 125.

Sasaki et al., "Protection of Corticospinal Tract Neurons After Dorsal Spinal Cord Transection and Engraftment of Olfactory Ensheathing Cells," GLIA, 2006, pp. 352-359, vol. 53.

Sasaki et al., "Transplantation of an Acutely Isolated Bone Marrow Fraction Repairs Demyelinated Adult Rat Spinal Cord Axons," GLIA, 2001, pp. 26-34, vol. 35.

Staba et al., "Cord-Blood Transplants from Unrelated Donors in Patients with Hurler's Syndrome," N. Engl. J. Med., May 6, 2004, pp. 1960-1969, vol. 350, No. 19.

Svendsen et al., "Long-Term Survival of Human Central Nervous System Progenitor Cells Transplanted into a Rat Model of Parkinson's Disease," Experimental Neurology, 1997, pp. 135-146, vol. 148, Article No. EN976634.

Takiguchi et al., "CTLA4IgG Gene Delivery Prevents Autoantibody Production and Lupus Nephritis in MRL/*lpr* Mice," Life Sciences, 2000, pp. 991-1001, vol. 66, No. 11, Elsevier.

Tamura et al., "Focal cerebral infarction in the rat: I. Operative technique and physiological monitorings for chronic model," No To Shinkei, 1986, vol. 38, No. 8, pp. 747-751.

Tille et al., "Mesenchymal Cells Potentiate Vascular Endothelial Growth Factor-Induced Angiogenesis in Vitro," Experimental Cell Research, 2002, pp. 179-191, vol. 280.

Toma et al., "Human Mesenchymal Stem Cells Differentiate to a Cardiomyocyte Phenotype in the Adult Murine Heart," Circulation, Jan. 1/8, 2002, pp. 93-98.

Tondreau et al., "Mesenchymal Stem Cells Derived from CD133-Positive Cells in Mobilized Peripheral Blood and Cord Blood: Proliferation, Oct4 Expression, and Plasticity," Stem Cells, 2005, pp. 1105-1112, vol. 23.

Tsuda et al., "Efficient BMP2 Gene Transfer and Bone Formation of Mesenchymal Stem Cells by a Fiber-Mutant Adenoviral Vector," Mole. Therapy, Mar. 2003, pp. 354-365, vol. 7, No. 3.

Utzschneider et al., "Transplantation of glial cells enhances action potential conduction of amyelinated spinal cord axons in the myelin-deficient rat," Proc. Natl. Acad. Sci., Jan. 1994, pp. 53-57, vol. 91, USA.

Villaron et al., "Mesenchymal stem cells are present in peripheral blood and can engraft after allogeneic hematopoietic stem cell transplantation," Haematologica, Dec. 2004, pp. 1421-1427, vol. 89, No. 12.

Willing et al., "Mobilized Peripheral Blood Cells Administered Intravenously Produce Functional Recovery in Stroke," Cell Transplant., 2003, pp. 449-454, vol. 12, USA.

Yandava et al., "'Global' cell replacement is feasible via neural stem cell transplantation: Evidence from the dysmyelinated *shiverer* mouse brain," Proc. Natl. Acad. Sci., Jun. 1999, pp. 7029-7034, vol. 96, USA.

Woodbury et al., "Adult Rat and Human Bone Marrow Stromal Cells Differentiate Into Neurons," J. Neurosci. Res., 2000, pp. 364-370, vol. 61.

Yamauchi et al., "Pre-administration of angiopoietin-1 followed by VEGF induces functional and mature vascular formation in a rabbit ischemic model," J. Gene Med., 2003, pp. 994-1004, vol. 5.

Zhang et al., "Human bone marrow stromal cell treatment improves neurological functional recovery in EAE mice," Exper. Neurology, 2005, pp. 16-26, vol. 195, Elsevier.

Zvaifler et al., "Mesenchymal precursor cells in the blood of normal individuals," Arthritis Res., 2000, pp. 477-488, vol. 2, No. 6.

Chen et al., "Intracerebral transplantation of bone marrow with BDNF after MCAo in rat," Neuropharmacology, 2000, 39:711-716.

Supplementary European Search Report completed May 27, 2009, mailed Jun. 5, 2009, in corresponding EP 04 74 6855, 3 pages.

Chen et al., "Human Bone Marrow Stromal Cell Cultures Conditioned by Traumatic Brain Tissue Extracts: Growth Factor Production," Journal of Neuroscience Research, Aug. 2, 2002, 69(5):687-691.

Erices et al., "Mesenchymal progenitor cells in human umbilical cord blood," British Journal of Hematology, 2000, 109:235-242.

Kuriwaka et al., "Isolation of mesenchymal stem cells in cord blood and placental blood, and induction of differentiation of such mesenchymal stem cells," Nihon Seikie-Geka-Gakkai Zasshie, 2002, 76(8):S1052, 2-D-7, with English translation of excerpt, 2 pages.

Mahmood et al., "Intracerebral Transplantation of Marrow Stromal Cells Cultured with Neurotrophic Factors Promotes Functional Recovery in Adult Rats Subjected to Traumatic Brain Injury," Journal of Neurotrauma, Dec. 1, 2002, 19(12):1609-1617.

Sanchez-Ramos et al,. "Adult Bone Marrow Stromal Cells Differentiate into Neural Cells in Vitro," Experimental Neurology, Jan. 1, 2000, 164:247-256.

Terashima et al., "Cell separation technology and application by a novel filter system," Cell, 2001, 33(11):436-439, with partial English translation, 1 page.

Zhao et al., "Human Bone Marrow Stem Cells Exhibit Neural Phenotypes and Ameliorate Neurological Deficits after Grafting into the Ischemic Brain of Rats," Experimental Neurology, 2002, 174:11-20.

* cited by examiner

FIG. 20
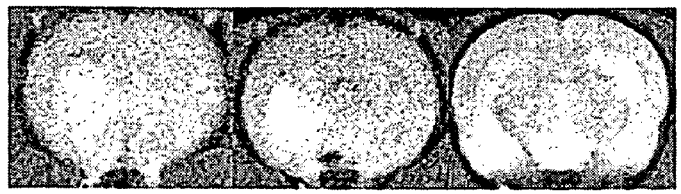
6 HRS AFTER CEREBRAL INFARCTION, 3 HRS AFTER TRANSPLANT
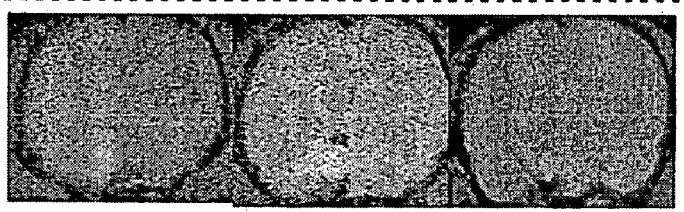
24 HRS AFTER CEREBRAL INFARCTION, 21 HRS AFTER TRANSPLANT
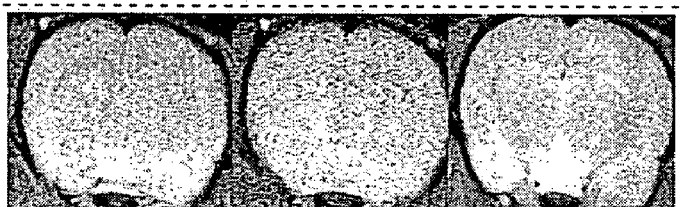
1 WEEK LATER
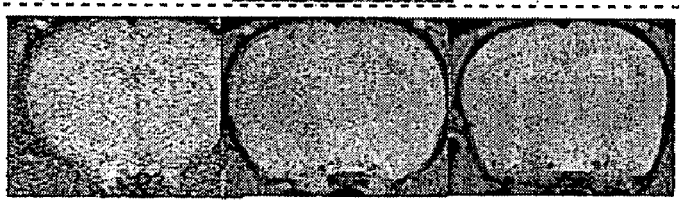
2 WEEKS LATER FIG. 21
6 HRS AFTER CEREBRAL INFARCTION, JUST BEFORE TRANSPLANT 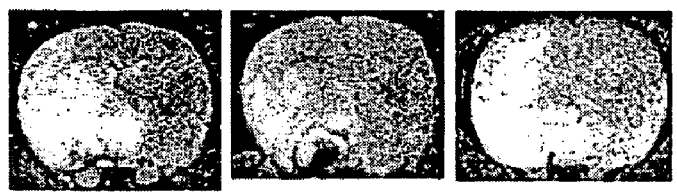
24 HRS AFTER CEREBRAL INFARCTION, 18 HRS AFTER TRANSPLANT 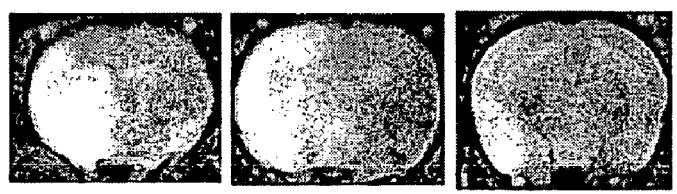
1 WEEK LATER 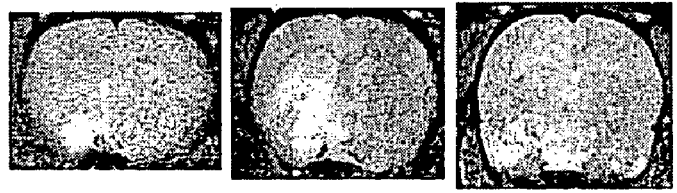
2 WEEKS LATER 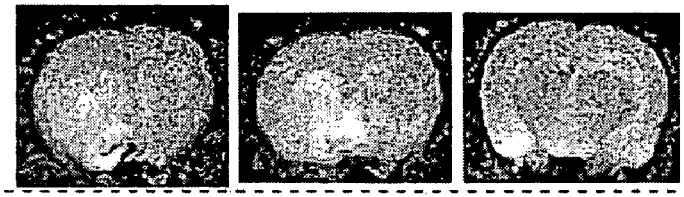
4 WEEKS LATER 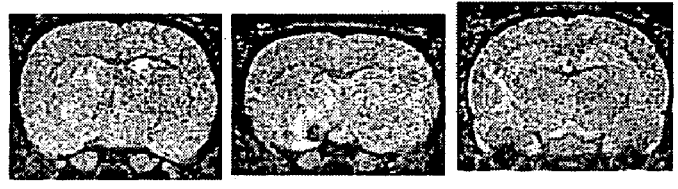

MSC CELLS
CONTROL                    G-CSF DAY 3 S.C.
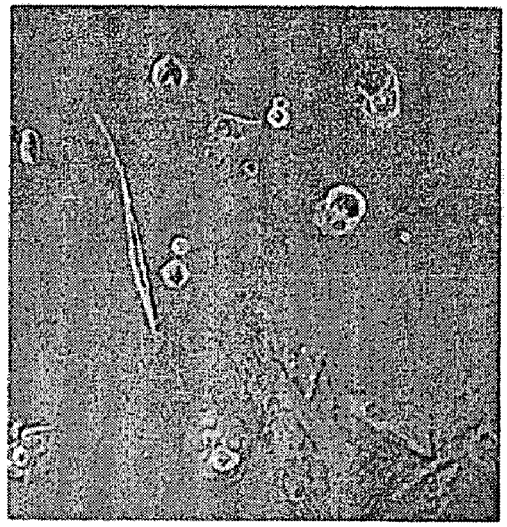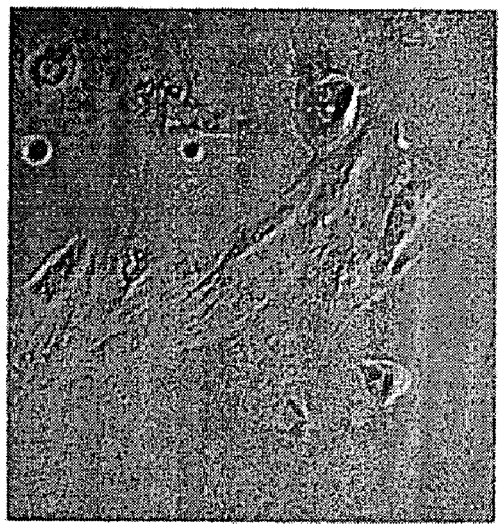
G-CSF + SCF DAY 7 S.C.           CORD BLOOD
FIG. 24

NF GFAP
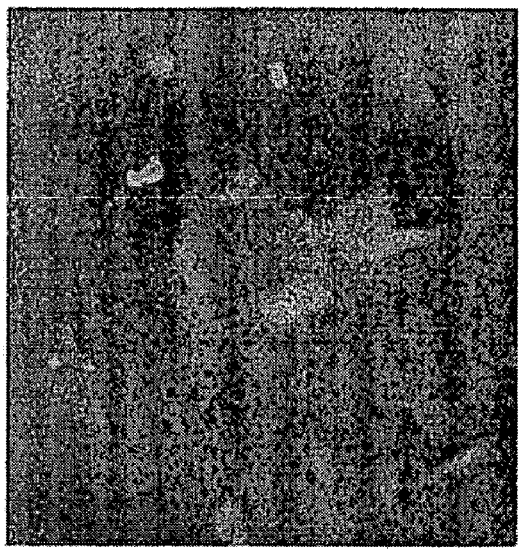 
RT-PCR (NF)　　　　　　　　　　RT-PCR (GFAP)
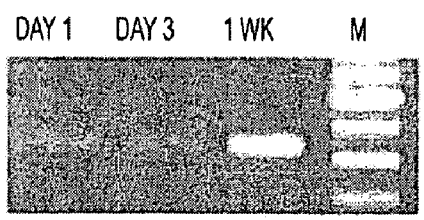 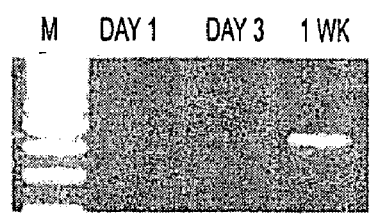
FIG. 26

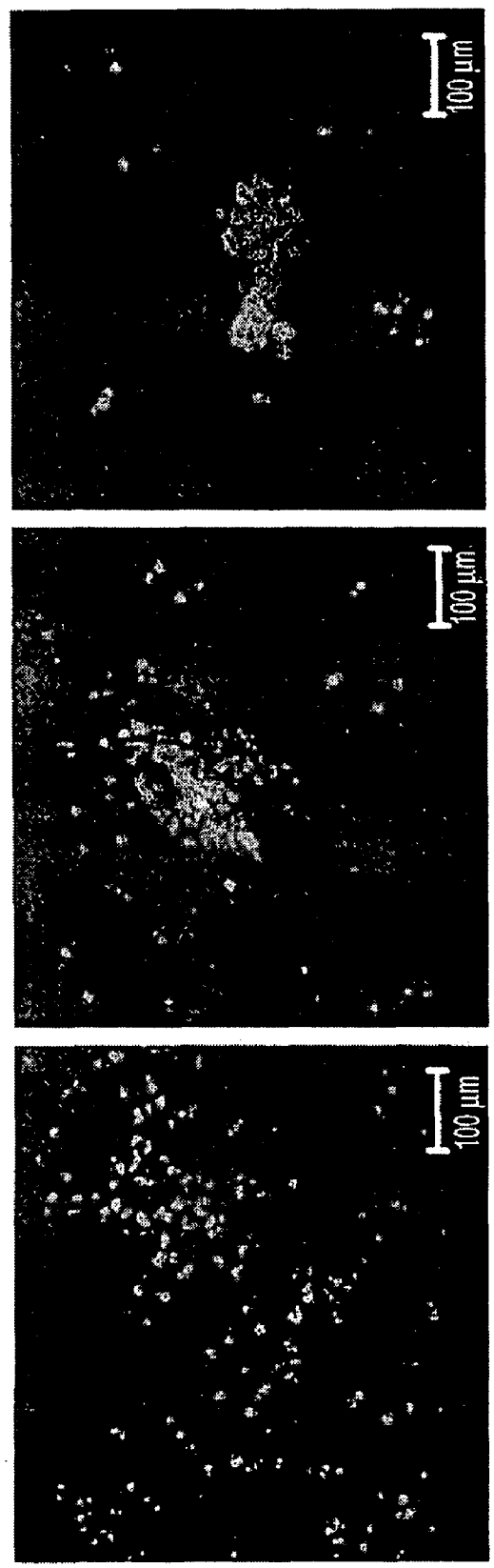

FIG. 36
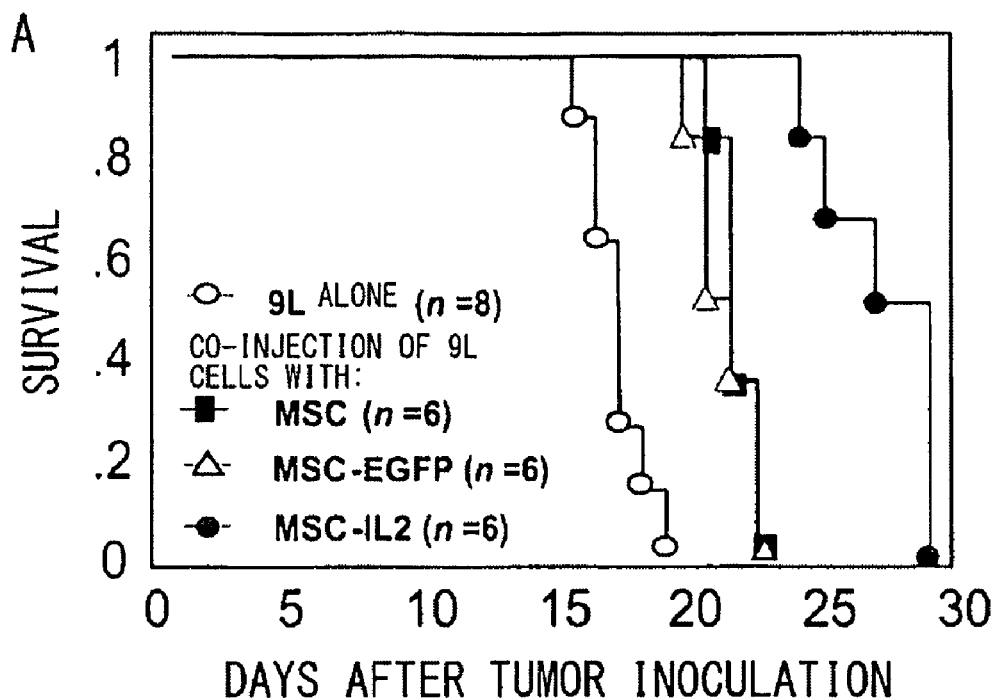
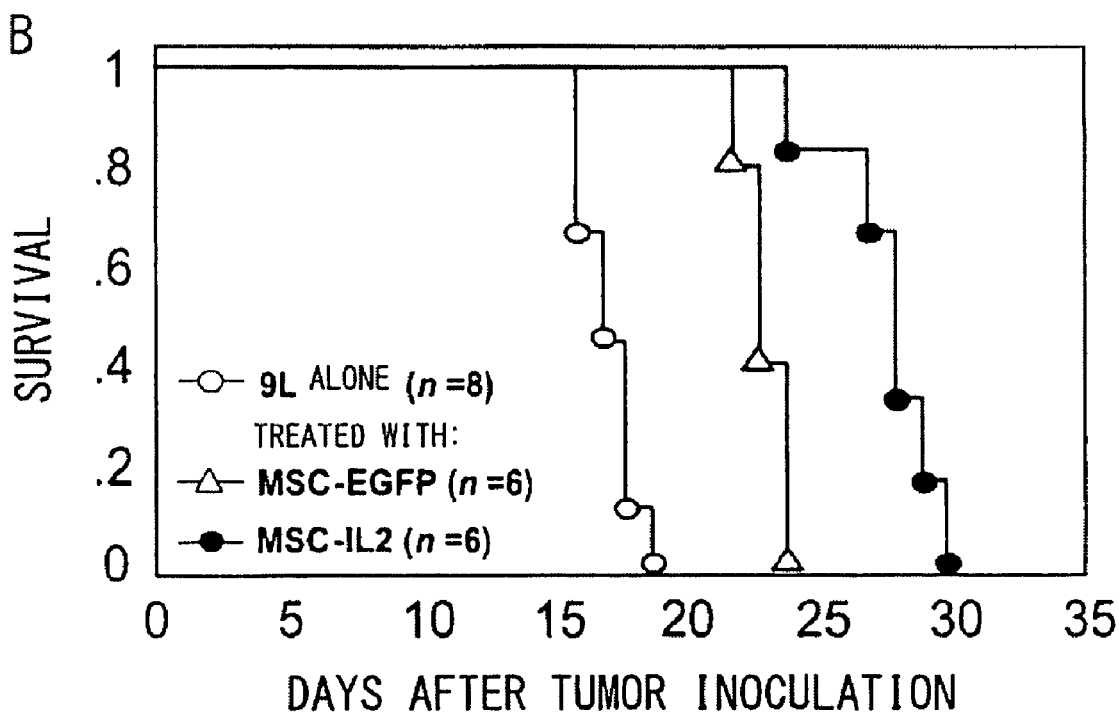

```
                           SEQUENCE LISTING

<160> NUMBER OF SEQ ID NOS: 10

<210> SEQ ID NO 1
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
cggaattcca ccatgaccat cctttcctt actatggtta                                40

<210> SEQ ID NO 2
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ccagatctat cttcccctt taatggtcaa tgta                                      34

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
tggaatcctg tggcatccat gaaac                                               25

<210> SEQ ID NO 4
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
taaaacgcag ctcagtaaca gtccg                                               25

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
```

```
cttagtctgg aggtggctac ataca                                           25

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gaggatagca gaagaactag gcact                                           25

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ggtcacttca catgccatag tcaa                                            24

<210> SEQ ID NO 8
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ggctcagttg gtactttgcg taa                                             23

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
attccgcgcc tctccctgtc tc                                              22

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gcttcatccg cctcctgtct gt                                              22
```

INTERNALLY ADMINISTERED THERAPEUTIC AGENTS FOR CRANIAL NERVE DISEASES COMPRISING MESENCHYMAL CELLS AS AN ACTIVE INGREDIENT

This application is a Continuation of application Ser. No. 11/377,610, filed Mar. 17, 2006, which is a Continuation-in-Part of application Ser. No. 10/562,202, which is a national phase application of PCT/JP04/009386 filed on Jun. 25, 2004. The entire of contents of application Ser. No. 10/562,202, include the specification, drawing, claims, sequence listing and abstract are hereby incorporated by reference.

TECHNICAL FIELD

The present invention relates to cranial nerve disease therapeutic agents for in vivo administration, which comprise mesenchymal cells, particularly bone marrow cells, cord blood cells, or peripheral blood cells, or cells derived from these cells as active ingredients.

BACKGROUND ART

In recent years regenerative medical techniques have been in the limelight. In regenerative medical techniques, disorders that the natural, inherent regenerative-healing ability of the human body cannot cure can be cured by regenerating organs and such using artificial proliferation of autologous cells, and then surgically conjugating these at the site of the lesions. Such cures have been successful in a wide variety of fields.

Transplantation of oligodendroglia (oligodendrocytes) (see Non-patent Documents 1 to 3), or myelin-forming cells, such as Schwann cells (see Non-patent Documents 4, 2, and 5) or olfactory ensheathing cells (see Non-patent Documents 6 to 8), can elicit remyelination in animal models and electrophysiological function may be recovered (see Non-patent Documents 9 and 5). It is not impossible to prepare such cells from patients or other persons for use in cell therapy; however, it is problematic since tissue material must be collected from either the brain or nerves.

Neural progenitor cells or stem cells derived from the brain have the ability to self-proliferate, and are known to differentiate into neurons and glial cells of various lineages (see Non-patent Documents 10 to 13). Upon transplantation into newborn mouse brains, human neural stem cells collected from fetal tissues differentiate into neurons and astrocytes (see Non-patent Documents 14 to 16), and can remyelinate axons (Non-patent Document 17). There have been reports of the remyelination and recovery of impulse conduction when neural progenitor cells derived from adult human brains are transplanted into demyelinated rodent spinal cords (Non-patent Document 18).

These studies have evoked great interest since they indicate the possibility of applying the above-mentioned cells in reparative strategies for neurological diseases (see Non-patent Documents 18, 14 to 16, and 19).

Recent studies have revealed that neural stem cells can produce hematopoietic cells in vivo, indicating that neural progenitor cells are not limited to nervous system cell lineages (see Non-patent Document 20). Further, when bone marrow interstitial cells are injected into newborn mouse lateral ventricles, they differentiate, to a very small extent, into cells expressing astrocyte markers (see Non-patent Document 21). Under appropriate cell culture conditions bone marrow interstitial cells are reported to produce a very small number of cells that express nervous system cell markers in vitro; however, it is unclear whether these cells are useful for neural regeneration (see Non-patent Document 22).

The present inventors have previously extracted and cultured nervous system cells (neural stem cells, neural progenitor cells) from adult human brains, and established some cell lines.

By studying the functions of these cells, the inventors discovered that neural stem cells are pluripotent and can self-reproduce (see Non-patent Document 18). Specifically, single-cell expansion of neural progenitor (stem) cells obtained from adult human brains was conducted to establish cell lines; the established cells were then subjected to in vitro clonal analysis. The results demonstrated that the cell lines were pluripotent (namely, had the ability to differentiate into neurons, astroglia (or astrocytes), and oligodendroglia (i.e., oligodendrocytes)) and had self-reproducing ability (namely, proliferation potency). Thus, these cells were confirmed to possess the characteristics of neural stem cells.

Transplantation of cultured neural stem cells, which were extracted from small amounts of neural tissue collected from the cerebrum of an individual, into a lesion of the brain or spinal cord of the individual, seems to be a widely applicable therapeutic method in autotransplantation therapy. However, although it doesn't cause symptoms of neurological deficiency, collecting tissues that contain neural stem cells from the cerebrum is not easy. Thus, considering the current need to establish therapeutic methods for various complicated diseases of the nervous system, it is crucial to establish safer and simpler methods for autotransplantation therapy. Thus, to obtain donor cells, the present inventors have developed techniques for collecting mononuclear cell fractions and the like from bone marrow cells, cord blood cells, or fetal liver cells, which is simpler than collecting neural stem cells (see Patent Document 1). Specifically, the present inventors have shown that mononuclear cell fractions prepared from bone marrow cells have the ability to differentiate into nervous system cells. They also have shown that cell fractions containing mesodermal stem cells (mesenchymal stem cells), stromal cells, and AC133-positive cells, which were separated from the mononuclear cell fraction, also had the ability to differentiate into nervous system cells.

Cranial nerve diseases can be treated by directly administering an affected part in the brain with cells that have the ability to differentiate into the above-mentioned nervous system cells. This technique, however, is very complicated and dangerous. There is therefore much demand for the development of simple and safe methods and agents for treating cranial nerve diseases.

Mesenchymal stem cells (MSCs) are thought to represent a very small proportion of cells in the mononuclear population of bone marrow. These cells will grow to confluency in appropriate culture conditions as flattened fibroblast-like cells, and have been suggested to differentiate into bone, cartilage, cardiac myocytes and neurons and glia both in vitro and in vivo. MSCs prepared from human bone marrow (BMSCs) have been used in clinical studies for metachromatic leukodystrophy, Hurler syndrome, myeloablative therapy for breast cancer [11], graft-versus-host disease, and stroke.

Human mesenchymal precursor cells found in the blood of normal subjects proliferated in culture with an adherent-spread morphology, and displayed cytoskeletal, cytoplasmic and surface markers ($CD34^-$, $CD45^-$, and $CD105^+$) of mesenchymal precursors. These cells had a capacity for differentiation into fibroblast, osteoblast, and adipocyte lineages. A canine $CD34^-$ fibroblast-like cell in the peripheral blood showed mesenchymal stem cell characteristics. Because peripheral blood is readily accessible, stem cells isolated from blood may be a good candidate for a cell therapy.

Transplantation of mesenchymal stem cells derived from bone marrow (BMSCs) after ischemia onset can reduce infarction size and improve functional outcome in rodent cerebral ischemia models. While intravenous injection of BMSCs reduces infarction size and improves functional outcome in a rat stroke model, the therapeutic benefit of MSC-like multipotent precursor cells derived from peripheral blood (PMSCs) transplantation in cerebral ischemia is still uncertain.

Although the potential of MSCs in peripheral blood (PMSCs) has been studied, it is not previously been known whether peripheral blood-derived plastic-adherent stem/precursor cells (PMSCs) can differentiate into a neural lineage or provide a therapeutic benefit for victims of stroke.

[Patent Document] WO 02/00849

[Non-patent Document 1] Archer D R, et al. 1994. Exp Neurol 125:268-77.

[Non-patent Document 2] Blakemore W F, Crang A J. 1988. Dev Neurosci 10:1-11.

[Non-patent Document 3] Gumpel M, et al. 1987. Ann New York Acad Sci 495:71-85.

[Non-patent Document 4] Blakemore W F. 1977. Nature 266: 68-9.

[Non-patent Document 5] Honmou O, et al. 1996. J Neurosci 16:3199-208.

[Non-patent Document 6] Franklin R J, et al. 1996. Glia 17:217-24.

[Non-patent Document 7] Imaizumi T, et al. 1998. J Neurosci 18(16):6176-6185.

[Non-patent Document 8] Kato T, et al. 2000. Glia 30:209-218.

[Non-patent Document 9] Utzschneider D A, et al. 1994. Proc Natl Acad Sci USA 91:53-7.

[Non-patent Document 10] Gage F H, et al. 1995. Proc Natl Acad Sci USA 92:11879-83.

[Non-patent Document 11] Lois C, Alvarez-Buylla A. 1993. Proc Natl Acad Sci USA 90:2074-7.

[Non-patent Document 12] Morshead C M, et al. 1994. Neuron 13:1071-82.

[Non-patent Document 13] Reynolds B A, Weiss S. 1992. Science 255:1707-10.

[Non-patent Document 14] Chalmers-Redman R M, et al. 1997. Neurosci 76:1121-8.

[Non-patent Document 15] Moyer M P, et al. 1997. Transplant Proc 29:2040-1.

[Non-patent Document 16] Svendsen C N, et al. 1997. Exp Neurol 148:135-46.

[Non-patent Document 17] Flax J D, et al. 1998. Nat Biotechnol 16:1033-9.

[Non-patent Document 18] Akiyama Y, et al. 2001. Exp Neurol.

[Non-patent Document 19] Yandava B D, et al. 1999. Proc Natl Acad Sci USA 96:7029-34.

[Non-patent Document 20] Bjornson C R, et al. 1999. Science 283:534-7.

[Non-patent Document 21] Kopen G C, et al. Proc Natl Acad Sci USA 96:10711-6.

[Non-patent Document 22] Woodbury D, et al. 2000. J Neurosci Res 61:364-70.

[Non-patent document 23] Friedenstein A J. Precursor cells of mechanocytes. Int Rev Cytol 1976; 47:327-359.

[Non-patent document 24] Majumdar M K, Thiede M A, Mosca J D et al. Phenotypic and functional comparison of cultures of marrow-derived mesenchymal stem cells (MSCs) and stromal cells. J Cell Physiol 1998; 176:57-66.

[Non-patent document 25] Kobune M, Kawano Y, Ito Y et al. Telomerized human multipotent mesenchymal cells can differentiate into hematopoietic and cobblestone area-supporting cells. Exp Hematol 2003; 31:715-722.

[Non-patent document 26] Toma C, Pittenger M F, Cahill K S et al. Human mesenchymal stem cells differentiate to a cardiomyocyte phenotype in the adult murine heart. Circulation 2002; 105:93-98.

[Non-patent document 27] Prockop D J. Marrow stromal cells as stem cells for nonhematopoietic tissues. Science 1997; 276:71-74.

[Non-patent document 28] Woodbury D, Schwarz E J, Prockop D J et al. Adult rat and human bone marrow stromal cells differentiate into neurons. J Neurosci Res 2000; 61:364-370.

[Non-patent document 29] Iihoshi S, Honmou O, Houkin K et al. A therapeutic window for intravenous administration of autologous bone marrow after cerebral ischemia in adult rats. Brain Res 2004; 1007:1-9.

[Non-patent document 30] Honma T, Honmou O, Iihoshi S et al. Intravenous infusion of immortalized human mesenchymal stem cells protects against injury in a cerebral ischemia model in adult rat. Exp Neurol 2005 (in press).

[Non-patent document 31] Nomura T, Honmou O, Harada K et al. I.V. infusion of brain-derived neurotrophic factor gene-modified human mesenchymal stem cells protects against injury in a cerebral ischemia model in adult rat. Neuroscience 2005; 136:161-169.

[Non-patent document 32] Koc O N, Day J, Nieder M et al. Allogeneic mesenchymal stem cell infusion for treatment of metachromatic leukodystrophy (MLD) and Hurler syndrome (MPS-IH). Bone Marrow Transplant 2002; 30:215-222.

[Non-patent document 33] Koc O N, Gerson S L, Cooper B W et al. Rapid hematopoietic recovery after coinfusion of autologous-blood stem cells and culture-expanded marrow mesenchymal stem cells in advanced breast cancer patients receiving high-dose chemotherapy. J Clin Oncol 2000; 18:307-316.

[Non-patent document 34] Aggarwal S, Pittenger M F. Human mesenchymal stem cells modulate allogeneic immune cell responses. Blood 2005; 105:1815-1822.

[Non-patent document 35] Bang O Y, Lee J S, Lee P H et al. Autologous mesenchymal stem cell transplantation in stroke patients. Ann Neurol 2005; 57:874-882.

[Non-patent document 36] Zvaifler N J, Marinova-Mutafchieva L, Adams G et al. Mesenchymal precursor cells in the blood of normal individuals. Arthritis Res 2000; 2:477-488.

[Non-patent document 37] Huss R, Lange C, Weissinger E M et al. Evidence of peripheral blood-derived, plastic-adherent CD34 (-/low) hematopoietic stem cell clones with mesenchymal stem cell characteristics. Stem Cells 2000; 18:252-260.

[Non-patent document 38] Brown R A, Adkins D, Goodnough L T. Factors that influence the collection and engraftment of allogeneic peripheral-blood stem cells in patients with hematologic malignancies. J Clin Oncol 1997; 15:3067-3074.

[Non-patent document 39] Auner H W, Zebisch A, Ofner P et al. Evaluation of potential risk factors for early infectious complications after autologous peripheral blood stem cell transplantation in patients with lymphoproliferative diseases. Ann Hematol 2005; 84:532-537.

[Non-patent document 40] Bender J G, Unverzagt K L, Walker D E et al. Identification and comparison of CD34-positive cells and their subpopulations from normal peripheral blood and bone marrow using multicolor flow cytometry. Blood 1991; 77:2591-2596.

[Non-patent document 41] Tondreau T, Meuleman N, Delforge A et al. Mesenchymal stem cells derived from CD133-positive cells in mobilized peripheral blood and cord blood: proliferation, Oct4 expression, and plasticity. Stem Cells 2005; 23:1105-1112.

[Non-patent document 42] Rochefort G Y, Vaudin P, Bonnet N et al. Influence of hypoxia on the domiciliation of mesenchymal stem cells after infusion into rats: possibilities of targeting pulmonary artery remodeling via cells therapies?. Respir Res 2005; 6:125.

[Non-patent document 43] Chen J, Li Y, Wang L, et al. Therapeutic benefit of intracerebral transplantation of bone marrow stromal cells after cerebral ischemia in rats. J Neurol Sci 2001; 189: 49-57.

[Non-patent document 44] Chopp M, Zhang X H, Li Y, et al. Spinal cord injury in rat: treatment with bone marrow stromal cell transplantation. Neuroreport. 2000; 11(13): 3001-3005.

[Non-patent document 45] Prockop D J. Marrow stromal cells as stem cells for nonhematopoietic tissues. Science 1997; 276:71-74.

[Non-patent document 46] Woodbury D, Schwarz E J, Prockop D J, et al. Adult rat and human bone marrow stromal cells differentiate into neurons. J Neurosci Res 2000; 61:364-370.

[Non-patent document 47] Kobune M, Kawano Y, Ito Y, et al. Telomerized human multipotent mesenchymal cells can differentiate into hematopoietic and cobblestone area-supporting cells. Exp Hematol 2003; 31:715-722.

[Non-patent document 48] Prockop D J, Gregory C A, Spees J L. One strategy for cell and gene therapy: Harnessing the power of adult stem cells to repair tissues. PNAS 2003; 100: 11917-11923.

[Non-patent document 49] Longa E Z, Weinstein P R, Carlson S, Cummins R. Reversible middle cerebral artery occlusion without craniectomy in rats. Stroke 1989; 20:84-91.

[Non-patent document 50] Nakamura Y, Wakimoto H, Abe J, et al. Adoptive immunotherapy with murine tumor-specific T lymphocytes engineered to secrete interleukin 2. Cancer Res 1994; 54:5757-5760.

[Non-patent document 51] Nakagawa I, Murakami M, Ijima K, et al. Persistent and secondary adenovirus-mediated hepatic gene expression using adenovirus vector containing CTLA4IgG Hum Gene Ther 1998; 9:1739-1745.

[Non-patent document 52] Takiguchi M, Murakami M, Nakagawa I, et al. CTLA4IgG gene delivery prevents autoantibody production and lupus nephritis in MRL/lpr mice. Life Sci 2000; 66:991-1001.

[Non-patent document 53] Neumann-Haefelin T, Kastrup A, de Crespigny A, et al. Serial MRI after transient focal cerebral ischemia in rats: dynamics of tissue injury, blood-brain barrier damage, and edema formation. Stroke 2000; 31:1965-1972.

[Non-patent document 54] Bederson J B, Pitts L H, Germano S M, Nishimura M C, et al. Evaluation of 2,3,5-triphenyltetrazolium chloride as a stain for detection and quantification of experimental cerebral infarction in rats. Stroke 1986; 17:1304-1308.

[Non-patent document 55] Villaron E M, Almeida J, Lopez-Holgado N, et al. Mesenchymal stem cells are present in peripheral blood and can engraft after allogeneic hematopoietic stem cell transplantation. Haematologica 2004; 89:1421-1427.

[Non-patent document 56] Willing A E, Vendrame M, Mallery J, et al. Mobilized peripheral blood cells administered intravenously produce functional recovery in stroke. Cell Transplant 2003; 12:449-454.

[Non-patent document 57] Hirouchi M, Ukai Y. Current state on development of neuroprotective agents for cerebral ischemia. Nippon Yakurigaku Zasshi 2002; 120:81-90.

[Non-patent document 58] Kurozumi K, Nakamura K, Tamiya T, et al. BDNF gene-modified mesenchymal stem cells promote functional recovery and reduce infarct size in the rat middle cerebral artery occlusion model. Mol Ther 2004; 9: 189-97.

[Non-patent document 59] Sasaki M, Hains B C, Lankford K L, et al. Protection of corticospinal tract neurons after dorsal spinal cord transection and engraftment of olfactory ensheathing cells. Glia. 2006; 53:352-359.

[Non-patent document 60] Chen X, Li Y. Wang L, et al. Ischemic rat brain extracts induce human marrow stromal cell growth factor production. Neuropathology 2002; 22:275-279.

[Non-patent document 61] Iuchino S, Zanotti L, Rossi B, et al. Neurosphere-derived multipotent precursors promote neuroprotection by an immunomodulatory mechanism. Nature 2005; 436: 266-271.

[Non-patent document 62] Keirstead H S, Ben-Hur T, Rogister B, et al. Polysialylated neural cell adhesion molecule-positive CNS precursors generate both oligodendrocytes and Schwann cells to remyelinate the CNS after transplantation. J. Neurosci 1999; 19:7529-7536.

[Non-patent document 63] Inoue M, Honmou O, Oka S, et al. Comparative analysis of remyelinating potential of focal and intravenous administration of autologous bone marrow cells into the rat demyelinated spinal cord. Glia 2003; 44: 111-118.

[Non-patent document 64] Sasaki M, Honmou O, Akiyama Y, et al. Transplantation of an acutely isolated bone marrow fraction repairs demyelinated adult rat spinal cord axons. Glia 2001; 35:26-34.

[Non-patent document 65] Hamano K, Li T S, Kobayashi T, et al. Angiogenesis induced by the implantation of self-bone marrow cells: a new material for therapeutic angiogenesis. Cell Transplant 2000; 9:439-443.

[Non-patent document 66] Bernstein D C, Shearer G M. Suppression of human cytotoxic T lymphocyte responses by adherent peripheral blood leukocytes. Ann NY Acad. Sci. 1988; 532:207-213.

[Non-patent document 67] Escolar M E, Poe M D, Provenzale J M et al. Transplantation of umbilical-cord blood in babies with infantile Krabbe's disease. The New England Journal of Medicine 2005; 352:2069-2081.

[Non-patent document 68] Staba S L, Escolar M L, Poe M, et al. Cord-blood transplants from unrelated donors in patients with Hurler's syndrome. N Engl J. Med. 2004; 350:1960-1969.

[Non-patent document 69] Zhang J, Li Y, Chen J, et al. Human bone marrow stromal cell treatment improves neurological functional recovery in EAE mice. Exp Neurol 2005; 195: 16-26.

[Non-patent document 70] Pluchino S, Quattrini A, Brambilla E, et al. Injection of adult neurospheres induces recovery in a chronic model of multiple sclerosis. Nature 2003; 422:688-694.

SUMMARY OF THE INVENTION

One aspect of this invention is a composition of peripheral blood-derived mesenchymal stem cells (PMSCs) that is over 70% positive for CD73, essentially 100% positive for CD90, essentially 100% negative for CD45 and essentially 100% negative for CD106. The term essentially 100% means nearly all the detectable cells, such as 99% or more, display or do not display as certain marker.

Another aspect of this present invention is a method of differentiating PMSCs into neural cells by
 a) obtaining peripheral blood from a subject or patient,
 b) optionally diluting the peripheral blood,
 c) optionally incubating the peripheral blood,
 d) centrifuging the peripheral blood in order to form a supernatant and a cell fraction,
 e) discarding the supernatant from the cell fraction,
 f) suspending the cell fraction in a culture medium,
 g) plating the suspended cells on a surface for tissue culturing,
 h) incubating the suspended cells for about 48 hours, wherein the cells form into a group of cells adhering the surface and a group of cells not adhering to the surface,
 i) eliminating the nonadherent cells,
 j) further incubating the adherent cells,
 k) optionally detaching and subculturing the adherent cells,
 l) detaching the adherent cells,
 m) suspending the adherent cells in a neural progenitor basal medium,
 n) plating the cells wherein PMSCs are formed, and
 o) harvesting the PMSCs.
PMSCs can be harvested by conventional means, such as by use of a centrifuge. In one embodiment of the present invention, the PMSCs form floating neurospheres prior to harvesting.

It is preferred to centrifuge at 300-500 G for about 2 to 5 minutes. The angle of the centrifuge tube can be about 40°-50° and the speed of the centrifuge can be about 1200 to about 3500 rpm. A suspension for separating or culturing PMSCs can be any commercially available neural progenitor base medium. Another aspect of the present invention involves a method of treating a patient who has suffered a stroke or who suffers from neural lesions caused by injury or disease, ischemia, infarction, Krabbe's disease, Hurler's syndrome, metachromatic leukodystrophy, or encephalomyelitis by injecting into the patient a therapeutically effective amount of PMSCs. The PMSCs can be injected, preferably injected intravenously. An intravenous injection can be made anywhere on the patient, such as in the arm or leg or other conventional locations. The treatment for stroke can be after a week of the occurrence of the stroke, less then a week, less than 36 hours, less than 24 hours, less than 12 hours or less 6 hours. The surface that the cells are cultured on can be any type of surface suitable for culturing cells such as a plastic or glass surface, a surface of a culturing dish or a culture medium surface.

DISCLOSURE OF THE INVENTION

The present invention was achieved under these circumstances, and an objective of the present invention is to provide safe techniques and agents for treating cranial nerve diseases. More specifically, an objective is to provide agents for treating cranial nerve diseases for in vivo administration, particularly for intravenous administration, comprising mesenchymal cells, particularly bone marrow cells, cord blood cells, or peripheral blood cells, or cells derived from these cells as an active ingredient.

The present inventors made intensive investigations to achieve the above objectives. Initially, they investigated the therapeutic effect on cranial nerve diseases of: collecting bone marrow cells from mouse bone marrow, separating only the mononuclear cell fraction therefrom, and using this isolated fraction as donor cells for intravenous administration to a rat cerebral infarction model. Consequently, they surprisingly found that not only local administration, but also intravenous administration of bone marrow cells exhibits a therapeutic effect on cranial nerve diseases such as cerebral infarction, spinal cord injuries, and demyelinating diseases.

The present inventors made further studies on the therapeutic effects of bone marrow stem cells (mesenchymal stem cells) on cranial nerve diseases by intravenously administering them to the above mentioned model animal in the same manner. They found that intravenous administration of bone marrow stem cells is very effective for treating cranial nerve diseases.

They also found that intravenous administration or local administration of autologous bone marrow cells or mesenchymal stem cells is effective for treating cranial nerve diseases. Compared to allotransplantation and xenotransplantation, autotransplantation is extremely advantageous in terms of therapeutic effects and further does not require immunosuppressive drugs.

As described above, the present inventors discovered the therapeutic effects of intravenously administering mesenchymal cells (mesenchymal stem cells), particularly bone marrow cells or mesenchymal stem cells, on cranial nerve diseases. The present invention has been achieved based on these findings. As shown below in the Examples, the present inventors have verified the therapeutic effects on cranial nerve diseases of intravenously administering the mesenchymal cells of the present invention by carrying out various medical or biological experiments and detailed analysis.

Specifically, mesenchymal cells (mesenchymal stem cells), and particularly bone marrow cells themselves, can become intravenously administered agents for therapies of cranial nerve diseases.

The above mentioned therapeutic effects are considered to be synergistic, including the neuroprotective and neural regenerative effects of bone marrow cells or mesenchymal stem cells. Accordingly, bone marrow cells or mesenchymal stem cells are expected to be intravenously administered cranial nerve protectants or cranial nerve regenerants.

The present invention relates to agents for treating cranial nerve diseases that are administered in vivo, and particularly that are intravenously administered, where the agents comprise mesenchymal cells, particularly bone marrow cells, cord blood cells, or peripheral blood cells, or cells derived from these cells as an active ingredient. The present invention also relates to agents for in vivo administration that exhibit neuroprotective or regenerative actions on cranial nerves, which comprise the above mentioned mesenchymal cells as an active ingredient, and use of the agents. More specifically, the present invention provides:

[1] A cranial nerve disease therapeutic agent for in vivo administration, comprising a mesenchymal cell as an active ingredient.
[2] The agent of [1], wherein the cranial nerve disease is cerebral infarction.
[3] An agent for in vivo administration, exhibiting neuroprotection and comprising a mesenchymal cell as an active ingredient.
[4] An agent for in vivo administration, exhibiting cranial nerve regeneration and comprising a mesenchymal cell as an active ingredient.
[5] The agent of any one of [1] to [4], wherein the in vivo administration is intravenous.

[6] The agent of any one of [1] to [5], wherein the mesenchymal cell is:
(a) a mesenchymal cell introduced with a BDNF gene, PLGF gene, GDNF gene, or IL-2 gene; or
(b) an immortalized mesenchymal cell introduced with an hTERT gene.

[7] The agent of any one of [1] to [6], wherein the mesenchymal cell is a mesenchymal stem cell.

[8] The agent of any one of [1] to [6], wherein the mesenchymal cell is a bone marrow cell, a cord blood cell, or a peripheral blood cell.

[9] A method for treating a cranial nerve disease comprising the in vivo administration to a patient of a therapeutically effective amount of the agent of any one of [1] to [8].

[10] The method of [9], wherein the bone marrow cell is an autologous cell of the patient.

[11] The method of [9] or [10], wherein the cranial nerve disease is cerebral infarction.

[12] The method of any one of [9] to [11], wherein the in vivo administration is intravenous administration.

[13] The method of any one of [9] to [12], wherein the mesenchymal cell is a bone marrow cell, a cord blood cell, or a peripheral blood cell.

The present invention provides cranial nerve disease therapeutic agents for in vivo administration, wherein the agents comprise mesenchymal cells (for example, bone marrow cells, cord blood cells, peripheral blood cells, mesenchymal stem cells, or cells derived from these cells) as an active ingredient.

Herein the term "in vivo administration" generally means administration at a site other than the head (brain). The in vivo administration includes intravenous administration, intramuscular administration, subcutaneous administration, and intraperitoneal administration, and of these intravenous administration is most preferred.

Herein the term "mesenchymal cells" preferably refers to, for example, bone marrow cells (mononuclear cell fraction of bone marrow cells; MCF (mononuclear cell fraction)), cord blood cells, peripheral blood cells, mesenchymal stem cells (MSCs), or cells derived from these cells. The mesenchymal cells of the present invention include, for example, mesenchyme-related cells, mesoblastic stem cells, and so on. Even if cells referred to as "mesenchymal cells" in the present invention are classified as cells other than mesenchymal cells in the future, the cells can still be suitably used in the present invention.

The stem cells included in bone marrow are hematopoietic stem cells and "mesenchymal stem cells (MSCs)". Herein "stem cells" generally mean undifferentiated cells with self-proliferation ability and the ability to differentiate into cells which have specific functions in physiological processes, such as the proliferation and differentiation of cells constituting living bodies. Hematopoietic stem cells are stem cells that differentiate into red blood cells, white blood cells, or thrombocytes. Mesenchymal stem cells may differentiate via neural stem cells into nerves, differentiate directly into nerves without going via neural stem cells, differentiate via stromal cells into nerves (but with low efficiency), differentiate into viscera, differentiate into the blood vascular system, or differentiate into bone, cartilage, fat, or muscle.

The present invention mainly uses mesenchymal stem cells (MSCs), but there is also the possibility of using hematopoietic stem cells and other stem cells (progenitor cells) in the body. The mesenchymal stem cells can be obtained from bone marrow cells, collected from the bone marrow. Bone marrow cells from which mesenchymal stem cells are not separated can also be used for the treatments, as for the mesenchymal stem cells, although the efficacy of the former is somewhat less the latter.

Preparing cells such as mesenchymal stem cells from the peripheral blood is also thought possible. In fact, the present inventors have successfully induced cultured cells, derived from cells contained in the peripheral blood, to differentiate into cells capable of developing cell markers of neural stem cells and nervous system cells (neurons and glial cells). G-CSF or SCF is not always necessary when inducing cells derived from the peripheral blood to differentiate into nervous system cells. Specially, the present inventors have found that, when mesoblastic stem cells (mesenchymal stem cells) prepared from a mononuclear cell fraction separated from bone marrow fluid or umbilical cord blood, or embryonic stem cells (ES cells), are cultivated in a basal culture medium, the mesoblastic stem cells (mesenchymal stem cell) or ES cells are induced to differentiate into neural stem cells, neurons, or glial cells. Accordingly, cells with functions equivalent to mesenchymal stem cells can be prepared by cultivating cells from peripheral blood, and such cells can be used in the present invention. The "basal culture media" is not limited, as long as they are regular culture media used in cell cultivation, and they are preferably DMEM (Dulbecco's modified essential medium) or NPBM (Neural progenitor cell basal medium: Clonetics). Other components of the above mentioned basal culture medium are not particularly limited, and preferably contains F-12, FCS, and/or Neural survival factors (Clonetics), and so on. The concentration within this culture medium may be, for example, 50% for F-12 and/or 1% for FCS. The $CO_2$ concentration of the culture medium is preferably 5%, but is not limited thereto.

As used herein, the term "mesodermal stem cell" refers to a cell constituting tissues embryologically categorized into the class of mesoderm, including blood cells. A "mesodermal stem cell" is also a cell that can make copies of itself (divide and proliferate), with the same potency as that of the original cell, and with the ability to differentiate into all cell types constituting mesodermal tissues. The mesodermal stem cell expresses, for example, the cell markers SH2(+), SH3(+), SH4(+), CD29(+), CD44(+), CD14(−), CD34(−), and CD45(−), but such cells are not limited to these markers. Furthermore, so-called mesenchyme-related stem cells are also included in the mesodermal stem cells of the present invention.

The above term "mesenchyme-related cell" refers to mesenchymal stem cells, mesenchymal cells, precursor cells of mesenchymal cells and cells derived from mesenchymal cells.

The term "mesenchymal stem cell" refers to stem cells that can be obtained from bone marrow, peripheral blood, skin, hair root, muscle tissue, uterine endometrium, blood, cord blood and primary cultures of various tissues. Furthermore, cells functionally equivalent to mesenchymal stem cells obtainable by culturing cells in the peripheral blood are also comprised in the mesenchymal stem cells of the present invention.

Preferred mesenchymal cells in the present invention are bone marrow cells and bone marrow stem cells (mesenchymal stem cell). Cord blood cells, peripheral blood cells, and fetal liver cells are also preferable examples in the present invention.

A preferred embodiment of bone marrow cells, cord blood cells, peripheral blood cells, and fetal liver cells in the present invention is a cell fraction which is isolated from bone marrow cells, cord blood cells, peripheral blood, or fetal liver and comprises cells capable of differentiating into nervous system cells.

In another embodiment, the cell fraction is a cell fraction containing mesoblastic stem cells characterized by SH2 (+), SH3 (+), SH4 (+), CD29 (+), CD44 (+), CD14 (−), CD34(−), and CD45(−).

Other examples of the cell fraction are cell fractions containing interstitial cells characterized by Lin(−), Sca-1(+), CD10(+), CD11D(+), CD44(+) CD45(+), CD71(+), CD90 (+), CD105(+), CDW123(+), CD127(+), CD164(+), fibronectin (+), ALPH(+), and collagenase-1 (+), or cell fractions containing cells characterized by AC133(+).

Cells contained in the above mentioned cell fractions are preferably cells capable of differentiating into nervous system cells.

The cell fractions in the present invention comprise mononuclear cell fractions, which were separated from bone marrow cells, and which contain cells characterized by their ability to differentiate into nervous system cells. Another embodiment is a mononuclear cell fraction separated from, for example, cord blood cells, peripheral blood cells, or fetal liver cells which contain cells characterized by their ability to differentiate into nervous system cells. Yet another embodiment is mesenchymal stem cells from the bone marrow that are released into the peripheral blood, and which are characterized by their ability to differentiate into nervous system cells. Active substance or agents, for example, can be used when mesenchymal stem cells are released into the peripheral blood, but these substances are not always necessary. Mesenchymal stem cells collected from the bone marrow and those derived from the peripheral blood possess common characteristics in the development of markers of neural stem cells and/or nervous system cells, but differ from each other in some properties, such as proliferation rate and rate of differentiation induction. The mesenchymal stem cells for use in the present invention are not limited to those collected from the bone marrow but also include those derived from the peripheral blood. Specifically, the "mesenchymal stem cells" in the present invention include both of these cells. In the present invention, the mesenchymal stem cells derived from the peripheral blood may also be simply referred to as "mesenchymal cells".

It is unclear whether the differentiation of cells contained in the cell fractions of the present invention into neural cells is caused by the transformation of so-called hematopoietic cells into neural cells, or, alternatively, by the differentiation of immature cells capable of differentiating into neural cells that are comprised in bone marrow cells, cord blood cells, or peripheral blood cells. However, the majority of the cells differentiating into neural cells are assumed to be stem or precursor cells, namely, cells having pluripotency and the ability to self-propagate. Alternatively, the cells differentiating into neural cells may be stem or precursor cells which have differentiated to some extent into endoderm or mesoderm.

Cells in a cell fraction of the present invention do not have to be proliferated with any trophic factors (but proliferation in the presence of trophic factors is possible). Thus, these cells are simple and practical from the standpoint of the development of autotransplantation technique for nervous system, and are very beneficial to the medical industry. In general, bone marrow cells, cord blood cells, or peripheral blood cells (cell fractions) of the present invention are derived from vertebrates, preferably from mammals (for example, mice, rats, rabbits, swine, dogs, monkeys, humans, etc.), but are not especially limited.

A cell fraction of the present invention can be prepared, for example, by subjecting marrow cells or cord blood cells collected from vertebrate animals to density-gradient centrifugation at 2,000 rpm in a solution for a sufficient time to ensure separation, depending on specific gravity, and then recovering the cell fraction with a certain specific gravity in the range of 1.07 to 1.1 g/ml. Herein, the phrase "a sufficient time to ensure separation, depending on specific gravity" refers to a time, typically about ten to 30 minutes, sufficient for the cells to shift to positions in the solution for density-gradient centrifugation that accord with their specific gravity. The specific gravity of the cell fraction to be recovered is within the range of 1.07 to 1.08 g/ml (for example, 1.077 g/ml). Solutions such as Ficoll solution and Percoll solution can be used for the density-gradient centrifugation, but there is no limit thereto. Furthermore, cord blood cells collected from vertebrate animals may be prepared in a similar manner as described above, and can be used as a cell fraction.

Specifically, first, bone marrow (5 to 10 µl) collected from a vertebrate animal is combined with a solution (2 ml L-15 plus 3 ml Ficoll), and then centrifuged at 2,000 rpm for 15 minutes to isolate a mononuclear cell fraction (approx. 1 ml). The mononuclear cell fraction is combined with culture solution (2 ml NPBM) to wash the cells, and then the cells are again centrifuged at 2,000 rpm for 15 minutes. Then, after removing the supernatant, the precipitated cells are recovered. In addition to the femur, sources for obtaining a cell fraction of the present invention include the sternum and the ilium, which constitutes the pelvis. Any other bone can serve as a source, as long as it is large enough. A cell fraction of the present invention can also be prepared from bone marrow fluid stored in a bone marrow bank, or from cord blood. When using cord blood cells, the cells can be obtained from cord blood stored in a bone marrow bank.

Another embodiment of the cell fractions of the present invention includes mononuclear cell fractions isolated and purified from bone marrow cells, cord blood cells, or peripheral blood cells, which contains mesodermal (mesenchymal) stem cells capable of differentiating into neural cells. A cell fraction containing mesodermal stem cells can be obtained, for example, by selecting cells with a cell surface marker, such as SH2 as described above, from the above-mentioned cell fraction obtained by centrifuging bone marrow cells, cord blood cells, or peripheral blood cells.

Furthermore, a cell fraction containing mesodermal stem cells (mesenchymal stem cells) capable of differentiating into neural cells can be prepared by subjecting bone marrow cells or cord blood cells collected from vertebrate animals to density-gradient centrifugation at 900 G in a solution for a sufficient time to ensure separation, depending on specific gravity, and then recovering the cell fraction with a certain specific gravity within the range of 1.07 to 1.1 g/ml. Herein, the phrase "a sufficient time to ensure separation, depending on specific gravity" refers to a time, typically about ten to 30 minutes, sufficient for the cells to shift to positions in the solution for density-gradient centrifugation that accord with their specific gravity. The specific gravity of a cell fraction to be recovered varies depending on the type of animal (for example, human, rat, or mouse) from which the cells have been derived. Solutions for density-gradient centrifugation include Ficoll solution and Percoll solution, but are not limited thereto.

Specifically, first, bone marrow (25 ml) or cord blood collected from a vertebrate animal is combined with an equal volume of PBS solution, and then centrifuged at 900 G for ten minutes. Precipitated cells are mixed with PBS and then recovered (cell density=approx. $4 \times 10^7$ cells/ml) to remove blood components. Then, a 5-ml aliquot thereof is combined with Percoll solution (1.073 g/ml), and centrifuged at 900 G for 30 minutes to extract a mononuclear cell fraction. The extracted mononuclear cell fraction is combined with a culture solution (DMEM, 10% FBS, 1% antibiotic-antimycotic solution) to wash the cells, and is centrifuged at 2,000 rpm for 15 minutes. Finally, the supernatant is removed, and the precipitated cells are recovered and cultured at 37° C. under 5% $CO^2$ atmosphere.

Another embodiment of a cell fraction of the present invention is a fraction of mononuclear cells isolated from bone marrow cells or cord blood cells, which contains stromal cells capable of differentiating into neural cells. Examples of stromal cells include cells characterized by Lin(−), Sca-1(+), CD10(+), CD11D(+), CD44(+), CD45(+), CD71(+), CD90 (+), CD105(+), CDW123(+), CD127(+), CD164(+), fibronectin (+), ALPH(+), and collagenase-1(+). A cell fraction containing stromal cells can be prepared, for example, by selecting cells with a cell surface marker, such as Lin as described above, from the above-mentioned cell fraction obtained by centrifuging bone marrow cells or cord blood cells.

Furthermore, such cell fractions can be prepared by subjecting bone marrow cells or cord blood cells collected from vertebrate animals to density-gradient centrifugation at 800 G in a solution for a sufficient time to ensure separation, depending on specific gravity, and then recovering the cell fraction with a certain specific gravity within the range of 1.07 to 1.1 g/ml. Herein, "a sufficient time ensuring separation depending on the specific gravity" indicates a time, typically about ten to 30 minutes, sufficient for the cells to shift to positions in the solution for density-gradient centrifugation that accord with their specific gravity. The specific gravity of the cell fraction to be recovered is preferably in the range of 1.07 to 1.08 g/ml (for example, 1.077 g/ml). Solutions for density-gradient centrifugation include Ficoll solution and Percoll solution, but are not limited thereto.

Specifically, first, bone marrow or cord blood collected from vertebrate animals is combined with an equal volume of a solution (PBS, 2% BSA, 0.6% sodium citrate, and 1% penicillin-streptomycin). A 5-ml aliquot thereof is combined with Ficoll+Paque solution (1.077 g/ml) and centrifuged at 800 G for 20 minutes to obtain a mononuclear cell fraction. The mononuclear cell fraction is combined with a culture solution (Alfa MEM, 12.5% FBS, 12.5% horse serum, 0.2% i-inositol, 20 mM folic acid, 0.1 mM 2-mercaptoethanol, 2 mM L-glutamine, 1 μM hydrocortisone, 1% antibiotic-antimycotic solution) to wash the cells, and then centrifuged at 2,000 rpm for 15 minutes. After centrifugation the supernatant is removed. The precipitated cells are collected and then cultured at 37° C. under 5% $CO^2$ atmosphere.

Another embodiment of a cell fraction of the present invention is a mononuclear cell fraction containing cells characterized by AC133(+) which can differentiate into neural cells, and which is isolated from bone marrow cells, cord blood cells, peripheral blood cells, or fetal liver tissues. Such cell fractions can be obtained, for example, by selecting cells with a cell surface marker of the above-mentioned AC133 (+) from the cell fraction obtained as described above by centrifuging bone marrow cells, cord blood cells, or peripheral blood cells.

Further, in other embodiments, the cell fractions can be obtained by subjecting fetal liver tissues collected from vertebrate animals to density-gradient centrifugation at 2,000 rpm in a solution for a sufficient time to ensure separation, depending on specific gravity, then recovering a cell fraction with a specific gravity in the range of 1.07 to 1.1 g/ml, and then recovering cells with AC133(+) characteristics from the cell fraction. Herein, "a sufficient time ensuring separation depending on specific gravity" refers to a time, typically about ten to 30 minutes, sufficient for the cells to shift to positions in the solution for density-gradient centrifugation that accord with their specific gravity. The solutions for density-gradient centrifugation include Ficoll solution and Percoll solution, but are not limited thereto.

Specifically, first, liver tissue collected from vertebrate animals is washed in L-15 solution, and then enzymatically treated for 30 minutes at 37° C. in an L-15 solution containing 0.01% DNaseI, 0.25% trypsin, and 0.1% collagenase. Then, the tissue is dispersed into single cells by pipetting. These single fetal liver cells are centrifuged by the same procedure as that described for the preparation of mononuclear cell fractions from femur in Example 1(1). The cells thus obtained are washed, and then AC133(+) cells are collected from the washed cells using an AC133 antibody. Thus, cells capable of differentiating into neural cells can be prepared from fetal liver tissues. The antibody-based recovery of AC133(+) cells can be achieved using magnetic beads or a cell sorter (FACS, etc.).

Transplanting any of these cell fractions containing mesodermal stem cells (mesenchymal stem cells), interstitial cells, or AC133-positive cells into demyelinated spinal cords can lead to efficient remyelination of demyelinated regions. In particular, the above-mentioned cell fractions containing mesodermal stem cells (mesenchymal stem cells) can favorably engraft and differentiate into nervous system cells or glial cells when transplanted into a cerebral infarction model.

The cells capable of differentiating into neural cells, which are contained in the above-mentioned cell fractions, include for example, neural stem cells, mesodermal stem cells (mesenchymal stem cells), interstitial cells, and AC133-positive cells which are contained in the above-mentioned cell fractions, but are not limited thereto as long as they can differentiate into neural cells.

The active ingredients of the cranial nerve disease therapeutic agents for in vivo administration of the present invention comprise not only bone marrow cells, cord blood cells, or peripheral blood cells, but also the above-mentioned cell fractions. In the present invention it is possible to administer mesenchymal cells such as bone marrow cells, cord blood cells, or peripheral blood cells without any modification. However, to improve the efficiency of therapy, they may be administered as agents (compositions) to which various agents have been added, or as cells to which genes with the function of increasing therapeutic effect have been introduced. The preparation of agents or transgenic cells of the present invention may comprise, but is not limited to:

(1) adding a substance that improves the proliferation rate of cells included in a cell fraction, or that enhances the differentiation of cells into nervous system cells, or introducing a gene having the same effect;
(2) adding a substance that improves the viability of cells in damaged neural tissues included in a cell fraction, or introducing a gene having the same effect (e.g., reduction of radicals);
(3) adding a substance that inhibits the adverse effects of damaged neural tissues on the cells in a cell fraction, or introducing a gene having the same effect;
(4) adding a substance that prolongs the lifetime of donor cells, or introducing a gene having the same effect (e.g., the hTERT gene);
(5) adding a substance that modulates the cell cycle, or introducing a gene having the same effect;
(6) adding a substance aimed at suppressing immunoreaction, or introducing a gene having the same effect;

(7) adding a substance that enhances energy metabolism, or introducing a gene having the same effect;
(8) adding a substance that improves the migration ability of donor cells in host tissues, or introducing a gene having the same effect;
(9) introducing a substance that improves blood flow (including the induction of angiogenesis), or a gene having the same effect (e.g., VEGF, angiopoietin, or PGF);
(10) adding a substance having neuroprotection activity, or introducing a gene having the same effect (e.g., BDNF, GDNF, NT, NGF, FGF, EGF, or PFG);
(11) adding a substance having an apoptosis inhibitory effect, or introducing a gene having the same effect; or
(12) adding a substance having an antitumor effect, or introducing a gene having the same effect (e.g., IL-2 or IF-β).

The present inventors verified that mesenchymal stem cells (MSCs) introduced with BDNF (brain-derived neurotrophic factor) gene, which is a nerve nutritional factor, have therapeutic effects on a rat cerebral infarction model, as shown in the Examples below. In addition, the present inventors confirmed that intravenous transplantation of MSCs introduced with the BDNF gene has therapeutic effects on cerebral infarction. Similarly, they have confirmed that intravenous transplantation of MSCs introduced with PLGF (placental growth factor) gene show therapeutic effects on cerebral infarction.

The present inventors have also found that MSCs introduced with genes other than the BDNF gene, such as the GDNF (glial cell line-derived neurotrophic factor), CNTF (ciliary neurotrophic factor), or NT3 (neurotrophin-3) gene, show therapeutic effects on cerebral infarction. They have verified that mesenchymal stem cells introduced with IL-2 gene have therapeutic effects on a rat brain tumor model. Thus, preferred embodiments of the mesenchymal cells for use in the present invention are mesenchymal cells introduced with the BDNF gene, PLGF gene, GDNF gene, or the IL-2 gene. Specifically, mesenchymal cells with an exogenous BDNF gene, PLGF gene, GDNF gene, or IL-2 gene in an expressible condition are preferably used as mesenchymal cells in the present invention.

Apart from the above genes, mesenchymal stem cells introduced with a gene such as the CNTF or NT3 gene are also preferred as specific examples of the mesenchymal cells in the present invention. Hereinafter, a mesenchymal stem cell (MSC) introduced with the "XX" gene may be referred to as "MSC-XX".

Combining the mesenchymal cells of the present invention with factors (genes) that are responsible for angiogenesis is expected to show significant therapeutic effects on treatments of cerebral infarction, since cerebral infarction shows symptoms of vascular occlusion. The present inventors have found that direct injection of the angiopoietin gene into cerebral infarctions exhibits significant angiogenetic effects, as shown in the Examples below. Specifically, MSCs introduced with a gene involved in angiogenesis, such as the angiopoietin gene, are expected to have therapeutic effects, particularly on cerebral infarctions.

Mesenchymal cells introduced with a desired gene in an expressible manner can be suitably prepared using techniques known to those skilled in the art.

The bone marrow fluids to be used in the present invention can be collected, for example, by anesthetizing (locally or systemically) vertebrate animals (including humans), puncturing a bone with a needle, and then aspirating with a syringe. The bones include, but are not limited to, the femur, sternum, and osilium, which forms the pelvis. Further, a procedure that involves directly puncturing the umbilical cord with a needle, and aspirating with a syringe to collect and store the cord blood at birth, has also become an established technique. Bone marrow cells are collected from subjects under local anesthesia, in an amount of preferably several milliliters per collection. Please note that this amount does not apply to case A below, but does apply to cases B and C.

Procedures for bone marrow collection include, but are not limited to, the following procedures:
(A) Transplanting Living Bone Marrow Cells When bone marrow cells are collected from humans, for example, bone marrow fluid is collected by an anesthetist from patients (the ilium and the like) under general anesthesia, after sufficient consideration of the safety of general anesthesia. A target number of cells for collection is $3\times10^9$ or more mononuclear leukocytes. It is assumed that the target cell number can be obtained from about 200 ml to about 400 ml of bone marrow fluid. The upper limit of the bone marrow amount to be collected is calculated in consideration of patient strain, and is calculated using the hemoglobin level (Hb level) immediately prior to bone marrow collection, and body weight of the patient, in consideration of patient strain. However, in the case of an elderly patient, where collection of the necessary amount of bone marrow fluid is problematic, a maximum amount should be collected based on the decision of the doctor in attendance at the collection of bone marrow fluid.

The upper limit of bone marrow to be collected depending on Hb level immediately prior to collection:
(1) Collect 12 ml or less per kg of patient body weight, when Hb level is less than 12.5 g/dl;
(2) Collect 15 ml or less per kg of patient body weight, when Hb level is less than 13.0 g/dl;
(3) Collect 18 ml or less per kg of patient body weight, when Hb level is less than 13.5 g/dl; or
(4) Collect 20 ml or less per kg of patient body weight, when Hb level is 13.5 g/dl or more.

Bone marrow fluid should not be collected when a patient suffers from cytopenia in the peripheral blood (a white blood cell count less than 2,000 per milliliter; neutrophil count less than 1,000 per milliliter; hemoglobin level less than 11.0 g/dl; platelet count less than $10\times10^4$ per milliliter) or when the patient suffers from hemorrhagic diathesis.

The collection of bone marrow from patients who use anticoagulants or antiplatelet agents should be carefully considered while performing, prior to bone marrow collection and general anesthesia, hemostasis-coagulation tests (FDP, fibrinogen, ATIII) which comprise bleeding time and ACT, and that can be performed as emergency tests.
(1) Patients Using Anti-platelet Agents (Such as Panaldine, Bufferin, and Bayaspirin):

Platelet function does not recover until seven days or more after discontinuation, and bone marrow collection in an acute stage may cause hemorrhage. Thus, bone marrow collection should be carefully performed. When bleeding time exceeds ten minutes, bone marrow collection should not be performed.
(2) Patents Using Anti-coagulants (Such as Warfarin):

Bone marrow should be collected after ACT has been normalized by intravenous injection of vitamin K (K1 or K2).

Bone marrow cells are intravenously administered by mixing bone marrow cells ($3\times10^9$ cells or more) with an equal amount of a diluent (antibiotic-free RPMI 1640) and intravenously injecting the mixture, for example. The entire quantity is expected to be about 400 to 2000 cc. Administration is as rapid as possible, but to inhibit coagulation during the administration period, heparin is generally co-injected.

For example, 250 cc of the collected bone marrow cell fluid is mixed with an equal amount of a diluent and 2500 units of heparin to make up 500 cc, the mixture is immediately filtrated through a filter to yield an intravenously injectable preparation, and intravenous administration of the preparation to a patient is begun immediately. Collection of bone marrow cell fluid is also continued during this time. This operation is repeated two to six times, and a set amount of bone marrow cell fluid is administered. The amount of heparin to be thus administered is about 5,000 to 15,000 units which is substantially the same as the safe and effective amount for which evidence in the acute stage of cerebral infarction is already obtained. However, when considering the continuation of bone marrow collection during administration, ACT is determined, and treatment such as neutralization with protamine is conducted as necessary. The time needed for collection is about two hours. The total amount of bone marrow fluid (including diluent) to be administered intravenously is about 2000 cc. Intravenous administration is completed in about three to four hours while sufficiently monitoring strain to the right heart, indicated by central venous pressure and so on. Note that about 2000 ml of bone marrow fluid (including diluent) is intravenously administered, and about 1000 ml of the bone marrow fluid is collected. Thus the volume of fluid applied to the patient is 1000 ml in three to four hours, which is not so large considering the volume load applied during conventional treatment of cerebral infarction.

Patients are preferably selected according to the following requirements, but are not limited thereto:
1. Patients aged 20 to 70;
2. Patients within 24 hours of onset;
3. Patients for whom diffusion-weighted MRIs show abnormalities in the supratentorial cerebral cortex, perforating region, or both;
4. Patients whose NINDS-III category is any of atherothrombotic cerebral infarction, lacunar infarction, or cardiogenic cerebral embolism;
5. Patients whose Modified Rankin Scale for the present episode is 3 or more;
6. Patents whose impaired consciousness rates 0 to 100 on the Japan Coma Scale.

Patients under the following conditions are preferably excluded.
1. Patients with improving symptoms and diagnosed as substantially asymptomatic or as TIA (transient ischemic attack) patients;
2. Patients diagnosed as having a causative lesion of a disorder other than obliterative cerebrovascular disorders, such as an intracranial hemorrhage, based typically on CT or MRI;
3. Patients with cardiogenic embolus where hemophilic alterations have already been observed by CT;
4. Patients in a coma with a severe consciousness disorder of 200 or more on the Japan Coma Scale;
5. Pregnant patients or patients at risk of pregnancy;
6. Patents with grave renal diseases, liver diseases, or digestive organ diseases;
7. Patents with malignant tumors;
8. Patients in whom grave abnormalities, such as severe ischemic heart disease, are suspected in the cardiovascular system;
9. Patients meeting the subject exclusion criteria for bone marrow fluid collection;
10. Patients for whom general anesthesia is judged as risky;
11. Patients with cerebellar infarction or brainstem infarction;
12. Patients who have undergone endovascular surgical treatment in the acute stage; or
13. Patients judged by the doctor in charge of treatment as unsuitable subjects for this treatment.

(B) Culturing, Preserving, and Administering Mesenchymal Stem Cells (MSCs) Collected from the Bone Marrow Fluid and So On:

Another embodiment of the intravenous administration of the present invention is, for example, the intravenous administration of MSCs collected from the bone marrow fluid and so on, then cultured, and preserved. Preferred conditions for collection, culture, and preservation of the bone marrow cells are as follows:

Specifically:
(1) Collect about 5 ml of bone marrow fluid from the ilium under local anesthesia;
(2) Extract MSCs from the collected bone marrow fluid, cultivate and proliferate, for example, using the method described in WO 02/00849;
(3) Cryopreserve in a preservation medium;
(4) Thaw the frozen MSCs as needed and intravenously administer thawed MSCs intact ($2 \times 10^8$ cells or more).

In the present invention, bone marrow fluid can be safely and easily collected under local anesthesia from almost all patients, since the amount of the bone marrow to be collected in the initial stages is about 3 ml to about 5 ml, and the strain on the body is small.

Since the collected mesenchymal stem cells, such as bone marrow stem cells, can be proliferated, they can be proliferated in advance to an amount required for treatment. The MSCs to be used in the present invention are preferably primary culture MSCs, and more preferably, primary culture MSCs of $2 \times 10^8$ cells or more. The mesenchymal stem cells proliferated by the above methods, or the therapeutic agents of the present invention can be preserved for long periods using a predetermined procedure, such as freezing. Preservation and thawing methods are as follows:

The cells are thawed in the following manner. First, equipment and materials such as a program freezer, a freezing bag F-100, liquid nitrogen, and a tube sealer are prepared. Reagents such as Trypsin/EDTA, DMSO, dextran autoserum, and D-MEM are also prepared.

After removing the culture medium, T/E is added, adherent cultured MSC cells are recovered, an equal amount of a cell washing fluid (D-MEM containing 2% autoserum) is added, and this is then centrifuged at 400 g for five minutes. The cell pellets are stirred with a cell-washing fluid (D-MEM containing 2% autoserum) and centrifuged at 400 g for five minutes. Next, the cells are stirred in 41 ml of a cell-preservation medium (D-MEM containing 50% autoserum). In this procedure, two 0.5 ml portions of the cell suspension are sampled using a 1 ml syringe, and the cells are counted. The stirred fluid is subjected to bacteriological and virological examinations to confirm it is uncontaminated by bacteria or viruses. Next, 10 ml of a cryoprotective fluid (5 ml of DMSO (Cryoserv) and 5 ml of 10% dextran 40) is added. The resulting suspension is packed into freezing bags at 50 ml per bag, and the specimen number is indicated on each bag. The bags are frozen in a program freezer, and the frozen bags are transferred to and stored in a liquid nitrogen tank.

The cells are thawed and washed as follows: First, equipment and materials such as a warm water bath, a clean work station, a centrifugal separator, a separating bag, and a tube sealer are prepared, and reagents such as 20% human serum albumin (or autoserum), physiological saline, and 10% dextran 40 are prepared. A freezing bag comprising the cells is removed from the liquid nitrogen tank and left to stand in the gaseous phase for five minutes, and at room temperature for two minutes. The bag is left to stand in the gaseous phase and at room temperature to prevent its explosion caused by the vaporization of liquid nitrogen. The bag is placed in a sterilized plastic bag to prevent leakage of its contents due to, for example, pinholes in the bag. The plastic bag is placed in a warm water bath and is thawed. After thawing, the entire quantity of the cell suspension is recovered in a blood bag (closure system) or tube (open system). The recovered cell suspension is added to an equal amount of a washing fluid (25 ml of 20% human serum albumin, 75 ml of physiological saline, and 100 ml of 10% dextran 40). The mixture is left to stand for five minutes to reach equilibrium, intracellular DMSO is removed, and the mixture is then centrifuged at 400 g for five minutes. The cell pellets are stirred with cell-washing fluid. The resulting cell suspension is administered in vivo to a patient, and again, two 0.5 ml portions of the cell suspension are sampled using a 1 ml syringe and subjected to a viability assay and bacteriological examination.

In the present invention, the primary culture MSCs, which were collected, cultivated, and preserved in advance, can be immediately thawed to an active state as needed, and can be immediately administered intravenously for treatment. Heparin is not used herein. The patient to be administered has no specific limitations.

(C) Administering Mesenchymal Stem Cells Immortalized by hTERT:

The present inventors succeeded in developing a method for stably inducing the differentiation and proliferation of large cell numbers (WO 03/038075). Generally, mesodermal stem cells (mesenchymal stem cells) are useful in the medical field of neural regeneration; however, the proliferation of such cells under culture conditions is limited to some extent. However, according to the studies of the present inventors, the in vitro introduction into stromal cells or mesenchymal stem cells of a viral vector containing, as an insert, an immortalization gene such as telomerase, was revealed to result in the continuation of cell proliferation, even after cycles of cell division, greatly extending the life span of the cells, and still retaining the same morphology as normal cells. The present inventors found that mesodermal stem cells (mesenchymal stem cells) immortalized by introducing an immortalization gene can be efficiently induced to differentiate into neural stem cells and nervous system cells under appropriate culture conditions.

Specifically, the inventors succeeded in inducing mesodermal stem cells (mesenchymal stem cells), which had been immortalized through the introduction of the immortalization gene hTERT, to differentiate into fat cells, chondroblasts, and osteoblasts, for example. Furthermore, the inventors induced the efficient differentiation of mesodermal stem cells (mesenchymal stem cells) immortalized by the introduction of the hTERT gene, into nervous system cells containing neural stem cells. The present inventors further revealed that demyelinated areas in the spinal cord can be repaired by transplanting these cells themselves (the mesodermal stem cells (mesenchymal stem cells)); neural stem cells differentiated from the mesodermal stem cells (mesenchymal stem cells); nervous system cells differentiated from neural stem cells which had been differentiated from the mesodermal stem cells (mesenchymal stem cells); and nervous system cells differentiated from the mesodermal stem cells (mesenchymal stem cells).

In addition, neural stem cells and nervous system cells whose differentiation was induced according to the above-described methods of the present invention, or by the mesodermal stem cells (mesenchymal stem cells) themselves having an immortalization gene introduced therein, are expected to be very useful in achieving neural regeneration.

When a cell is immortalized by introducing an oncogene or such, the character of the cell is also transformed. In contrast, when a cell is immortalized by introducing an immortalization gene, as in the present invention, the cell retains its original character. In addition, in cases where an immortalization gene has been introduced, the gene can be removed after sufficient proliferation.

Mesenchymal cells introduced with an immortalization gene can also be used for intravenous administration in the present invention as appropriate.

Since technique (C) can yield a large quantity of cells, a larger number of cells can be intravenously administered. Preferably, $1 \times 10^9$ or more cells can be administered. This is a tremendous advantage, since therapeutic effect increases as the number of administered cells increases.

The cranial nerve disease therapeutic agents for in vivo administration of the present invention, comprising mesenchymal cells as an active ingredient, can be formulated according to methods known to those skilled in the art. For example, the agents can be used parenterally in the form of an abacterial solution or suspension for injection, combined with water or other pharmaceutically acceptable liquid. The agents can be formulated, for example, by appropriate combination with pharmacologically acceptable carriers or vehicles (specifically, sterile water, physiological saline, vegetable oils, emulsifiers, suspending agents, surfactants, stabilizers, fillers, vehicles, antiseptic agents, and binders), into the form of generally acceptable unit dosages as required in drug manufacturing procedures. The amount of active ingredient in these pharmaceutical preparations is set so as to yield an appropriate volume within an indicated range. An aseptic composition for injection can be formulated using a vehicle such as distilled water for injection, according to regular preparation procedures.

Aqueous solutions for injection include, for example, physiological saline and isotonic solutions containing other adjuvants such as glucose, D-sorbitol, D-mannose, D-mannitol, or sodium chloride. These aqueous solutions may be used in combination with appropriate solubilizers, such as alcohols, more specifically ethanol and polyalcohols, such as propylene glycol and polyethylene glycol; and nonionic surfactants such as Polysorbate 80™ and HCO-50.

Oily liquids include sesame oil and soy bean oil. These can be used in combination with a solubilizer such as benzyl benzoate or benzyl alcohol. Buffers such as phosphate buffer and sodium acetate buffer; soothing agents such as procaine hydrochloride; stabilizers such as benzyl alcohol and phenol; and antioxidants may also be combined. Injections prepared in this way are generally packaged into appropriate ampules.

In vivo administration of the agents to patients is preferably parenteral administration. Specifically, it is a single dose intravenous administration, but can be a multiple dose administration. The administration can be conducted over a short period or continuously over a long period. More specifically, the administration includes injection-type and dermal administration-type administrations. Injection-type administration includes intravenous injection, intraarterial injection, selective intraarterial injection, intramuscular injection, intraperitoneal injection, hypodermic injection, intracerebroventricular injection, intracranial injection, and intraspinal injection, and of these intravenous injection is preferred.

Intravenous injection enables transplantation by a regular blood transfusion procedure, does not require surgery or local anesthesia of the patient, and reduces the burden on both patient and doctor. Intravenous injection is preferable in that it also enables bedside transplantation. Considering future advances in emergency medicine, administration may also be possible during ambulance transportation or at the scene of an episode.

Further, due to their high capacity for migration, cells comprised in a cell fraction of the present invention can be used as carriers (vectors) for genes. For example, the cells are expected to be useful as vectors for the gene therapy of various neurological diseases, such as cerebral infarction and brain tumor.

Cranial nerve diseases of the present invention include cerebral infarction, cerebral stroke, encephalorrhagy, subarachnoidal hemorrhage, and brain tumor, of which cerebral infarction is preferred. The cause can be any of atherothrombotic cerebral infarction, cardiogenic cerebral embolism, and lacunar stroke categorized in NINDS-III (Classification of Cerebrovascular Diseases (the third edition) by NINDS (National Institute of Neurological Disorders and Stroke)). The cranial nerve diseases also include neurological diseases associated with head injuries, such as head injuries and cerebral contusion; ischemic cranial nerve injuries; traumatic cranial nerve injuries; cranial nerve degenerative diseases; and metabolic nerve diseases, but are not limited to these, as long as they are diseases caused by abnormalities in the cranial nerve.

In vivo administration, such as intravenous administration of the mesenchymal cells of the present invention enables neuroprotection in the brain and cranial nerve regeneration. Accordingly, the present invention provides agents for in vivo administration that exhibit neuroprotective effects and comprise mesenchymal cells as active ingredients. The term "neuroprotection" herein refers to the effect of saving cranial neurons that would be damaged or die without treatment.

In addition, the present invention provides agents for in vivo administration that exhibit cranial nerve regeneration and that comprise mesenchymal cells as active ingredients. Herein the term "cranial nerve regeneration" means the effect of regenerating cranial nerve cells to recover their function, or therapeutic effects obtained from this effect.

Furthermore, the present invention relates to methods of treating cranial nerve diseases, including the in vivo administration (preferably intravenous) of a therapeutically effective amount of an agent of the present invention to a patient.

To reduce the risk of transplant rejection, mesenchymal cells such as bone marrow cells, cord blood cells, or peripheral blood cells in the agents for use in the above mentioned therapeutic methods are preferably cells collected from the patient, or cells derived therefrom (autologous cells derived from the patient) (autotransplantation treatment), unless a special operation such as immunosuppression is conducted. This is preferable there is no need for the concomitant use of immunosuppressive drugs. Allotransplantation is possible if immunosuppression is carried out; however, autotransplantation treatments can be expected to exhibit significantly greater therapeutic effect.

When autotransplantation treatment is difficult, cells derived from another person or from another animal for medical use can be used. These cells may be cryopreserved.

The autologous cells can be any undifferentiated cells collected from a patient, cells prepared by subjecting undifferentiated mesenchymal stem cells collected from a patient to gene manipulation, and cells prepared by inducing differentiation of undifferentiated mesenchymal stem cells collected from a patient.

The agents of the present invention (mesenchymal cells such as bone marrow cells) can be suitably administered to patients by the above-mentioned methods, for example. Doctors can administer the agents of the present invention to patients by appropriately modifying the above-described methods.

The therapeutic methods of the present invention are not limited to humans. In general, the methods of the present invention can also be conducted in the same manner, using mesenchymal cells, on non-human mammals, such as mice, rats, rabbits, pigs, dogs, and monkeys.

The inventors have found that fibroblast-like adherent cells with phenotypic characteristics resembling those of mesenchymal stem cells prepared from the bone marrow can be cultured from peripheral blood. These cells showed proliferation and differentiation into neural lineages in vitro, confirmed by immunocytochemistory and RT-PCR.

Mesenchymal stem cell populations obtained from rat peripheral blood and bone marrow of the rat metaphysis easily expanded in vitro and exhibited a fibroblast-like morphology. Flow cytometry analysis to study the surface protein expression on undifferentiated BMSCs and PMSCs indicated that the myeloid progenitor antigen CD45 was not expressed by these cells. On the other hand, PMSCs expressed CD73 (SH3), which has been used to characterize mesenchymal stem cells. In addition, nestin expression by PMSCs and BMSCs and their ability to grow in suspension in defined culture conditions brought them nearer to a neurosphere phenotype. When nestin-positive neurospheres were dissociated and plated onto an adherent surface without growth factors, neuronal and glial differentiation was observed The present inventors have shown that rat PMSCs proliferated, highly transformed to nestin-positive neural stem cells (neurospheres), and differentiated into neuronal or glial cells in vitro. Thus, autologous peripheral blood is indicated as an important source of cells for a cell therapy, since they are easy to isolate and expand for autotransplantation with little risk of rejection.

The inventors have also shown that intravenous infusion of MSCs, derived from either bone marrow or peripheral blood, 6 hours after permanent MCAO in the rat results in reduction in infarction volume, improvement in cerebral blood flow, induction of angiogenesis, MSC accumulation in the ischemic brain, and improvement in behavioral performance. PMSCs derived from peripheral blood, expanded in culture and intravenously infused contributed to the therapeutic benefits in the rat MCAO model with a large effect.

A characteristic feature of the BMSCs derived from rat bone marrow is the marker profile of CD45 (−), CD73 (+), CD90 (+), CD106 (−) cell surface phenotype. PMSCs derived from peripheral blood expressed a similar pattern of cell surface antigens and cellular morphology (flattened and spindle-shaped adherent cells) in culture, suggesting similarity of the two cell populations.

The mechanisms of therapeutic benefits of MSCs transplantation for stroke, may result from neuroprotection and angiogenesis. A number of neurotrophic factors have been reported to have therapeutic effects on cerebral infarction. These include BDNF, GDNF, NGF, EGF, and bFGF. Mechanisms proposed for the neuroprotective effect of these agents include anti-apoptotic activity, free radical scavenging, anti-inflammatory activity, and anti-glutamate excitotoxicity.

An advantage of PMSCs for transplantation studies is that they can be easily and safely obtained in large numbers from blood, which is a less invasive proceed than extracting from bone marrow.

MSCs also provide several angiogenic growth factors such as VEGF and bFGF, which may prevent endothelial cells from ischemic damage or stimulate angiogenesis. These cells produce soluble mediators that down-regulate immune responses which could also contribute to neuroprotection. Hemodynamic changes of cerebral blood flow after MCAO with and without MSCs transplantation were analyzed by PWI. While both control and MSCs transplantation groups showed improvement of rCBF in the lesion, recovery of rCBF was greater in the MSC transplantation groups than control groups. Moreover, histological examination of capillary vessels in ischemic lesion indicated that MSCs transplantation group showed greater angiogenesis. These data suggest that the improvement of cerebral blood perfusion plays an important role in the mechanism of therapeutic effects of MSC transplantation.

The present invention can be used to treat neurological damage caused by injury and neurological diseases including Krabbe's disease, Hurler's syndrome, metachromatic leukodystrophy, and stroke. Improved neurological function in experimental autoimmune encephalomyelitis (EAE) has been reported following intravenous infusion of human MSCs and neurosphere-derived multipotent precursors. Suggested mechanisms include reduction of inflammatory infiltration, remyelination, and elevation of trophic factors that may be neuroprotective or stimulate oligodendrogliosis. The present invention may have the advantage of exerting multiple therapeutic effects at various sites and times within the lesion as the cells respond to a particular pathological microenvironment.

In the working examples, the centrifuge used was one supplied by Kubota. Cells were injected intravenously into rats by injection into the femoral vein of the rat in the leg.

All prior art documents cited herein are hereby incorporated by reference into this specification.

BRIEF DESCRIPTION OF THE DRAWINGS

FIG. 20 shows photographs indicating the therapeutic effect over time of intravenous MSC administration in the hyperacute stage of severe cerebral infarction.

FIG. 21 shows photographs indicating examples of the therapeutic effect over time of intravenous MSC administration in the acute stage of severe cerebral infarction.

FIG. 24 shows photographs of adherent cultured cells, such as mesenchymal stem cells obtained from the peripheral blood in an untreated group or in a group pre-administered with G-CSF or SCF factor by hypodermic injection.

Figure 25:
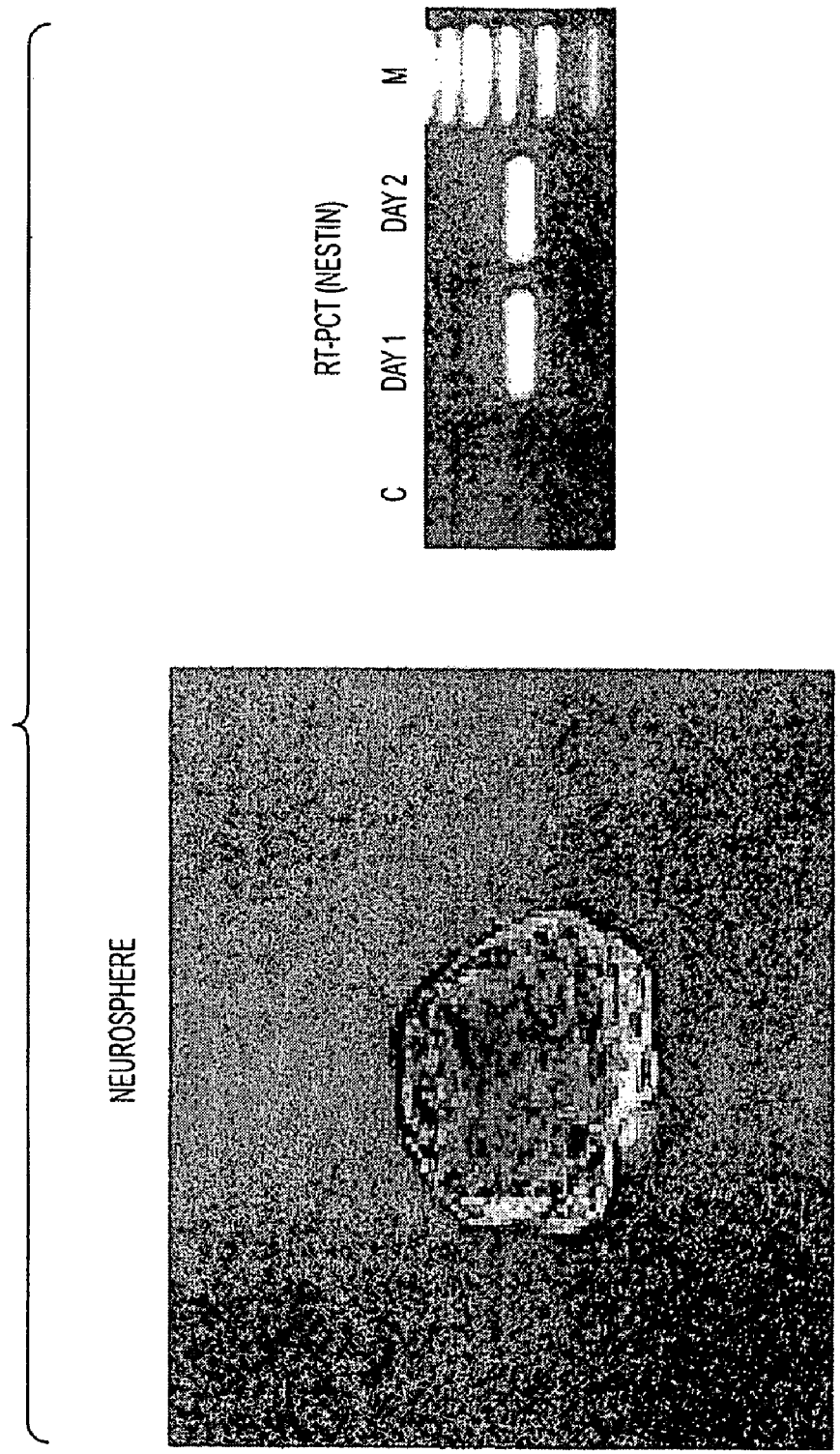

The left view of FIG. 25 is a photograph showing that it was possible to induce the differentiation of adherent cultured cells into neural stem cells (Neurospheres). The right view of FIG. 25 is a photograph showing that it was also possible to confirm nestin expression using RT-PCR.

The upper half of FIG. 26 shows photographs indicating that the cells shown in FIG. 25 could be induced to differentiate into neurons (NF-positive cells) and glial cells (GFAP-positive cells). The lower half of FIG. 26 shows photographs indicating that the expression of both NF and GFAP could also be confirmed by RT-PCR.

Figure 27:
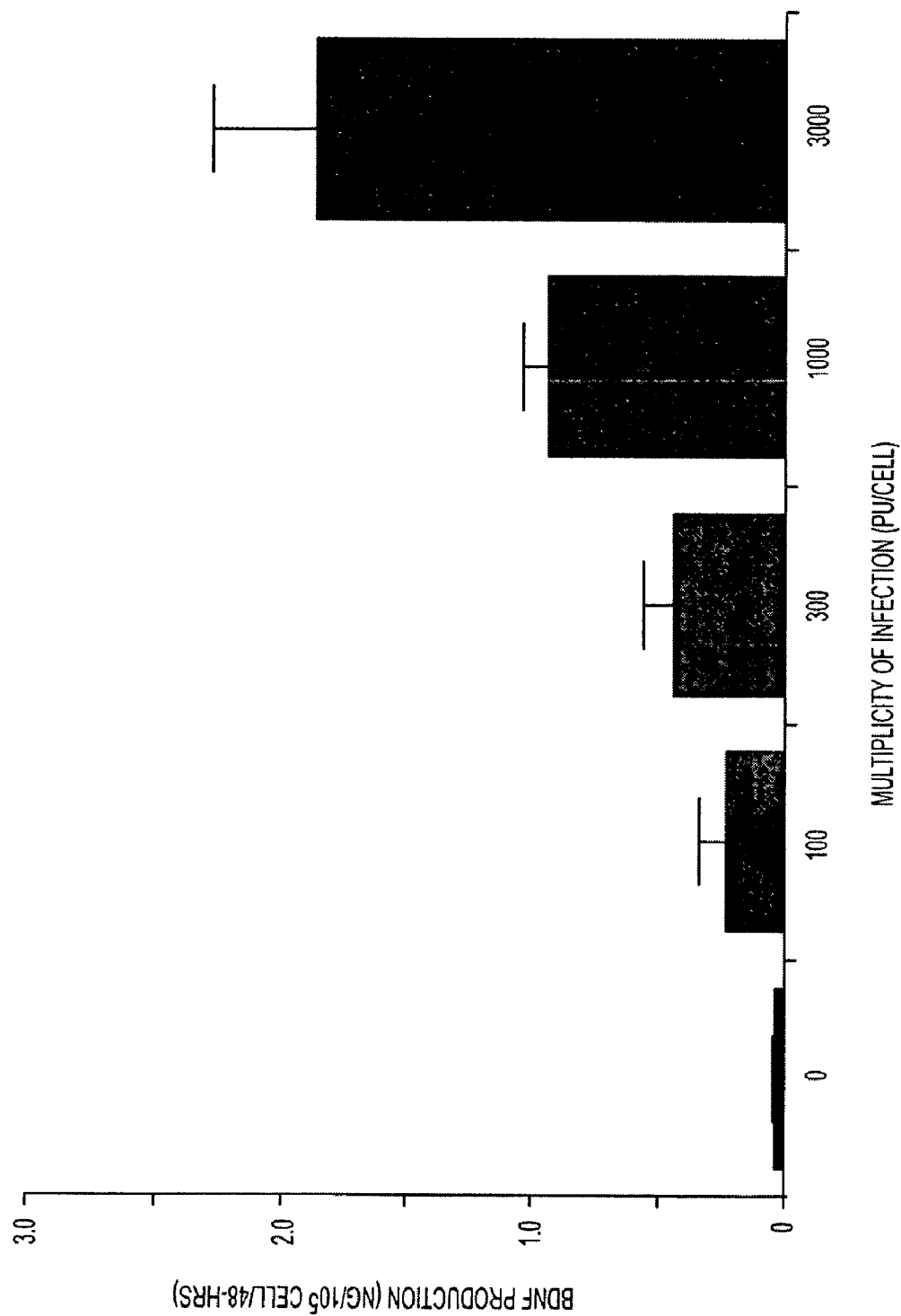

FIG. 27 is a graph showing that culturing MSCs results in BDNF production. MSCs transfected with AxCAhBDNF-F/RGD (MSC-BDNF) at MOIs of 100, 300, 1000, and 3000 pu/cell secreted $0.230\pm0.110$, $0.434\pm0.122$, $0.931\pm0.101$, and $1.860\pm0.41$ ng/$10^5$-cells of BDNF, respectively, 48 hours later. Untransfected MSCs also produced BDNF ($0.0407\pm0.0059$ ng/$10^5$ cell/48-hr).

Figure 28:
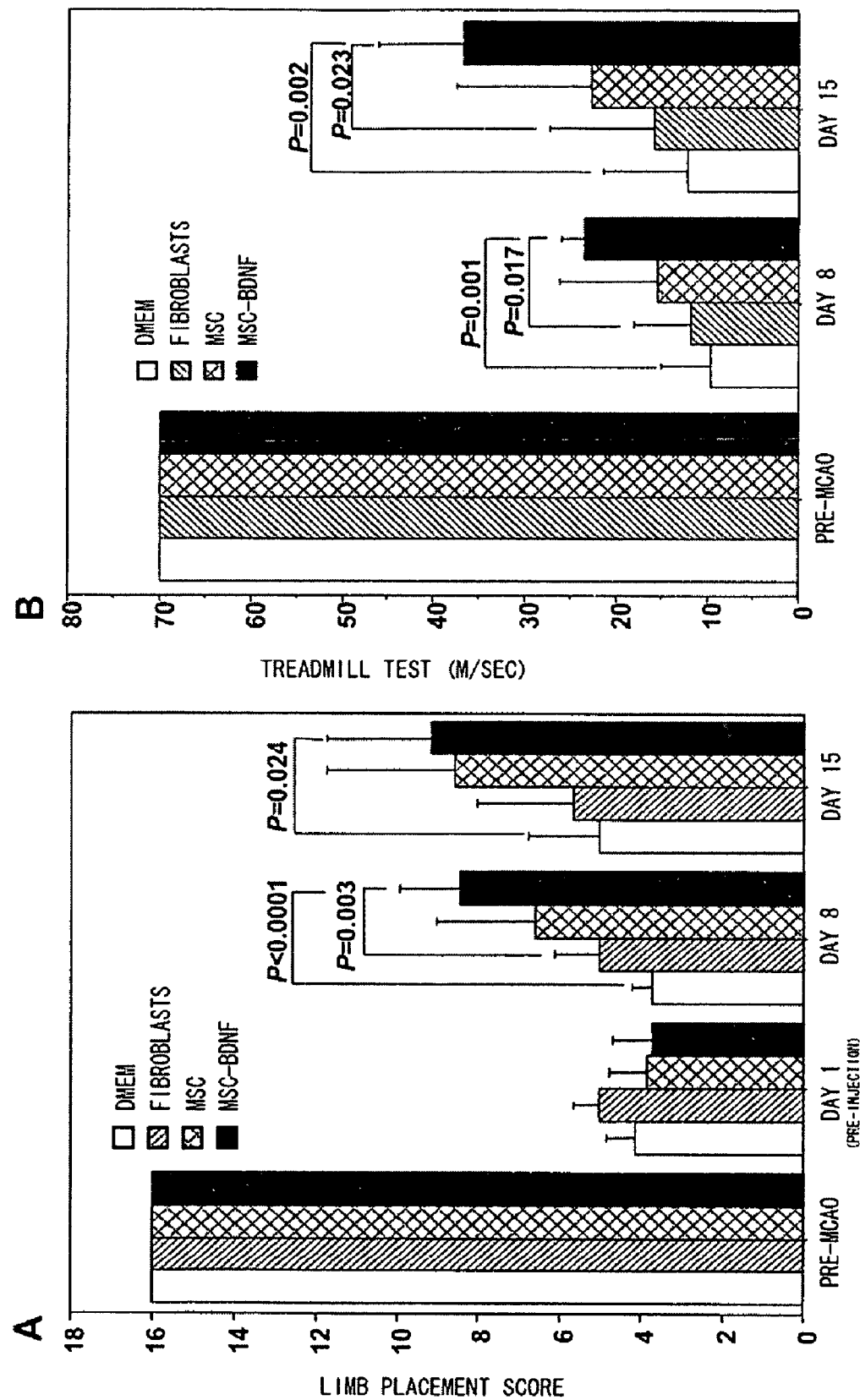

FIG. 28 shows graphs indicating evaluations of cerebral ischemia-induced neural deficiency.
A: Leg placement impairment was evaluated according to the following scale: 0: severe neural deficiency, 16: no neural deficiency. The four ischemia groups showed no statistical difference in leg-placement score, one day after MCAO and before intracranial administration of MSCs. Eight days after MCAO, MSC-BDNF-treated rats had significantly higher leg-placement scores than control DMEM rats (P=0.0001) and fibroblast-treated rats (P=0.003). Fifteen days after MCAO, the scores of MSC-BDNF-treated rats had similarly increased compared to the scores of the DMEM group (P=0.024).
B: Prior to MCAO the average treadmill speeds were compared between the groups. Eight days after MCAO, rats in the MSC-BDNF group achieved a significantly higher speed than those in the control DMEM (P=0.001) and the fibroblast-treated (P=0.017) group. The speed in MSC-BDNF group remained different (significantly higher than the control DMEM (P=0.002) and the fibroblast group (P=0.023)) until Day 15.

Figure 29A:
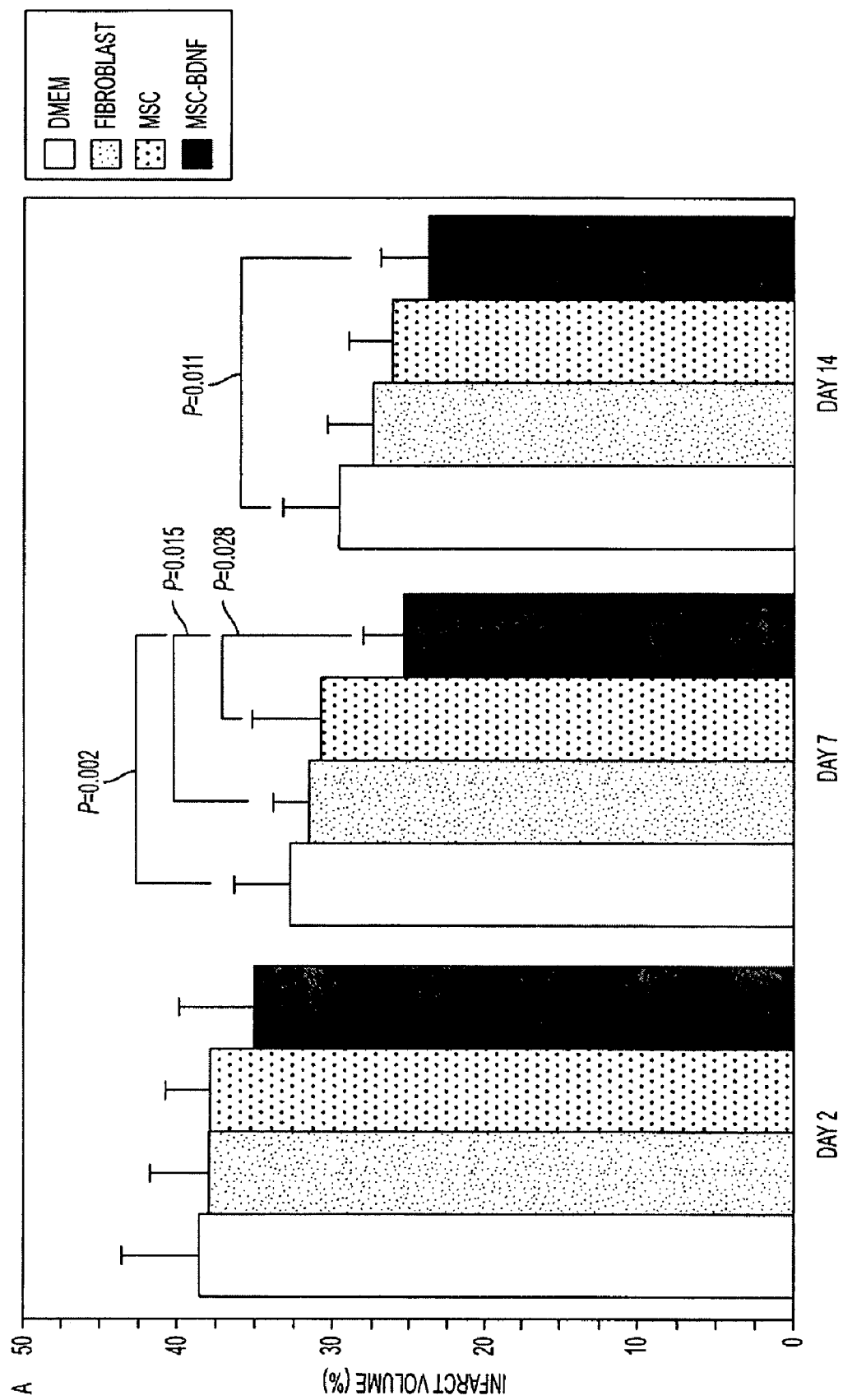

FIG. 29A is a graph of T2-weighted images (T2W) of rats administered with DMEM, fibroblasts, MSCs, or MSC-BDNF taken two, seven, and 14 days after MCAO. Seven days after MCAO, the MSC-BDNF-treated rats showed a significant reduction in HLV (%) as compared to rats treated with DMEM (P=0.002), fibroblasts (P=0.015), or MSCs (P=0.028). Fourteen days after MCAO, the MSC-BDNF-treated rats showed a significant reduction in HLV (%) compared with the DMEM-treated rats (P=0.011).

Figure 29B:
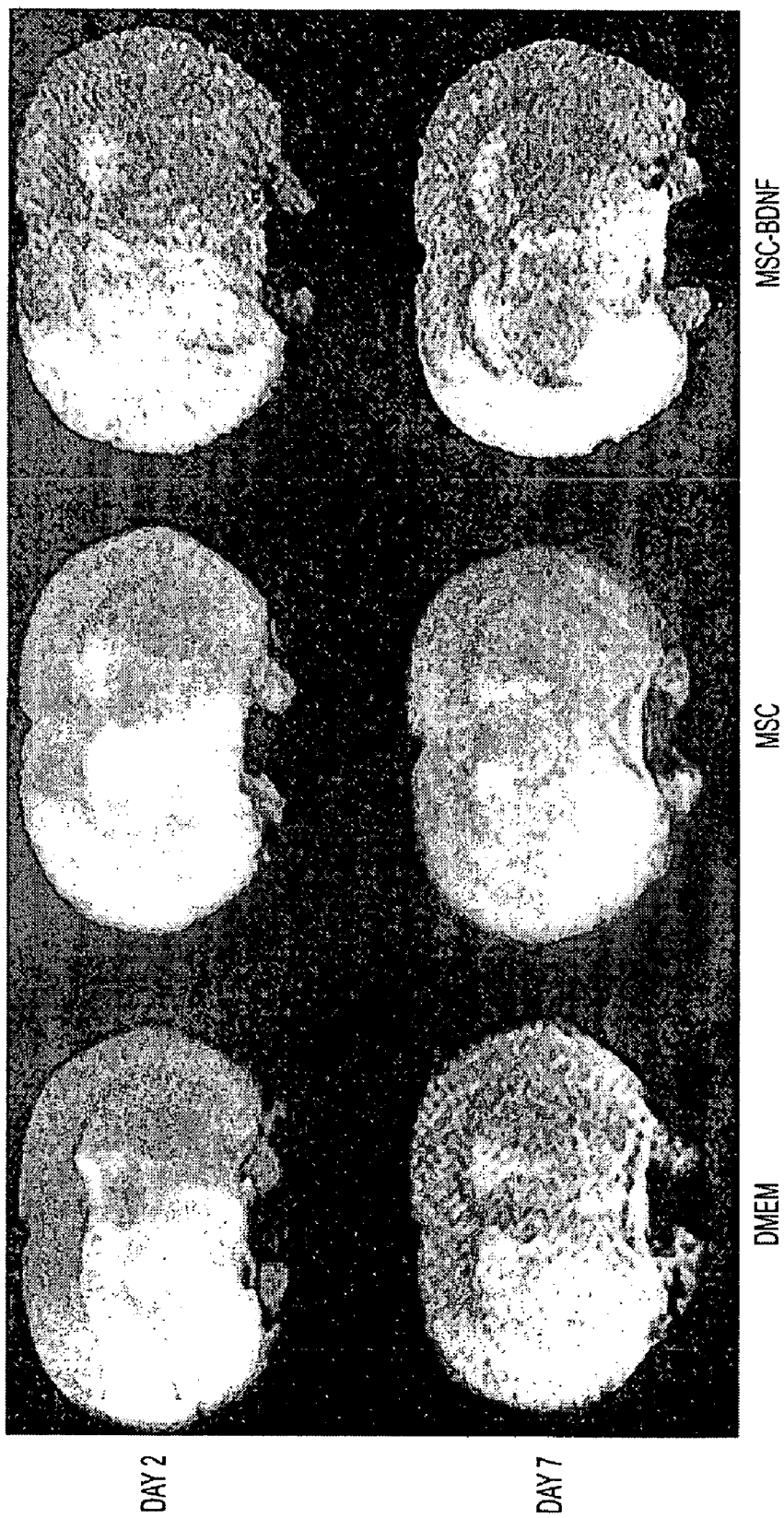

FIG. 29B shows photographs of representative T2W images of rats administered with DMEM, MSCs, or MSC-BDNF, taken two and seven days after MCAO. Compared to the other groups on Day 7, the MSC-BDNF group showed a reduction in ischemic injury volume.

Figure 30:
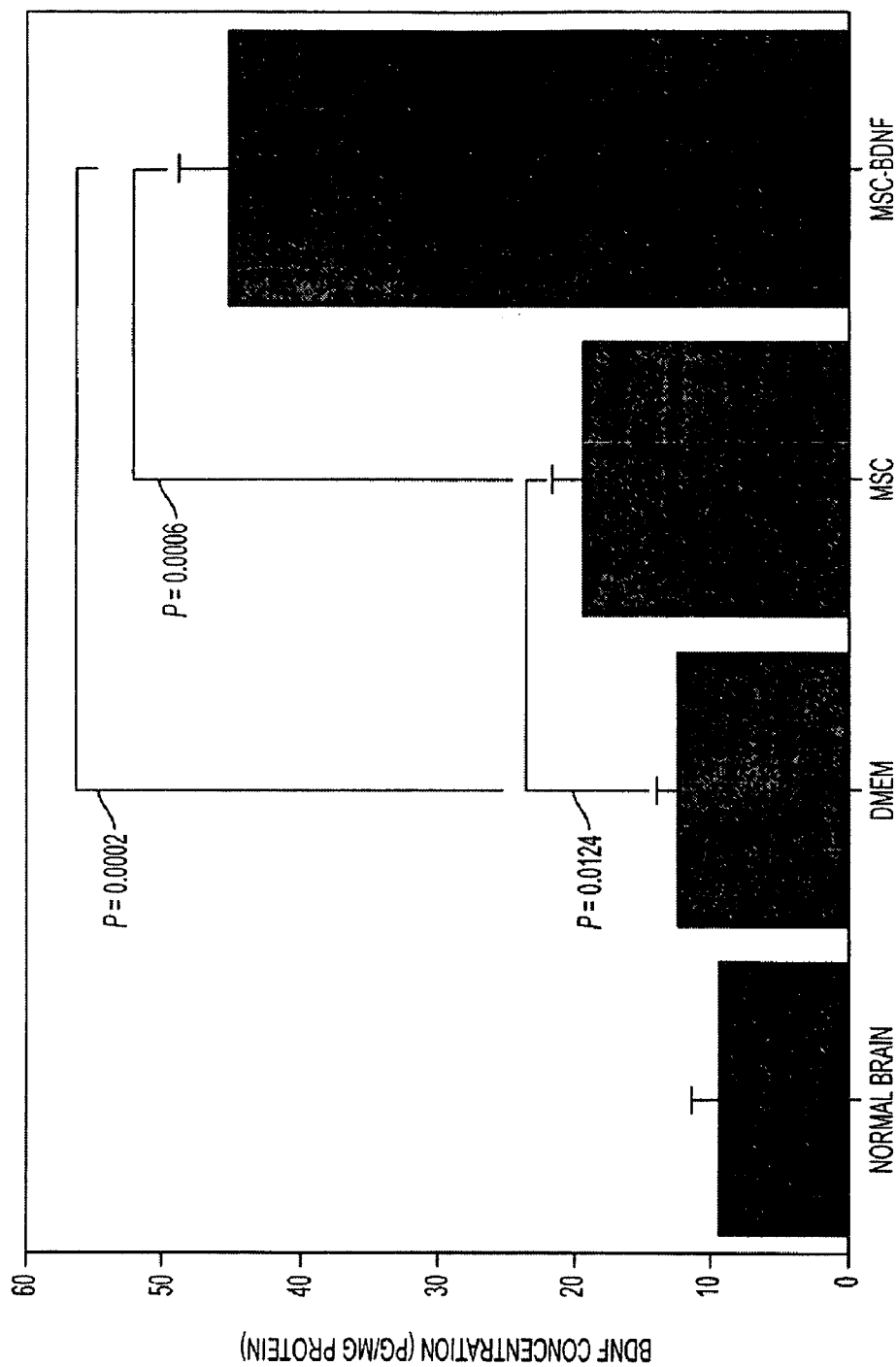

FIG. 30 is a graph showing in vivo BDNF production levels. The MSC-BDNF-transplanted rats showed a significantly increased BDNF level in the ischemic hemisphere seven days after MCAO compared to rats treated with DMEM (P=0.0002) or MSCs (P=0.0006). Compared to the DMEM-treated rats, the MSC-treated rats also showed a significantly increased BDNF level in the ischemic hemisphere (P=0.0124).

FIG. 31 shows diagrams indicating the presence of cells having a DNA fragment in the ischemic penumbra and at the site of application after MCAO.
A: Photographs showing that compared to the DMEM-treated rats, the MSC-BDNF-treated rats had virtually no TUNEL-positive cells. FITC=green (TUNEL-positive), PI=red (nucleus), magnification ×200.
B: Photographs A magnified by 630 times.

Figures 31A, 31B:
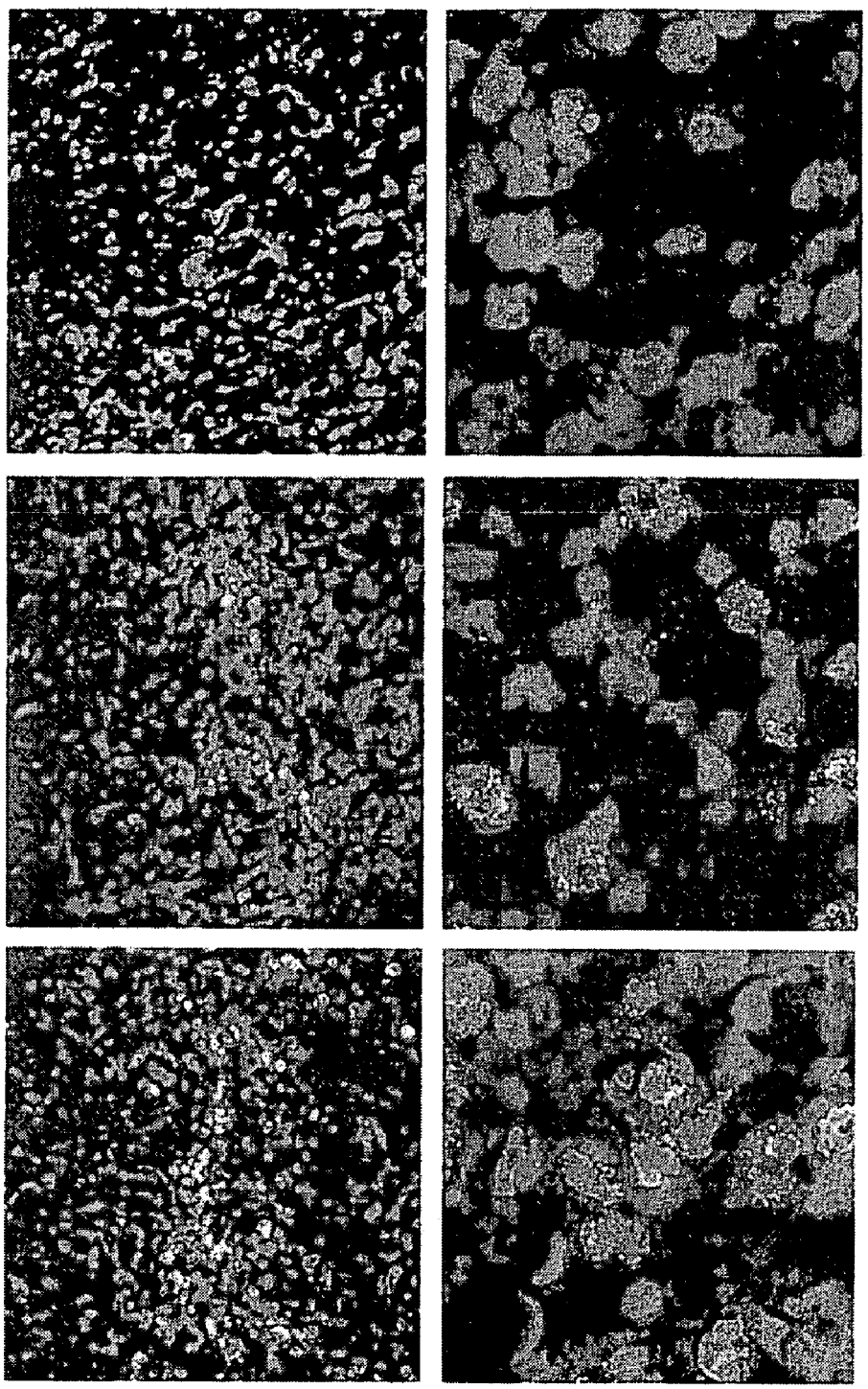
Figure 31C:
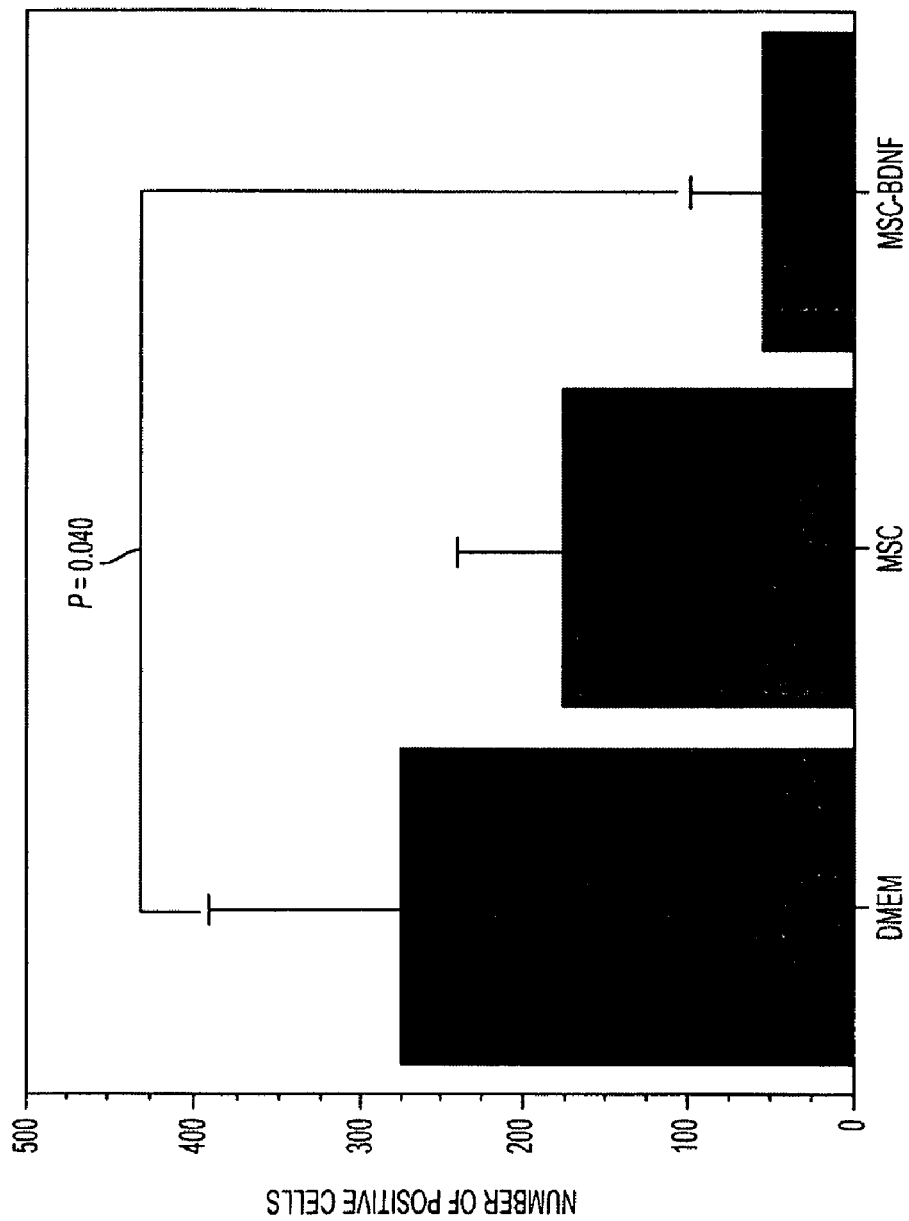

FIG. 31C is a graph showing that animals treated with MSC-BDNF in the ischemic boundary zone showed a significant reduction in TUNEL-positive cells compared to DMEM-administered animals (P=0.013).

FIG. 31D shows photographs indicating that fewer positive cells were detected in the MSC-BDNF-treated rats than in the MSC-treated rats. A large number of DsR-positive MSCs were detected within 2 mm of the administration site. FITC (green, TUNEL-positive), DsR (red, MSC).

Figure 32:
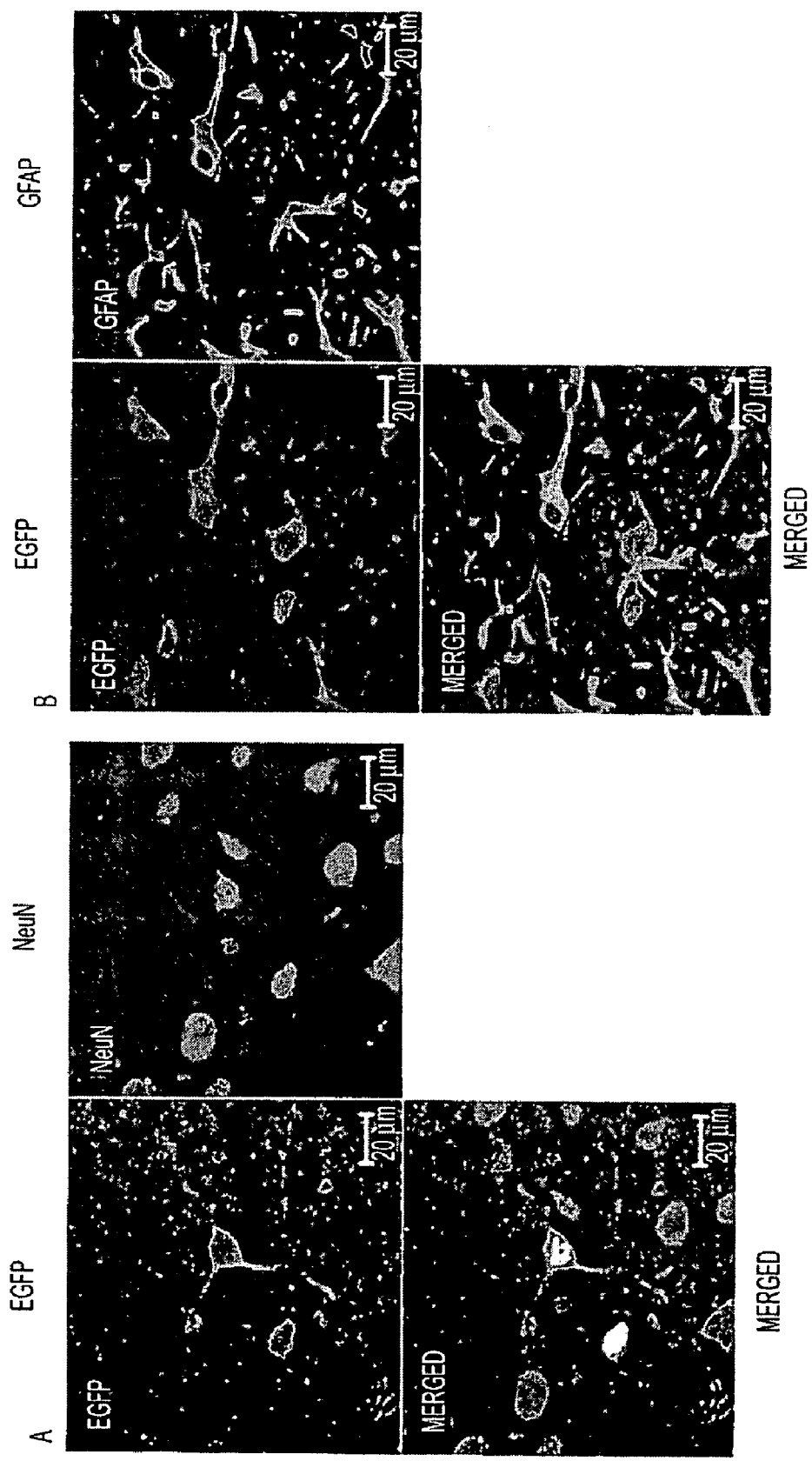

FIG. 32 shows micrographs indicating morphological characteristics of exogenous MSCs and endogenous brain cells in the rat brain. Double-immunofluorescence staining revealed that EGFP cells were localized near the administration site. In the brains of recipient rats, EGFP cells (green), neurogenic nucleus antigen (NeuN; A) and glial fibrillary acidic protein (GFAP; B) were found using confocal laser scanning microscopy. Scale bar: 20 μm.

FIGS. 33a to 33e are graphs showing the expression of surface antigens in rat MSCs analyzed by flow cytometry. The MSCs were labeled with monoclonal antibodies specific to the antigen to be presented. Dead cells were removed by front and side scattering. FIGS. 33f to 33i are photographs indicating the differentiation of rat MSCs into typical mesenchymal cells. Osteogenic differentiation of primary MSCs or MSC-IL2s was detected by von Kossa staining. Adipogenic differentiation of primary MSCs (h) or MSC-IL2s (i) was detected by Oil Red O staining.

Figure 34:
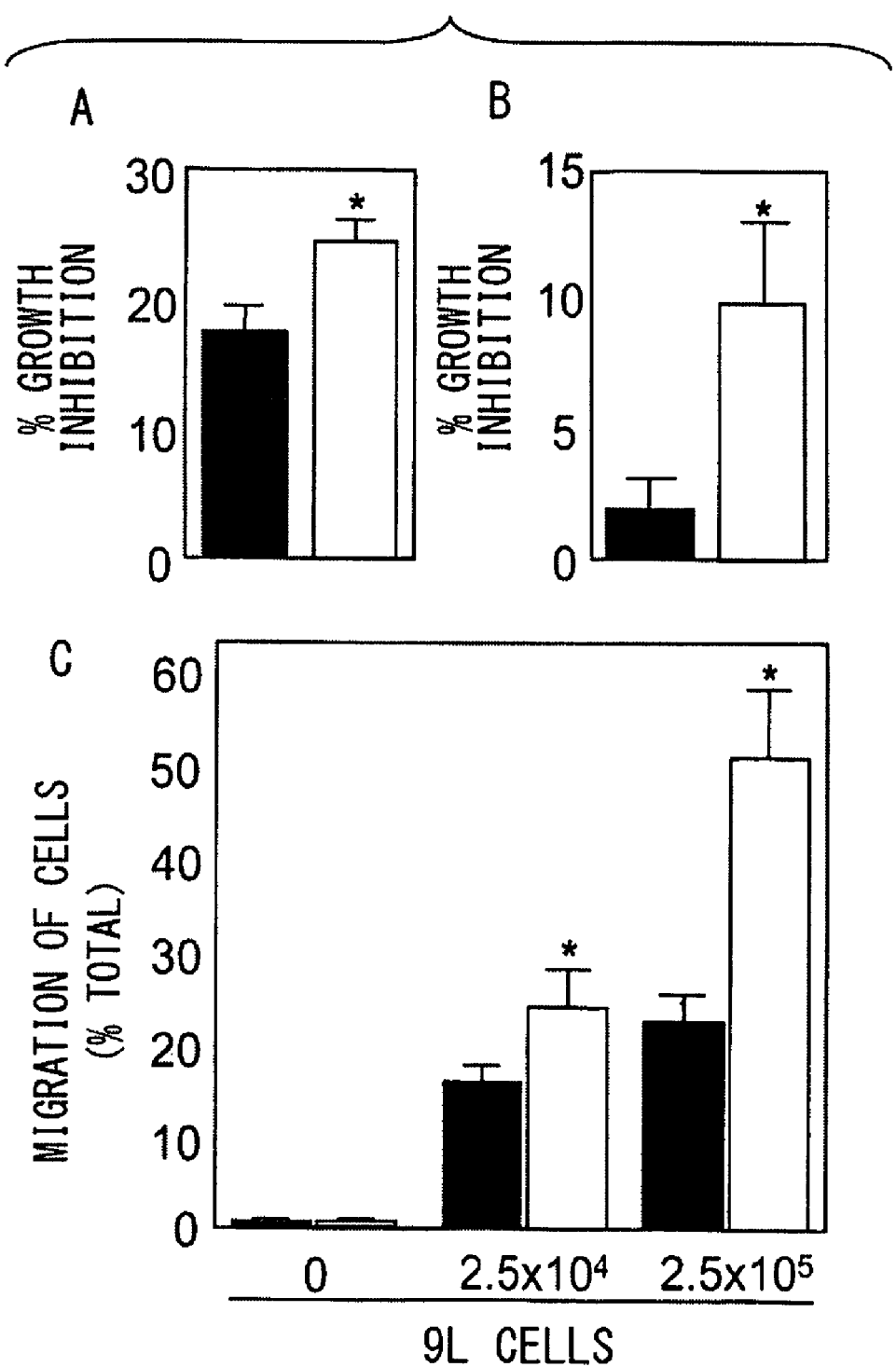

FIG. 34 shows graphs indicating the antitumor effect and migration capability of MSCs. Filled bars represent NRK cells, and open bars represent MSC cells. (a): 9L cells ($5\times10^4$ cell/well) were co-cultured with MSC or NRK cells ($5\times10^3$ cell/well). (b): MSC or NRK cells were inoculated at a concentration of 1×10⁵ cells in a Transwell Insert, and 9L cells (5×10³ cell/well) were placed in wells. The 9L cells were counted four days later. All data are expressed by proliferation inhibitory percentage (%)=[1-(number of 9L cells co-cultured with MSC or NRK cells/number of 9L cells cultivated alone)]×100. Graph (c) shows the results of a migration assay. $^{125}$I-deoxyuridine-labeled cells (5×10⁴) isolated using a filter of 8 μm pore size were then placed in the upper chamber of a Transwell, and 9L cells were placed in the lower chamber. After 24-hours of incubation, radioactivity in the lower chamber was determined. The results of the cell migration assay are expressed as ratios of the cell number in the lower chamber to the total cell number in the chamber.

Figure 35:
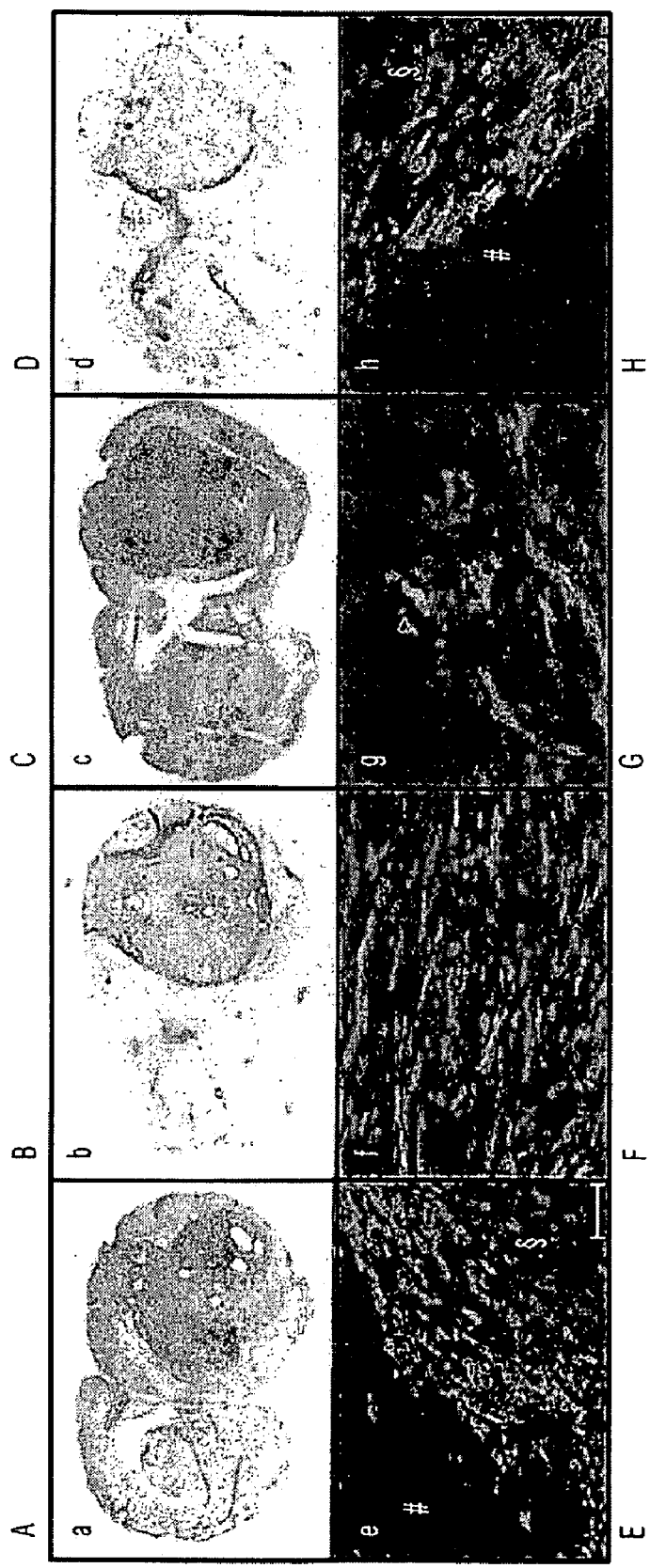

FIG. 35 shows photographs indicating the distribution and migration of MSCs in rats with glioma. 9L-DsR cells (4×10⁴) were transplanted, and 4×10⁵ of MSC-EGFP were administered into the tumor or to the contralateral hemisphere three days after the inoculation of the tumor. The rats were euthanized 14 days after tumor inoculation and their brains were excised. (a) and (b) are micrographs of a brain preparation where MSC-EGFP were administered into the tumor. (c) and (d) are micrographs of a brain preparation where MSC-EGFP were administered to the contralateral hemisphere. (a) and (c) are H-E stained, and (b) and (d) are immunohistochemically stained using an anti-GFP monoclonal antibody. (e) to (h) are fluorescent micrographs of the brain where MSC-EGFP were administered into the tumor. (e) shows a boundary zone between glioma and normal parenchyma. (f) shows the inside of the tumor, and (g) shows a terminal microsatellite. (h) is a fluorescent micrograph of a boundary zone between tumor and normal parenchyma where MSC-EGFP were administered to the contralateral hemisphere.

FIG. 36 shows graphs indicating the effects of IL2 genetically modified MSCs on surviving rats to which 9L cells were inoculated. Survivorship was analyzed using a log-rank test based on the Kaplan-Meier method. (a) shows the viabilities of rats, with or without MSC inoculation, after inoculation of 9L cells. (b) shows the viabilities of rats, with or without inoculation of MSC, into the tumor three days after tumor inoculation.

Figure 37:
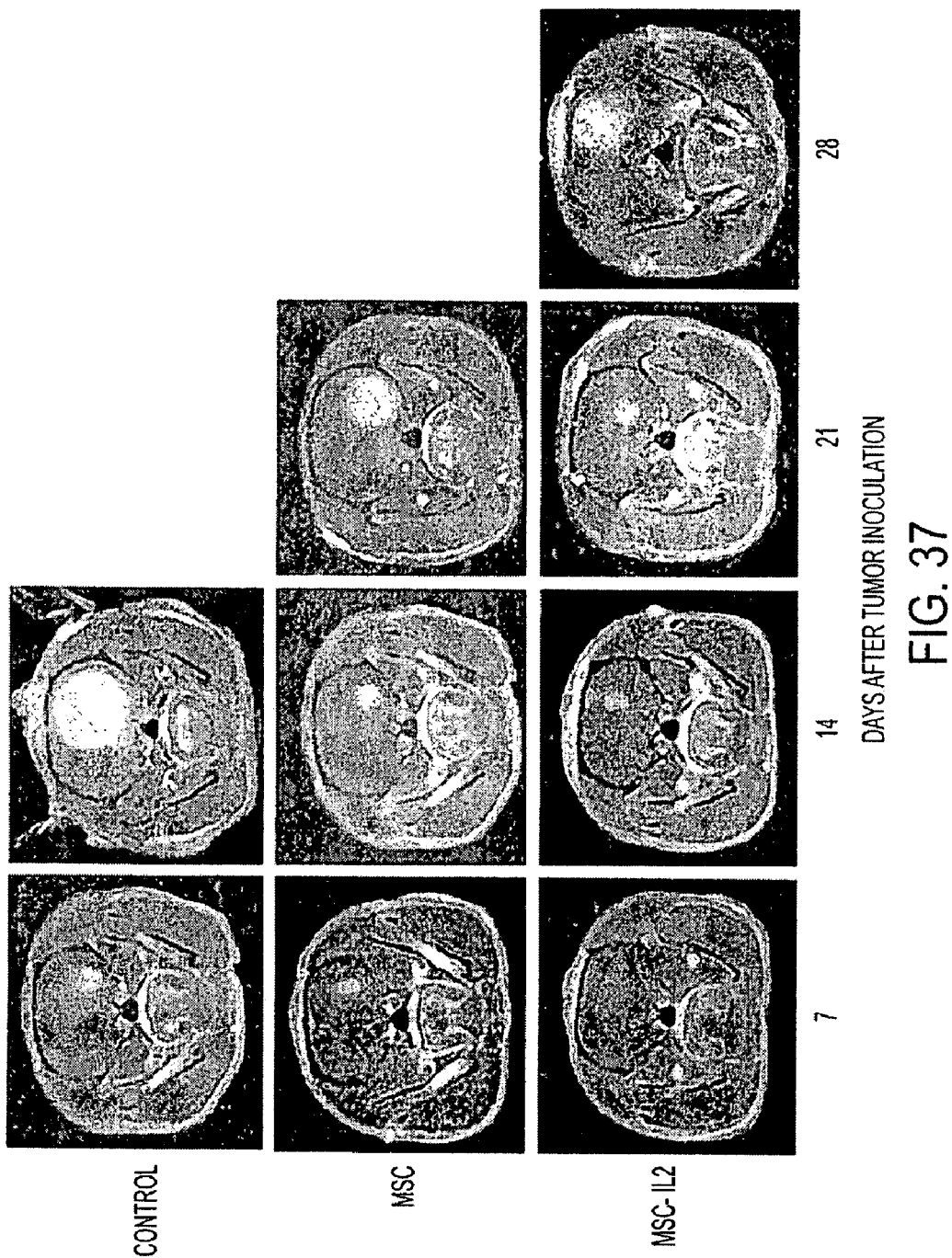

FIG. 37 shows photographs of representative MRIs (Gd-DTPA-enhanced T1-weighted coronal images). 9L glioma were inoculated, or not inoculated, with MSCs three days after tumor inoculation. All animals were subjected to magnetic resonance imaging analysis every seven days. The tumor volume (mm³) was calculated as the sum of image thickness and the area (mm²) of Gd-DTPA-enhanced portions in each imaged region.

Figure 38:
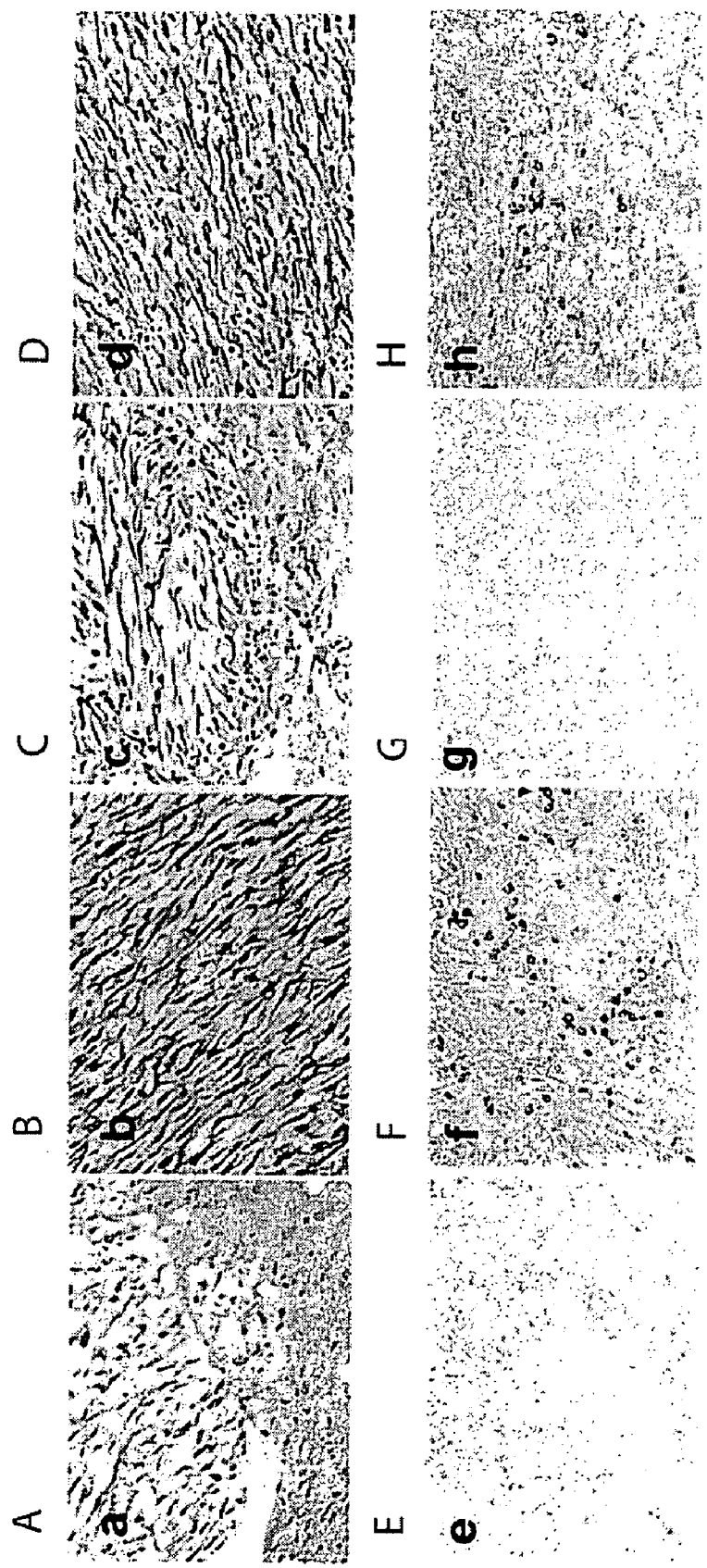

FIG. 38 shows photographs indicating the results of histological analysis of glioma administered with genetically modified MSCs. Glioma inoculated with unmodified MSCs (a and b) or with MSC-IL2s (c and d) were histologically analyzed using hematoxylin and eosin staining. The invasion of CD4-positive lymphocytes in glioma after inoculation with unmodified MSCs (e) or MSC-IL2s (f) was detected using a monoclonal antibody W3/25. The invasion of CD8-positive lymphocytes in glioma after inoculation of unmodified MSCs (g) or MSC-IL2s (h) was detected using a monoclonal antibody OX-8.

Figure 39:
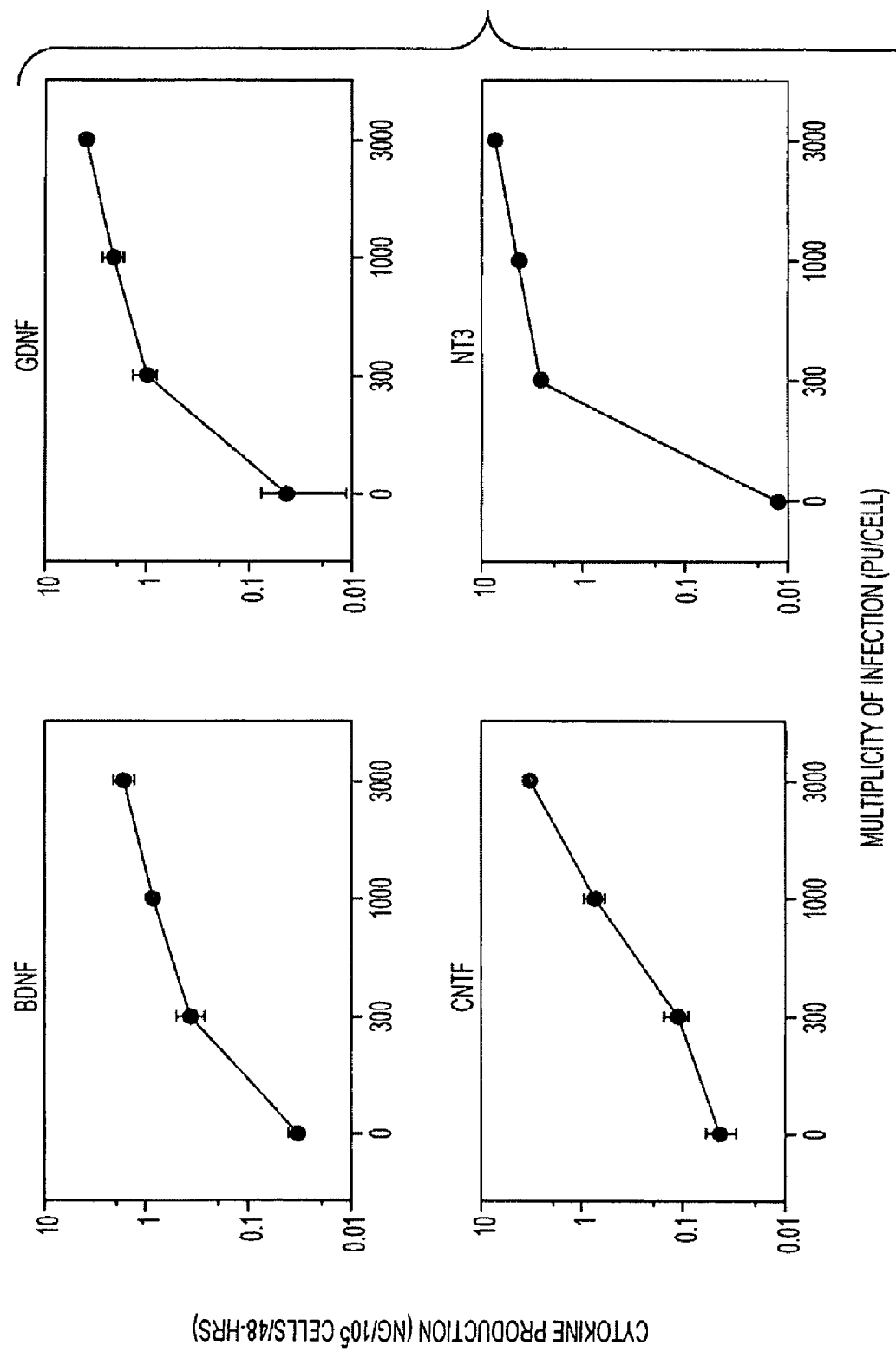

FIG. 39 shows graphs indicating the results of investigating the production of BDNF, GDNF, CNTF, and NT3 by MSCs introduced with the BDNF, GDNF, CNTF, and NT3 genes. The y-axis indicates cytokine production (ng/10⁵ cell/48-hr), and the x-axis indicates the multiplicity of infection (pu/cell).

Figure 40:
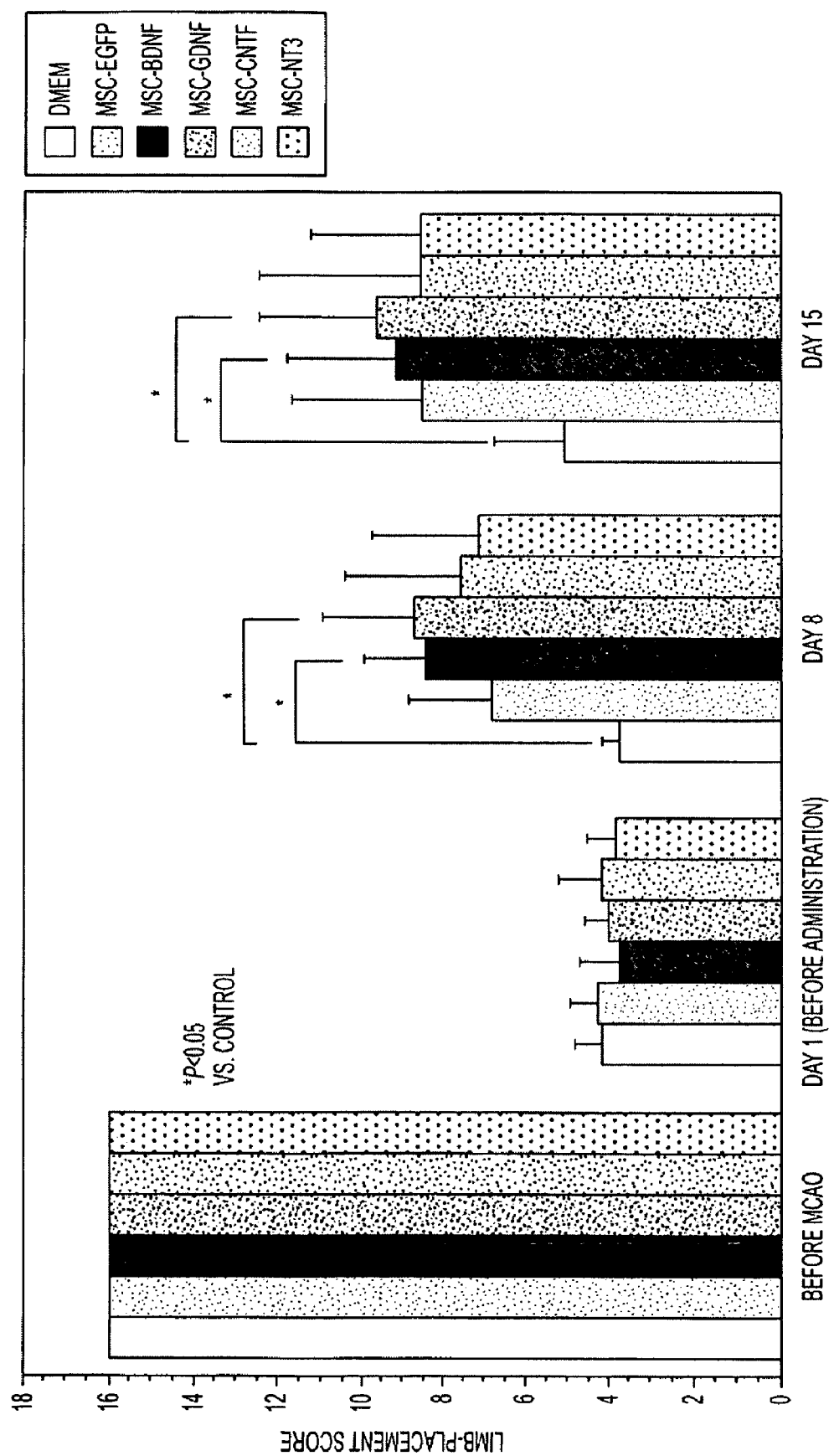

FIG. 40 is a graph showing the results of assessing neurological disorders induced by cerebral ischemia. In addition to the BDNF gene, the GDNF, CNTF, or NT3 gene was introduced into MSCs, the resulting cells were transplanted to a cerebral infarction region, and a limb placement test was conducted. The y-axis indicates the leg-placement score, and the x-axis indicates data before MCAO, one day after MCAO (before injection), eight days after MCAO, and 15 days after MCAO, respectively.

Figure 41:
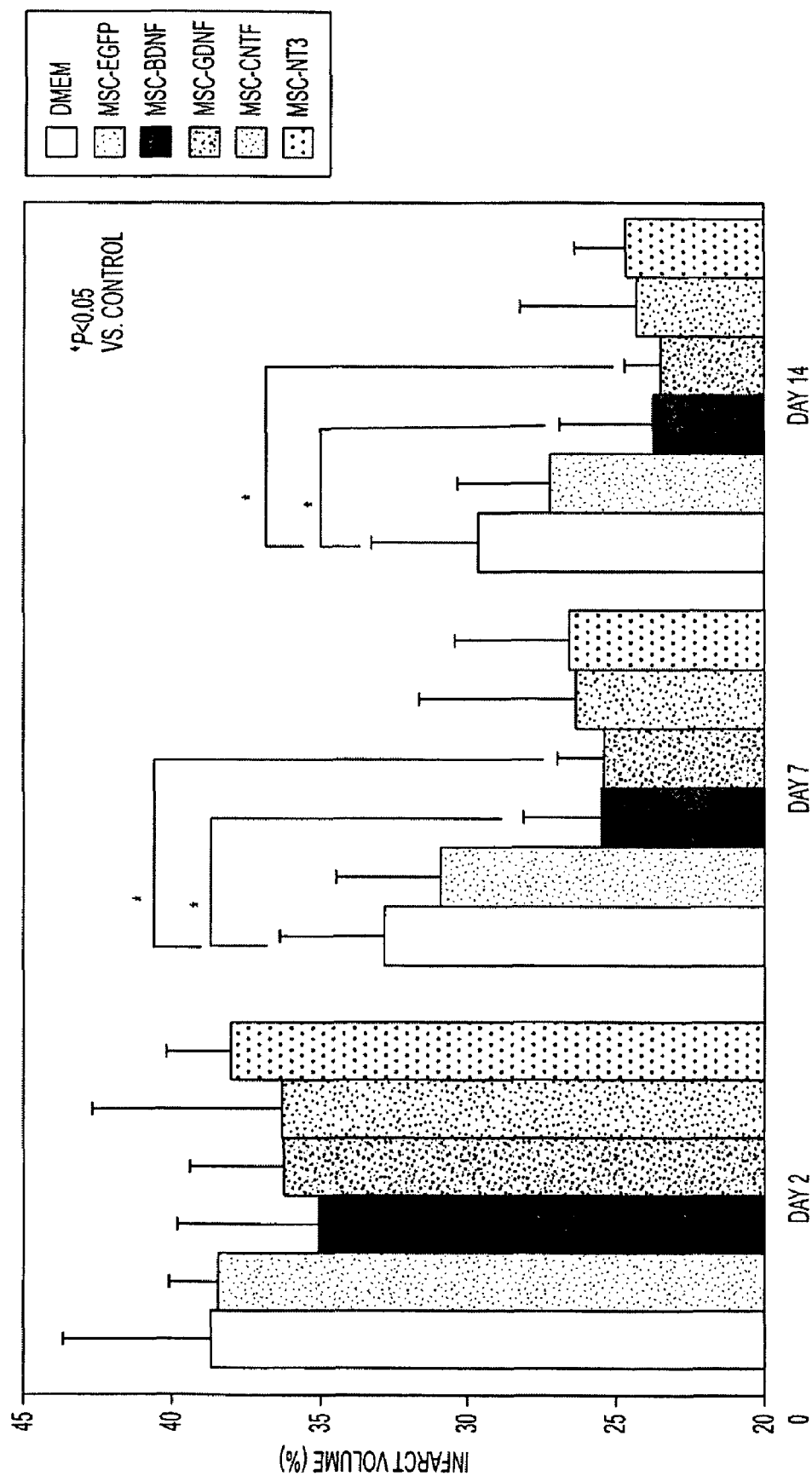

FIG. 41 is a graph showing the infarct volume (HLV) after local transplantation treatment of MSC-BDNF and MSC-GDNF. The y-axis indicates the infarct volume (%), and the x-axis indicates data two days, seven days, and 14 days after MCAO, respectively.

Figure 42:
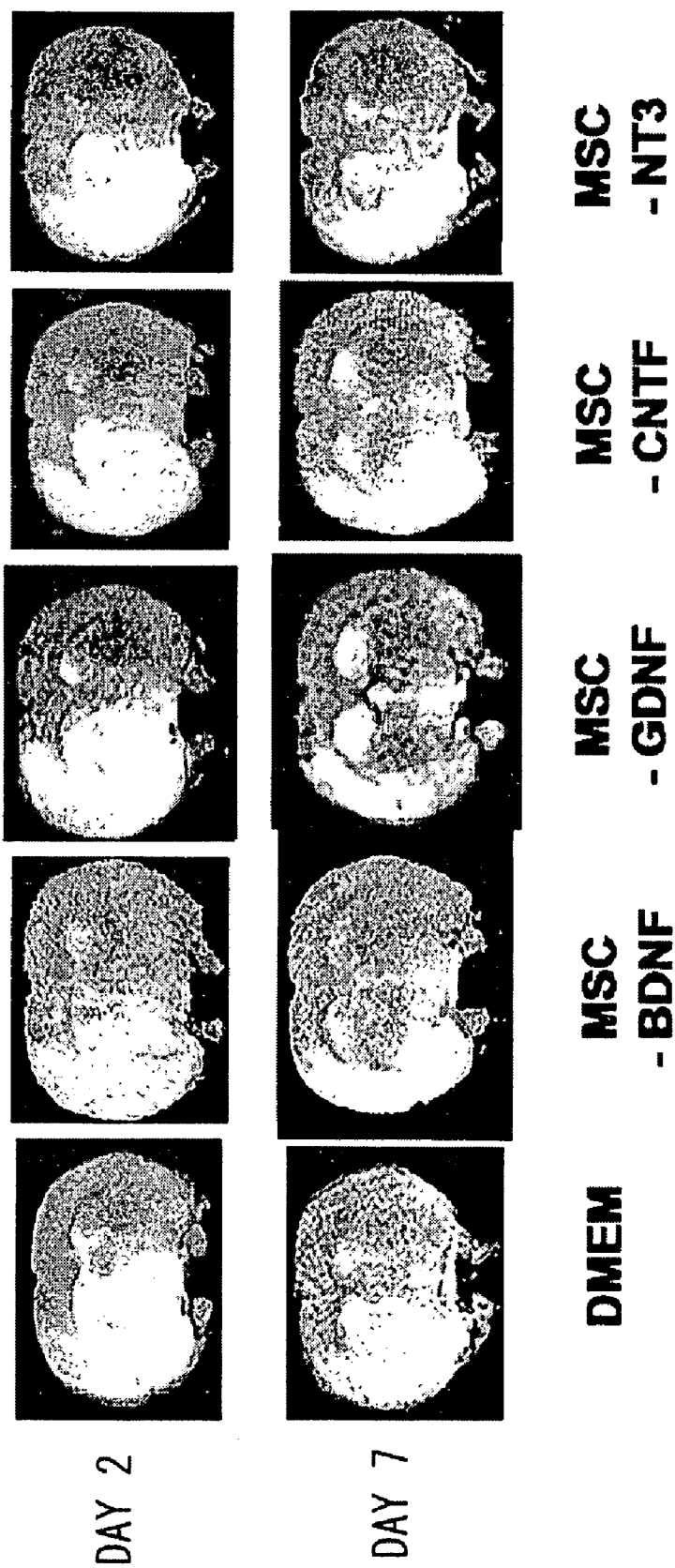

FIG. 42 shows photographs of representative T2-weighted (T2W) images of rats after local administration of DMEM, MSC-BDNF, MSC-GDNF, MSC-CNTF, or MSC-NT3, taken two days and seven days after MCAO.

Figure 43:
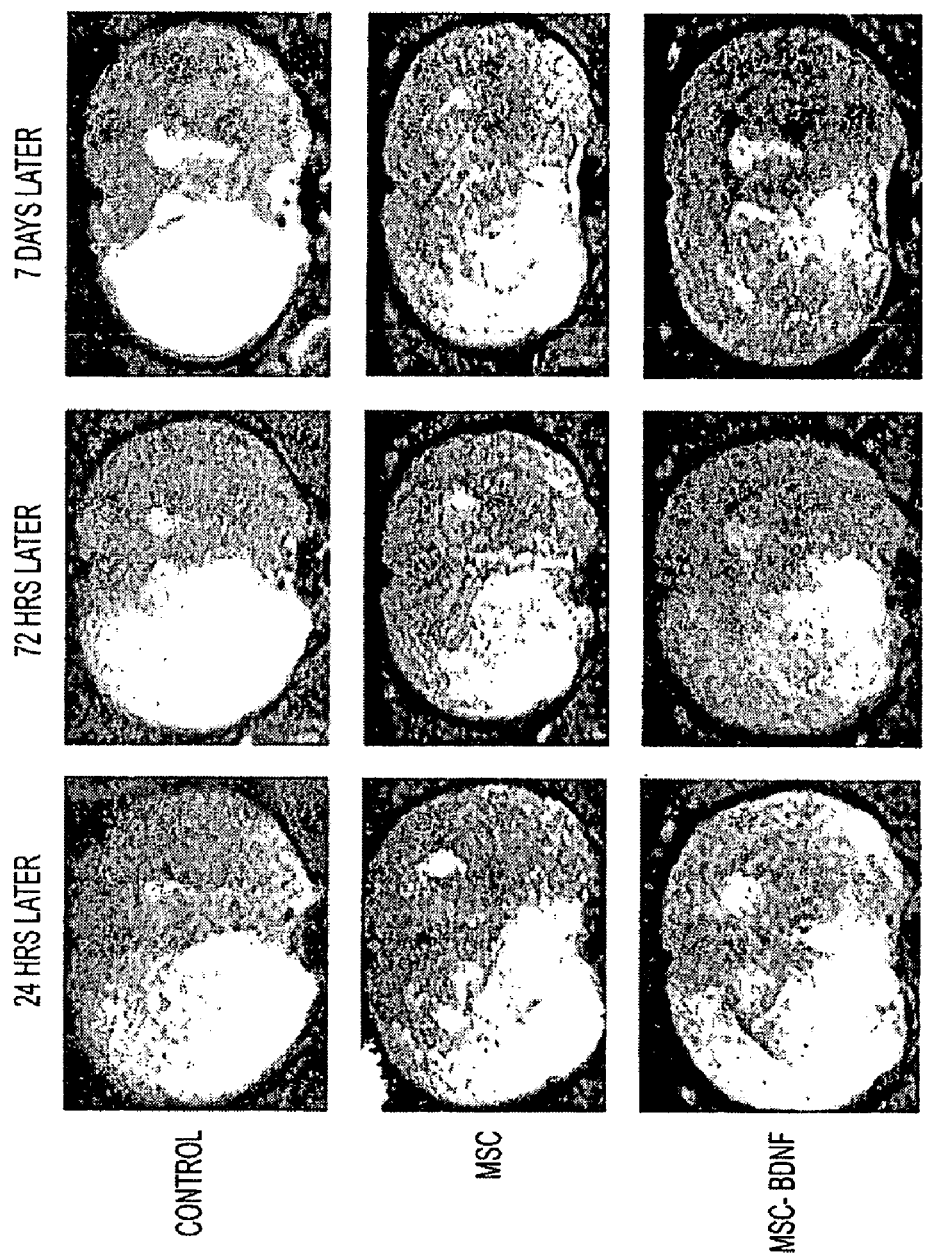

FIG. 43 shows photographs of MRI images of the group intravenously administered with MSC-BDNF, the group intravenously administered with MSC, and an untreated group (control), taken 24 hours, 72 hours, and seven days after MCAO.

Figure 44:
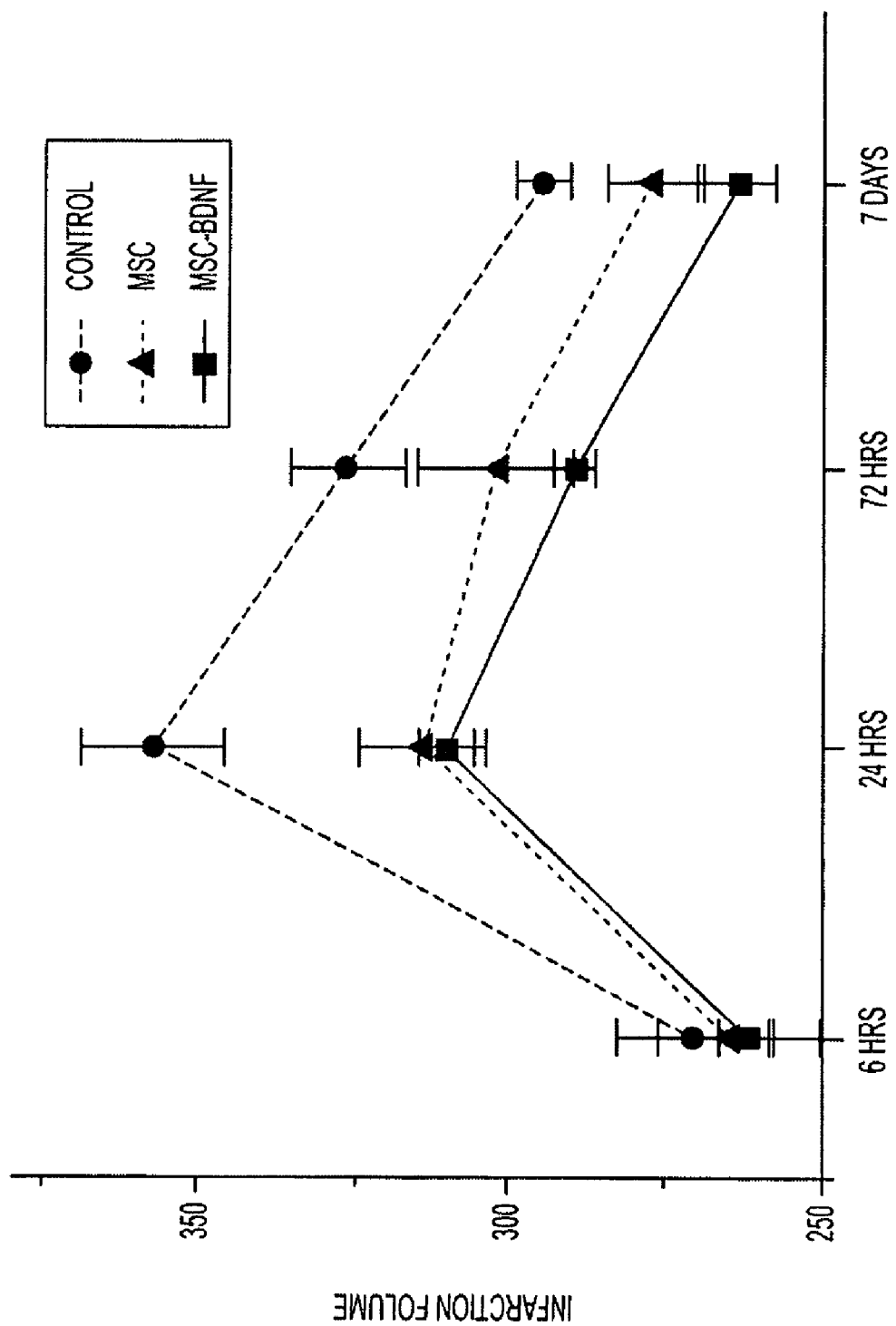

FIG. 44 is a graph showing changes in cerebral infarct volume after MCAO of the group intravenously administered with MSC-BDNF, the group intravenously administered with MSC, and an untreated group (control). The y-axis indicates the infarct volume, and the x-axis indicates data six hours, 24 hours, 72 hours, and seven days after MCAO, respectively.

Figure 45:
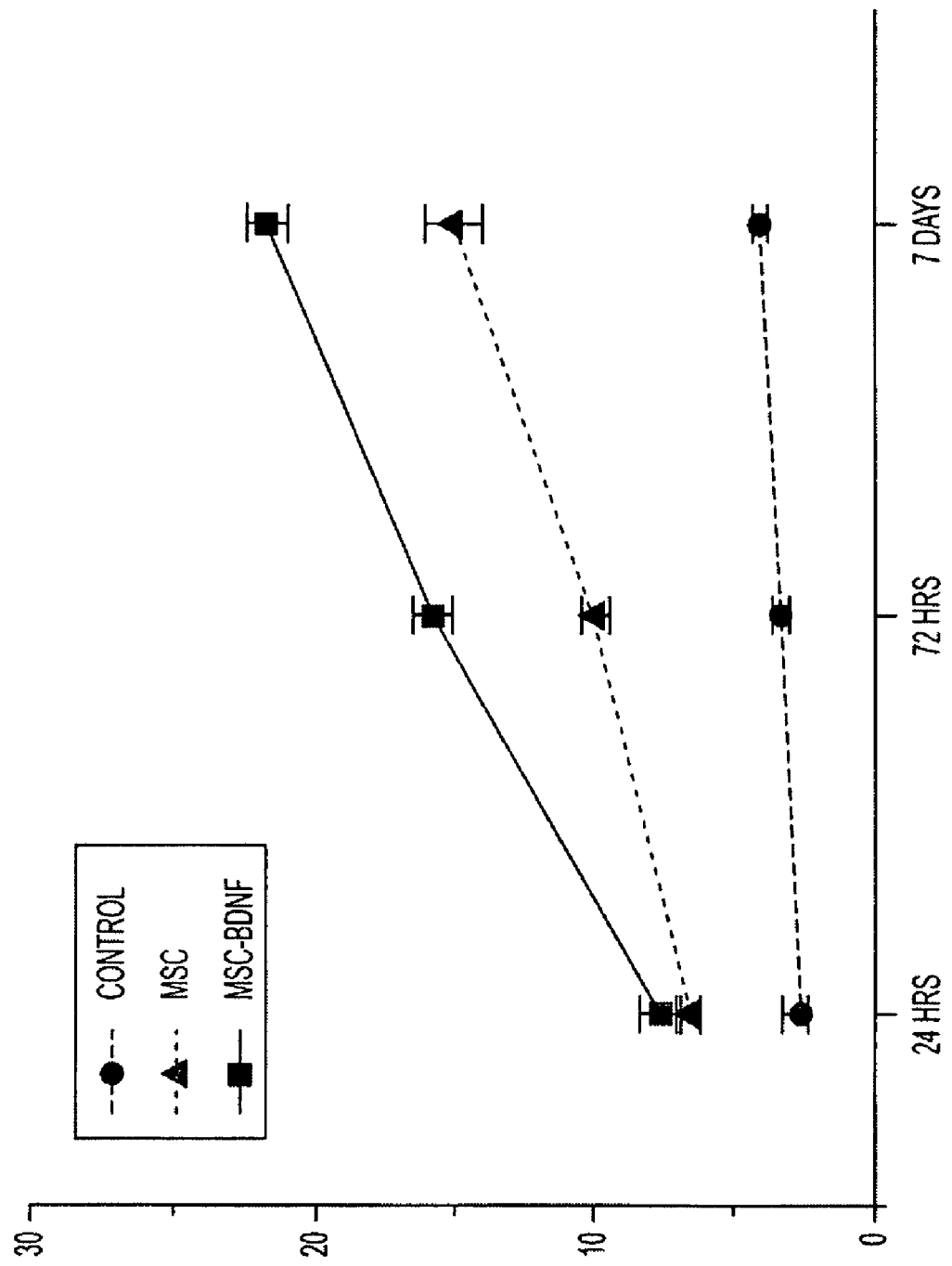

FIG. 45 is a graph showing treadmill test results of the group intravenously administered with MSC-BDNF, the group intravenously administered with MSC, and an untreated group (control) after MCAO. The y-axis indicates the highest running speed, and the x-axis indicates data 24 hours, 72 hours, and seven days after MCAO, respectively.

Figure 46:
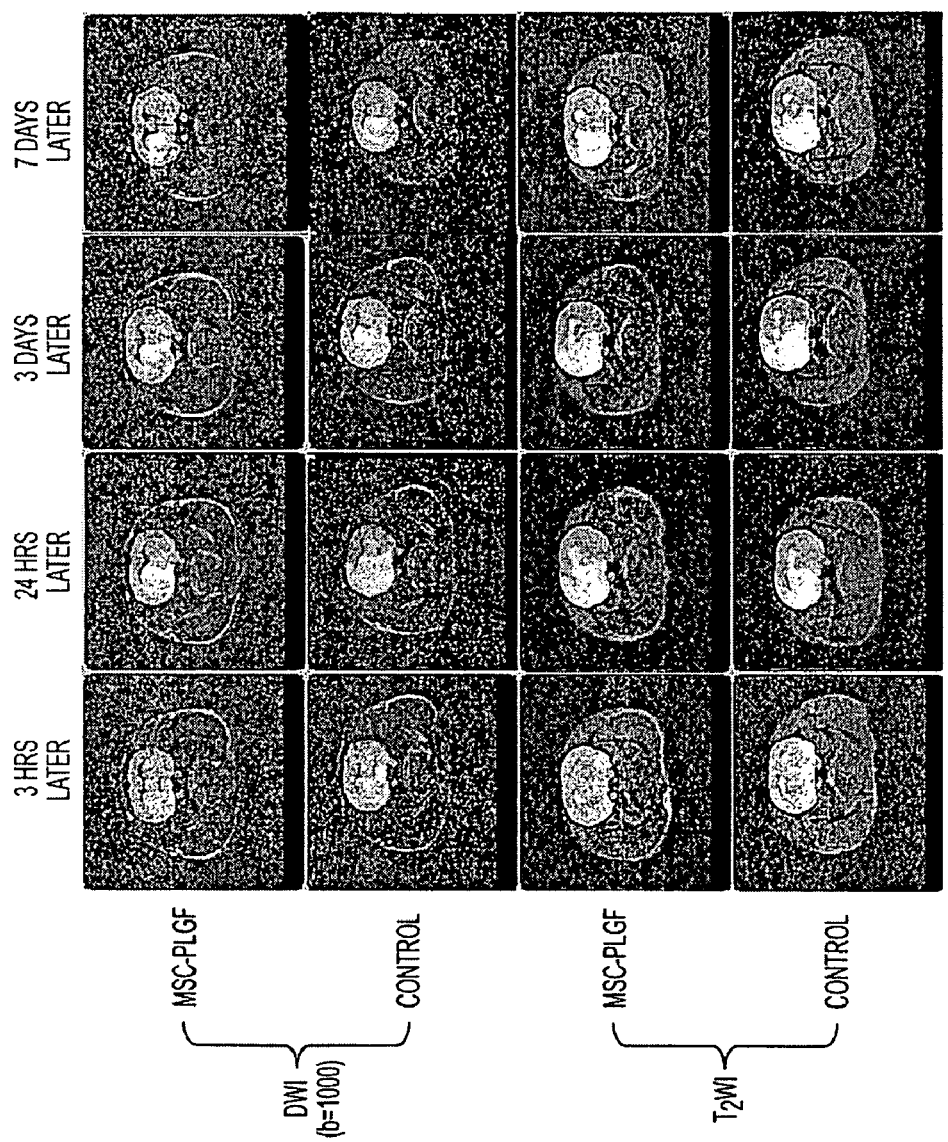

FIG. 46 shows photographs of DW2 (b=1000) images and T₂WI images in MRI analysis of the cerebral infarctions of an untreated group (control) and a group intravenously administered with MSC-PLGF (administered three hours after MCAO), observed at three hours, 24 hours, three days, and seven days after MCAO, respectively.

Figure 47:
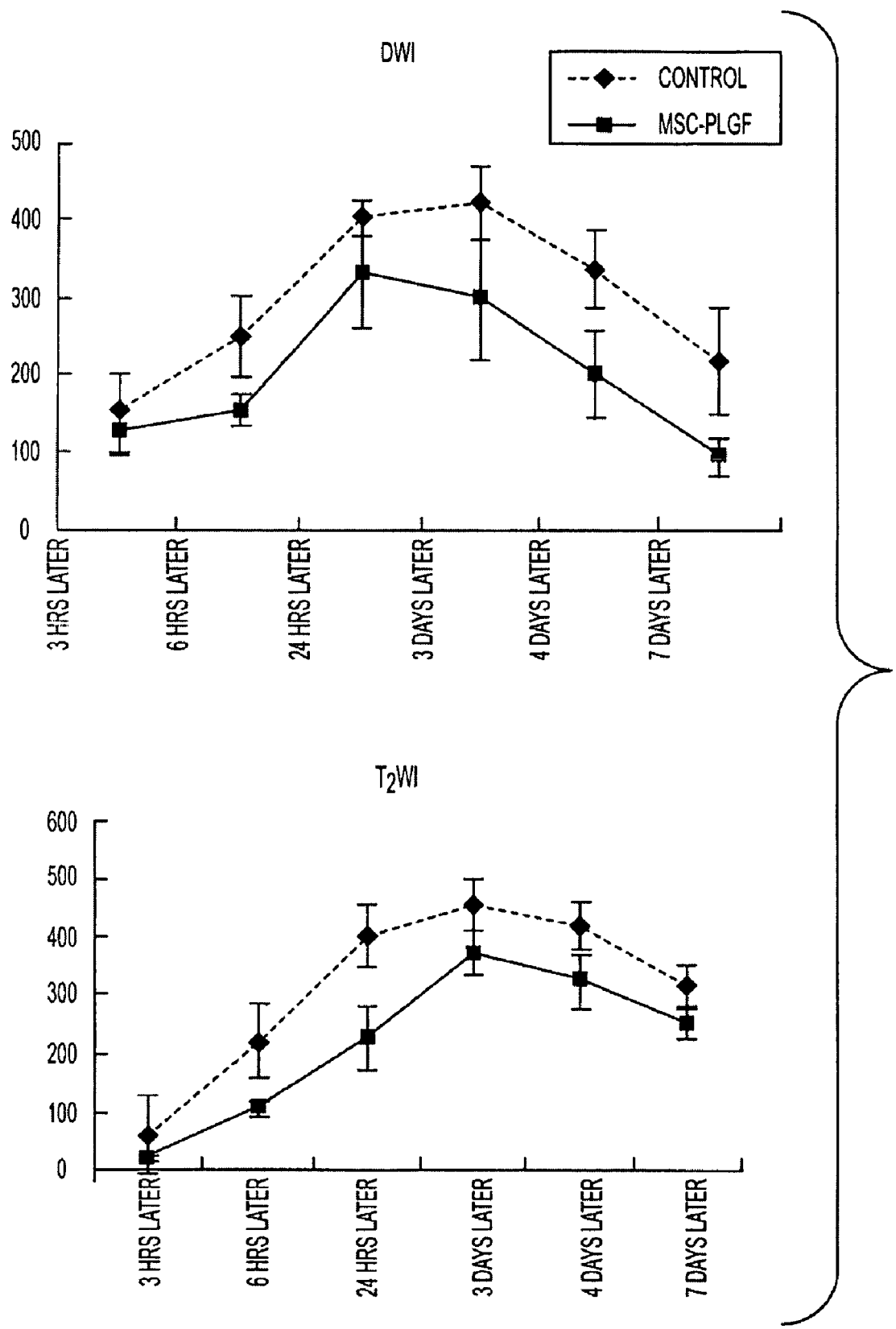

FIG. 47 shows graphs indicating the results of quantifying the volume of a region showing abnormal signals developed after MCAO, observed in MRI analysis over time. The upper graph shows the results using DWI images, and the lower graph shows the results using T₂WI images.

Figure 48:
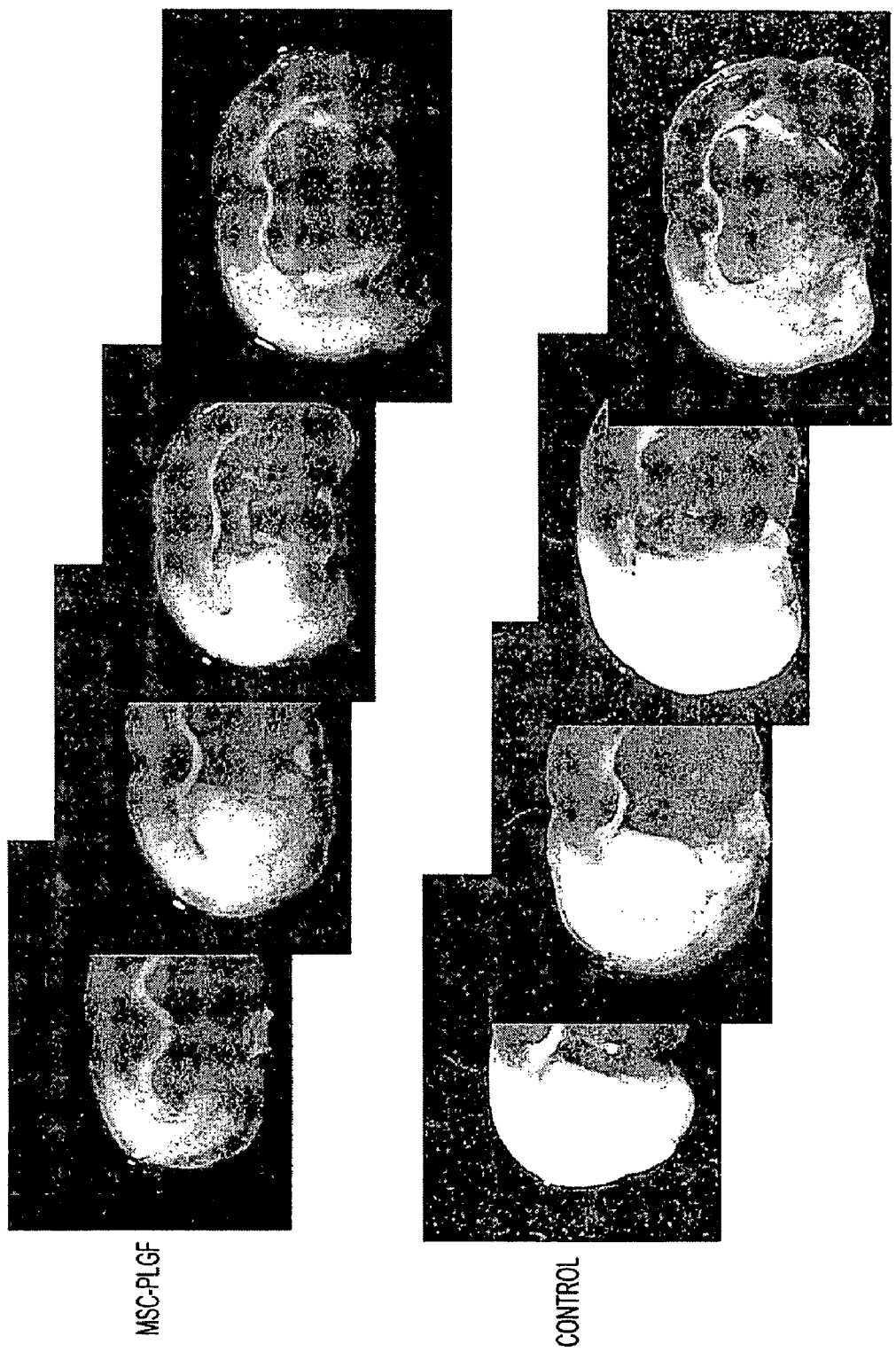

FIG. 48 shows photographs of the brain tissues of the untreated group (control) and the group intravenously administered with MSC-PLGF, which tissues were stained with TTC seven days after MCAO. The upper photographs show the MSC-PLGF treated group, and the lower photographs show the untreated group (control).

Figure 49:
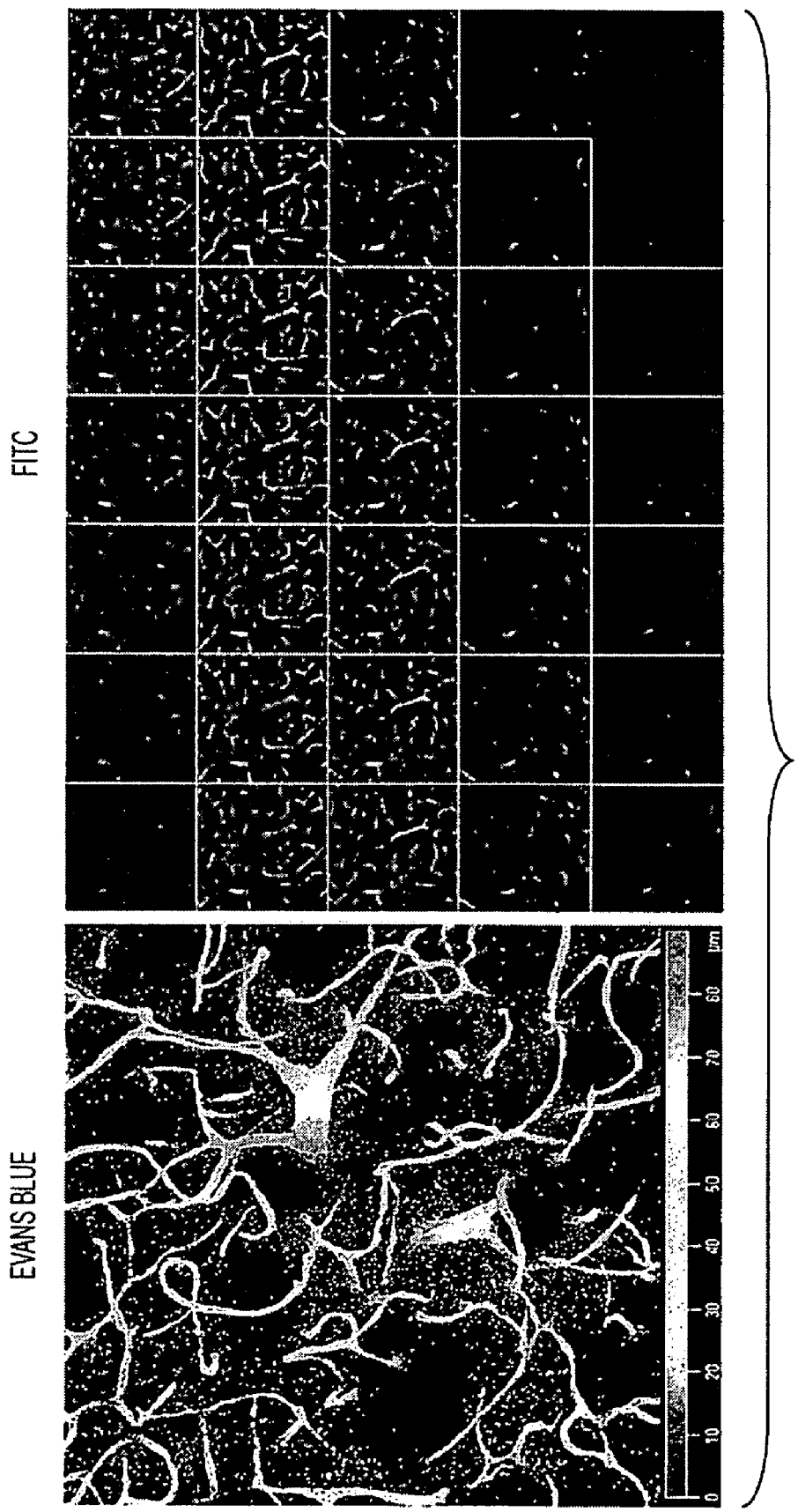

FIG. 49 shows photographs of the blood vascular system of a normal rat visualized by staining with Evans Blue and FITC dextran. The left photograph shows the results using Evans Blue, and the right photograph shows the result using FITC dextran.

Figure 50:
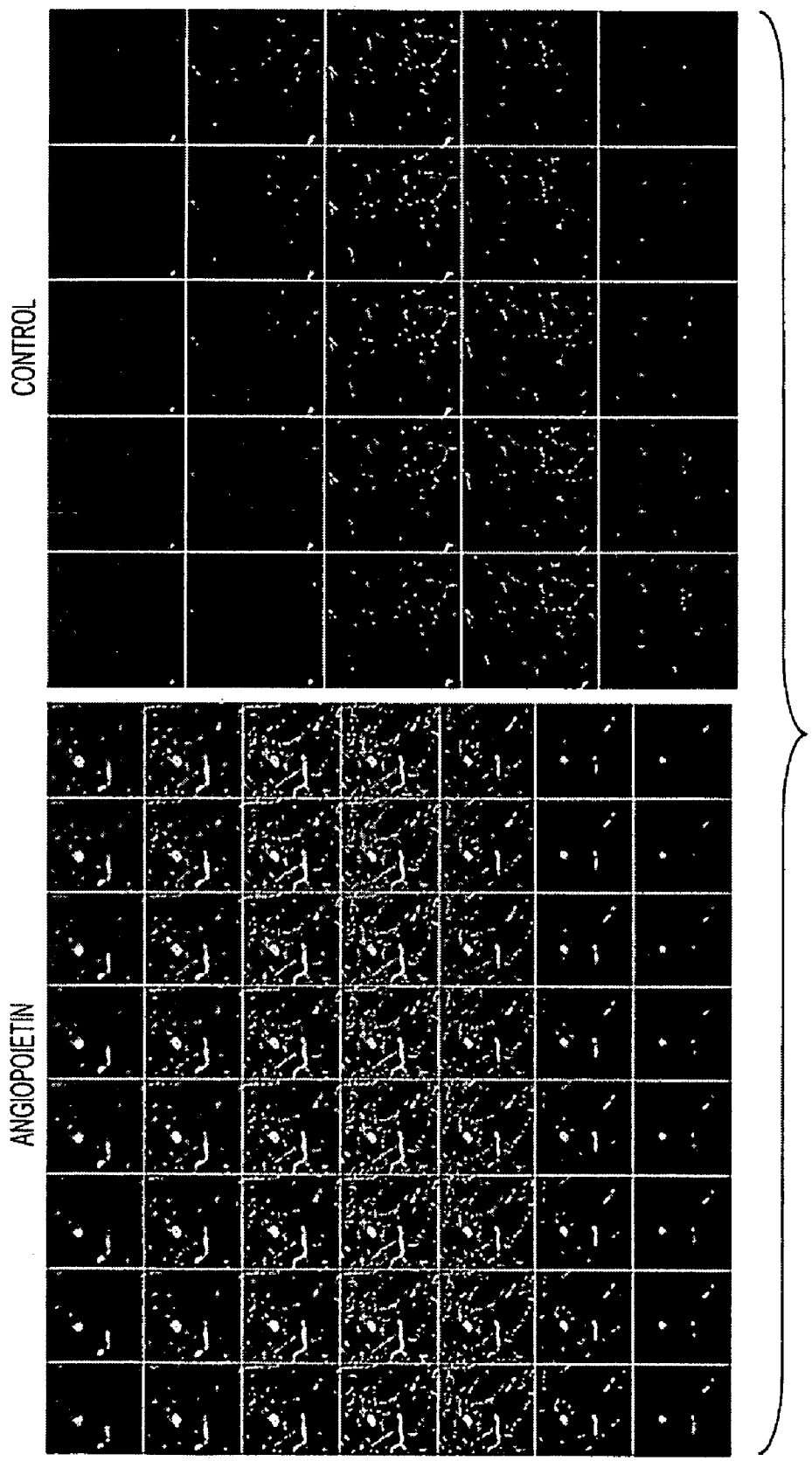

FIG. 50 shows photographs of the results of using FITC to visually compare angiogenesis induction in an MCAO-model rat, locally injected with the angiopoietin gene using an adenoviral vector, and in an untreated MCAO-model rat. The left images show results for the MCAO-model rat which was injected with the gene (Angiopoietin), and the right images show results for the MCAO-model rat that was not injected with the gene (control).

Figure 51:
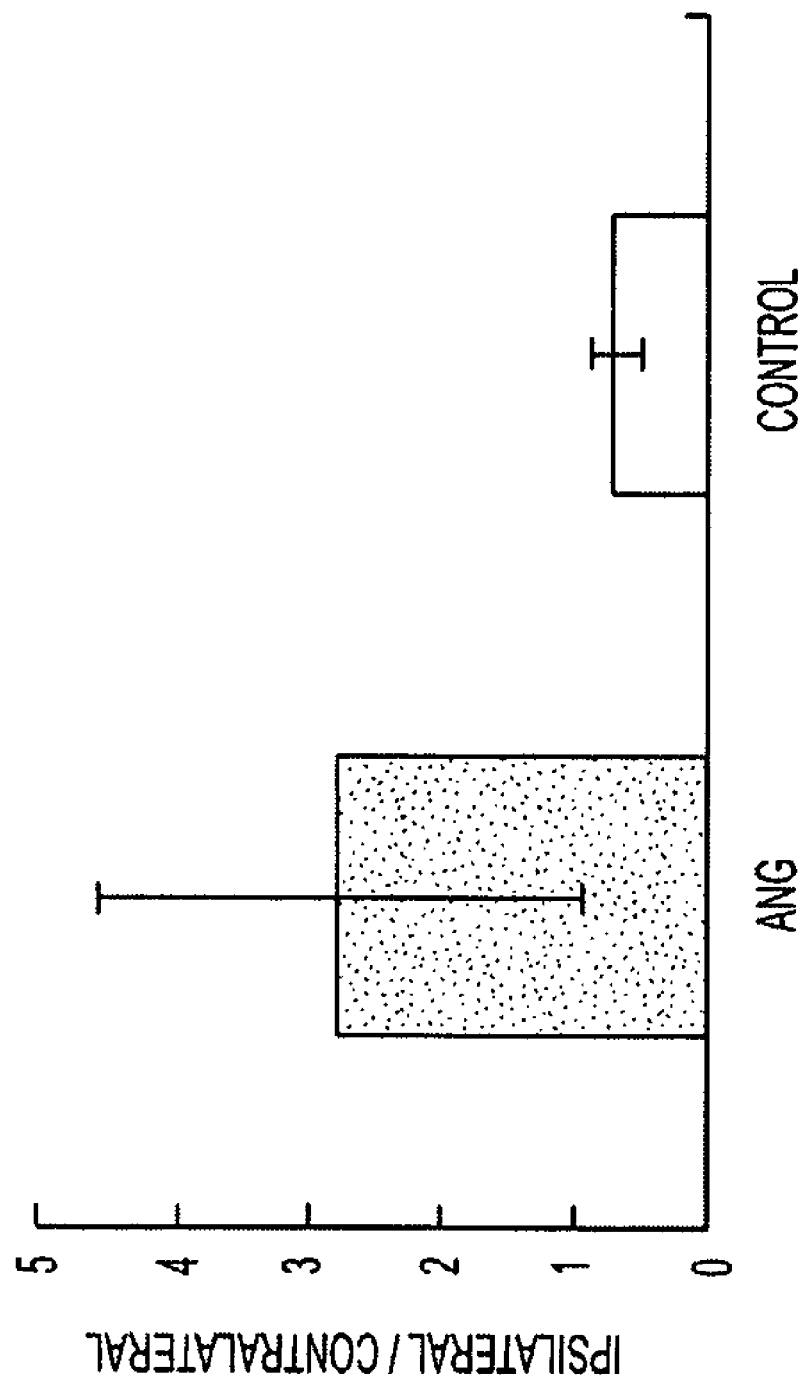

FIG. 51 is a graph showing the results of quantifying the ipsilateral/contralateral ratio using FITC. In FIG. 51, "ANG" represents angiopoietin treatment.

Figure 52:
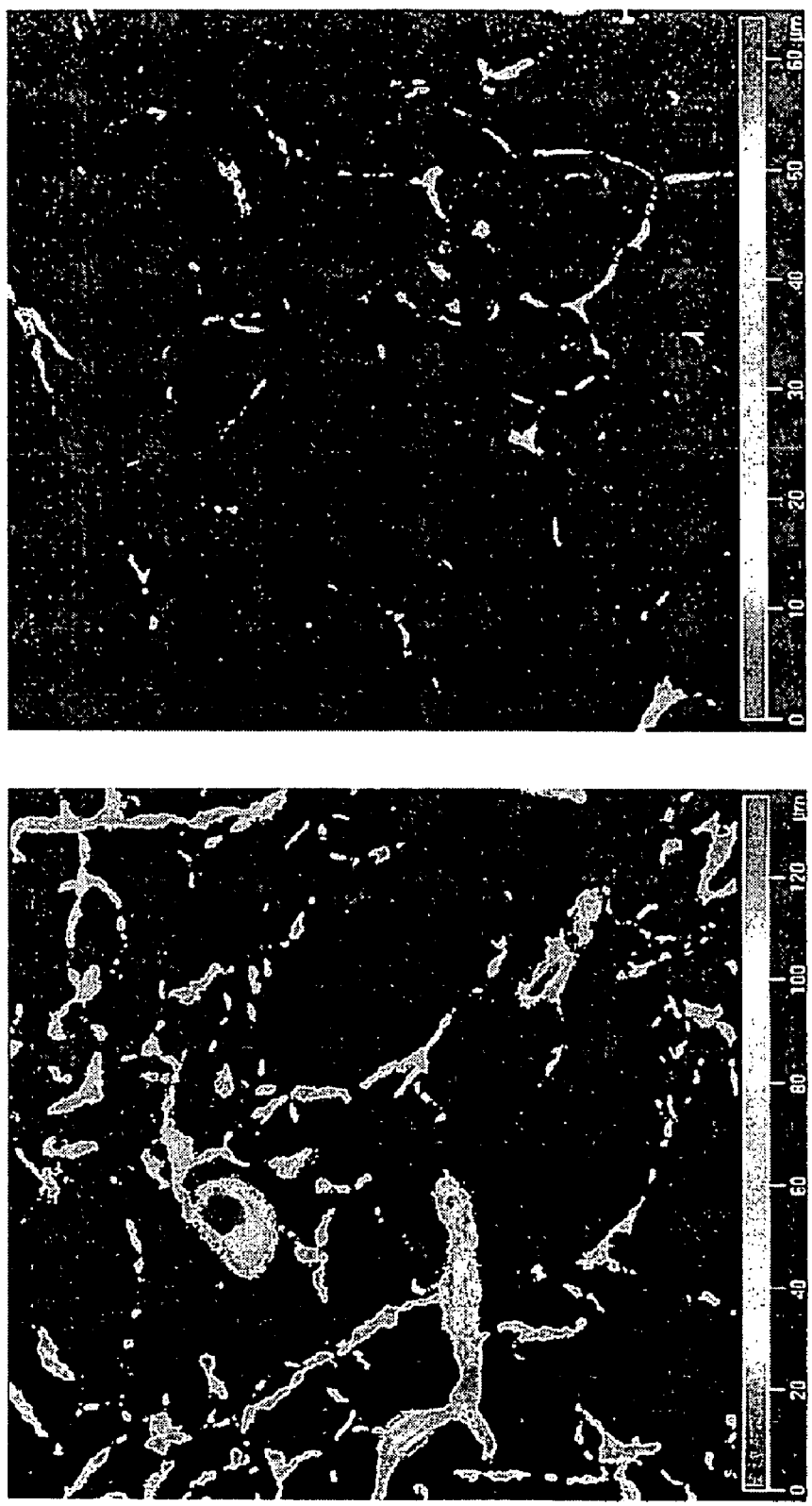

FIG. 52 shows photographs indicating the results of using Evans Blue staining to visually compare angiogenesis induction in MCAO-model rats injected, and not injected, with a gene. The left photograph shows results for the MCAO-model rat injected with the gene (Angiopoietin), and the right photograph shows results for the MCAO-model rat not injected with the gene (control).

Figure 53:
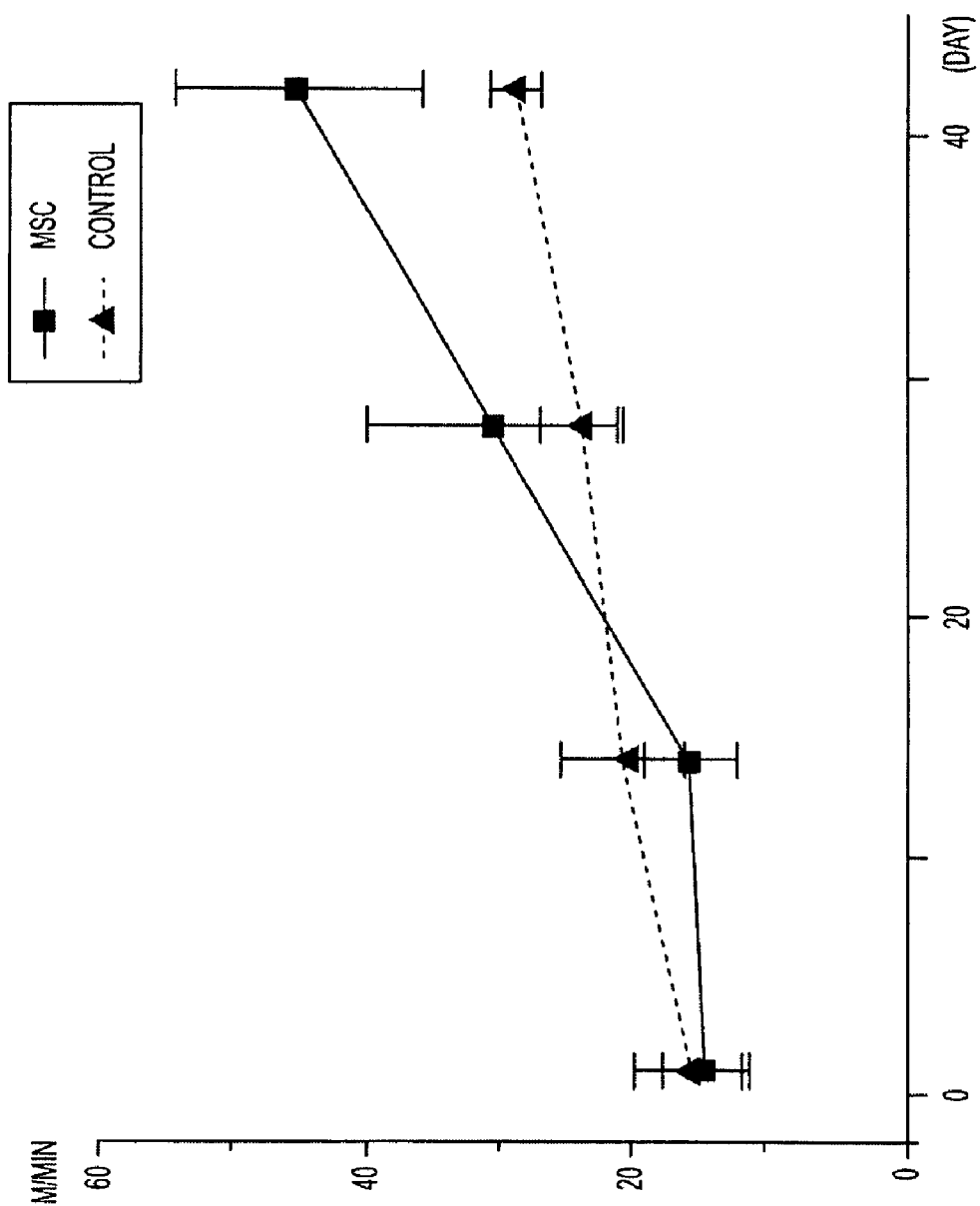

FIG. 53 is a graph showing the results of a treadmill test on an MSC-administered group, in which MSCs were locally administered in the chronic stage after cerebral infarction, and an untreated group (control). The y-axis indicates the highest running speed, and the x-axis indicates the number of days after MSC administration.

Figure 54:
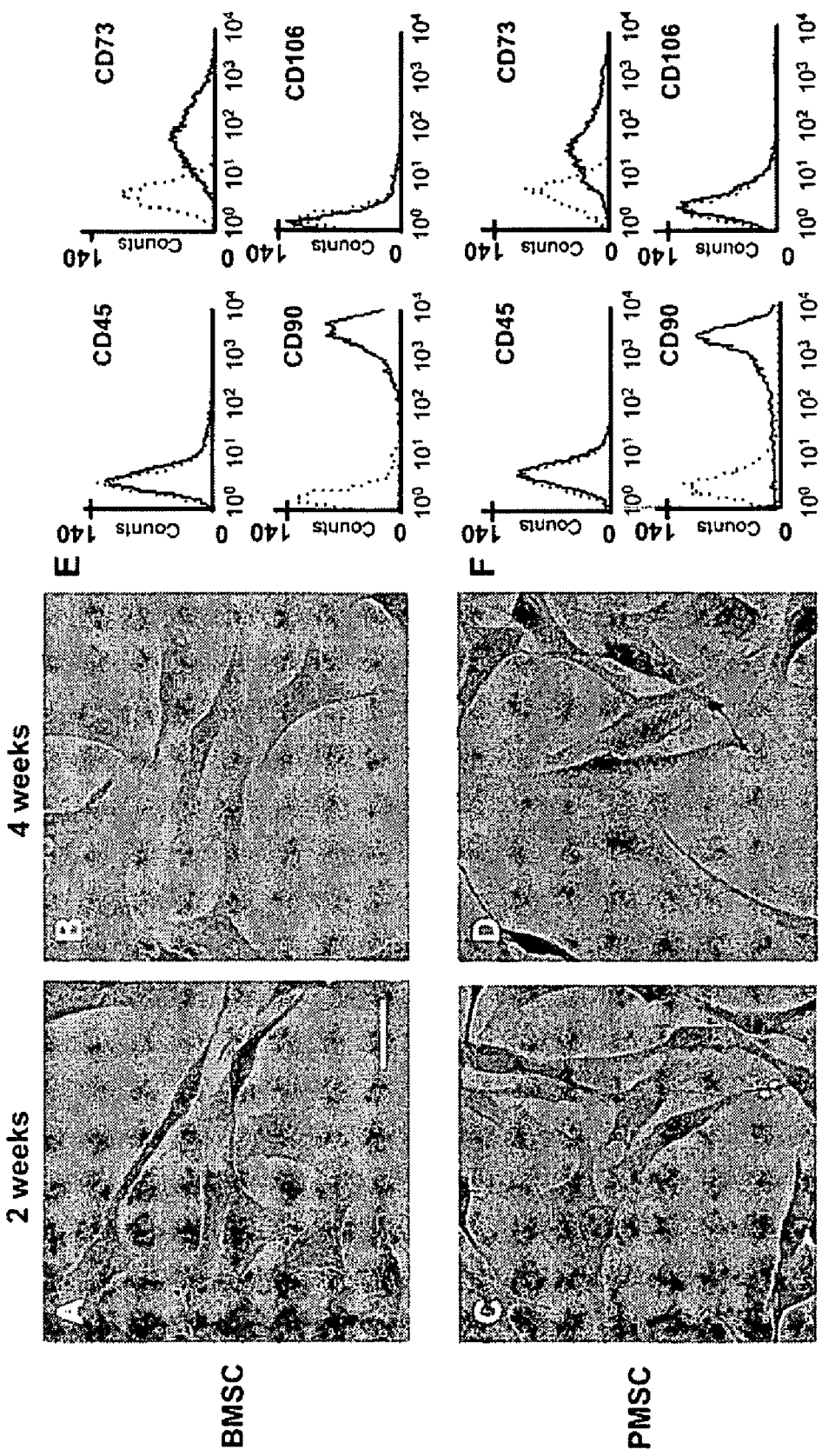

FIG. 54 shows phase-contrast photomicrograph of May-Giemsa stained BMSCs (A) and PMSCs (B) at 2 and 4 weeks in culture, respectively. Flow cytometric analysis of cultured BMSCs (E) and PMSCs (F) with CD45, CD73, CD90, and CD106 antibodies. Dotted lines in each panel indicate isotype-matched mouse IgG antibody control staining. Scale bar=10 µm.

Figure 55:
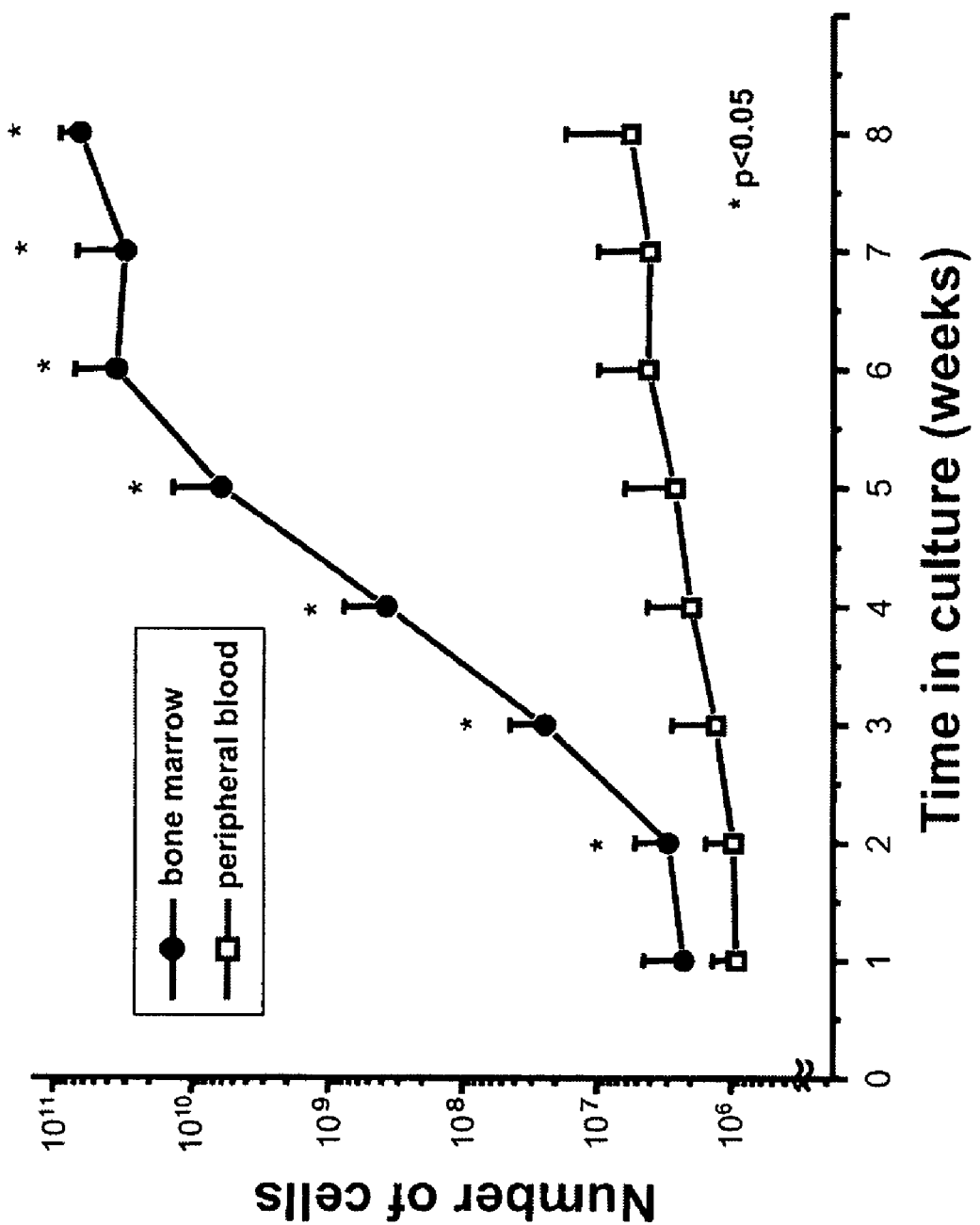

FIG. 55 shows culture expansion of BMSCs (black) and PMSCs (open square). The cell numbers of both MSCs were counted at each week. Error bars represent one SD from the mean. *p<0.05 (n=16).

Figure 56:
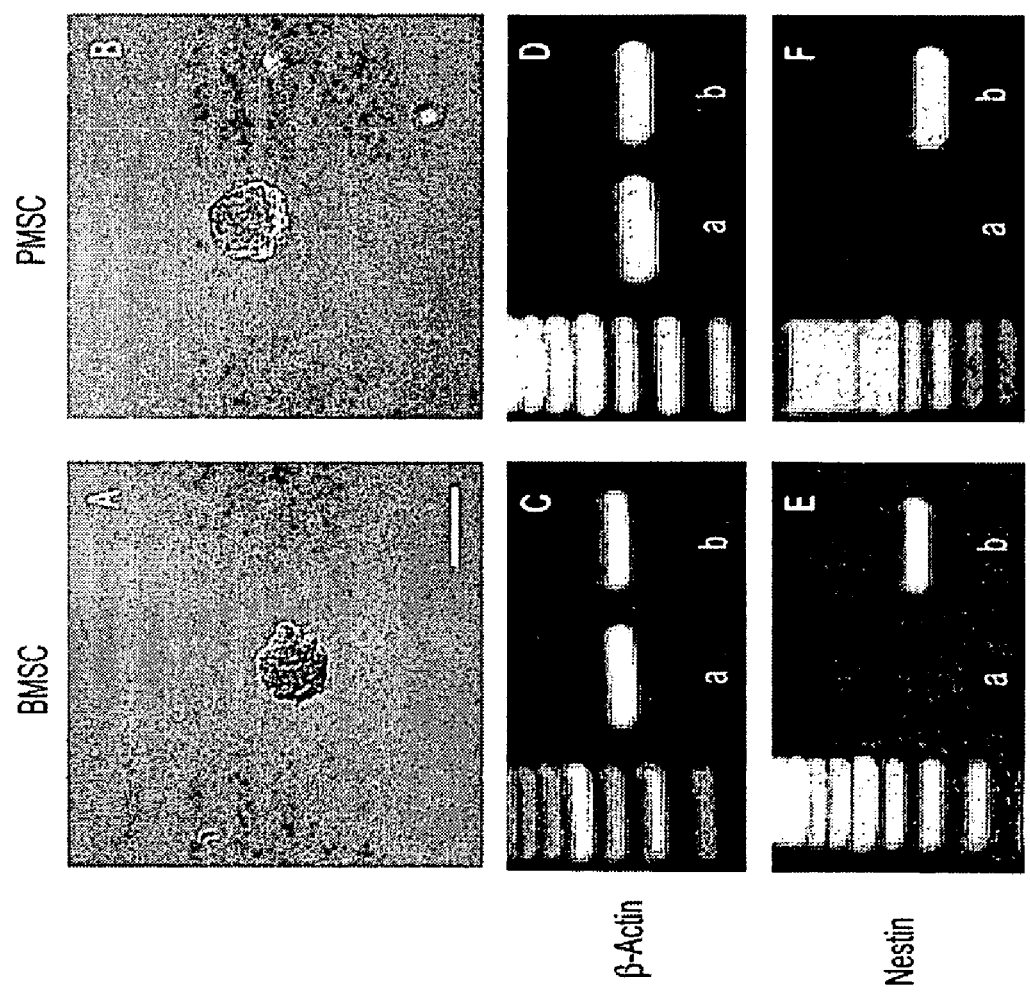

FIG. 56 shows transformation from MSCs to nestin-positive neurospheres. When BMSCs (A) and PMSCs (B) were placed in NPBM with growth factors and were inhibited to adhere on the culture dish, the cells formed neurospheres (Scale bar=20 µm). RT-PCR analysis demonstrated that neurospheres transformed from BMSCs showed nestin-positivity (E-b), which was negative before transformation (E-a). Nestin also became positive following transformation of PMSCs (F-b), which was negative in the primary PMSCs (E-a). C and D showed control mRNA expression of β-Actin of BMSCs and PMSCs, respectively.

Figure 57:
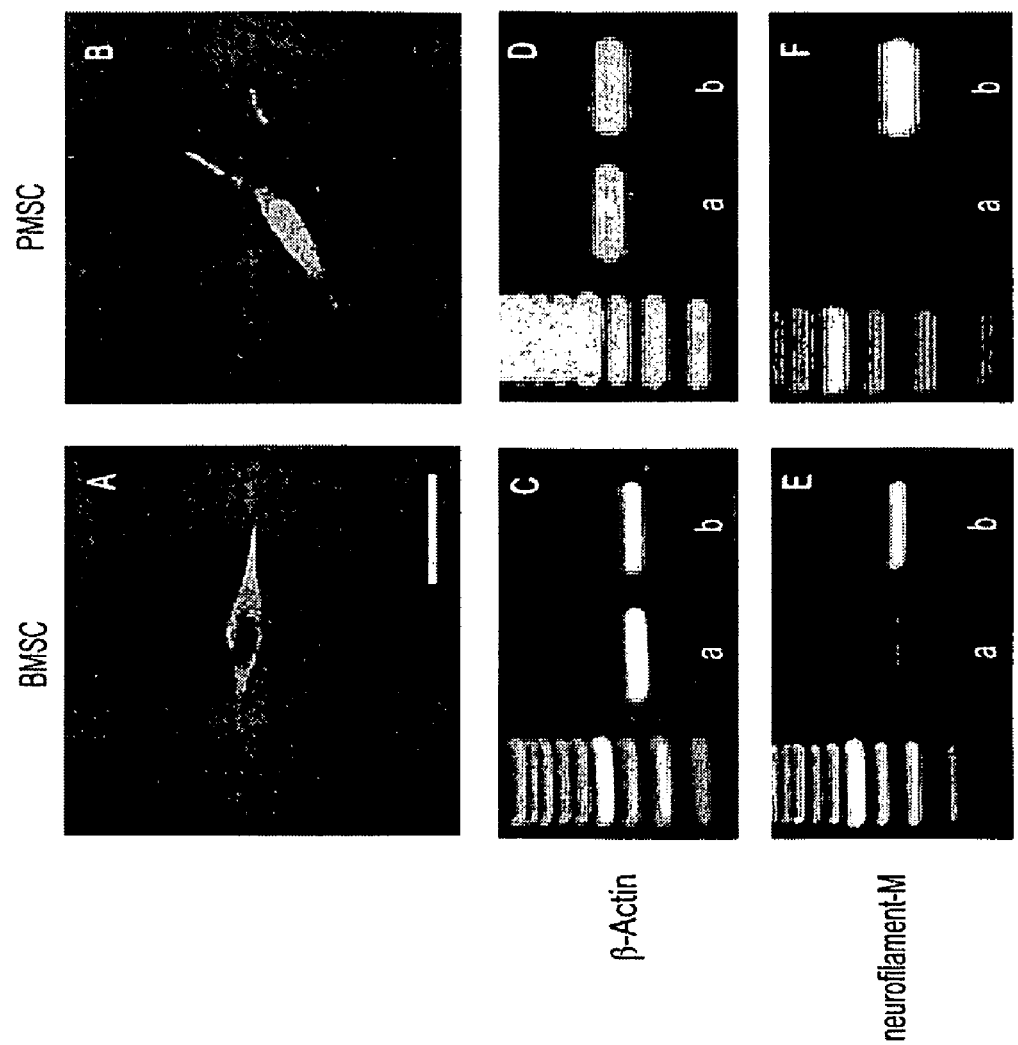

FIG. 57 shows Neurofilament expression in differentiated neurosphere cells. Cells differentiated from neurospheres which had been transformed from BMSCs (A) or PMSCs (B) showed NF-M positivity in culture. RT-PCR analysis demonstrated that BMSCs (A) and PMSCs (B) differentiated from neurospheres showed NF-M positivity (E-b; F-b), which was negative in neurospheres (E-a; F-a). C and D showed control mRNA expression of β-Actin of BMSCs and PMSCs, respectively. Scale bar=10 µm.

Figure 58:
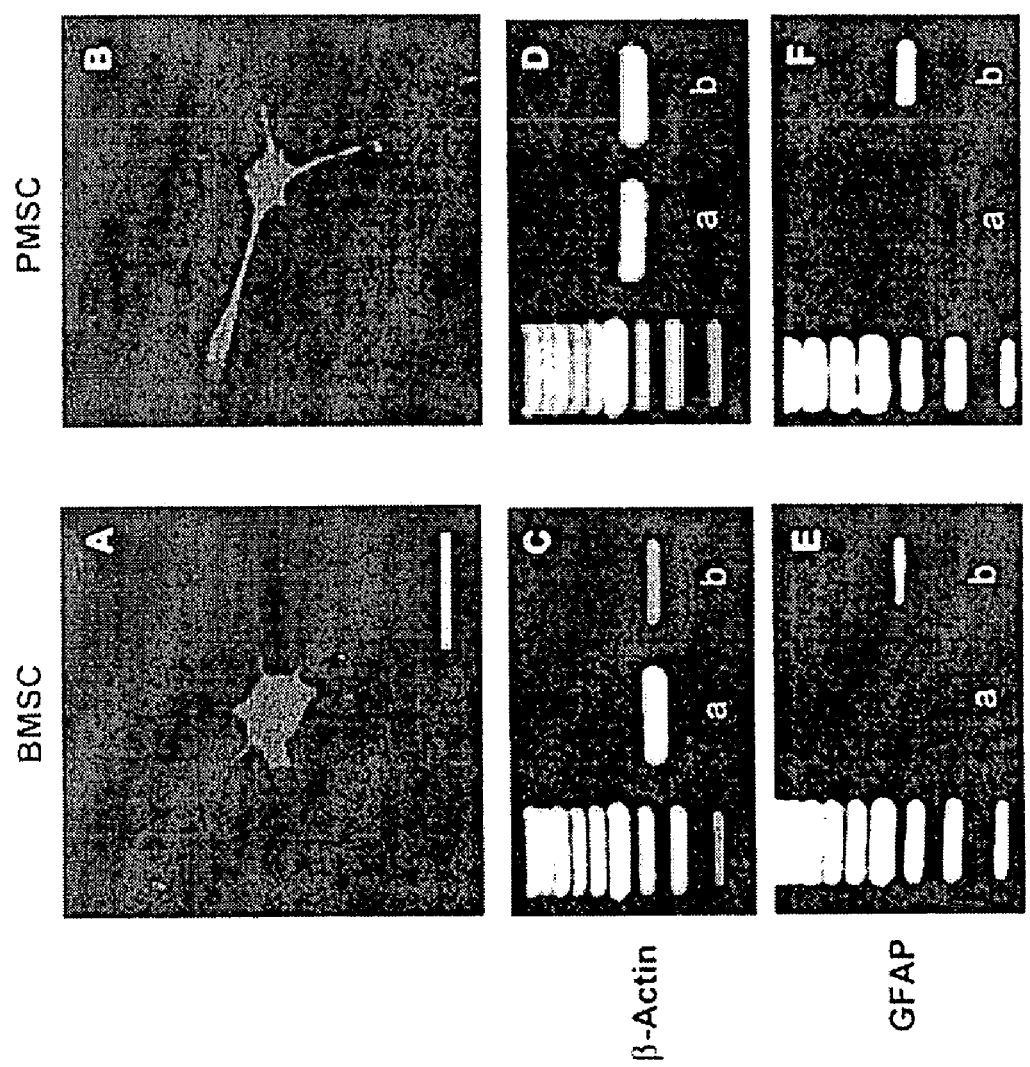

FIG. 58 shows GFAP expression in differentiated neurosphere cells. Immunocytochemical analysis indicated that BMSCs (A) and PMSCs (B) differentieted from neurospheres showed GFAP positivity in culture. RT-PCR analysis demonstrated that cells differentiated from neurospheres which had been transformed from BMSCs showed the GFAP positivity (E-b), which was negative in neurospheres (E-a). GFAP also became positive following differentiation in the PMSCs group (F-b), which was negative before induction (E-a). C and D demonstrated the mRNA expression of β-Actin of BMSCs and PMSCs for control, respectively. Scale bar=10 µm.

Figure 59:
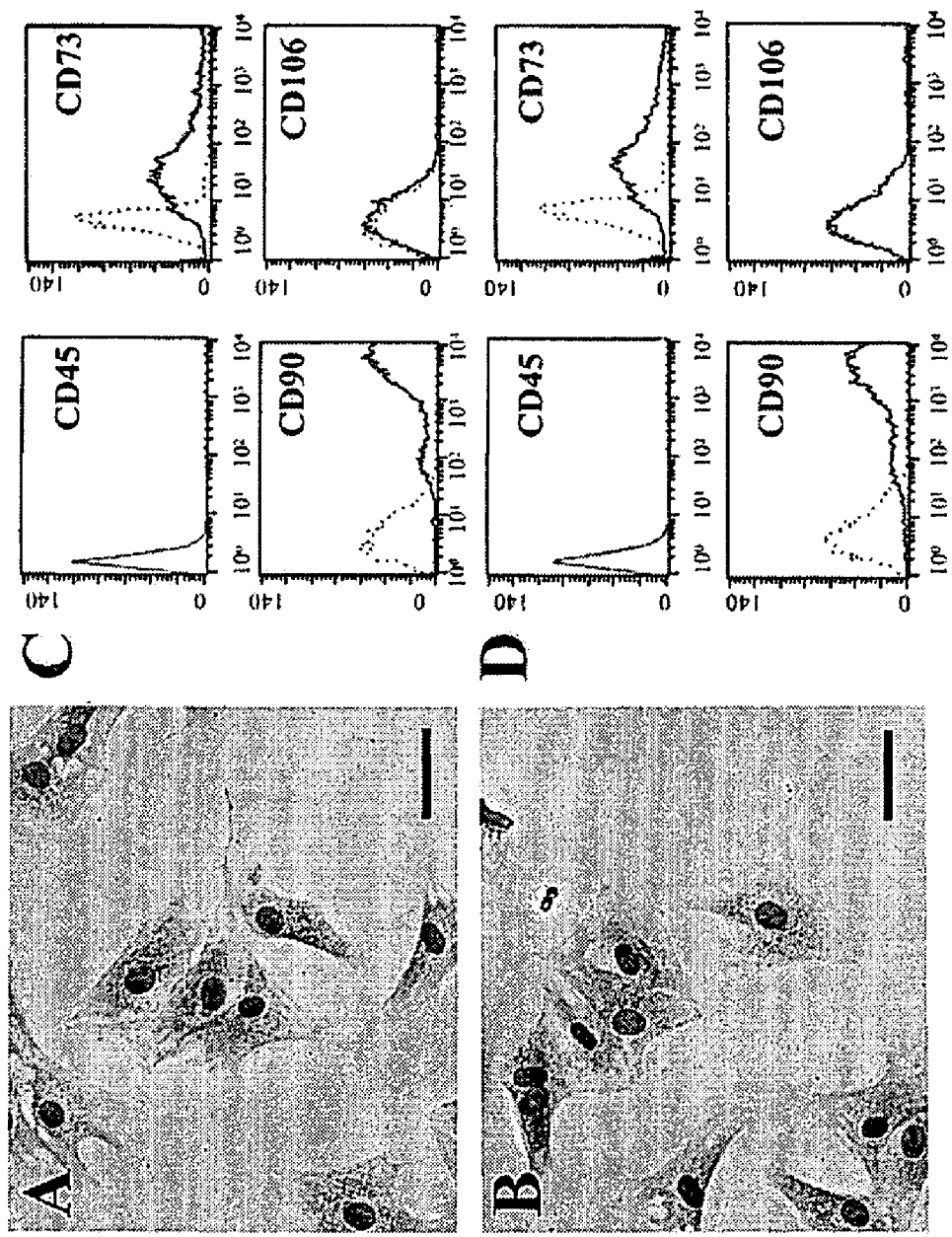

FIG. 59 shows May-Giemsa staining of BMSCs (A) and PMSCs (B) (scale bar=20 µm). Flow cytometric analysis of surface antigen expression on BMSCs (C) and PMSCs (D). The cells were immunolabeled with FITC-conjugated and PE-conjugated monoclonal antibody specific for the indicated surface antigen. Dead cells were eliminated by forward and side scatter.

Figure 60:
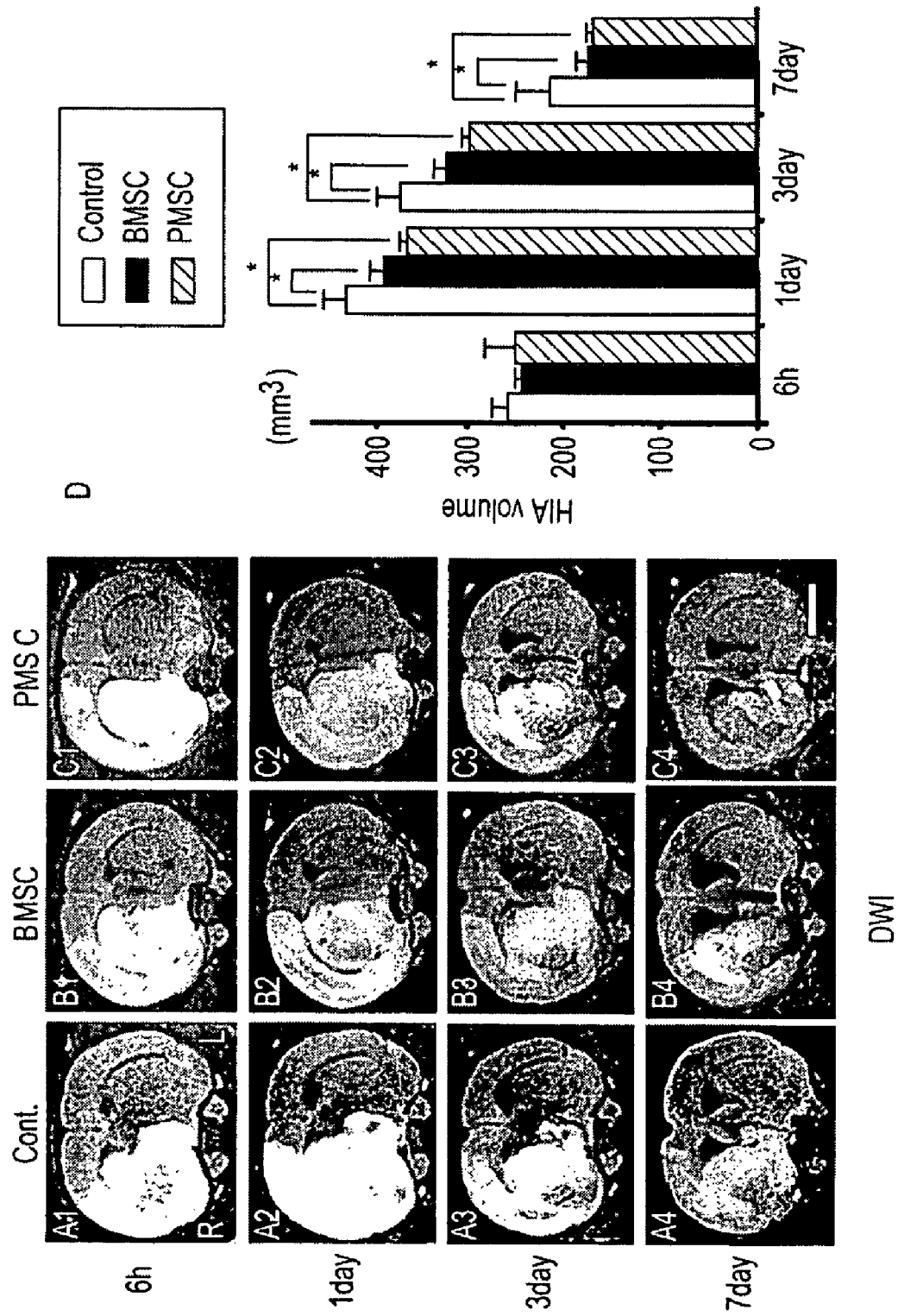

FIG. 60 shows evaluation of the ischemic lesion volume with Diffusion Weighted Images (DWI). BMSCs or PMSCs were intravenously-injected immediately after the initial MRI scanning (6 hrs after MCAO). Images obtained 6 hrs, 1, 3, and 7 days MCAO in medium-injected (A1-4), BMSC-treated (B1-4), and PMSC-treated group ($C_{1-4}$). Summary of lesion volumes evaluated with DWI in each groups (D). Scale bar=3 mm. *P<0.05

Figure 61:
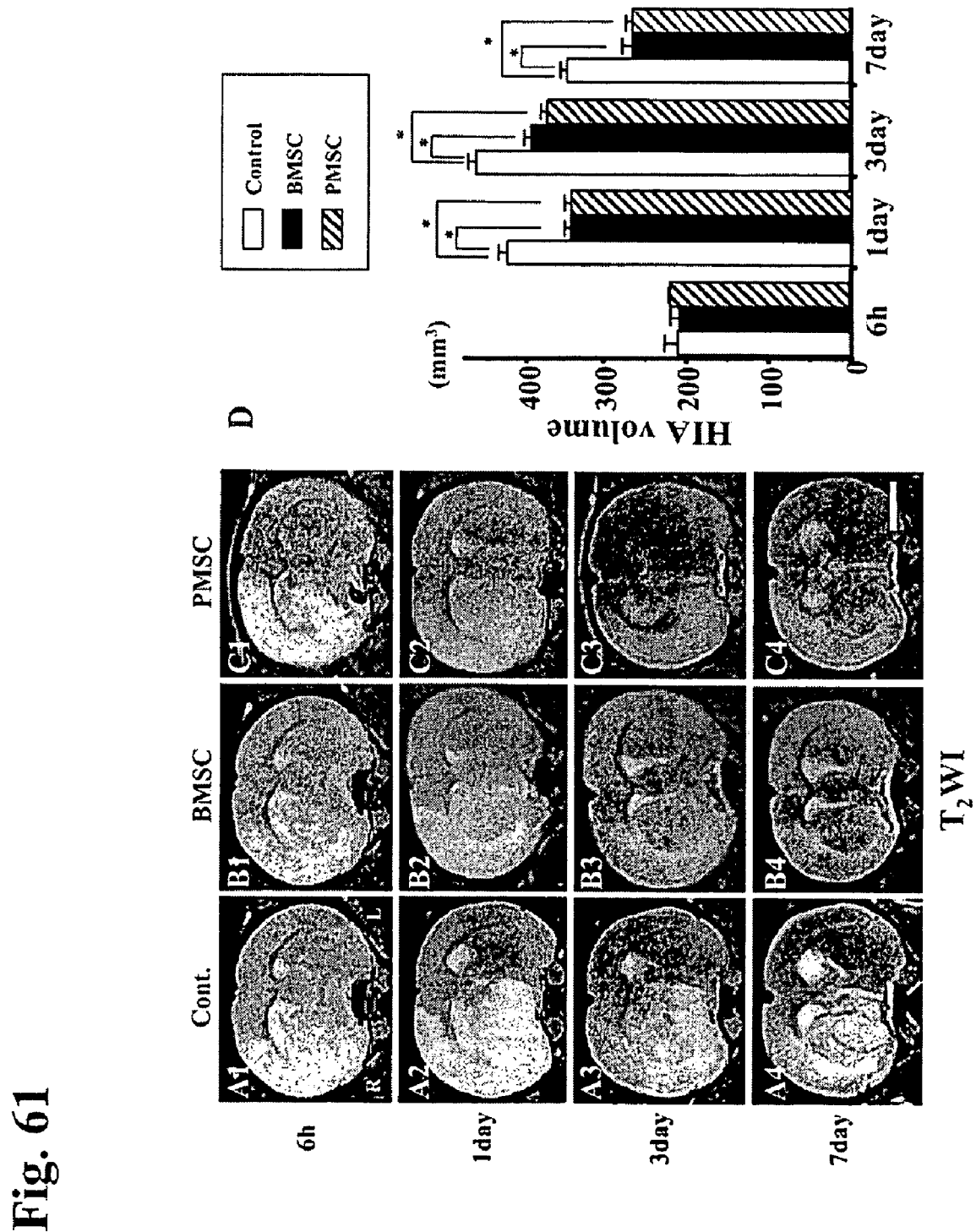

FIG. 61 shows evaluation of the ischemic lesion volume with $TB_{2B}$Weighted Images ($TB_{2B}$WI). BMSCs or PMSCs were intravenously-injected immediately after the initial MRI scanning (6 hours after MCAO). Images obtained 6 hrs, 1, 3, and 7 days MCAO in medium-injected (A1-4), BMSC-treated (B1-4), and PMSC-treated group ($C_{1-4}$). Summary of lesion volumes evaluated with $TB_{2B}$WI in each groups (D). Scale bar=3 mm. *P<0.05

Figure 62:
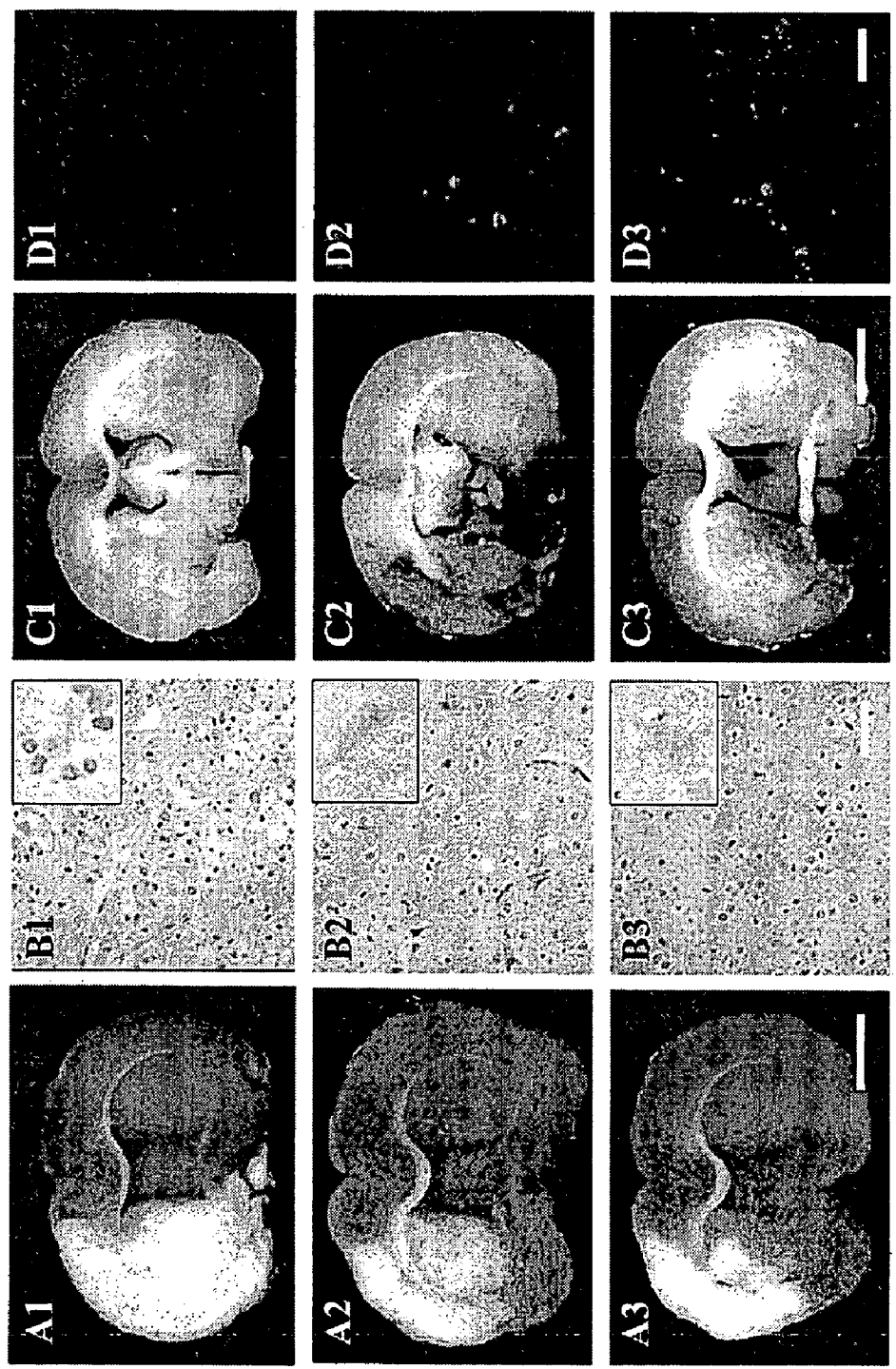

FIG. 62 shows TTC Brain sections slices stained with 2,3,5-triphenyl tetrazolium chloride (TTC) to visualize the ischemic lesions 7 days after MCAO. TTC-stained brain slices from medium-injected MCAO model rats (A1), following BMSC-treated (A2), and PMSC-treated (A3) groups. The Sections were also stained with hematoxylin and eosin at 7 days post-MCAO. Although a larger number of inflammatory cells were obvious in the lesion without cell transplantation (B1), parenchymal brain tissue was greatly preserved in the BMSC-treated (B2) and PMSC-treated group (B3). Inflammatory cells in the lesion were shown in insert of B1. On the other hand, preserved neurons in the lesion were shown in insert of B2 and B3. Intravenously-administrated BMSCs and PMSCs accumulated in and around the ischemic lesion hemisphere. BMSCs and PMSCs were transfected with the reporter gene LacZ. Transplanted LacZ-positive MSCs (blue cells) were present in the ischemic lesion (BMSCs: C2; PMSCs: C3). Brain from control (without LacZ transfected MSCs transplantation) injected animals with comparable X-gal staining is shown in C1. Confocal images (BMSCs: D2; PMSCs: D3) demonstrating a large number of LacZ-positive cells in the lesion hemisphere. Confocal image of non-treated group is shown in D1. Scale bar=3 mm (A and C), 40 µm (B), and 50 µm (D).

Figure 63:
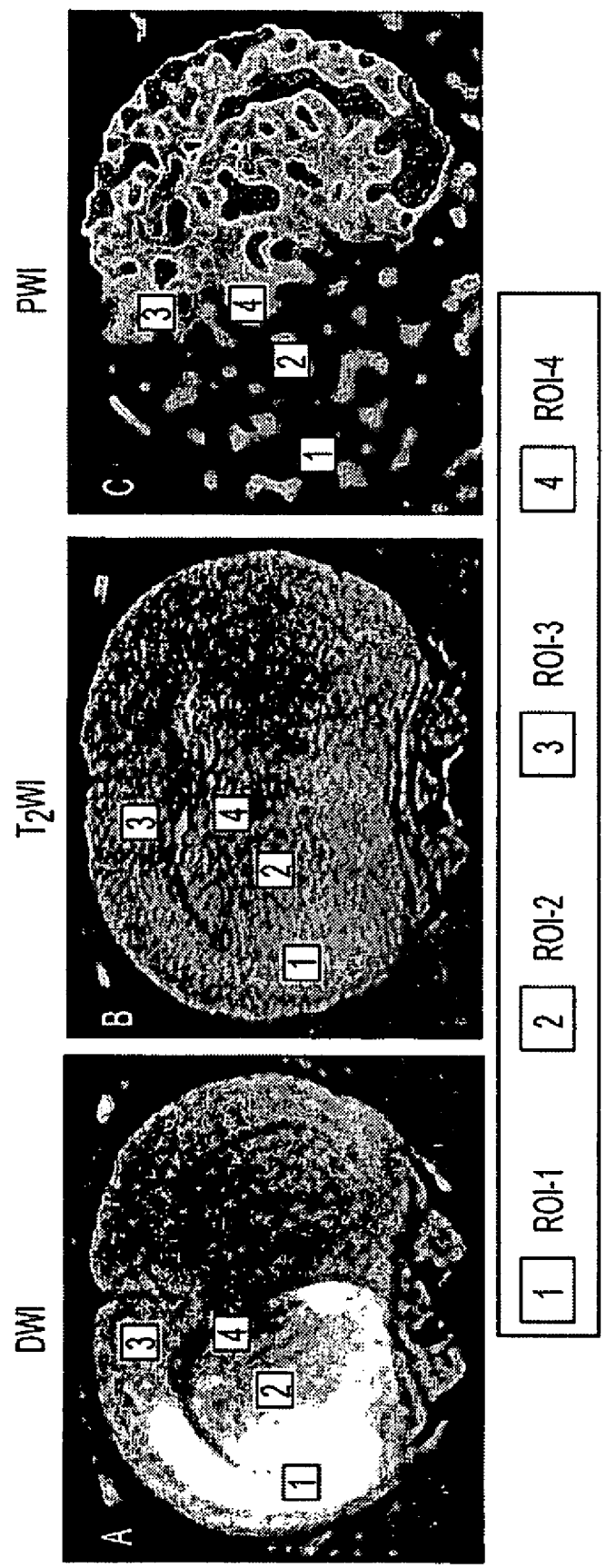

FIG. 63 shows region of interest (ROI) for dynamic susceptibility contrast-enhanced perfusion weighted imaging (PWI) analysis. PWI analysis was carried out at four regions of interest (ROI) indicated by the boxed numbered areas on the lesion side of the brain.

Figure 64:
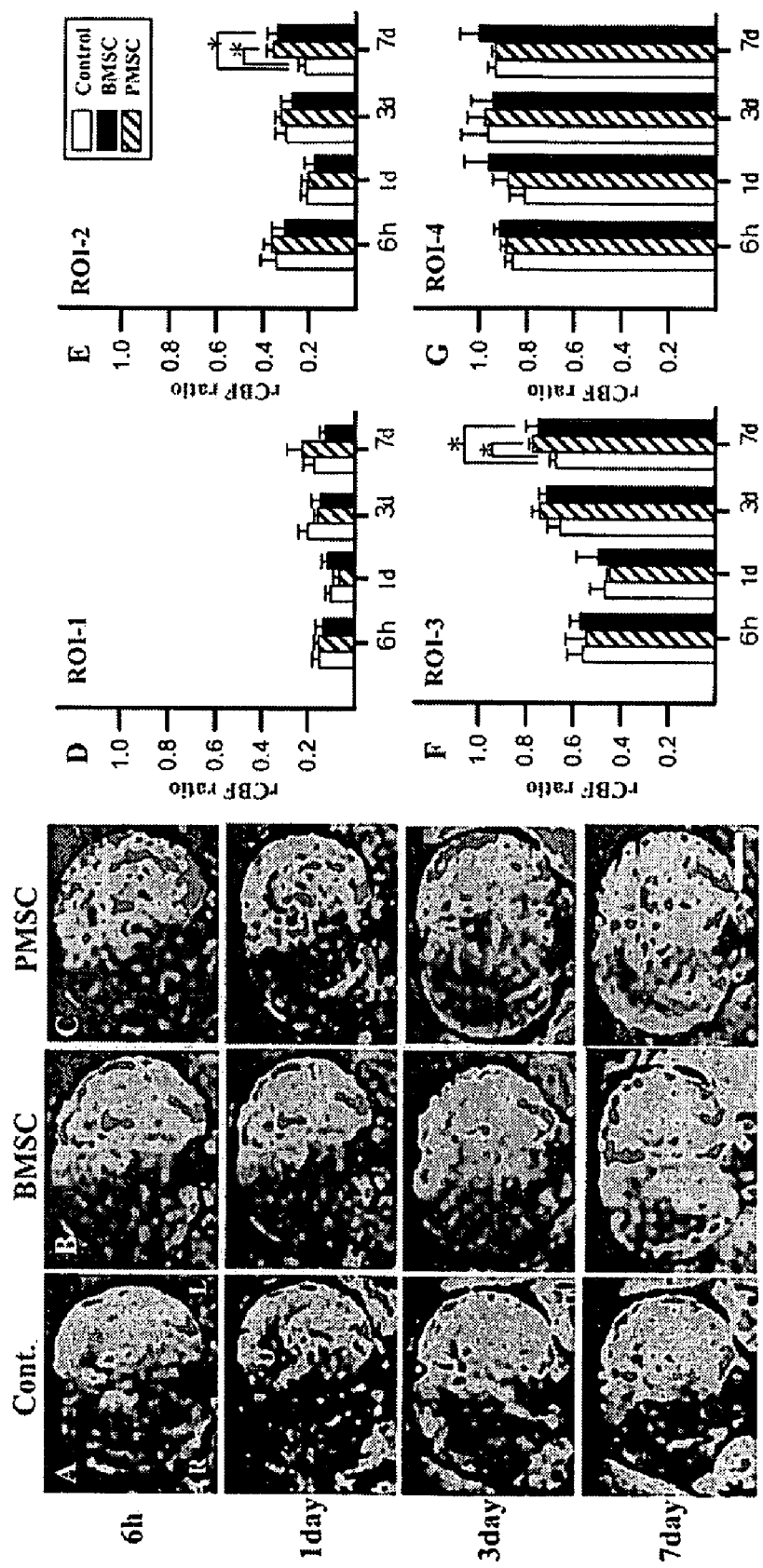

FIG. 64 shows evaluation of hemodynamic state (rCBF maps) with Perfusion Weighted Images (PWI). BMSCs or PMSCs were intravenously-injected immediately after the initial MRI scanning (6 hours after MCAO). Images obtained 6 hrs, 1, 3, and 7 days MCAO in medium-injected (A), BMSC-treated (B), and PMSC-treated group (C). Summary of rCBF evaluated with PWI in each groups (D-G), ROI-1 (D), ROI-2 (E), ROI-3 (F), and ROI-4 (G). rCBF ratio (ischemic lesion/contralateral lesion) at 6 hrs, 1, 3, and 7 days after MCAO are summarized in figure D-G. Scale bar=3 mm, *P<0.05.

Figure 7:
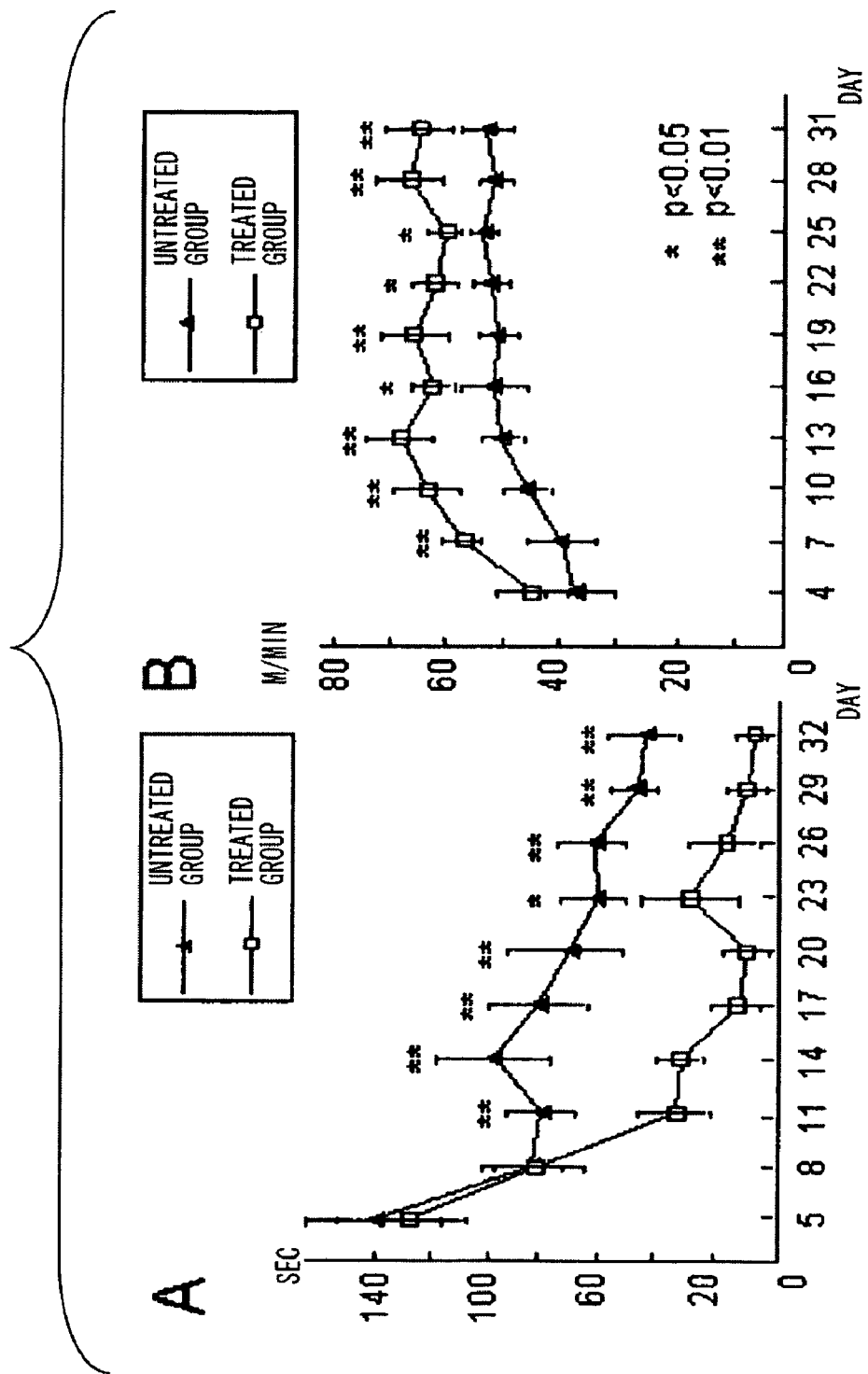
FIG. 7 shows graphs indicating the therapeutic effects of transplantation. (A) shows the results of investigating higher brain functions (memory and learning) in a Morris water maze test and (B) is a graph indicating the results of a treadmill stress test. Filled triangles indicate the untreated group, and open squares indicate the treated group. *$p<0.05$, **$p<0.01$.
Figure 65:
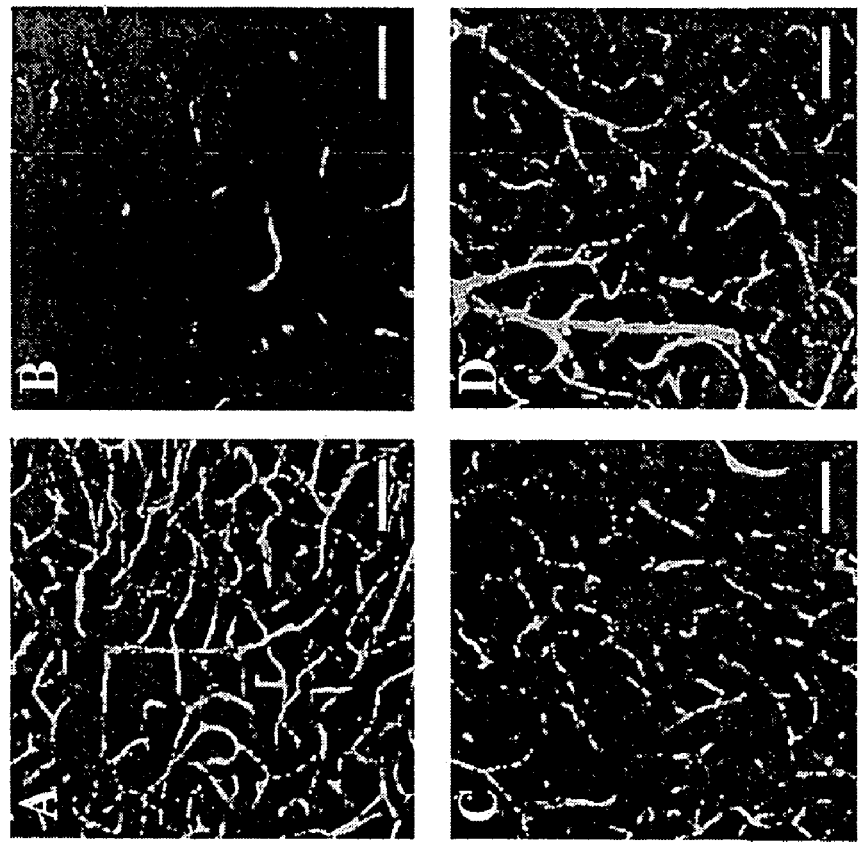

FIG. 65 shows seven days after MCAO, the angiogenesis in boundary zone was analyzed using a three-dimensional analysis system. FIG. 7A shows the three-dimensional capillary image with systemically perfused FITC-dextran in the normal rat brain. The total volume of the micro vessels in the sampled lesion site decreased 7 days after MCAO (B), but was greater in the BMSC-treated group (C) and the PMSC-treated group (D). Scale bar=100 µm.

Figure 66:
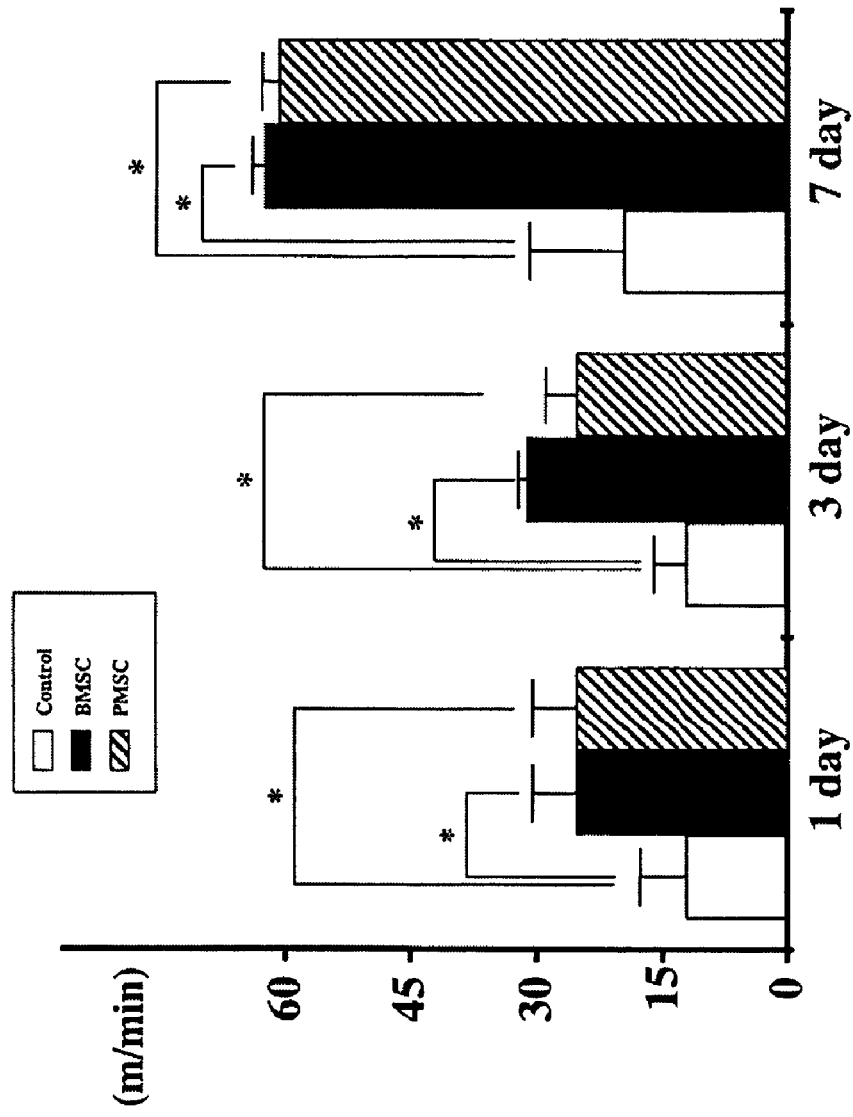

FIG. 66 shows the treadmill stress test demonstrated that maximum speed at which the rats could run on motor driven treadmill was faster in the BMSCs and PMSCs rats than control. Velocity is plotted for three times after MCAO induction.

WORKING EXAMPLES

The present invention will be illustrated in further detail with reference to several Examples below, which by no means limit the scope of the invention.

Example 1

Transient Middle Cerebral Artery Occlusion Model

A rat middle cerebral artery occlusion model was used as a stroke model. Transient middle cerebral artery occlusion (MCAO) was induced for 45 minutes using the intravascular occlusion method (E. Z. Longa, P. R. Weinstein, S. Carlson, R. Cummins, Reversible middle cerebral artery occlusion without craniectomy in rats, Stroke 20 (1989) 84-91).

Adult male Sprague-Dawley rats (n=113) weighing 250 to 300 g were anaesthetized with 5% isoflurane, and the anesthesia was mechanically maintained with 1.5% isoflurane in a gaseous mixture of 70% $N_2O$ and 30% $O_2$ under artificial ventilation. The rectal temperature was maintained at 37° C. using an infrared heat lamp. A cannula was inserted into the left femoral artery during surgery, for measuring blood pH, $pO_2$, and $pCO_2$. The tip of a 20.0 to 22.0 mm long 3-0 surgical suture (Dermalon: Sherwood Davis & Geck, UK) was rounded by heating near a flame, and was advanced from the external carotid artery into the lumen of the internal carotid artery, to thereby occlude the origin of the middle cerebral artery (MCA). The tip of the surgical suture was extracted from the internal carotid artery 45 minutes after MCAO, and reperfusion was conducted.

The physiological parameters (rectal temperature, blood pH, $PO_2$, $PCO_2$, and blood pressure) of all mice were maintained within normal ranges during surgery and transplant treatment, and no statistical difference was found between experimental groups.

Example 2

Preparation of Bone Marrow Cells

Autologous bone marrow was collected from the femur of MCAO rats, one and a half hours prior to bone marrow cell transplant.

The rats were anaesthetized with ketamine (75 mg/kg) and xylazine (10 mg/kg; i.p.). A 1 cm incision was made in the skin, a small hole (2×3 mm) was punctured in the femur using an air drill, and 1 ml of bone marrow was aspirated using a 22-gauge needle. The collected samples were diluted and suspended in a medium containing 2 ml of L-15 medium and 3 ml of Ficoll (Amersham Biosciences). After centrifugation at 2,000 rpm for 15 minutes, mononuclear cell fractions were collected and resuspended in 2 ml serum-free medium (NPMM: Neural Progenitor Cell Maintenance Medium; Clonetics, San Diego, Calif., USA). Following a second centrifugation (2,000 rpm, 15 minutes), cells were suspended in 1 ml of NPMM.

Example 3

Experimental Groups

The experiment was conducted using 11 groups (n=88). Nothing was administered to the Group 1 (control) rats after MCAO (n=8). The rats in Groups 2 to 6 were intravenously administered with just the medium (without donor cell administration), 3, 6, 12, 24, and 72 hours after MCAO (n=8 for each group). The rats in Groups 7 to 11 were intravenously administered with the autologous bone marrow cells ($1.0 \times 10^7$ cells), 3, 6, 12, 24, and 72 hours after MCAO (each group n=8). Six rats in each group were used to calculate the infarct volume, and the others were used for other histological analyses.

Example 4

Intravenous Administration of Autologous Bone Marrow Cells to Rat Cerebral Infarction Model LacZ gene was introduced into the bone marrow cells (mononuclear cell fraction: MCF) before transplantation to the rat cerebral infarction model (transient middle cerebral artery occlusion model).

Adex1CAlacZ adenovirus was used to transduce the LacZ gene into the bone marrow cells. The details of the construction procedures are described in another document (I. Nakagawa, M. Murakami, K. Ijima, S. Chikuma, I. Saito, Y. Kanegae, H. Ishikura, T. Yoshiki, H. Okamoto, A. Kitabatake, T. Uede, Persistent and secondary adenovirus-mediated hepatic gene expression using adenoviral vector containing CTLA4IgG, Hum. Gene Ther. 9 (1998) 1739-1745. Y. Nakamura, H. Wakimoto, J. Abe, Y. Kanegae, I. Saito, M. Aoyagi, K. Hirakawa, H. Hamada, Adoptive immunotherapy with murine tumor-specific T lymphocytes engineered to secrete interleukin 2, Cancer Res. 54 (1994) 5757-5760. M. Takiguchi, M. Murakami, I. Nakagawa, I. Saito, A. Hashimoto, T. Uede, CTLA4IgG gene delivery prevents autoantibody production and lupus nephritis in MRL/lpr mice, Life Sci. 66 (2000) 991-1001.). This adenoviral vector has an adenovirus serotype-5 genome that lacks the E1A, E1B, and E3 regions to prevent viral replication. Instead of the E1A and E1B domains, the vector comprises the lacZ gene, which is a β-galactosidase gene of *Escherichia coli*. The lacZ gene is comprised between a CAG promoter, which comprises a cytomegalovirus enhancer and a chicken β-actin promoter (H. Niwa, K. Yamamura, J. Miyazaki, Efficient selection for high-expression transfectants with a novel eukaryotic vector, Gene 108 (1991) 193-199.), and a rabbit β-globin polyadenylation signal. This recombinant adenovirus was propagated in 293 cells and was then isolated. Viral solutions were stored at −80° C. until use. The autologous bone marrow cells ($1.0 \times 10^7$ cells), together with 50 MOI of Adex1CalacZ, were placed in DMEM containing 10% fetal bovine serum at 37° C. to allow the adenovirus to infect in vitro.

The same rats from which bone marrow cells were collected were then subjected to MCAO. Then, a total volume of 1 ml of a liquid (NPMM) containing about $1 \times 10^7$ mononuclear cells, just prepared from the autologous bone marrow, was administered to the left femoral vein.

Two weeks after transplantation, cells that expressed β-galactosidase were detected in vivo.

First, the brains of the deeply anaesthetized rats were removed, fixed by leaving to stand in a phosphate buffer to which 0.5% glutaraldehyde had been added. The brain was cut into slices (100 μm) with a vibratome, and the sections were incubated at 37° C. overnight in a X-Gal developer (phosphate buffered saline containing 35 mM $K_3Fe(CN)_6$/35 mM $K_4Fe(CN)_6 \cdot 3H_2O$/2 mM $MgCl_2$) with X-Gal in a final concentration of 1 mg/ml. Blue reaction products were formed within the cells and thus those cells expressing β-galactosidase were detected.

The cross section of each brain slice was observed under a dissecting microscope, and recorded with an image analyzer. The slices were then fixed by being left to stand overnight in a phosphate buffer to which 4% paraformaldehyde had been added, being dehydrated, and then embedded in paraffin. Slices (5 μm) were cut, and the presence of the blue reaction product (the β-galactosidase reaction product) was evaluated using a light microscope (Zeiss: Axioskop FS). Some sections were counter stained with hematoxylin and eosin.

Figure 1:
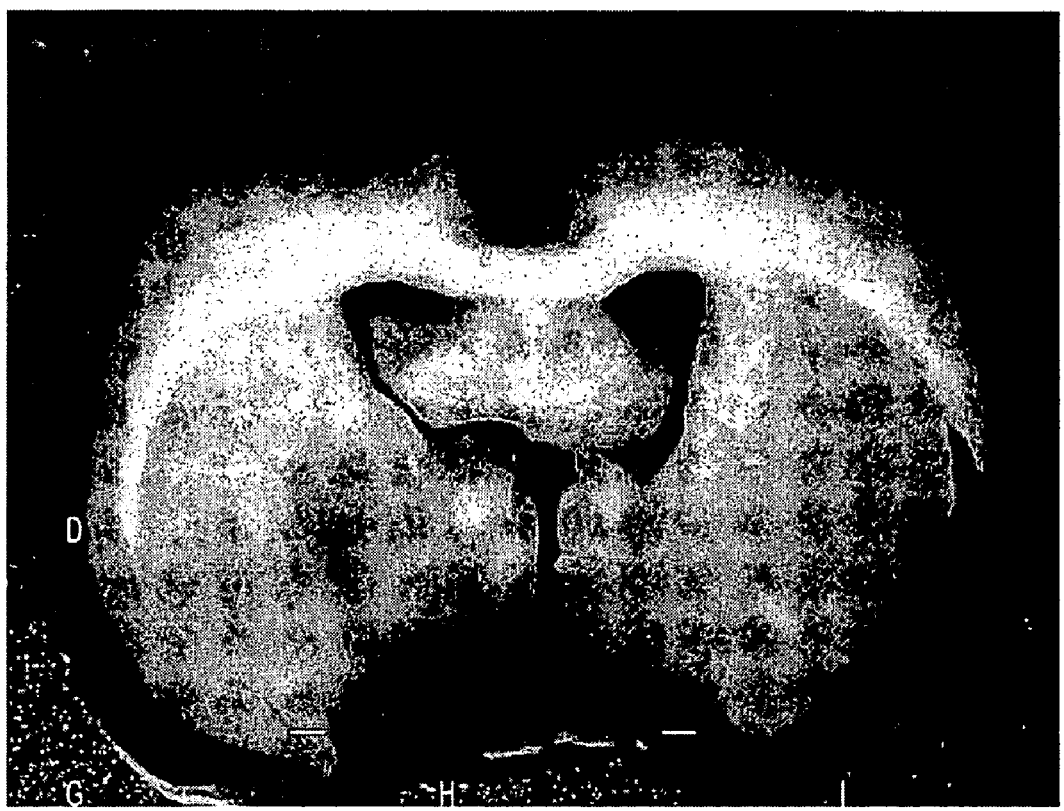
FIG. 1 is a photograph showing the therapeutic effect of intravenous administration of MCF cells on a rat cerebral infarction model (transient middle cerebral artery occlusion model). The intravenously administered MCF cells accumulated in the cerebral infarction area.

X-gal develops a blue color in the host brain tissue, and thus donor MCF cells were visualized as blue cells in host brain tissue (FIG. 1). Intravenously administered MCF cells accumulated in the cerebral infarction area.

Example 5

Figure 2:
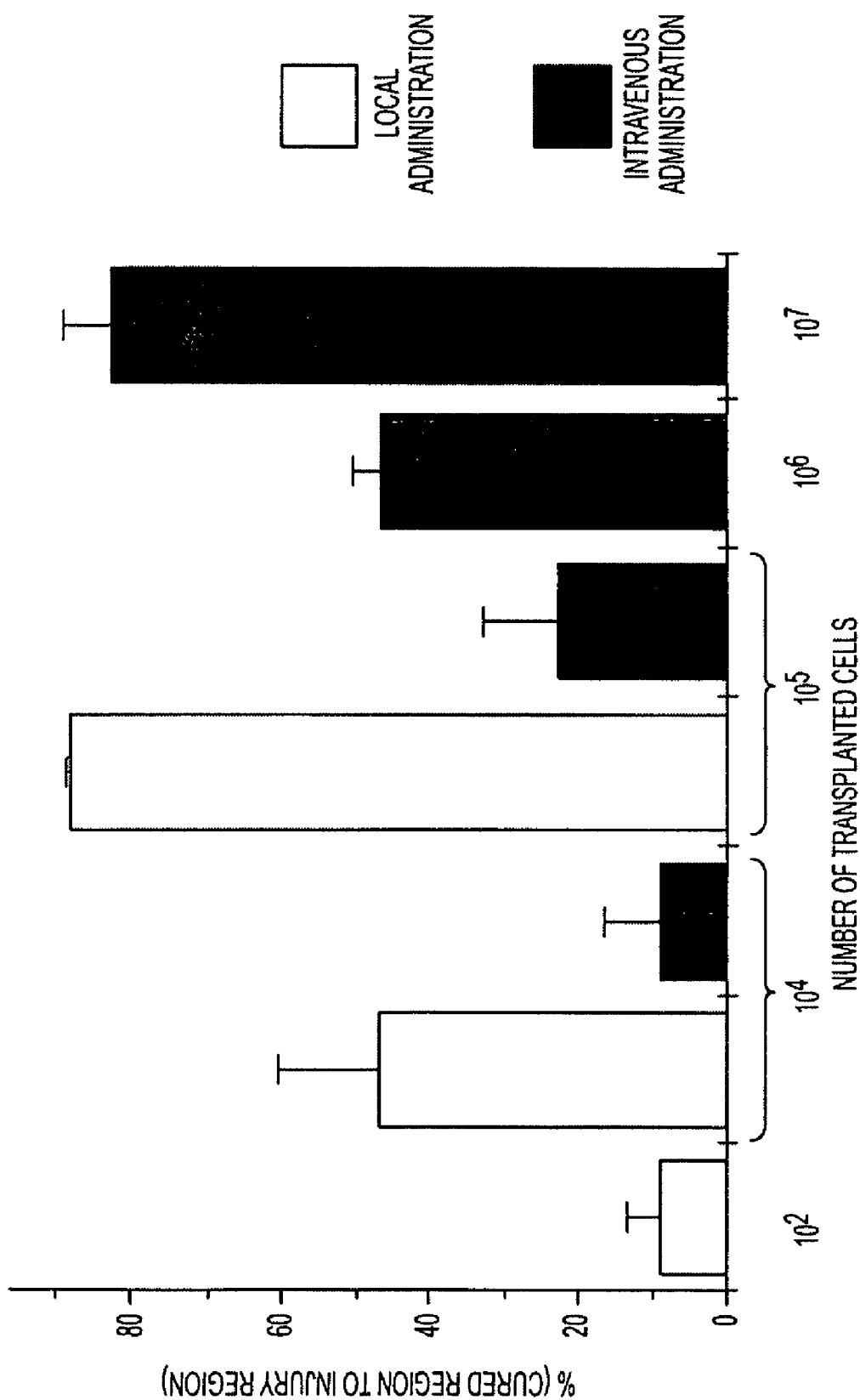
FIG. 2 is a graph showing the results of investigating the therapeutic effect of locally and intravenously administered MCFs, in which open bars indicate local administration and filled bars indicate intravenous administration.

The Effect of Local and Intravenous Administration of MCF on Therapeutic Effects The experimental results show that therapeutic effect increases with an increasing number of transplanted cells (FIG. 2). The results also demonstrate that intravenous administration requires about one hundred times as many cells as local administration to attain substantially the same therapeutic effect. Conversely, when one hundred times as many cells are intravenously administered than locally administered, intravenous administration can be expected to exhibit substantially the same therapeutic effect as local administration.

Example 6

Therapeutic Effects of Autologous MCF Transplant on Rat Cerebral Infarction Model Autologous MCF ($1 \times 10^7$ cells) were transplanted to the rat cerebral infarction model (transient middle cerebral artery occlusion model: 45 minutes).

The extent of infarction lesions was examined using 2,3,5-triphenyltetrazolium chloride (TTC) staining (J. B. Bederson, L. H. Pitts, S. M. Germano, M. C. Nishimura, R. L. Davis, H. M. Bartkowski, Evaluation of 2,3,5-triphenyltetrazolium chloride as a stain for detection and quantification of experimental cerebral infarction in rats, Stroke 17 (1986) 1304-1308.). Normal brain is stained red by this method.

Two weeks after transplantation, the rat was deeply anaesthetized with sodium pentobarbital (50 mg/kg, i.p.). The brain was carefully removed and was sliced into 1 mm coronal sections using a vibratome. Fresh brain sections were immersed for 30 minutes in 37° C. physiological saline containing 2% 2,3,5-triphenyltetrazolium chloride (TTC).

Figure 3:
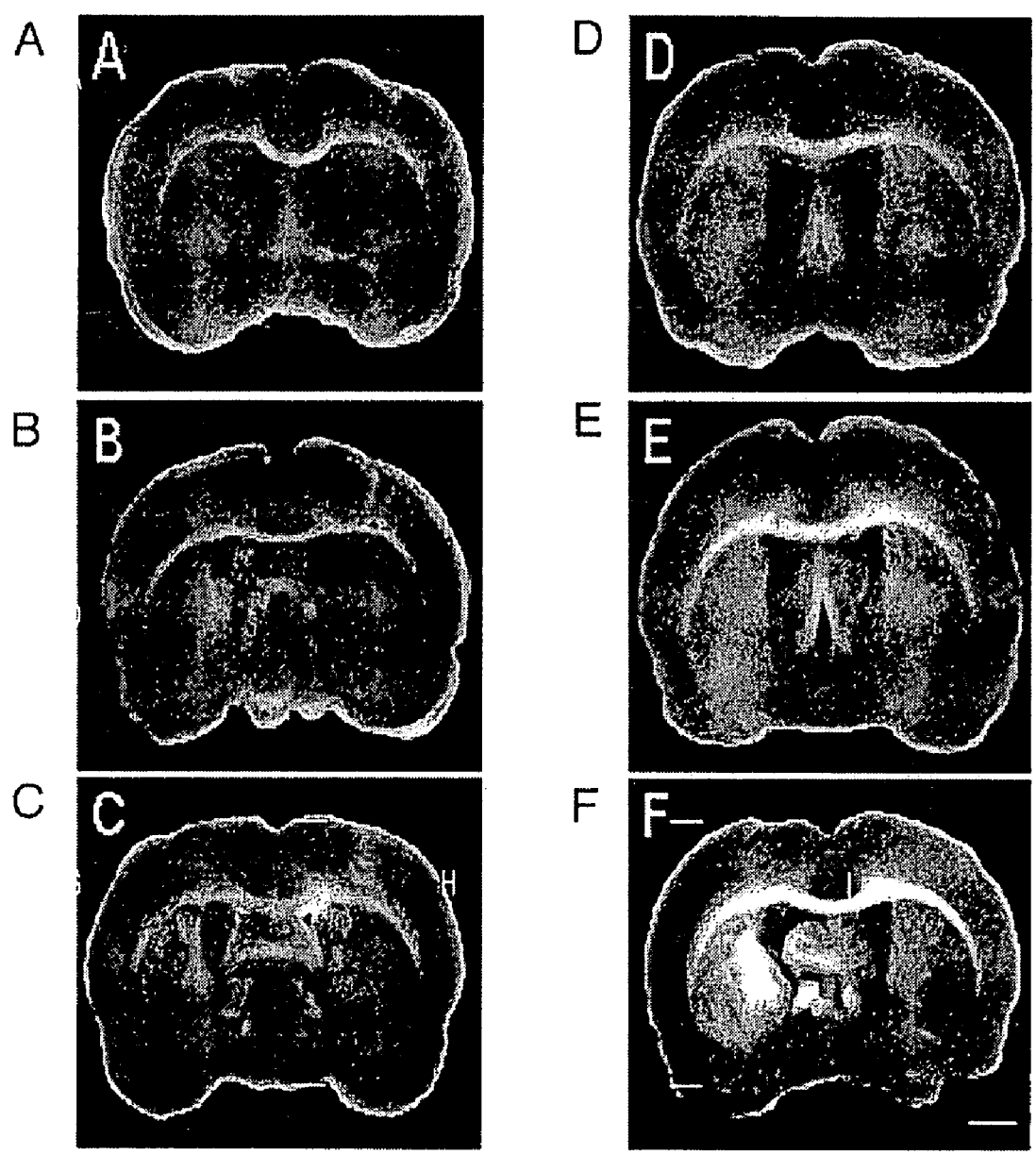
FIG. 3 shows photographs depicting the therapeutic effect of transplanting autologous MCFs ($1 \times 10^7$ cells) to a rat cerebral infarction model (transient middle cerebral artery occlusion model: 45 minutes) three hours after cerebral infarction (A), six hours after cerebral infarction (B), 12 hours after cerebral infarction (C), 24 hours after cerebral infarction (D), or 72 hours after cerebral infarction (E), or the untreated group (F).

As a result, the cerebral infarcted area (including both the cortex and basal ganglia) was slightly stained, and a white image of the cerebral infarction was clearly visualized in the brain of the MCAO model rats (FIG. 3).

The cross-sectional area of infarction in each brain section was examined with a dissecting microscope, and was measured using NIH image, which is image analyzing software. Infarct areas in all brain sections were added, and the total infarct volume of each brain was calculated.

The infarct volumes were statistically analyzed. Data are expressed as "mean ±SD". Differences between the groups were assessed by ANOVA using the Scheffes post hoc test for identifying differences between groups. Differences were deemed statistically significant at $p<0.05$.

Histological analysis of ischemic lesions to which no cells had been administered (the controls) revealed that ischemic lesions were found with reproducibility and consistency, and that their average volume was $258\pm55$ mm$^3$ (n=6) (FIG. 3F). Of the occlusion indices used for the infarct model, ischemia as determined by TTC was highest in the striatum (caudate-putamen), globus pallidus, and septal nucleus, and was relatively mild in the cortex.

Using the same infarction parameters, the bone marrow cells were intravenously administered 3, 6, 12, 24 and 72 hours after infarct induction. At all these time points the transplantations reduced the infarct volume, but better results were obtained when transplantation was conducted in the early stages after ischemia induction. When the autologous bone marrow cells were intravenously administered three hours after MCAO, virtually no infarct was detected (FIG. 3A); changes in TTC staining were barely detected, but a slight inflammatory response was detected in the target infarcted lesion. When the cells were administered six hours after MCAO, the intensity of TTC staining was reduced in the infarct at the basal ganglia ($40\pm28$ mm$^3$, n=6) (FIG. 3B). The infarct gradually increased when the cells were administered 12 hours ($80\pm25$ mm$^3$, n=6, FIG. 3C), 24 hours ($140\pm18$ mm$^3$, n=6, FIG. 3D), and 72 hours ($180\pm22$ mm$^3$, n=6, FIG. 3E) after MCAO.

The therapeutic effect was more remarkable when the transplant was conducted earlier. However, it is noticeable that a certain degree of therapeutic effect was obtained even when the treatment was conducted 72 hours after cerebral infarction.

The therapeutic effect is considered to be a synergy of the effects of neuroprotection and neural regeneration. The sooner after cerebral infarction that the transplant is conducted, the greater the neuroprotection exhibited. Further, when treatment is conducted relatively late, the neuroprotective effect is relatively weak, but the neural regeneration effect becomes stronger instead.

Figure 4:
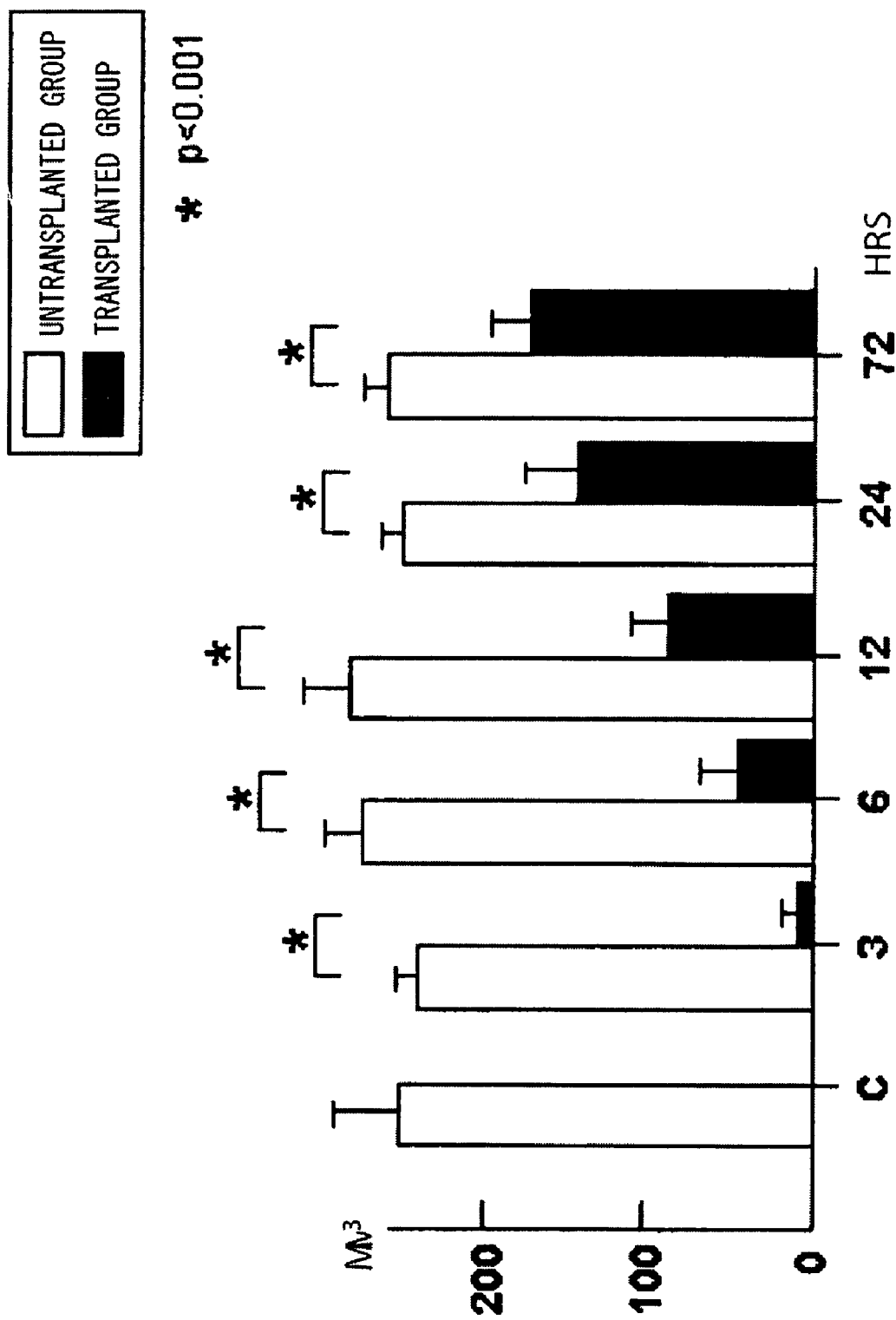
FIG. 4 shows a graph of the results of the above-mentioned FIG. 3, in which open bars indicate data of the untransplanted group, and filled bars indicate data of the transplanted group. *<0.001.

The obtained results were quantified and shown in the histogram of FIG. 4 as the infarct volumes in the control (group without cell implants), and in the infarction model animals (groups to which cells were transplanted), which were administered with the cells 3, 6, 12, 24, and 72 hours after MCAO.

Example 7

Effects of Intravenous Administration of Autologous MCF to Rat Cerebral Infarction Model Autologous MCFs ($1 \times 10^7$ cells) introduced with LacZ were intravenously administered to the rat cerebral infarction model after induction of MCAO. The bone marrow cells were identified in vivo.

The phenotype of the transplanted cells in vivo was analyzed using a laser scanning confocal microscope (n=5). Rats were deeply anaesthetized with sodium pentobarbital (50 mg/kg, i.p.), and the heart was perfused first with PBS, then with a fixative solution containing 4% paraformaldehyde in 0.14 M Sorensen's phosphate buffer (pH 7.4). The brain was removed, fixed for 24 hours in a 4° C. phosphate buffer containing 4% paraformaldehyde, and dehydrated in 0.1M PBS solution containing 30% sucrose. The tissue was placed in O.C.T. compound (Miles Inc.), frozen in liquid nitrogen, and sliced into 10 μm thick coronal sections using a cryostat. The sections were dried on silane-coated slide glass.

To identify the type of cells derived from the donor bone marrow, a double labeling study was conducted using antibodies against β-galactosidase (polyclonal rabbit anti-β-galactosidase antibody (IgG) labeled with Alexa Fluor 594, CHEMICON), neurons (monoclonal mouse anti-neuron-specific enolase antibody (IgG) labeled with Alexa Fluor 488 [NSE], DAKO) and astrocytes (monoclonal mouse anti-glial fibrillary acidic protein antibody (IgG) labeled with Alexa Fluor 488 [GFAP], SIGMA). The primary antibodies were labeled with Alexa Fluor 488 or Alexa Fluor 594, using a Zenon mouse or rabbit IgG labeling kit (Molecular Probes) according to the manufacturer's instruction. The tissue sections were dried on silane-coated slide glass, then washed with PBS (three times for five minutes), treated for 30 minutes with PBS containing 0.1% Triton-X at room temperature, and incubated for ten minutes with a blocking solution (Protein Block Serum Free, DAKO) at room temperature. The tissue sections were further reacted with two types of primary antibodies at room temperature for 60 minutes, then washed with PBS (three times for five minutes). After immunostaining, the slide glass was covered with a glass cover using a fluorescence mounting medium (DAKO). Alexa Fluor 488 (green) and Alexa Fluor 594 (red) were excited using a 488 nm laser beam derived from an argon laser, and a 543 nm laser beam derived from an He—Ne laser, respectively. Confocal images were obtained using a laser scanning confocal microscope (Zeiss) and software (Zeiss).

The transplanted MCF cells were treated with X-gal to visualize the donor cells in blue.

Figure 5:
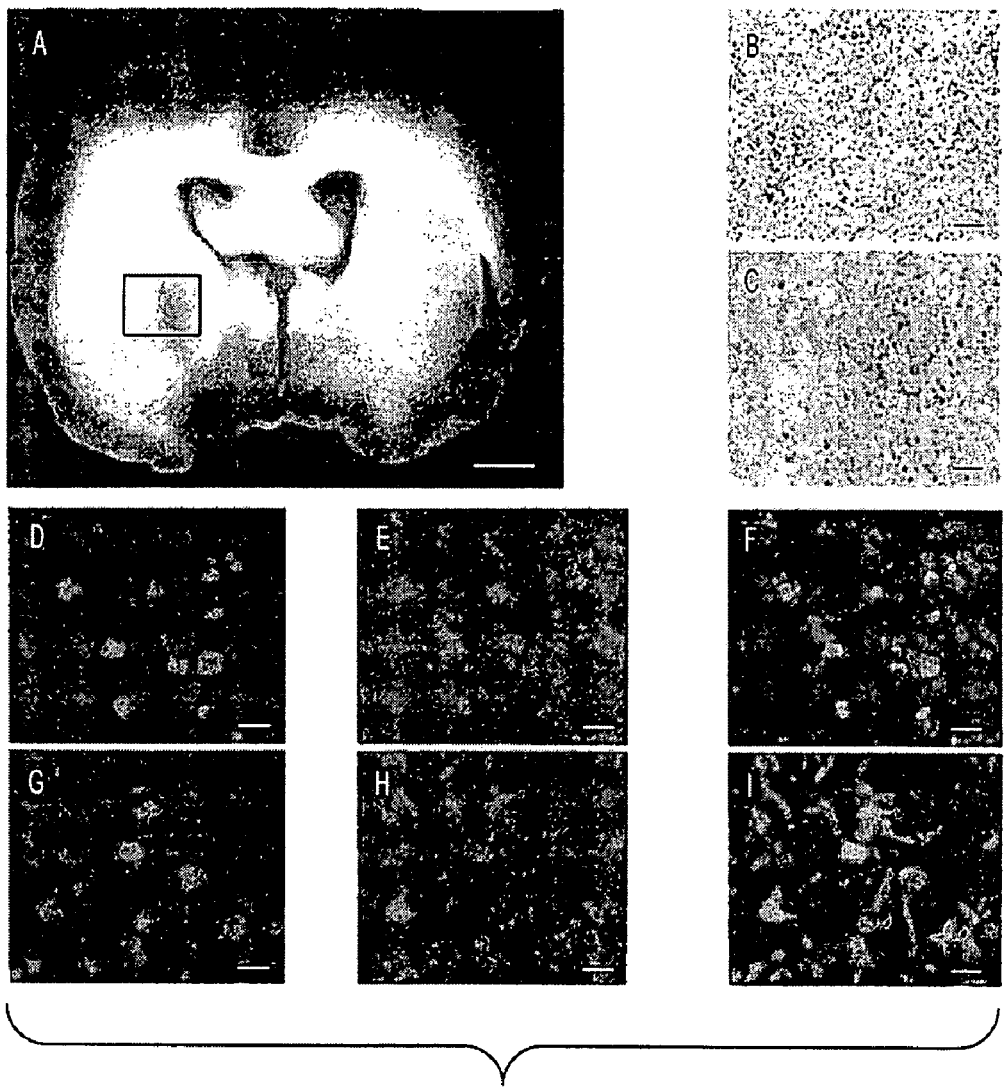
FIG. 5 shows photographs depicting the result of intravenously administering autologous MCFs ($1 \times 10^7$ cells) to a rat cerebral infarction model, in which A shows transplanted MCF cells (blue) accumulating in a cerebral infarction area. B is a photograph obtained by high power magnification of the region indicated by the open square in A (HE staining). C is a visualized image of the same region as in B (in blue) after treatment with x-gal; many transplanted MCF cells (blue) have accumulated; LacZ-positive cells (D) are found to be NSE-positive (E), and F is a merged view of D and E; LacZ-positive cells (G) are found to be GFAP-positive (H), and I is a merged view of G and H.

The results showed the transplanted donor cells accumulated inside and around the cerebral infarction. FIG. 5A shows a coronal section of the infarcted region comprising accumulated LacZ-positive cells. Examination with a light microscope indicates that many cells are present in and around the ischemic lesion (FIG. 5B), and most of these cells were LacZ-positive donor cells (FIG. 5C). Immunohistochemical analysis showed that some of the LacZ-positive donor cells express NSE, a neuron marker (FIG. 5E) or GFAP, an astrocyte marker (FIG. 5H). FIGS. 5F and 5I each show composite images of the LacZ, NSE, and GFAP images. No clear fluorescence signal was found in the control group. These results indicate that at least some of transplanted bone marrow cells can differentiate into neuronal (FIGS. 5E and 5F) and glial cell lineages (FIGS. 5H and 5I).

Example 8

Migration of Transplanted MCF Cells into the Brain

Figure 6:
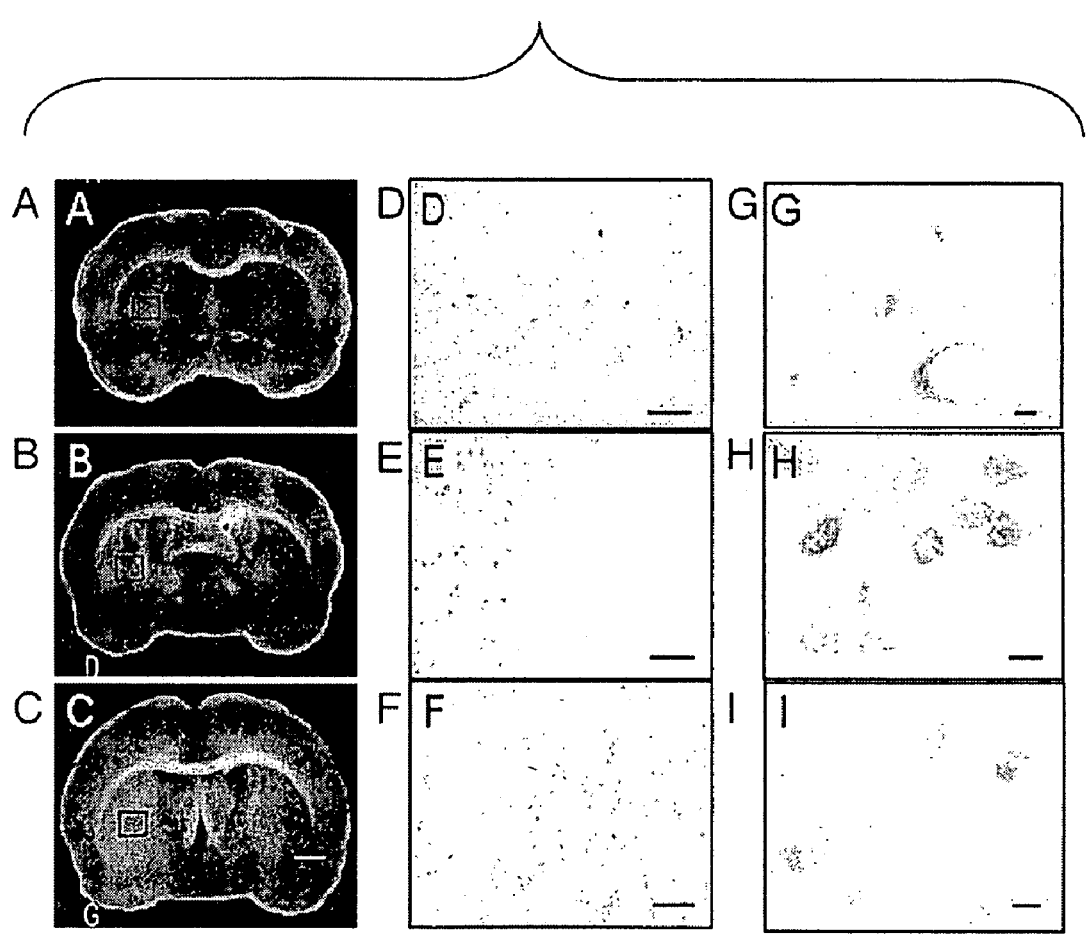
FIG. 6 shows photographs depicting the very frequent migration of transplant MCF cells into the brain. The cells were transplanted three hours after cerebral infarction (A), 12 hours after cerebral infarction (B), or 72 hours after cerebral infarction (C). D and G show the region indicated by the open square in A after staining; E and H show the region indicated by the open square in B after staining; and F and I show the region indicated by the open square in C after staining.

The transplanted MCF cells migrated into the brain at a high rate (FIG. 6). This migration varies with transplant time after cerebral infarction. For example, in cases where the cells were intravenously administered three hours after MCAO and infarct volume was reduced (FIG. 6A), LacZ-positive cells were observed both in the blood vessel tissue and in the parenchymal brain tissue of the protected lesion, indicating that the transplanted cells migrated to sites that would undergo cerebral infarction and be irreversibly damaged unless treated, and these cells exhibited remarkable neuroprotective effects, saving nervous system cells which would ordinarily have been killed (FIGS. 6D and G). When autologous bone marrow cells were administered 12 hours after MCAO (FIG. 6B), the pathophysiological features were more complex. A relatively large number of blue donor cells were found in areas thought to be severely damaged due to ischemic stress, but a smaller number of donor cells were present in non-damaged regions of the lesions (FIGS. 6E and 6H). In addition to the neuroprotective effect that was observed above, a neural regenerative effect was also found (FIGS. 6A, 6D, and 6G). In contrast, when the autologous bone marrow cells were administered 72 hours after MCAO, ischemic damage was much greater (FIG. 6C), and fewer transplanted cells were found in the lesions (FIGS. 6F and I). The neuroprotective effect observed above (FIGS. 6A, 6D, and 6G) was relatively small; however, a strong neural regenerative effect was observed. It should be noted, however, that even in this group TTC assays showed that cerebral infarction was suppressed by bone marrow cell transplantation.

Example 9

Confirmation of Therapeutic Effects of MCF Transplantation by Ethological Examination The therapeutic effects of MCF transplantation were verified by two ethological examinations: a Morris water maze test to evaluate learning and memory behaviors, and a treadmill stress test to evaluate motor function.

Higher brain functions (memory, learning) were studied by a modified water maze test (n=10) based on Morris's method (R. G. M. Morris, Spatial localization does not depend upon the presence of local cues, Learn Motiv. 12 (1981) 239-260.). Intravenous administration of autologous bone marrow or sham administration was conducted 12 hours after infarction induction.

The device comprised a white steel tank, 1.3 m in diameter and filled with water until 30 cm deep. The water was opacified with white tempera paint, and was held at 24° C. The walls of the space comprised visual cues, and these remained in the same positions during the experiment. In every training trial, a round ceramic platform 8 cm in diameter was placed 2.5 cm from the water surface in one quadrant of the tank. On Day 1 of training, a single habituation trial was conducted by placing each rat on the hidden platform for 60 seconds. If a rat fell or jumped from the platform, the rat was saved from the water and returned to the platform. Quadrant search and swimming speed were monitored with a video camera mounted to the ceiling and connected to a computer tracked image analysis system.

Treadmill stress tests were also conducted. Intravenous administration of the autologous bone marrow or sham administration was conducted 12 hours after infarction induction.

Rats were trained by making them run at a speed of 20 m/min on a motor-driven treadmill with a slope of 0° for 20 minutes per day, two days a week. The rats were placed on a moving belt that faced away from an electrified grid, and the rats were made to run in a direction opposite to that of the belt's movement. Namely, the rats need to run forwards to avoid a shock (intensity 1.0 mA) to the paw. Only those rats which had learned to avoid the weak electric shock were included in the test (n=10). The maximum speeds of the rats running on the motor-driven treadmill were recorded.

The behavioral scores recorded in the Morris water maze test and the treadmill stress test were statistically analyzed. Data are expressed as "mean ±SD". Differences between the groups were evaluated by ANOVA using Scheffe's post hoc test for identifying differences between groups. The difference was deemed statistically significant at $p<0.05$.

The experimental data show that improvements in behavior were observed in both tests (each n=10) (FIGS. 7A and 7B). No dyskinesis was apparent in normal time observation of both the untransplanted group and the transplanted group. However, the treadmill test revealed that the treated rats had higher running speeds on the motor-driven treadmill than the untreated rats (FIG. 7B). This reveals that transplantation markedly improved the motor function deterioration due to cerebral infarction. Severe dyskinesis can potentially affect swimming speed, but the mild hypokinesis of the present invention is not thought to lead to poor performance in the Morris water maze test.

Example 10

Chronological MRI Analysis of Therapeutic Effects

MRI was used to chronologically examine the therapeutic effects on living animals. This method is used in clinical examinations and treatments, and data obtained by this method can be clinically applied without modification, and are very useful.

Initially, rats were anaesthetized with ketamine (75 mg/kg) and xylazine (10 mg/kg, i.p). Each rat was placed in an animal holder/MRI probe apparatus and positioned inside a magnet. The rat's head was fixed in an imaging coil. A superconducting magnet (Oxford Magnet Technologies) of 7 Tesla, having an internal diameter of 18 cm, interfaced to a Biospec I spectrometer (Bruker Instruments) was used in every MRI determination. T2-weighted images were obtained from coronal sections 0.5 mm thick using visual field 3 cm, TR=3000 ms, TE=30 ms, and reconstructed using a 128×128 image matrix.

Figure 8:
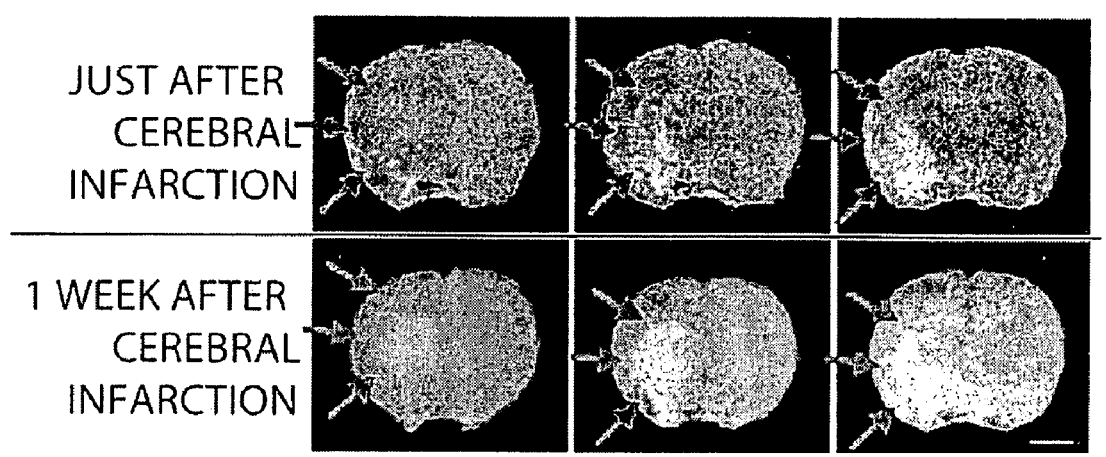
FIG. 8 shows photographs depicting the MRI test results of rats with cerebral infarction. The upper row shows data immediately after cerebral infarction and the lower row shows data one week after cerebral infarction. Scale bar: 5 mm.

Rats in which a cerebral infarction had been induced were examined using MRI, and abnormal signals were detected from about three hours after the cerebral infarction. Specifically, a cerebral ischemic region was detected as a High Intensity Area (HIA) in MRI ($T_2$WI) (FIG. 8, upper row). The abnormal signals remained in the untreated group (FIG. 8, lower row) to eventually form a cerebral infarcted area.

Example 11

Therapeutic Effects of Using Mesenchymal Stem Cells

The intravenous administration of bone marrow cells (mononuclear cell fraction: MCF) exhibited significant therapeutic effects on cerebral infarction. Mesenchymal stem cells (MSCs), which exist in about 0.1% of MCF, were also used for treatment and their therapeutic effects were confirmed. Mesenchymal stem cells c an be easily sampled, cultivated, proliferated, and preserved.

Figure 9:
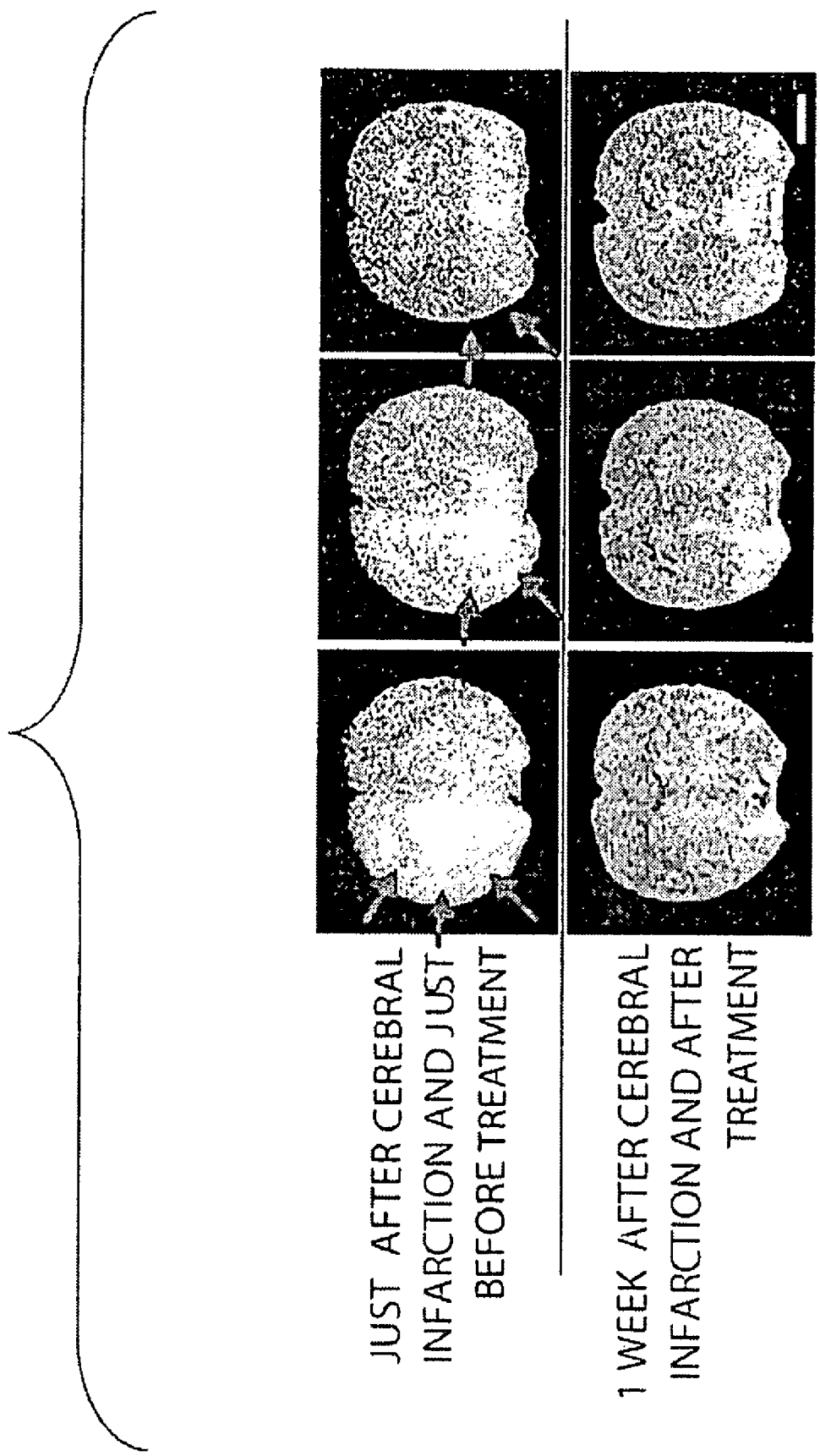
FIG. 9 shows photographs depicting the therapeutic effects of using MSCs. The upper row shows data immediately after cerebral infarction and immediately before treatment, and the lower row shows data after treatment conducted one week after the cerebral infarction. Scale bar: 5 mm.

MSCs ($1\times10^7$ cells) were administered to the rats with cerebral infarction of FIG. 8. The cells were intravenously administered 12 hours after cerebral infarction, and abnormal signals (HIA), having appeared in MRI tests after cerebral infarction (FIG. 9, upper row), then disappeared from re-tests one week after treatment (FIG. 9, lower row).

Thus, intravenous administration of MSCs was proven to treat cerebral infarction, which is untreatable at current medical levels.

Example 12

Relationship Between Number of Transplanted MSC Cells and Therapeutic Effects MSCs ($1\times10^4$ to $1\times10^7$ cells) were intravenously administered 12 hours after cerebral infarction.

To clarify the efficacy of MSCs and hTERT-MSCs transplants in reducing ischemic lesion volume, cells in different concentrations ($1\times10^4$ to $1\times10^7$ cells) were intravenously administered 12 hours after infarction induction, and cerebral images (T2-weighted images) of all tested animals were obtained 12 hours after MCAO and one week after intravenously administering different concentrations of hTERT-MSCs. Initial infarct volumes were estimated using in vivo MRI.

Figure 10:
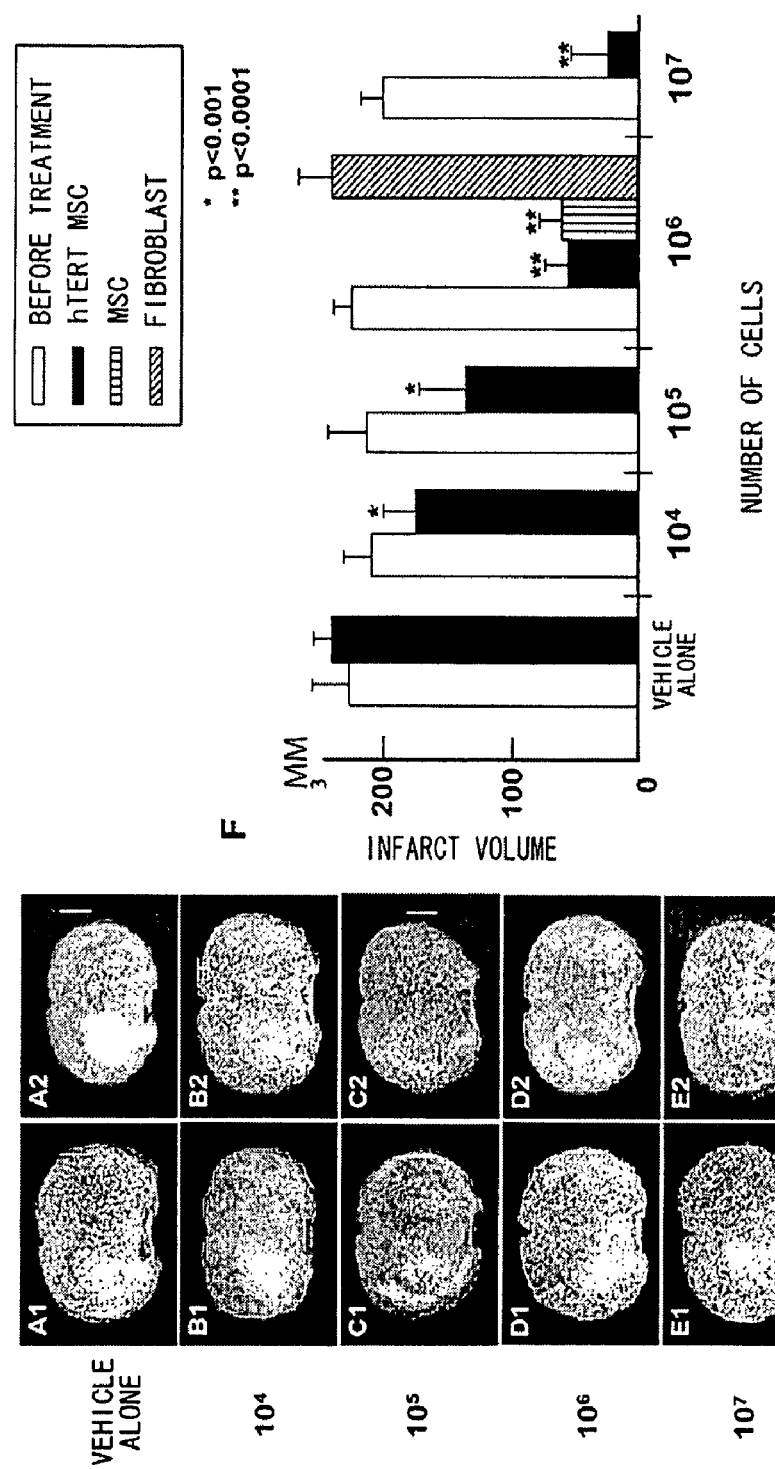
FIG. 10 shows photographs and a graph indicating the results when MSCs ($1 \times 10^4$ to $1 \times 10^7$ cells) were intravenously administered 12 hours after the cerebral infarction.

The left row of FIG. 10(A1-E1) shows simple cerebral images obtained from five rats, 12 hours after injury. These coronal forebrain sections were obtained at the caudate-putamen complex level. An ischemic damaged site is seen as a high-intensity region. The contralateral brain tissue shows normal signals, enabling comparison.

The infarct volume ($mm^3$) was evaluated by analyzing the high-intensity regions in a series of images collected from the entire cerebrum. Estimated infarct volumes were constant among the tested animals ($214\pm23$ $mm^3$, n=25).

MRI analysis did not find any change in infarct size when the vehicle (medium) alone was administered (FIG. 10A2). The infarct volume decreased with an increasing number of intravenously administered hTERT-MSCs. When $10^4$ hTERT-MSCs were administered, the infarct volume slightly decreased, showing a slight therapeutic effect (FIG. 10B2) ($176\pm21$ $mm^3$, n=5). The reduction in infarct volume escalated and the therapeutic effects became apparent upon administration of $10^5$ cells ($138\pm36$ $mm^3$, n=5) and $10^6$ cells ($56\pm18$ $mm^3$, n=5) (FIGS. 10C2 and 10D2). The infarct volume was most reduced when $10^7$ cells were administered; a virtually complete therapeutic effect could be expected (FIG. 10E2) ($23\pm31$ $mm^3$, n=5). The abnormal signals (HIA) observed before treatment (FIGS. 10A1, B1, C1, D1, and E1) remained unchanged if treatment was not conducted (FIG. 10A2), but disappeared partially or almost completely after treatment (FIGS. 10B2, C2, D2, and E2).

In another test, primary MSCs were also intravenously transplanted. Transplantation of $10^6$ primary MSCs reduced the infarct volume to the same extent as in tests using the same number of hTERT-MSCs (FIG. 10F) ($61\pm18$ $mm^3$, n=5, vs. $56\pm18$ $mm^3$, n=5, p=0.69). A supplemental sham control experiment was conducted using $10^6$ dermal fibroblasts (FIG. 10F). Transplantation of $10^6$ dermal fibroblasts did not show a reduction in infarct volume ($240\pm27$ $mm^3$, n=5, p=0.95).

The therapeutic effect on cerebral infarction of intravenously administering MSCs correlated with the number of transplanted cells. Namely, the therapeutic effect was higher when more cells were transplanted.

Figure 11:
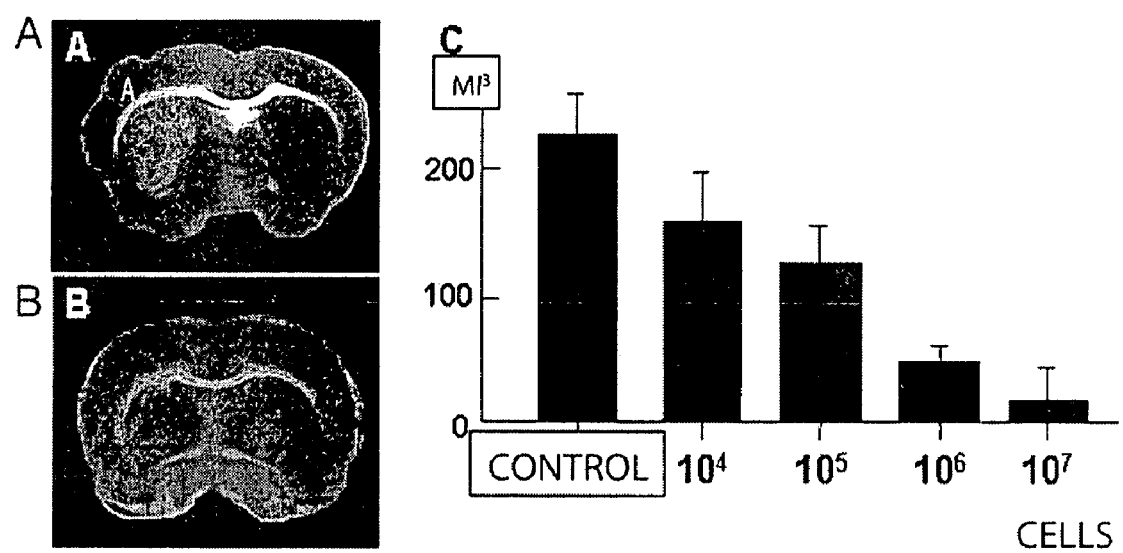
FIG. 11 shows photographs and a graph of results that histologically support the results of FIG. 10. Compared to the untreated group (A), a marked therapeutic effect can be seen in the treated group (B: transplantation of $1 \times 10^6$ cells). (C) shows quantified histological results.

Histological verification was also conducted (FIG. 11).

After evaluation of lesion volume by MRI analysis, and before and after cell administration, the rats were perfused, stained with 2,3,5-triphenyltetrazolium chloride (TTC), and second independent measurements of infarct volume were obtained. Normal brain tissues were generally stained with TTC, but the infarction lesions were not stained or were slightly stained. FIG. 1A shows a TTC stain result obtained one week after MCAO without cell transplantation. Staining on the lesion side was mainly observed in the corpus-striatum. The lesion volume was calculated by measuring the region with reduced TTC staining in the forebrain. As with MRI analysis, infarct size decreased with an increasing number of transplanted cells. Evaluation by TTC staining showed that intravenous administration of $10^7$ hTERT-MSCs markedly decreased the lesion volume (FIGS. 11B and C).

Example 13

Accumulation of Transplanted Donor Cells

MSCs ($1\times10^6$ cells) introduced with LacZ or GFP were intravenously administered to the rat cerebral infarction model 12 hours after MCAO.

The cultured cells were rinsed with phosphate buffered saline (PBS) and fixed at 4° C. for 15 minutes in a fixative solution containing 4% paraformaldehyde in 0.14M Sorensen's phosphate buffer (pH 7.4). The fixed cells were incubated in a blocking solution containing 0.2% Triton X-100 and 5% normal goat serum for 15 minutes, then incubated with primary antibodies. The primary antibodies used were anti-neuron specific enolase (NSE; 1:1000 polyclonal rabbit anti-NSE, Nitirei) antibody, anti-glial fibrillary acidic protein (GFAP; 1:200 polyclonal rabbit anti-GFAP, Nitirei) antibody, and anti-Nestin (Nestin; 1:5000 murine monoclonal anti-Nestin, Chemicon) antibody. For visualizing the primary antibodies, goat anti-mouse IgG antibody and goat anti-rabbit IgG antibody with fluorescein (FITC) (1:100, Jackson ImmunoResearch Laboratories, Inc.), or an alkaline phosphatase reaction (Zymed) were used according to the manufacturer's instruction. After immunostaining, a glass cover was placed on a microscopic slide glass using a mounting medium (Dako) cell-side down. Photographs were taken using an immunofluorescent microscope (Axioskop FS; Zeiss).

The FITC fluorochrome (green) and rhodamine fluorochrome (red) were excited using a 488 nm laser beam derived from an argon laser and a 543 nm laser beam derived from a He—Ne laser, respectively. Confocal images were obtained using a confocal laser scanning microscope (Zeiss) and software (Zeiss).

As shown in FIGS. 10 and 11, transplant treatment significantly reduced infarct volume, however, hTERT-MSCs expressing GFP were found mainly at the striatum (most infarction was identified in the untransplanted rats).

Figure 12:
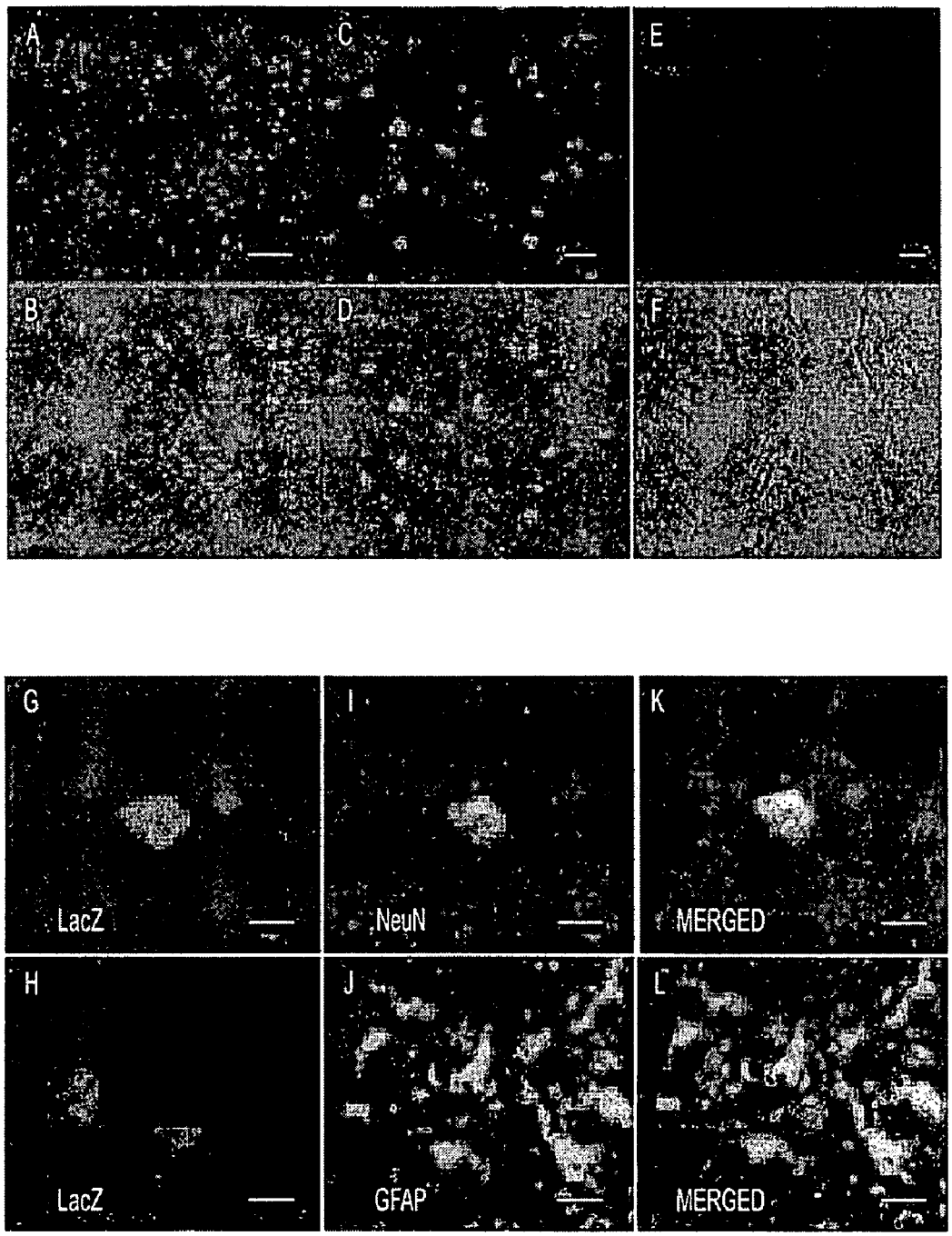
FIG. 12 shows photographs indicating the results of intravenous administration of MSCs ($1 \times 10^6$ cells) to a rat cerebral infarction model. The transplanted donor cells accumulated at areas of cerebral infarction (A, B, C, and D). Photographs A and C are photofluorograms, and photographs C and D are photofluorograms merged with regular photographs. The untransplanted group showed no donor cells (E and F). Some of the transplanted donor cells differentiated into neurons (G, I, and K) and glial cells (H, J, and L). LacZ-positive cells (G) were found to be NSE-positive (I). Photograph K shows photograph G merged with photograph I. LacZ-positive cells (H) were found to be GFAP-positive (J). Photograph L shows photograph H merged with photograph J. Scale bars: 250 µm (A and B), 10 µm (C to F), and 5 µm (G to L).

FIGS. 12A and 12B show merged confocal images of GFP fluorescence and transmitted light image, at low and high power, respectively, where the images are of the striatum on the infarcted side. Note the abundance of GFP-positive cellular-like elements. GFP-expressing cells were mainly concentrated in the corpus-striatum, but a few were found throughout the affected hemisphere. No GFP expression was found in images obtained from the contra lateral striatum, to which infarction had not been introduced. These data indicate that systemically administered cells reached the lesion site.

An immunohistochemical study was conducted to identify immature neurons (NeuN) and astrocytes (GFAP) in the infarcted sites of rats transplanted with LacZ-transferred hTERT-MSCs.

As a result, a small number of NeuN-positive cells and GFAP-positive cells were co-stained with LacZ (FIGS. 12G to L).

The transplanted donor cells accumulated in the cerebral infarction region (FIGS. 12A, B, C, and D). Under a fluorescent microscope, MSC in host brain tissue becomes green. Donor cells were not found in the untransplanted group (FIGS. 12E and F). Some of the donor cells differentiated into neurons (FIGS. 12G, I, and K) and glial cells (FIGS. 12H, J, and L).

Example 14

Confirmation of Therapeutic Effects of MSC Intravenous Administration by Metabolic Analysis The therapeutic effects of intravenous administration of MSCs on cerebral infarction were examined in terms of metabolism.

Specifically, NAA and lactate levels in the brain before and after cell transplantation were determined using magnetic resonance spectroscopy (MRS). Correlations have been reported between NAA signals and the presence of normal neurons, and between an increase in lactate and neuronal death (Barker, P. B., Gillard, J. H., van Zijl, P. C., Soher, B. J., Hanley, D. F., Agildere, A. M., Oppenheimer, S. M. and Bryan, R. N., Acute stroke: evaluation with serial proton MR spectroscopic imaging, Radiology, 192(3) (1994) 723-32.). MRS analyses of NAA and lactate levels were conducted in the lesioned and non-lesioned hemispheres 12 hours after MCAO induction.

MRS was conducted at TR=1500 msec, TE=20 msec, average=1024, voxel size 2.5×2.5×2.5 mm$^3$. The brain was accurately positioned by holding the rat's head in the flat skull position, and locating the center of an imaging section 5 mm posterior to the rhinal fissure.

Figure 13:
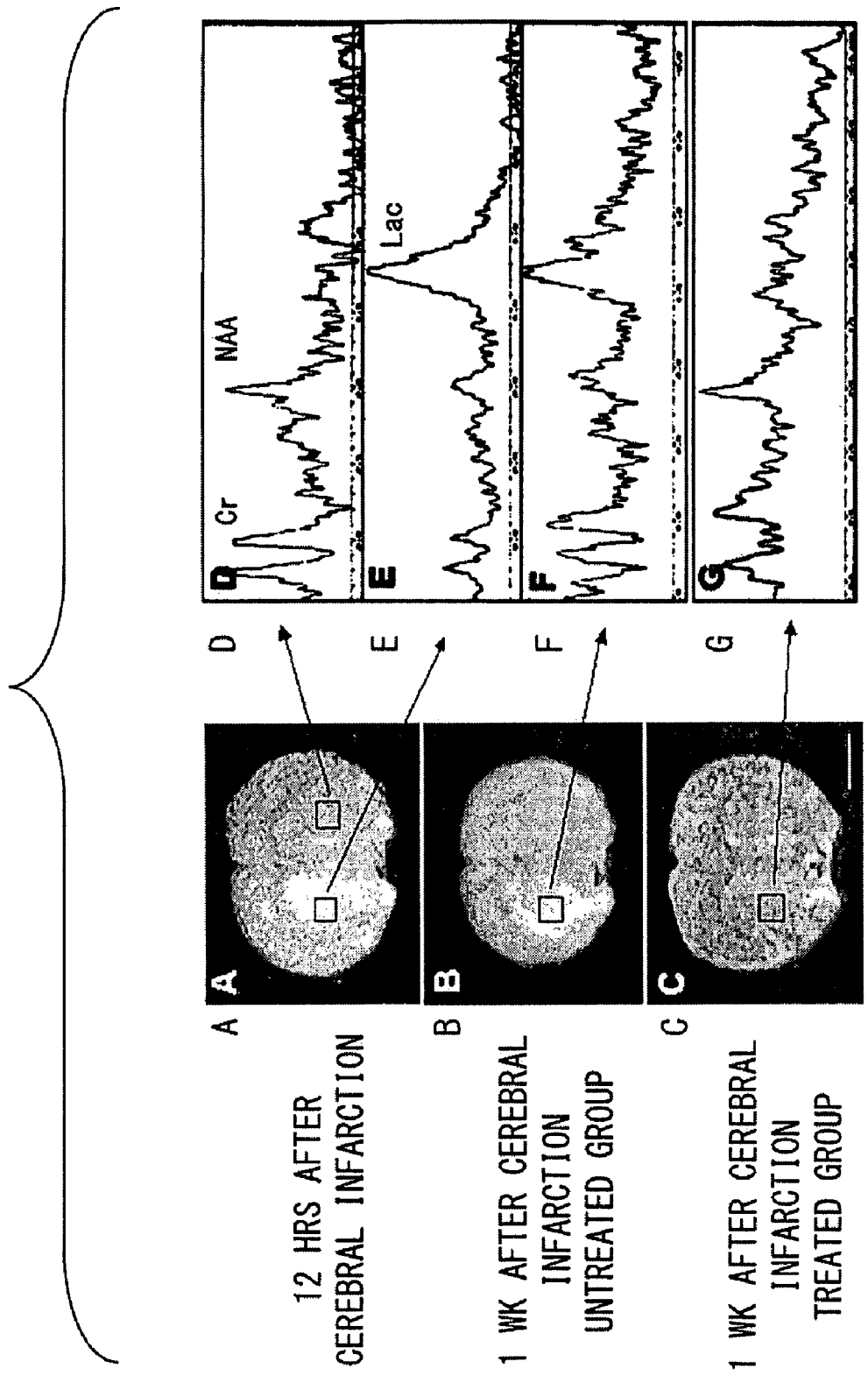
FIG. 13 shows photographs and graphs indicating the therapeutic effects of intravenous MSC administration, as investigated by magnetic resonance spectroscopy (MRS).

Consequently, the therapeutic effects of intravenous administration of MSCs on cerebral infarction were also verified in terms of metabolism. Normal hemispheres showed the highest NAA levels and no lactate signal (FIGS. 13A and D). In contrast, the lesioned sides showed low NAA levels and high lactate signals (FIGS. 13A and E). Without cell transplant, NAA signals were low and lactate signals were high one week after infarction induction (FIGS. 13B and F). In contrast, after intravenous administration of 10$^7$ hTERT-MSCs, NAA signals were present, and lactate signals were low, indicating that the brain tissue was protected by the transplant treatment (n=5) (FIGS. 13C and G).

Example 15

Confirmation of Therapeutic Effects of MSC Transplantation by Ethological Analysis Two tests were conducted to evaluate the behavioral abilities of infarction-induced rats and transplanted rats: a Morris water maze test and a treadmill stress test. These behavioral tests were started one week after infarction induction, and were conducted alone or together with cell transplantation.

Figure 14:
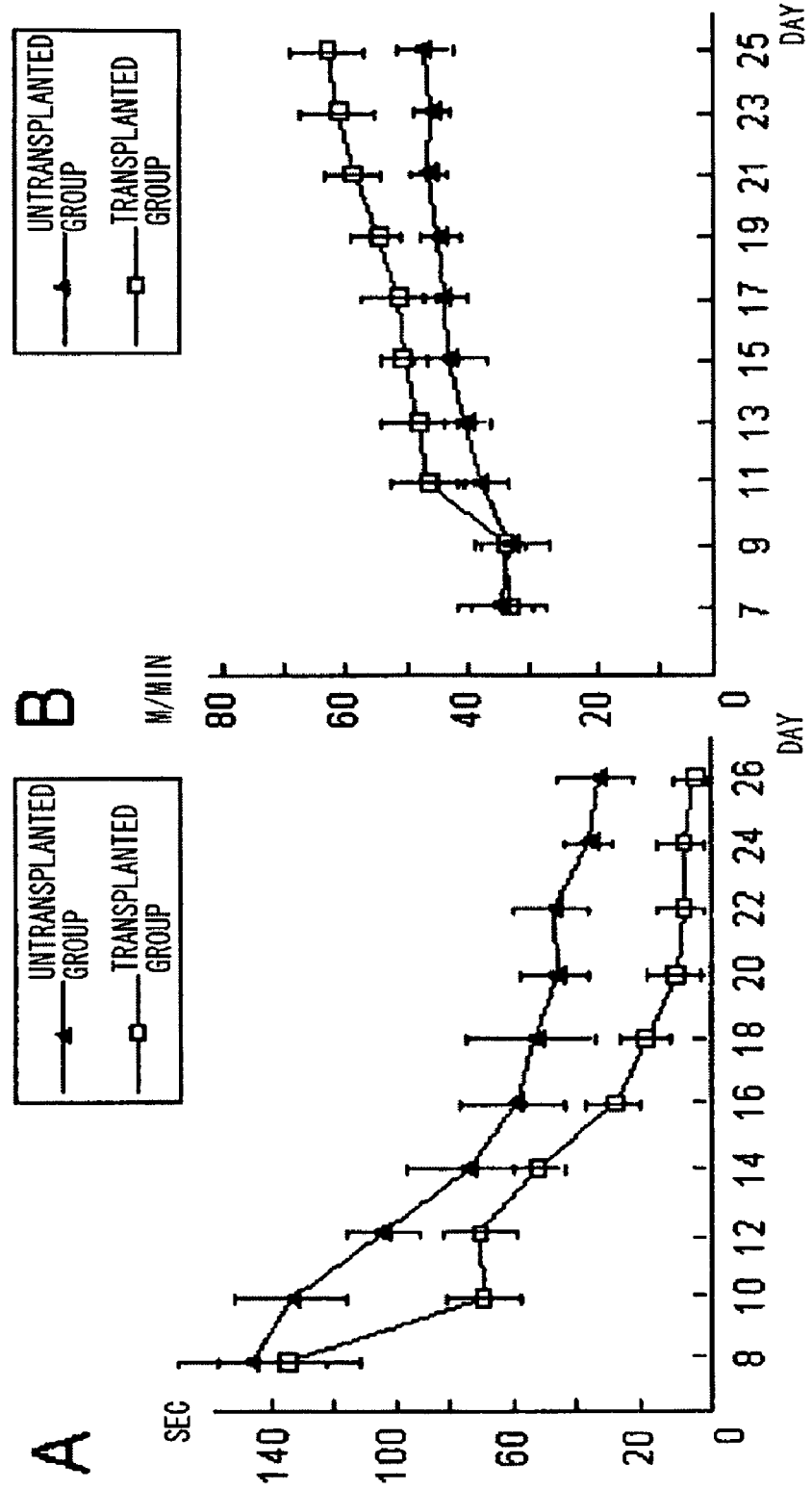
FIG. 14 shows graphs indicating the therapeutic effects of MSC transplantation, as investigated by ethological examination.

The Morris water maze test was conducted every other day. Control rats learned to mount the platform within several seconds (Morris, R. G. M., Spatial localization does not depend upon the presence of local cues., Learn Motiv, 12 (1981) 239-260.). It took about 140 seconds for MCAO-induced rats to execute the test. Rats without transplants showed stepwise improvement, and had learned to mount the platform in about 40 seconds on Day 26 of the test. The time required for MCAO-induced rats intravenously injected with hTERT-MSCs to get on the platform gradually decreased, and they mounted the platform within several seconds by Day 26 of the test, indicating that transplantation results in remarkable improvement (FIG. 14A).

In the treadmill stress test, the maximum treadmill velocity of control rats (without infarcts) reached about 60 m/min. The maximum velocity in the treadmill test one week after MCAO induction alone, or one week after MCAO induction along with transplantation, was about 35 m/min (FIG. 14B). The untreated rats showed an increase in treadmill velocity from 11 days after infarction induction, and gradually improved over 25 days at the most (46.3+6.1, n=10). The cell-transplanted group showed an even greater improvement in treadmill velocity, with their maximum speed 25 days after injury approaching that of the control group (62.0+7.2, n=10). These results revealed that the transplants remarkably improve the motor function deterioration due to cerebral infarction.

Example 16

Therapeutic Effects of MSC on Severe Cerebral Infarction

The therapeutic effects of the regenerative medical technique using MSCs were studied on rats with severe cerebral infarction (permanent middle cerebral artery occlusion model), to determine from what level of tissue damage the treatment can facilitate recovery. In contrast to the transient middle cerebral artery occlusion model used in Examples 1 to 15, the model used was one in which the middle cerebral artery was permanently occluded. This model was prepared under the same conditions as the model used in Examples 1 to 15, except for occlusion time.

Figure 15:
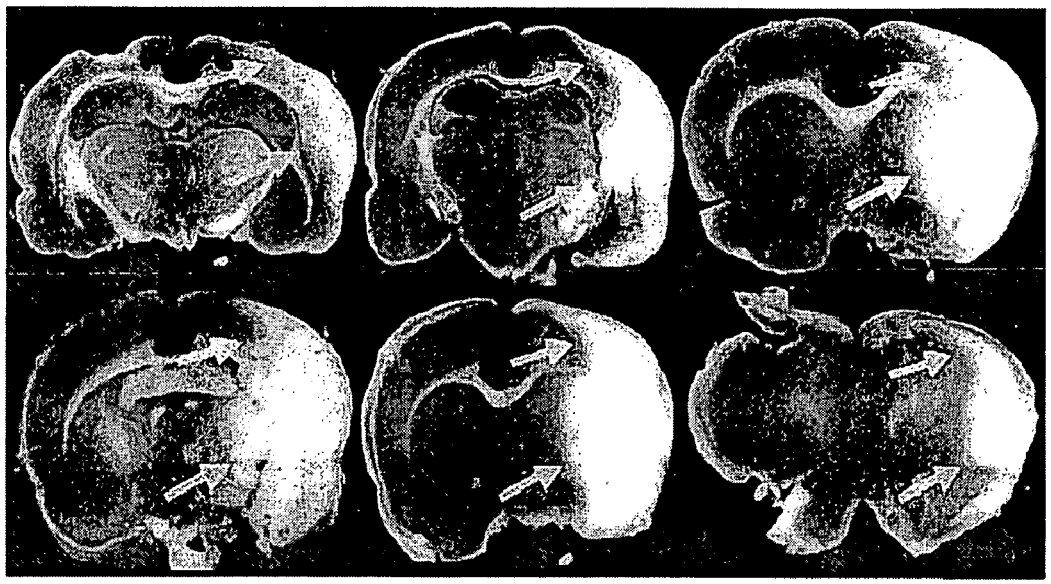
FIG. 15 shows photographs indicating the results of investigating the therapeutic effects of MSCs on a rat permanent middle cerebral artery occlusion model.

Compared to the previously mentioned rat cerebral infarction model (the transient middle cerebral artery occlusion model: 45 min), those rats with severe cerebral infarction showed a broader cerebral infarct area (FIG. 15, the portion stained white by TTC staining).

Figure 16:
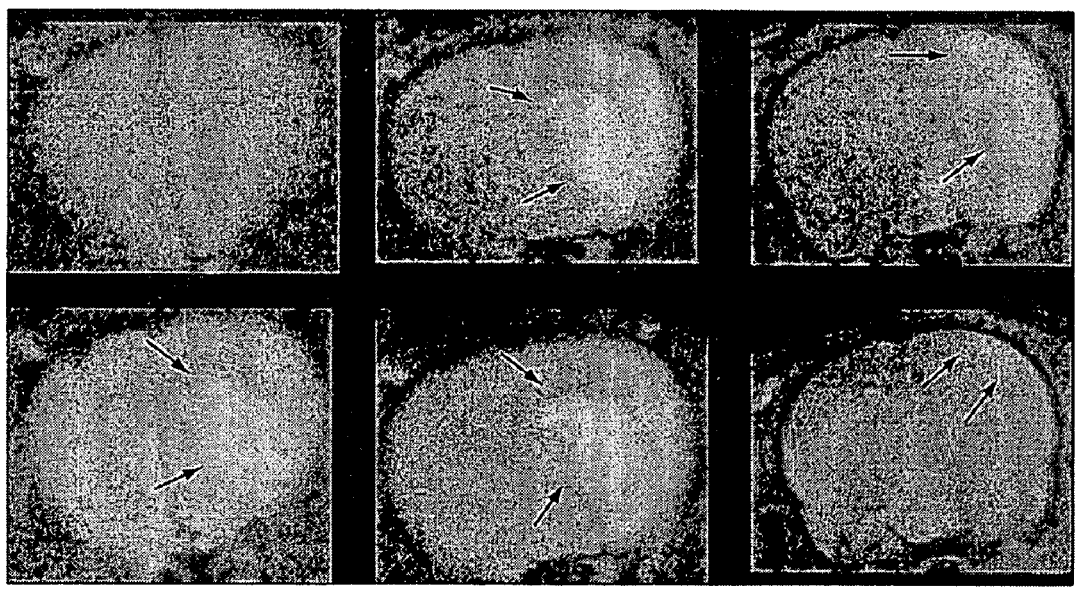
FIG. 16 shows photographs indicating that abnormal signals are also detected in concordance with a cerebral infarction area in MRI examination of severe cerebral infarction (rat permanent middle cerebral artery occlusion model).
Figure 17:
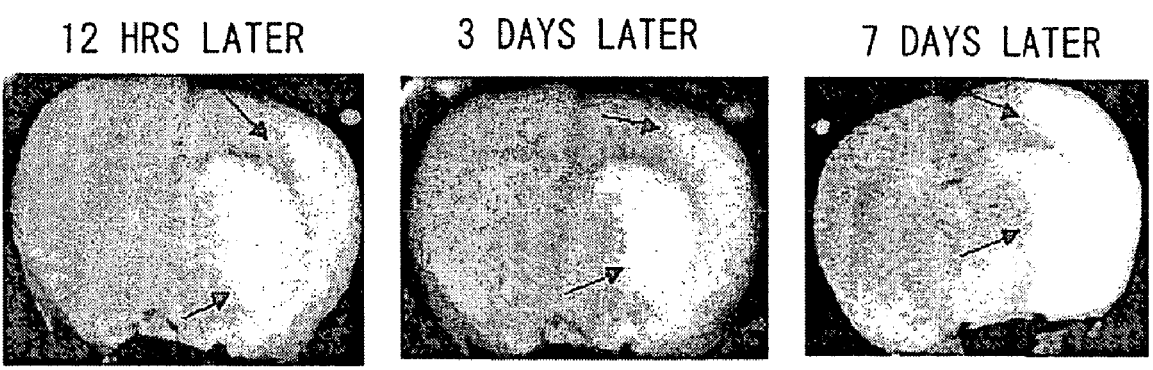
FIG. 17 shows photographs indicating that when cerebral infarction is not treated the clarity of the above-mentioned abnormal signal of FIG. 16 in cerebral infarction (HIA in MRI) increases with time (12 hours, three days, and seven days after cerebral infarction).

Abnormal signals in concordance with cerebral infarction were also detected in the severe cerebral infarction by MRI analysis (FIG. 16). Without treatment, the abnormal signals (HIA in MRI) due to cerebral infarction became more clear with time (12 hours, three days, and seven days after) (FIG. 17).

Figure 18:
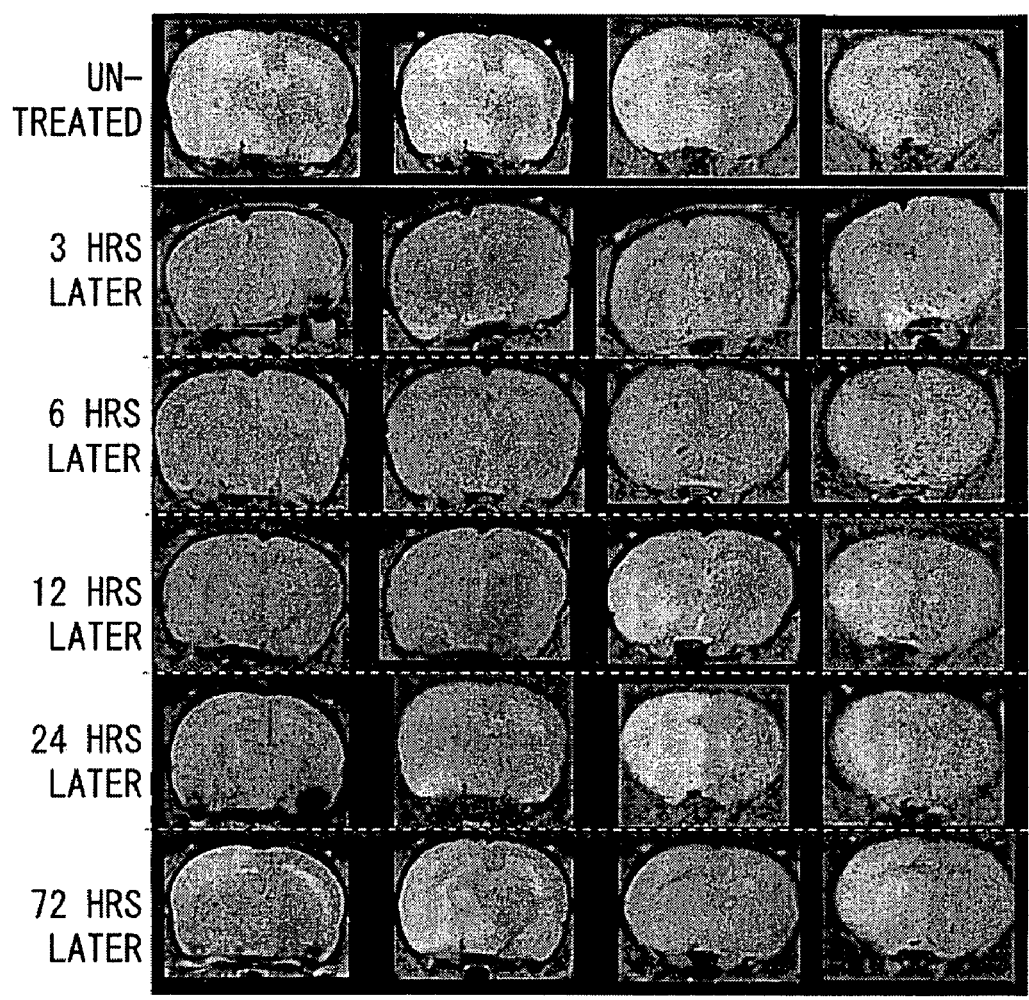
FIG. 18 shows photographs of MRI images showing the results of intravenous administration of mesenchymal stem cells (MSCs) ($1\times10^6$ cells) to a rat permanent middle cerebral artery occlusion model. Results are divided according to time elapsed from the onset of disorder to the administration of MSCs. The images show data without treatment, and for treatment three hours, six hours, 12 hours, 24 hours, and 72 hours after onset, indicated sequentially from the upper row. Each image was obtained by MRI examination ($T_2$WI) one week after the onset of cerebral infarction. The cerebral infarction is white in these images.

MSCs ($1 \times 10^6$ cells) were intravenously administered to rats with severe cerebral infarction (rat permanent middle cerebral artery occlusion model). Therapeutic effects were investigated by MRI analyses ($T_2WI$) one week after the cerebral infarction. The cerebral infarction appeared white. Transplants were timed three hours, six hours, 12 hours, 24 hours, and 72 hours after cerebral infarction. Cerebral infarction lesions were clearly observed in the untreated group (uppermost row), but hardly observed in the group intravenously administered with MSC three hours after cerebral infarction (FIG. 18). Specifically, intravenous administration of MSCs also had a remarkable therapeutic effect on severe cerebral infarction. This therapeutic effect was more prominent the earlier that transplant was conducted. It should be noted, however, that some degree of therapeutic effect is observed even when treatment is conducted 24 hours or more after the cerebral infarction.

The therapeutic effect is considered to be a synergy of the effects of neuroprotection and neural regeneration. The sooner after cerebral infarction that transplant is conducted, the stronger the neuroprotective and antihydropic actions. When the transplant is conducted relatively late, the neuroprotection becomes relatively weak, but the neural regeneration becomes strong instead.

Figure 19:
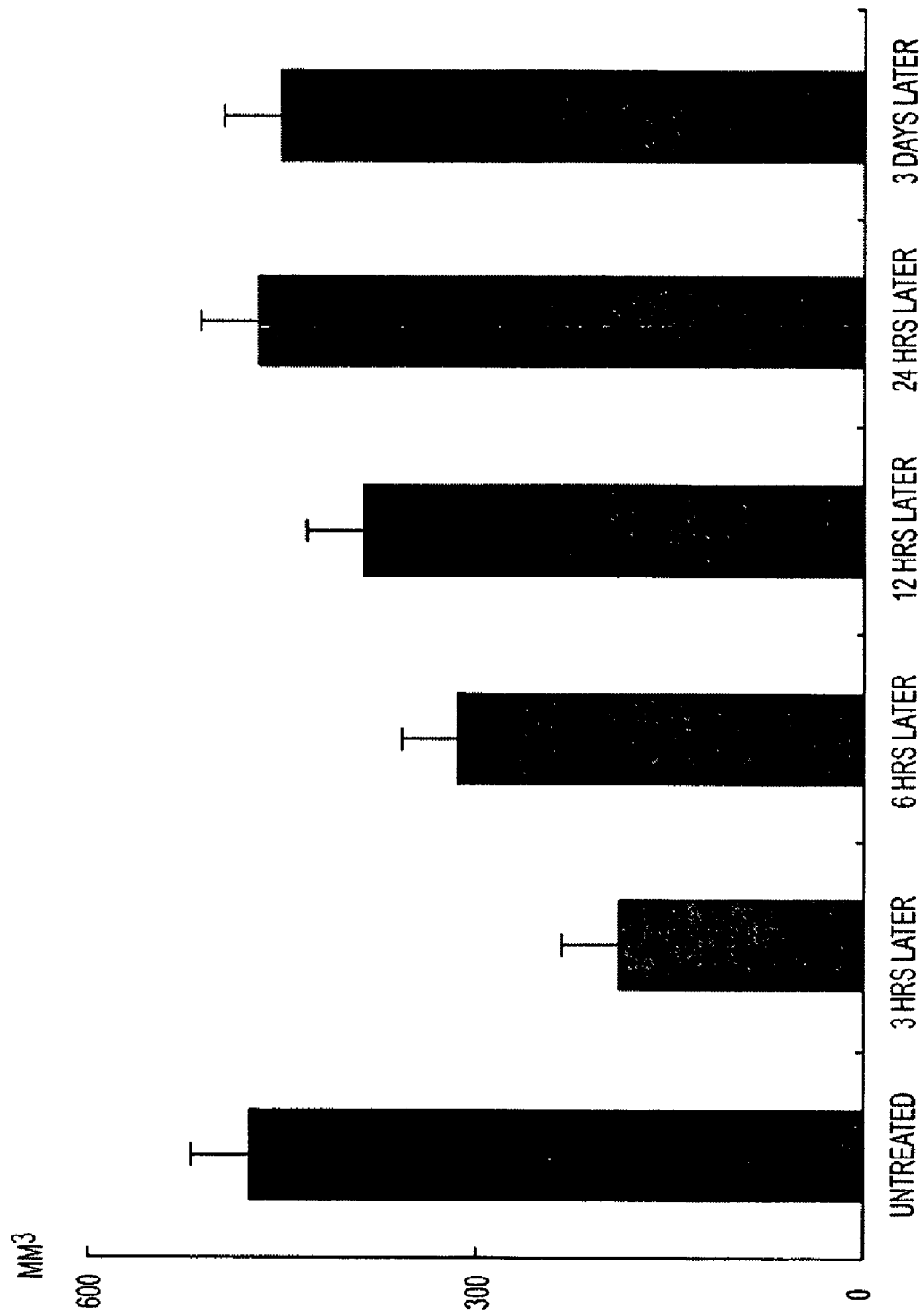
FIG. 19 shows a graph indicating the results of intravenously administering mesenchymal cells ($1\times10^6$ cells) to severe cerebral infarctions (a rat permanent middle cerebral artery occlusion model), in which the cerebral infarction area is quantitatively determined in terms of the infarct volume.

FIG. 19 is a graph quantifying results of intravenous administration of MSCs ($1 \times 10^6$ cells) to severe cerebral infarctions (rat permanent middle cerebral artery occlusion model), determined as cerebral infarct volume. The results are divided by the time elapsed between the disorder onset and MSC administration. This graph shows that the untreated group had an infarct volume of about 500 mm$^3$, but the group treated three hours after MCAO had an infarct volume of only 200 mm$^3$, indicating significant effect. When treatment was conducted within 12 hours of MCAO, the infarct volume was clearly reduced compared to that in the untreated group. The earlier the treatment, the greater the reduction in infarct volume, which means a good prognosis.

Example 17

Effects of Intravenous Administration of MSC on Severe Cerebral Infarction in Hyper Acute Stage The chronological therapeutic effects of intravenous MSC administration on severe cerebral infarction in the hyper acute stage were investigated.

When MSCs ($1 \times 10^6$ cells) were intravenously administered to severe cerebral infarction three hours after induction of the cerebral infarction, the abnormal signals (HIAs) that appeared in MRI tests then disappeared several days into the treatment, and this effect continued (FIG. 20). The therapeutic effects of MSCs are exhibited relatively early after administration, and rather than continuing these effects, the predominant therapeutic effects of intravenous MSC administration in the acute stage of cerebral infarction may be neuroprotection and antihydropic action.

Example 18

Effects of Intravenous MSC Administration on Severe Cerebral Infarction in the Acute Stage The chronological therapeutic effects of intravenous MSC administration on severe cerebral infarction in the acute stage were examined. When MSCs ($1 \times 10^6$ cells) were intravenously administered to severe cerebral infarction six hours after the cerebral infarction, the abnormal signals (HIAs) that appeared in MRI tests immediately before treatment gradually disappeared after treatment (18 hours, one week, two weeks, and four weeks after the transplant treatment) (FIG. 21). These therapeutic effects were not observed in the untreated group (no data).

Example 19

Viability in Severe Cerebral Infarction Upon Intravenous MSC Administration

MSCs ($1 \times 10^6$ cells) were intravenously administered to severe cerebral infarctions (rat permanent middle cerebral artery occlusion model), and changes in viability after disorder onset were examined and plotted on a graph.

Figure 22:
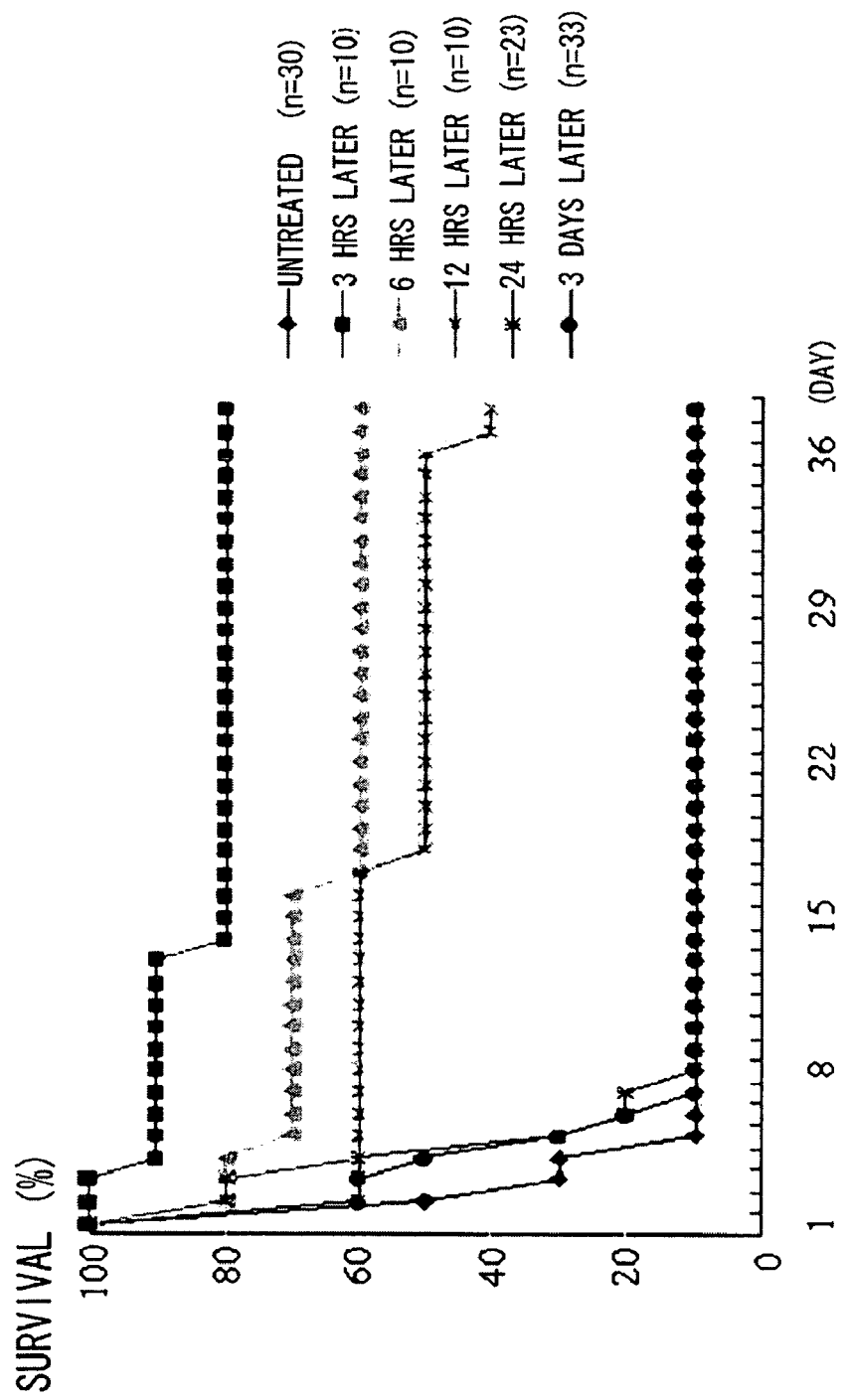
FIG. 22 shows a graph of the viability after the onset of disorder upon intravenous administration of mesenchymal stem cells (MSCs) ($1\times10^6$ cells) to severe cerebral infarction (rat permanent middle cerebral artery occlusion model). The results are divided according to the time elapsed from the onset of disorder until the administration of mesenchymal stem cells. An "n" denotes the number of samples.

The graph demonstrates that treatment by intravenous MSC administration markedly improved viability in severe cerebral infarction (rat permanent middle cerebral artery occlusion model) (FIG. 22). Without treatment, 90% of these same cerebral infarction model rats died; however, when MSCs ($1 \times 10^6$ cells) were intravenously administered three hours after cerebral infarction, 80% of the rats survived. This revealed that viability increases the earlier that treatment is started. Viability after treatment is also outstanding.

Example 20

Effects of MSC Transplantation Treatment on Clinical Symptoms of Severe Cerebral Infarction MSC transplant treatment was conducted on severe cerebral infarction, and clinical symptoms were studied.

Figure 23:
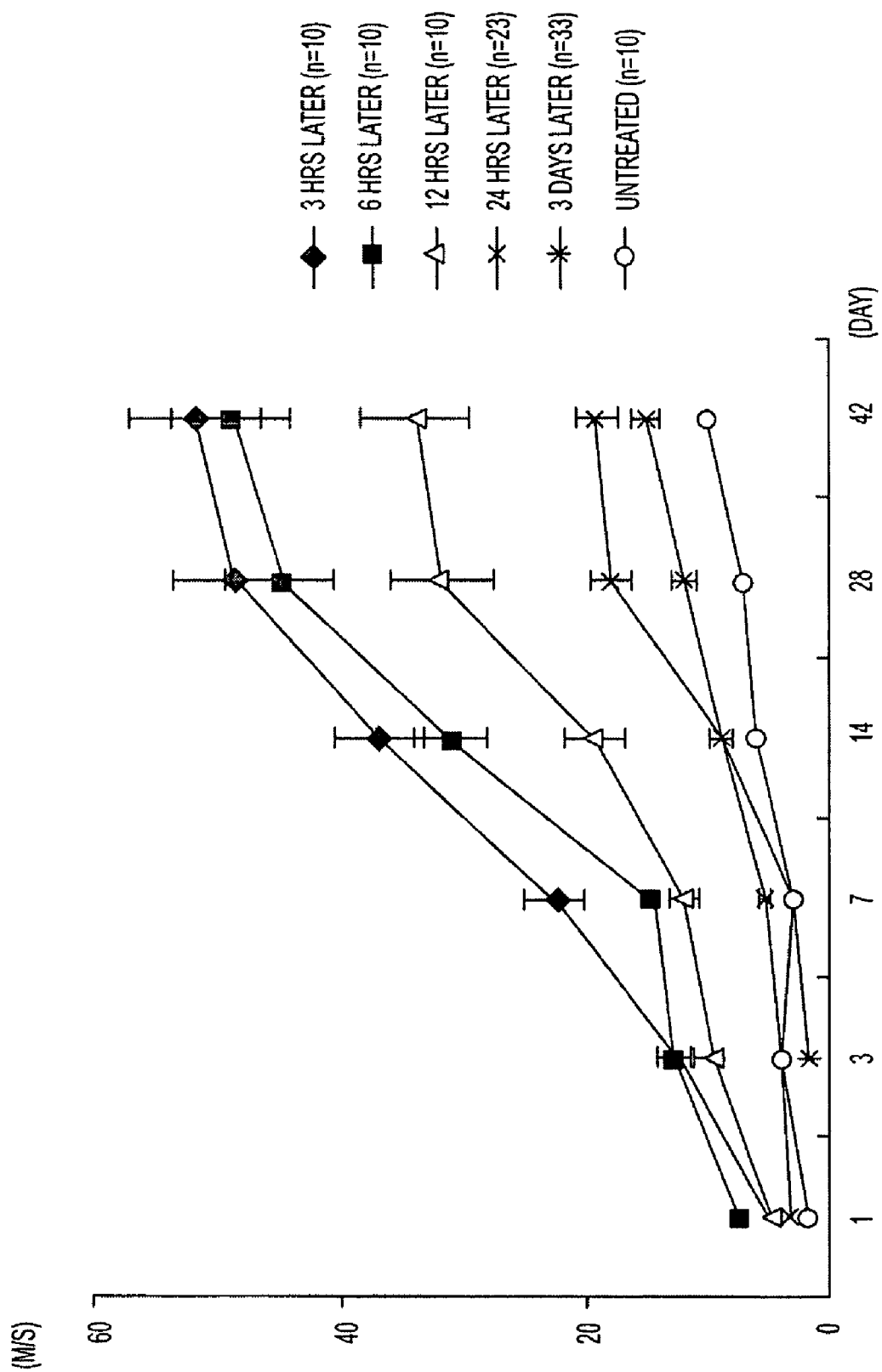
FIG. 23 shows a graph indicating clinical symptoms after MSC transplant therapy for severe cerebral infarction.

The MSC transplant treatment significant improved clinical symptoms of severe cerebral infarction (FIG. 23). Treadmill stress tests demonstrated that transplantation markedly improved motor function, once deteriorated by cerebral infarction.

Example 21

Induction of Differentiation of Adherent Cultured Cells Derived from Peripheral Blood into Neural Stem Cells or Nervous System Cells Adherent cultured cells such as mesenchymal stem cells were obtained from the peripheral blood. A large number of these cells were revealed to be obtainable by hypodermically injecting a factor such as g-CSF or SCF in advance (FIG. 24).

The obtained adherent cultured cells could be induced to differentiate into neural stem cells (Neurosphere). The expression of Nestin could be verified through RT-PCR (FIG. 25).

The obtained adherent cultured cells could also be induced to differentiate into neurons (NF-positive cells) and glial cells (GFAP-positive cells). The expressions of NF and GFAP could each be verified by RT-PCR (FIG. 26).

The following Examples 22 to 31 investigate the therapeutic effects of transplanting transgenic stem cells to the brain parenchyma a relatively long time after the onset of cerebral infarction.

Example 22

Preparation of Cells

Human bone marrow (BM) was obtained from the posterior iliac crest of healthy adult volunteers after obtaining their informed consents. This test was approved by the Institutional Review Board of Sapporo Medical University. BM mononuclear leukocytes were plated on 150 cm$^2$ plastic tissue culture flasks and incubated overnight. After washing away the free cells, the adherent cells were cultured at 37° C. in Dulbecco's modified essential medium (DMEM) containing 10% heat-inactivated fetal bovine serum (FBS) (GIBCO BRL, Rockville, Md.) in a humidified atmosphere of 5% $CO_2$.

After reaching confluence, the cells were harvested and used for gene transfection with a retroviral vector, BABE-hygro-hTERT (Kawano, Y., et al. (2003). Ex vivo expansion of human umbilical cord hematopoietic progenitor cells using a co-culture system with human telomerase catalytic subunit (hTERT)-transfected human stromal cells. Blood 101, 532-540.). MSCs within 40 population doublings (PD) were used in this study.

The morphological features of the MSCs were the same as those previously described by Kobune et al. (Kobune, M., et al. (2003). Telomerized human multipotent mesenchymal cells can differentiate into hematopoietic and cobblestone area-supporting cells. Exp Hematol 31, 715-722.). Adult normal human dermal fibroblasts (NHDF-Ad) were obtained from TAKARA BIO INC. (Japan) and were cultured in DMEM containing 10% FBS as described above.

Example 23

Adenoviral Vector

An adenoviral vector (AxCAEGFP-F/RGD) carrying a gene for RGD-mutated fiber together with a humanized variant of *Aequoria Victoria* green fluorescent protein (enhanced GFP: EGFP) under the control of CA promoter (chicken β-actin promoter with CMV-IE enhancer) was constructed according to known procedures (Nakamura, T., Sato, K. and Hamada, H. (2002). Effective gene transfer to human melanomas via integrin-targeted adenoviral vectors. Hum Gene Ther 13, 613-626., Dehari, H., et al. (2003). Enhanced antitumor effect of RGD fiber-modified adenovirus for gene therapy of oral cancer. Cancer Gene Ther 10, 75-85.).

The EGFP gene fragment was isolated from the pEGFP vector (BD Biosciences Clontech, Palo Alto, Calif.) and inserted into the pCAcc vector (PCAEGFP) (Yamauchi, A., et al. (2003). Pre-administration of angiopoietin-1 followed by VEGF induces functional and mature vascular formation in a rabbit ischemic model. J Gene Med in press). The cosmid vector pWEAxCAEGFP-F/RGD so generated, together with ClaI- and EcoT221-digested DNA-TPC from Ad5dlx-F/RGD, were co-transfected into human embryonic kidney 293 cells. Adenoviral EGFP expression vector, AxCAEGFP-F/RGD, obtained from isolated plaques, was expanded in these cells and purified by cesium chloride ultracentrifugation (Kanegae, Y., et al. (1995).

Efficient gene activation in mammalian cells by using recombinant adenovirus expressing site-specific Cre recombinase. Nucleic Acids Res 23, 3816-3821.).

Another adenoviral vector (AxCADsR-F/RGD) carrying a gene for RGD-mutated fiber together with a humanized Discosoma red fluorescent protein (DsR) under the control of the CA promoter was constructed as described above.

Human BDNF cDNA was cloned by a polymerase chain reaction using total RNA extracted from primary culture MSCs as the template (RT-PCR). The identity of the BDNF cDNA obtained in this manner was verified by sequencing and comparing with the GenBank sequence XM_006027. The human BDNF primer sequence was: forward 5'-CG-GAATTCCACCATGACCATCCTTTTCCT-TACTATGGTTA-3' (SEQ ID NO: 1); and reverse 5'-CCA-GATCTATCTTCCCCTTTTAATGGTCAATGTA-3' (SEQ ID NO: 2).

A plasmid was obtained by inserting the BDNF cDNA into the pCAcc vector between the EcoRI site and the Bgl II site, and was named pCAhBDNF. The plasmid pCAhBDNF was digested by ClaI and the fragment containing the BDNF cDNA expression unit was isolated by agarose gel electrophoresis. The adenoviral BDNF expression vector pWEAx-CAhBDNF-F/RGD was prepared using Lipofectamine 2000 (Invitrogen Corporation, Tokyo, Japan).

Before using the viral vector, the concentration and titer of the virus was evaluated, and the viral stocks were examined for potential contamination with replication competent viruses. To determine viral concentration (particle unit (pu)/ml), the viral solution was incubated in 0.1% sodium dodecylsulfate, and $A_{260}$ was measured (Nyberg-Hoffman, C., Shabram, P., Li, W., Giroux, D. and Aguilar-Cordova, E. (1997). Sensitivity and reproducibility in adenoviral infectious titer determination. Nat Med 3, 808-811.). The viral titers of AxCAhBDNF-F/RGD, AxCAEGFP-F/RGD, and AxCADsR-F/RGD were $4.35 \times 10^{11}$, $5.38 \times 10^{11}$, and $1.03 \times 10^{12}$ pu/ml, respectively.

Example 24

Adenovirus Infection

Adenovirus-mediated gene transfection was performed as previously described (Tsuda, H., et al. (2003). Efficient BMP2 gene transfer and bone formation of mesenchymal stem cells by a fiber-mutant adenoviral vector. Mol Ther 7, 354-365.).

Briefly, the cells were seeded onto 15 cm plates at a density of $2 \times 10^6$ cells per plate. MSCs were exposed to 7.5 ml of a DMEM suspension containing infectious viral particles at 37° C. for 60 minutes. The cells were infected with AxCAh-BDNF-F/RGD, AxCAEGFP-F/RGD, and AxCADsR-F/RGD at MOIs of $1 \times 10^3$, $4 \times 10^3$, and $4 \times 10^3$ pu/cell, respectively. The medium was then removed, and the cells washed with DMEM once, and then re-cultured with normal medium for 24 hours, and transplanted into the brain.

Example 25

In vitro Detection and Quantitative Analysis of Immunoreactive Human BDNF

MSC cells transfected with AxCAhBDNF-F/RGD (MSC-BDNF) at MOIs of 100, 300, 1000, and 3000 pu/cell secreted BDNF at rates of 0.230±0.110, 0.434±0.122, 0.931±0.101, and 1.860±0.410 ng/$10^5$ cell/48-hr, respectively. Untransfected MSCs also produced BDNF protein at a rate of 0.0407±0.0059 ng/$10^5$ cell/48-hr. BDNF production level of MSC-BDNF cells transfected at an MOI of 1000 pu/cell was 23 times more than in uninfected MSCs (FIG. 27).

Example 26

Transient MCAO Animal Model and Intracerebral Transplantation

The use of animals in this study was approved by the Animal Care and Use Committee of Sapporo Medical University, and all procedures were conducted according to institutional guidelines.

Rats were anaesthetized with 3.5% halothane, and were kept unconscious using a face mask and 1.0% to 2.0% halothane in 70% $N_2O$ and 30% $O_2$. After surgery, the animals were placed under a heat lamp to maintain their body temperatures at 37° C. Local cerebral ischemia was induced in male Wistar rats (each 250 to 300 g) by endovascular middle cerebral artery occlusion (Tamura, A., Gotoh, O. and Sano, K. (1986). [Focal cerebral infarction in the rat: I. Operative technique and physiological monitorings for chronic model]. No To Shinkei 38, 747-751.). A 5-0 monofilament nylon suture with a silicone-coated tip was gradually inserted through an arteriotomy in the right common carotid artery through the internal carotid artery to a point about 18 mm distal to the bifurcation of the carotid artery. The nylon suture was extracted 90 minutes into the transitory occlusion, to recover blood flow in the brain.

Donor MSCs were transplanted to the brain according to the method described by Goto et al. (Goto, S., Yamada, K., Yoshikawa, M., Okamura, A. and Ushio, Y. (1997). GABA receptor agonist promotes reformation of the striatonigral pathway by transplant derived from fetal striatal primordia in the lesioned striatum. Exp Neurol 147, 503-509.).

After confirming the induction of ischemic brain injury using the behavioral tests described below, the animals were randomized for transplantation. The animals were anaesthetized with intraperitoneal (IP) injection of ketamine (2.7 to 3 mg/100-g) and xylazine (0.36 to 0.4 mg/100-g) and positioned in a Narishige stereotaxic frame (Model SR-6N, Narishige Co., Ltd., Japan). Using a 26-gauge Hamilton syringe, 5 μl of a suspension of 5×$10^5$ MSCs in serum-free DMEM was injected to the right dorsolateral striatum 4 mm beneath the skull surface and 3 mm lateral to the bregma level over 2.5 minutes (Paxinos, G., Watson, C., Pennisi, M. and Topple, A. (1985). Bregma, lambda and the interaural midpoint in stereotaxic surgery with rats of different sex, strain and weight. J Neurosci Methods 13, 139-143.). This position was approximately the ischemic boundary zone. To prevent rejection of human MSCs transplants, the transplanted rats were intraperitoneally administered with cyclosporine A (10 mg/kg/day).

Example 27

Therapeutic Effects of MSC-BDNFs (Experiment 1)

Experiment 1 was conducted 14 days after MCAO to test the therapeutic effectiveness of MSC-BDNF. Experimental groups were as follows:

Group 1 (control): Rats in which the ischemic boundary zone was injected with DMEM 24 hours after MCAO (n=7);

Group 2: Rats in which the ischemic boundary zone was transplanted with fibroblasts 24 hours after MCAO (NHDF-Ad) (n=6);

Group 3: Rats in which the ischemic boundary zone was injected with MSCs 24 hours after MCAO (n=7); and Group 4: Rats in which the ischemic boundary zone was transplanted with MSC-BDNFs 24 hours after MCAO (n=7).

LPT was performed one, eight, and 15 days after MCAO, and a treadmill stress test was performed eight and 15 days after MCAO. MRI was performed on days two, seven, and 14.

(1) Limb Placement Test (LPT) (FIG. 28A)

LPTs included eight subtests, described by Johansson and coworkers (Ohlsson, A. L. and Johansson, B. B. (1995). Environment influences functional outcome of cerebral infarction in rats. Stroke 26, 644-649.), and were conducted 24 hours after ischemia induction.

Briefly, the four limbs of the rats were evaluated using the top and edges of a counter top. For each subtest, animals were scored as follows: 0=unable to place their limbs; 1=partial and/or delayed (by more than 2 seconds) placement of their limbs; and 2=immediate and correct limb placement.

The neurological scores prior to MCAO were similar for all animals. One day after MCAO, prior to intracerebral MSC injection, there was no statistical difference in limb-placement score between the four ischemic groups. Eight days after MCAO, the MSC-BDNF-administered rats achieved significantly high limb-placement scores (8.43±1.52) compared to the control DMEM rats (3.71±0.49, P=0.0001) and the fibroblast-administered rats (5.00±1.10, P=0.003). Fifteen days after MCAO, the MSC-BDNF-administered rats scored 9.14±2.61, which was significantly higher than the scores seen in the DMEM group (5.00±1.73, P=0.024). In contrast, on both Day 8 and Day 15 the MCS-administered rats did not achieve higher scores than the DMEM- or fibroblast-administered control rats.

(2) Treadmill Test (FIG. 28B)

In the treadmill test, rats were placed on an accelerating treadmill (Model MK-680, Muromachi Kikai Co., Ltd., Japan) (Mokry, J. (1995). Experimental models and behavioural tests used in the study of Parkinson's disease. Physiol Res 44, 143-150.). The rats were made to run on a belt, the speed of which gradually increased by 10 m/s every 10 seconds to a maximum speed of 70 m/s, and were made to maintain the middle position on that belt. When a rat could no longer run, the trial was officially ended. The maximum speed at which each animal could run was measured. The rats were tested eight and 15 days after MCAO. Average treadmill speeds prior to MCAO were comparable between groups. Eight days after MCAO, the rats of the MSC-BDNF group achieved significantly higher speeds (23.4±2.6 m/s) compared to the control DMEM- (9.57±5.6 m/s; P=0.001) and fibroblast-treated (11.8±6.2 m/s; P=0.017) groups. These differences were maintained even on Day 15. The MSC-BDNF, control DMEM, and control fibroblast groups showed speeds of 36.6±9.5, 12.1±9.4 (P=0.002), and 15.8±11.3 (P=0.023), respectively. MSC-treated rats showed no enhancement in recovery on Day 8 or Day 15.

(3) Reduction in Infarct Volume after MSC-BDNF Treatment, as Determined by MRI (FIGS. 29A and 29B)

MRI was conducted on all the animals two, seven, and 14 days after MCAO. The animals were anaesthetized prior to MRI. The MRI device comprised a superconductive magnet of 7 T and 18 cm in diameter, connected to a UNITYINOVA console (Oxford Instruments, UK, and Varian, Inc., Palo Alto, Calif.) via an interface. The animals were fixed in the same position during imaging. Multislice T2-weighted spin echo MR images (TR 3000 msec, TE 40 msec, field of view 40×30 mm, section thickness 2 mm, gapless) were obtained.

The disposition of the ischemic area was evaluated by calculating the percent hemisphere lesion volume (% HLV) from the T2-weighted images using imaging software (Scion Image, Version Beta 4.0.2, Scion Corporation). Ischemic tissue in each section was marked, and the infarct volume was calculated considering the thickness of the section (2 mm/section). To avoid overestimating infarct volume, a corrected infarct volume (CIV) was calculated according to the following equation, as described by Neumann-Haefelin et al. (Neumann-Haefelin, T., et al. (2000). Serial MRI after transient focal cerebral ischemia in rats: dynamics of tissue injury, blood-brain barrier damage, and edema formation. Stroke 31, 1965-1972; discussion 1972-1963.):

$$CIV = (LT - (RT - RI)) \times d$$

In this equation, LT represents the area of the left hemisphere in $mm^2$; RT represents the area of the right hemisphere in $mm^2$; RI represents the infarcted area in $mm^2$; and d represents the thickness of the section (2 mm). The relative infarct volume (% HLV) is expressed as a percentage of right hemisphere volume.

Hyper intensity areas were summed over the six central MR images in the T2-weighted images, and lesion volume was expressed as percent contralateral hemisphere lesion volume (% HLV). All groups showed a reduction in % HLV from Day 2 to Day 14. Two days after MCAO, no significant difference in % HLV was found among the MSC-BDNF (35.0±4.8%), DMEM (38.7±4.9%), fibroblast (37.9±3.8%), and MSC (37.8±2.8%) groups, but the % HLV of the MSC-BDNF group was somewhat reduced compared to the other groups.

In contrast, seven days after MCAO, the rats of the MSC-BDNF group showed a significant reduction in % HLV (25.4±2.8%) compared to the control DMEM (32.8±4.9%; P=0.002), control fibroblast- (31.6±2.2%; P=0.015), and control MSC-treated (30.8±4.3%; P=0.028) groups. After fourteen days, the rats of the MSC-BDNF group showed a significant reduction in % HLV (23.7±3.2%) compared to the DMEM control (29.6±3.6%; P=0.011).

Compared to the control DMEM and fibroblast groups, the MSC-treated rats did not show any significant recovery in % HLV seven days (30.8±4.3%) or 14 days (26.2±2.9%) after MCAO.

Example 28

In vivo BDNF Production Level (Experiment 2; FIG. 30)

In Experiment 2, growth factors were measured in the following animal groups:
Group 1 (control): Normal rats (n=3),
Group 2 (control): DMEM-injected rats (n=3),
Group 3: MSC-injected rats (n=3), and
Group 4: Rats injected with MSC-BDNF to the ischemic boundary zone 24 hours after MCAO.

The rats were sacrificed seven days after MCAO to measure BDNF concentration in the local brain tissue.

The present inventors determined the BDNF level in the local brain tissue seven days after MCAO using sandwich ELISA.

MSCs were transfected in vitro at different MOIs (pu/cell), and culture supernatants were collected 48 hours later for analysis. Seven days after MCAO, the rats were anaesthetized by the intraperitoneal administration of ketamine (4.4 to 8 mg/100 g) and xylazine (1.3 mg/100 g), the brain was removed and sliced while on ice into coronal sections (200 mg) from −1.0 to 1.0 mm bregma of the ischemic hemisphere, and these were stored at −80° C. until use. Each tissue sample was suspended in an equal weight of a homogenate buffer (1 ml; 137 mM NaCl, 20 mM Tris, 1% NP40, 1 mM PMSF, 10 µg/ml aprotinin, 1 µg/ml leupeptin, 0.5 mM sodium vanadate) and homogenized with a Dounce homogenizer. The homogenate was centrifuged (10,000 g) at 4° C. for ten minutes, and the supernatant (5 µg/µl) was collected for analysis. The BDNF concentration of each of the samples (analyzed in triplicate) was quantified using a commercially available BDNF ELISA kit (Promega, Madison, Wis.).

The MSC-BDNF-transplanted rats showed significantly increased BDNF levels in the ischemic hemisphere (45.2±14.8 pg/mg protein) as compared to the DMEM- (12.5±1.9 pg/mg protein; P=0.0002) or MSC-injected rats (19.3±5.5 pg/mg protein; P=0.0006). The MSC-treated rats also showed significantly increased BDNF levels in the ischemic hemisphere as compared to the DMEM-treated rats (P=0.0124).

Example 29

Nuclear DNA Fragmentation in MSC-BDNF-treated Animals (Experiments 3A and B; FIG. 31)

Experiment 3A was conducted to evaluate the intensity of DNA fragmentation in brain cells seven days after ischemia. The experimental groups herein are as described in Experiment 2. The rats were sacrificed seven days after MCAO to evaluate their brain tissue using TUNEL staining.

Seven days after MCAO, the rats were anaesthetized and transcardially perfused, initially, with phosphate-buffered saline (PBS) and then with PBS containing 4% paraformaldehyde (PFA). The brains were excised, immersed for two days in PBS containing 4% PFA, and 30 µm frozen sections (coronal coordinates bregma −1.0 to 1.0 mm) were sliced in a cryostat at −20° C. DNA fragmentation of cells in the ischemic boundary zone was detected with an In Situ Apoptosis Detection Kit (Takara Biomedicals, Shiga, Japan) using the terminal deoxynucleotidyl transferase (dUTP) nick-end labeling (TUNEL) technique (Gavrieli, Y., Sherman, Y. and Ben-Sasson, S. A. (1992). Identification of programmed cell death in situ via specific labeling of nuclear DNA fragmentation. J Cell Biol 119, 493-501.). Specifically, after protease digestion, the sections were incubated in a mixture of terminal deoxynucleotidyl transferase and fluorescein isothiocyanate-labeled dUTP (green). The sections were then counterstained with PI (propidium iodide), which stains red. In these sections the MSCs that were transfected with AxCADsR-F/RGD were stained red. The total number of positive red cells was counted in three 1×1 $mm^2$ regions of the inner boundary zone (Hayashi, T., Abe, K. and Itoyama, Y. (1998). Reduction of ischemic damage by application of vascular endothelial growth factor in rat brain after transient ischemia. J Cereb Blood Flow Metab 18, 887-895.). Sections 100 µm thick were prepared using a vibratome and incubated at 4° C. overnight with a primary antibody diluted with PBS containing 3% BSA and 0.1% Triton X-100. The primary antibodies used in this study were anti-neuronal nuclear antigen (NeuN: mAb377; Chemicon International, Temecula, Calif., USA) and anti-glial fibrillary acidic protein (GFAP: G3893, Sigma) antibodies. After rinsing in PBS, the sections were incubated at room temperature for one hour with a fluorescent secondary antibody (Alexa Fluor 594 goat anti-mouse IgG (H+L): A-11032, Molecular Probes, Inc.).

Seven days after MCAO the number of TUNEL-positive cells (green) in the ischemic boundary zones of MSC-BDNF-injected animals was significantly less than in the DMEM-injected group (275±73 vs. 55.0±41.0; P=0.013). In contrast, there were significantly more of these cells in the MSC-injected animals than in the DMEM-injected animals (173.0±64.9 vs. 55.0±41.0; P=0.20) (FIGS. 31A, B, and C).

In Experiment 3B, DNA fragmentation on Day 7 was determined in animals transplanted with MSC-DsR— (Group 2; n=3) or MSC-BDNF-DsR— (Group 3; n=3), as well as in control animals (Group 1; n=3).

A large number of DsR-positive MCS cells were detected less than 2 mm from the injection site. The MSC-BDNF-treated animals showed a reduced number of TUNEL-positive transplanted MSCs in the injection site, as compared to the MSC group (FIG. 31D). In addition, compared to the MSC group, the MSC-BDNF-treated animals showed a reduced number of TUNEL-positive cells near MSCs in the injection site.

Example 30

MSC Phenotypes (Experiment 4; FIG. 32)

Experiment 4 was conducted to determine cell morphology on Day 7. Experimental groups included DMEM-injected control rats (Group 1; n=3), MSC-EGFP-transplanted rats (Group 2; n=3), and MSC-BDNF-EGFP-transplanted rats (Group 3; n=3). Rats were sacrificed seven days after MCAO to morphologically evaluate brain tissue.

To determine whether or not MSCs in the ischemic area expressed a neuronal phonotype, morphological examinations were conducted seven days after MCAO. Some transplanted MSCs were immunopositive to the neuron marker NeuN and astrocyte marker GFAP. Some displayed fibrous projections, while others had a round shape. The transplanted MSC-BDNFs showed similar features to those of the MSCs.

Example 31

Data Analyses

The data shown in Examples 22 to 31 are presented as "means ±standard deviation (SD)". The data from the limb placement and treadmill tests were analyzed using one-way ANOVA and then Games Howell's post hoc tests. The HLV data were analyzed using one-way ANOVA and then Tukey's HSD post hoc tests. The ELISA data were compared between individual groups using Student's t-tests. TUNEL-positive cell numbers were compared between individual groups using one-way ANOVA and then Sheffe's post hoc tests. Significance was assumed if the P value was <0.05.

The following Examples 32 to 44 examine the therapeutic effects of transgenic stem cell transplants on brain tumors.

Example 32

Establishment of Cell Lines

A 9L rat glioma cell line (syngenetic with Fisher 344 rats) and normal rat kidney (NRK) cells were maintained in Dulbecco's Modified Eagle's Medium (DMEM, Sigma-Aldrich Inc., St Lewis, Mo., USA) supplemented with 10% heat-inactivated fetal bovine serum (FBS, Invitrogen Life Technologies Inc., Grand Island, N.Y., USA), 2 mM L-glutamine, 50 μg streptomycin, and 50 units/ml penicillin. To biologically label the 9L cells, pDsR2-N1 plasmid encoding humanized Discosoma red fluorescent protein (DsRed2) under the control of a CMV promoter was purchased from BD Biosciences Clontech (Palo Alto, Calif., USA). Using a DNA complex prepared at a ratio of 1 μg DNA: 2.5 μl of NeuroPORTER reagent (Gene Therapy Systems, Inc., San Diego, Calif., USA), pDsR2-N1 was transfected using NeuroPORTER to cells at 50% to 60% confluence. 24 hours after the transfection DsRed2-positive cells were isolated using FACScalibur (Becton Dickinson Co., Franklin Lakes, N.J., USA), and further purified by repeating selection 72 hours after the transfection. The isolated DsRed2-positive 9L cells were selected in DMEM supplemented with 10% FBS and 1 mg/ml G418 (Invitrogen Life Technologies) for 14 days to establish a stable cell line (9L-DsR).

Example 33

MSC Preparation

MSCs were prepared from bone marrow according to previously reported procedures (Tsuda H et al. Efficient BMP2 gene transfer and bone formation of mesenchymal stem cells by a fiber-mutant adenoviral vector. Mol Ther 2003; 7: 354-365.).

Briefly, Fischer 344 rats (nine weeks of age, male) were sacrificed by cervical dislocation, the femur and tibias were cut from the soft tissues, and the epiphyses were removed using rongeurs. The mid shaft bone marrow tissues of the femur and tibias were then flushed into normal medium (DMEM supplemented with 10% FBS, 100 unit/ml penicillin, 100 μg/ml streptomycin, 0.25 μg/ml amphotericin-B, and 2 mM L-glutamine). The bone marrow was successively aspirated into syringes using needles of gradually decreasing size (18, 20, and 22 gauge, respectively) to give a single cell suspension. The primary culture MSCs were seeded in normal medium at a density of $5 \times 10^7$ cells per 10-cm culture dish. Four days after initial culture, the medium was replaced with fresh normal medium to remove non-adherent cells.

MSCs were maintained at 37° C. and 5% $CO_2$, and consumed medium was exchanged with fresh medium every four days.

Example 34

Adenoviral Vectors and in vivo Gene Transduction

An adenoviral vector with modified fiber encoding human IL-2 (AxCAhIL2-F/RGD) has been already described (Dehari H et al. Enhanced antitumor effect of RGD fiber-modified adenovirus for gene therapy of oral cancer. Cancer Gene Ther 2003; 10: 75-85.). Another adenoviral vector (AxCAE-GFP-F/RGD) with RGD mutated-fiber and a humanized variant of Aequoria victoria green fluorescent protein (enhanced GFP: EGFP) under the control of CA promoter (chicken β-actin promoter with CMV-IE enhancer) was constructed as already described (Dehari H et al. Enhanced antitumor effect of RGD fiber-modified adenovirus for gene therapy of oral cancer. Cancer Gene Ther 2003; 10: 75-85., Nakamura T, Sato K, Hamada H. Effective gene transfer to human melanomas via integrin-targeted adenoviral vectors. Hum Gene Ther 2002; 13: 613-626.).

An EGFP gene fragment was isolated from the pEGFP vector (BD BIOSCIENCES CLONTECH, Palo Alto, Calif., USA) and inserted into the pCAcc vector (Yamauchi A et al. Pre-administration of angiopoietin-1 followed by VEGF induces functional and mature vascular formation in a rabbit ischemic model. J Gene Med 2003; 5: 994-1004.) (pCAE- GFP). An expression cassette containing the EGFP gene was isolated by restriction enzyme digestion with ClaI, and inserted into the ClaI site of cosmid vector pL. The thus-generated cosmid vector pLEGFP, together with ClaI- and EcoT22I-digested DNA-TPC derived from AdSdlx-F/RGD, were co-transfected into human embryonic kidney 293 cells. Plaques produced from the transfected 293 cells were isolated and evaluated using restriction enzyme digestion of the viral genome. AxCAEGFP-F/RGD, which is an adenoviral EGFP expression vector with RGD fiber, obtained from the isolated plaques, was proliferated in the 293 cells. All adenoviral vectors were proliferated in the 293 cells and purified by cesium chloride ultracentrifugation.

After purification, the virus was dialyzed against phosphate-buffered saline (PBS) containing 10% glycerol, and stored at −80° C. Viral titer was determined in terms of particle units (pu) by spectrophotometry at $A_{260}$ nm (Dehari H et al. Enhanced antitumor effect of RGD fiber-modified adenovirus for gene therapy of oral cancer. Cancer Gene Ther 2003; 10: 75-85.). Ex vivo adenoviral gene transduction of primary culture MSCs has been described. (Tsuda H et al. Efficient BMP2 gene transfer and bone formation of mesenchymal stem cells by a fiber-mutant adenoviral vector. Mol Ther 2003; 7: 354-365.).

Briefly, one day before adenoviral infection, $5 \times 10^5$ MSCs were inoculated on a 10-cm culture dish. The cells were infected by incubating at 37° C. in 5% $CO_2$ for one hour with 5 ml of a preserved viral solution containing either 1000 pu/cell of AxCAEGFP-F/wt or AxCAhIL2-F/RGD. After infection, the cells were washed twice with PBS (pH 7.4) and supplemented with 10 ml of normal medium.

Example 35

Characteristics of Primary Culture Rat MSCs

The present inventors analyzed the surface antigens on rat primary culture MSCs using flow cytometry.

The phenotypes of the primary culture MSCs were analyzed using FACScalibur (Becton, Dickinson and Company). In summary, cells were washed twice with PBS containing 0.1% bovine serum albumin (BSA). After labeling with anti-rat CD73 (SH3), CD45, or CD11b/c monoclonal antibody (Pharmingen, San Diego, Calif., USA), the cells were labeled with a secondary antibody: goat anti-mouse IgG antibody (Immunotech, Marseille, France) combined with fluorescein isothiocyanate. Mouse $IgG_1$-labeled cells (Immunotech) or mouse $IgG_{2a}$-labeled cells were analyzed as controls with matching isotypes.

Figure 33:
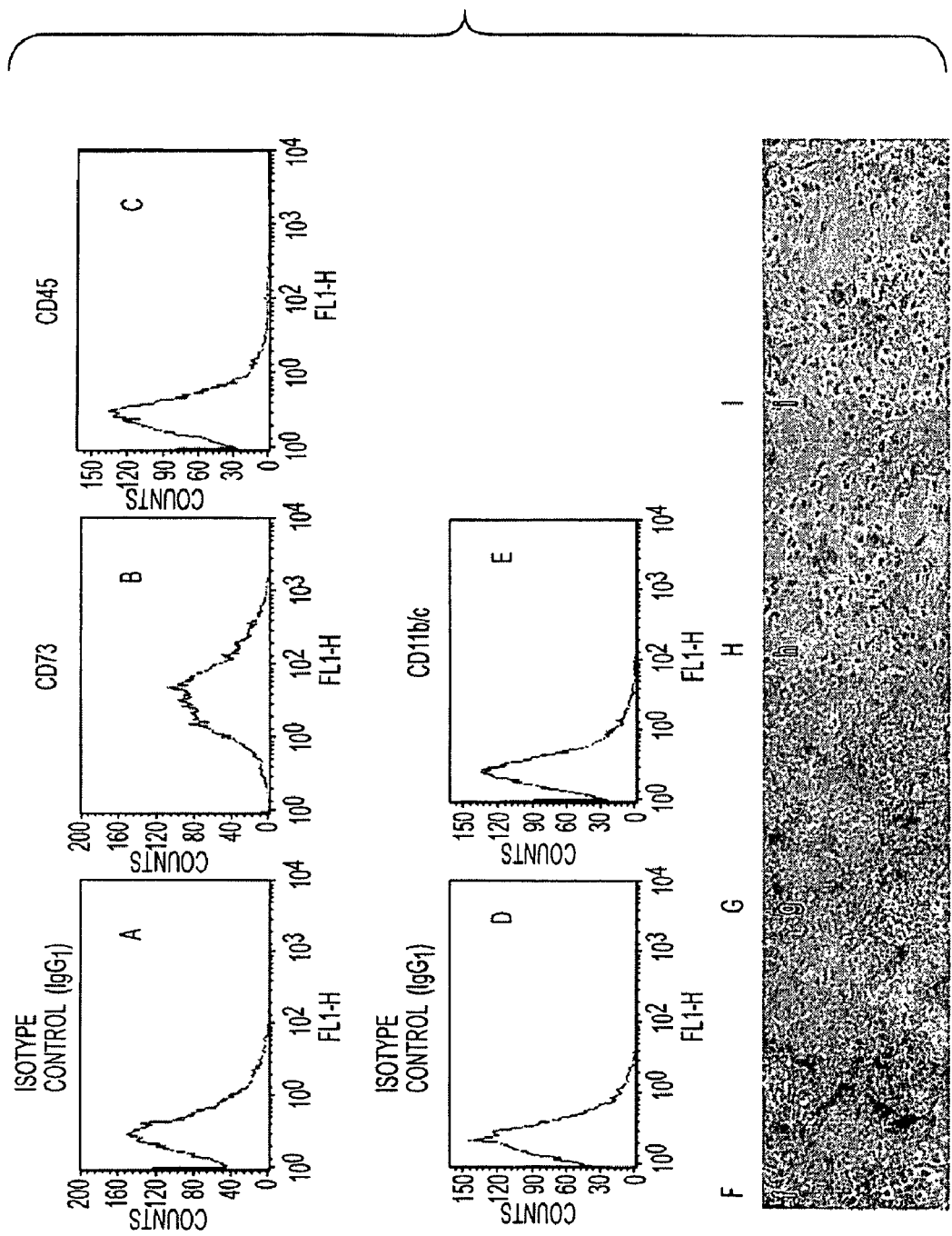

The cultured rat MSC cells were CD73 antigen-positive (FIG. 33b). This antigen has been reported as a typical mesenchymal surface antigens on human MSCs (Kobune M et al. Telomerized human multipotent mesenchymal cells can differentiate into hematopoietic and cobblestone area-supporting cells. Exp Hematol 2003; 31: 715-722.). No contamination by hematopoietic cells (CD45 or CD11/b) was detected in the MSC cultures of the present inventors (FIGS. 33c and 33e).

Example 36

The in vitro Capacity of MSCs for Differentiation into Mesenchymal Cells

The present inventors similarly investigated the differentiation of rat MSCs into typical mesenchymal lineages.

The in vitro capacities for differentiation of the rat primary culture MSCs or genetically modified MSCs into typical mesenchymal lineages were evaluated as previously described (Tsuda H et al. Efficient BMP2 gene transfer and bone formation of mesenchymal stem cells by a fiber-mutant adenoviral vector. Mol Ther 2003; 7: 354-365., Kobune M et al. Telomerized human multipotent mesenchymal cells can differentiate into hematopoietic and cobblestone area-supporting cells. Exp Hematol 2003; 31: 715-722.).

In summary, MSC cells were treated with an osteogenic differentiation medium supplemented with 80 μg/ml vitamin C phosphate (Wako Pure Chemical Industries, Ltd., Osaka, Japan), 10 mM sodium β-glycerophosphate (CALBIOCHEM, San Diego, Calif., USA), and $10^{-7}$ M dexamethasone (Sigma-Aldrich Inc.), or an adipogenic differentiation medium supplemented with 0.5 μM hydrocortisone, 500 μM isobutylmethylxanthine, and 60 μM indomethacin. The differentiation medium was exchanged every three days until Day 21.

To confirm osteogenic differentiation, cells were fixed with 10% formalin for ten minutes and stained with 5% silver nitrate (Sigma-Aldrich) for 15 minutes to detect deposition of minerals (von Kossa staining).

To detect adipogenic differentiation, the cells were fixed with 10% formalin for 15 minutes and stained with a fresh Oil Red 0 solution (a 3:2 mixture of 0.5% isopropanol stock solution of Oil Red 0 and distilled water) to detect lipid droplet formation in cell cultures.

The present inventors' cultured rat MSCs were able to differentiate into osteocyte lineage (FIG. 33f) and adipocyte lineage (FIG. 33h). The capacities of primary culture MSCs for differentiation in to osteogenic and adipogenic lineages were not affected by LI-2 gene modification using the adenoviral vector (FIGS. 33g and 33i).

Example 37

Effects of MSCs on in vitro Proliferation of 9L Cells

It is unclear whether or not in vivo administration of MSCs to brain tumors affects tumor growth. However, MSCs are known to produce cytokines such as fibroblast growth factor (FGF), and other tumor growth factors (TGFs) capable of supporting tumor growth (Tille J C, Pepper M S. Mesenchymal cells potentiate vascular endothelial growth factor-induced angiogenesis in vitro. Exp Cell Res 2002; 280: 179-191.). The present inventors initially evaluated the effects of MSC co-culture on the growth of 9L glioma cells in vitro.

The present inventors cultured Ds-Red2 (humanized Discosoma red fluorescent protein)-labeled 9L cells (9L-DsR) ($5 \times 10^4$ cell/well) alone or with MSC ($5 \times 10^3$ cell/well) or with normal rat kidney (NRK) cells ($5 \times 10^3$ cell/well) in a 6-well plate for 72 hours. The cells were then trypsinized and counted. The number of 9L-DsR cells was determined using a flow cytometer (FACScalibur).

As is shown in FIG. 34a, the proliferation of 9L cells co-cultured with MSCs (24.5±1.9% inhibition) was significantly inhibited compared to those co-cultured with NRK cells (17.4±1.9% inhibition, $p < 0.01$).

To determine the effect of soluble factors released from MSCs on the proliferation of 9L cells, the present inventors used a two-chamber culture system.

MSC or NRK cells were inoculated to DMEM containing 10% FBS in a Transwell Insert (pore size 0.4 μm, Costar Corporation, Cambridge, Mass., USA) at a density of $1 \times 10^5$ cell/Transwell. 9L cells were inoculated to DMEM containing 10% FBS in a well at a density of $5 \times 10^3$ cell/well. The co-cultures were incubated for 72 hours and the cells were directly counted to determine proliferation in the co-culture system. All data are expressed as percent inhibition, calculated according to the following equation:

Percent Growth Inhibition=[1−(Cell number of 9L-DsR co-cultured with MSC or NRK cells/Cell number of 9L-DsR cells cultured alone)]×100.

As shown in FIG. 34b, significant growth suppression of 9L cells was also effected by MSCs but was not affected by the NRK cells cultivated in the different chamber (9.8±3.1% and 1.8±1.2%, respectively, P<0.01).

These results show that the MSCs themselves have a direct antitumor effect against 9L glioma cells in vitro, which is mediated by a soluble factor.

Example 38

In vitro Migration Capability of MSCs

The present inventors evaluated the migratory nature of MSCs towards glioma cells in vitro.

A cell migration assay was conducted using a culture dish with two chambers: a Transwell (Costar Corporation). Cells were metabolically labeled with $^{125}$I-deoxyuridine ($^{125}$U-IUDR, Amersham Biosciences Corp., Piscataway, N.J., USA).

In summary, $1\times10^5$ cell/ml cells were cultured for 24 hours in a medium containing 0.1 μCi/ml $^{125}$I-IUDR. Next, the cells were washed with DMEM three times and re-suspended in the same medium. $^{125}$I-IUDR-labeled cells ($5\times10^4$ cells) were placed in an upper chamber 8 μm in pore size, and the 9L cells were placed in a lower chamber. The Transwell was left stand at 37° C. in 5% $CO_2$ for 24 hours, and the cells in the lower chamber were lysed with 1 N NaOH. The radioactivity of the cellular lysate was assessed using a gamma counter. Results of cell migration assay are expressed as percentages (count in the lower chamber as a % of the total cell count).

Neither MSC nor NRK cells spontaneously migrated, but adding 9L cells to the lower chamber stimulated spontaneous migration (FIG. 34c). Migration activity increased dose-dependently with an increasing number of 9L cells. The migration capacity of MSCs was found to be significantly higher than that of NRK cells (p<0.01).

Example 39

Migration and Tumor-tropism of Transplanted MSCs

Having established the in vitro migration capability of MSCs, the present inventors investigated whether or not transplanted MSCs migrate in vivo through a normal brain parenchyma toward intracranial gliomas.

To evaluate the intracranial distribution of MSCs, $4\times10^4$ 9L-DsR glioma cells were intracranially inoculated to the right basal glioma, and three days later $4\times10^5$ EGFP (enhanced green fluorescent protein)-labeled MSC (MSC-EGFP) cells were directly injected into the glioma or into the contralateral hemisphere. Fourteen days after tumor inoculation, the rat brain under deep anesthesia was perfused with PBS and then with 4% paraformaldehyde. The excised brain was fixed with 4% paraformaldehyde overnight and equilibrated with PBS containing 30% sucrose for 48 hours. The fixed brain was embedded in OTC compound (Miles, Inc., Elkhart, Ind., USA), snap frozen in liquid nitrogen, and stored at −70° C. The tissue was cryo-sectioned to 20 μm thick and stained with hematoxylin and eosin (H-E), or immunohistochemically stained with an anti-GFP monoclonal antibody (BD Sciences Clontech). The sections stained with the first antibody were visualized using VECTASTATIN Kit (Vector Laboratories, Burlingame, Calif., USA). Imaging was conducted with a Zeiss-Pascal microscope (Carl Zeiss, Inc., Thornwood, N.Y., USA).

As is shown in FIGS. 35a and 35c, a large glioma mass intensively stained with hematoxylin was found in all rats inoculated with the 9L cells. The glioma mass occupied the right hemisphere and caused the midline to be shifted toward the left hemisphere. Most of the gene-labeled MSCs were observed in the boundary zone between the tumor and the normal parenchyma, but after intratumoral injection some of them relatively evenly infiltrated into the tumor bed (FIG. 35b). MSCs did not migrate into the distal brain parenchyma or to the contralateral hemisphere.

Confocal laser microscopy revealed accumulation of EGFP-positive MSCs. Most of them maintained their spindle-like shape at the edge of the DsRed-positive tumor (FIG. 35e).

The MSCs existed in concordance with glioma cells, which spread from the main tumor (FIG. 35g). In contrast, MSCs inoculated into the contralateral hemisphere migrated away from the initial injection site along the corpus callosum towards the glioma cells (FIG. 35d). Most of these MSCs remained in the corpus callosum and at the edge of the adjacent tumor (FIG. 35h).

MSCs also infiltrated the tumor. Having confirmed the excellent migration capacity and glioma-tropism of MSCs after intracranial transplantation, therapeutic genetically modified cells for treating experimental glioma were therefore prepared in subsequent steps.

Example 40

Human IL-2 Production by Genetically Modified MSCs

The human IL-2 (hIL-2) was selected as a therapeutic gene since the antitumor effects of IL-2 on 9L glioma cells has been sufficiently established in rat models (Rhines L D et al. Local immunotherapy with interleukin-2 delivered from biodegradable polymer microspheres combined with interstitial chemotherapy: a novel treatment for experimental malignant glioma. Neurosurgery 2003; 52: 872-879; discussion 879-880., Iwadate Y et al. Induction of immunity in peripheral tissues combined with intracerebral transplantation of interleukin-2-producing cells eliminates established brain tumors. Cancer Res 2001; 61: 8769-8774.). Human IL-2-transfected MSCs (MSC-IL2s) were prepared by infection with a modified adenoviral vector, as previously described (Tsuda H et al. Efficient BMP2 gene transfer and bone formation of mesenchymal stem cells by a fiber-mutant adenoviral vector. Mol Ther 2003; 7: 354-365.). The rat primary culture MSCs have low expression levels of adenoviral receptor and Coxsackie-adenoviral receptor (CAR), and are relatively resistant to wild type adenoviral infection. A fiber-mutant vector was therefore used.

To measure human interleukin-2 (IL-2) production by MSCs transfected with the human IL-2 gene, MSCs were inoculated to a 24-well plate in triplicate at a density of $10^4$ cell/well, twelve hours prior to adenoviral infection. Next, the cells were infected with AxCAhIL2-F/RGD and incubated for 72 hours. The concentration of human IL-2 in the culture supernatant was measured using ELISA (IL-2 Immunoassay Kit; R&D Systems, Inc., Minneapolis, Minn., USA).

A high level of hIL-2 was detected in the supernatant of MSCs infected with a relatively low concentration of AxCA-hIL2-F/RGD (8.6±0.5 and 24.0±1.7 ng/ml/$10^4$ cell/72 h at 300 and 1000 particle units/cell, respectively). This agrees with the present inventor's previous findings. This high-level IL-2 production further increased dose-dependently with increasing adenoviral concentration.

Example 41

Prolonged Survival of Glioma-bearing Rats Transplanted with IL-2 Gene-transfected MSCs The present inventors investigated whether or not MSC-IL2s provide in vivo therapeutic benefits.

Male Fisher 344 rats (seven to eight weeks of age, 200 to 240 g) were purchased from Japan SLC, Inc. (Hamamatsu, Japan). The animals were anaesthetized and placed in a stereotaxic apparatus (Narishige Scientific Instrument Lab., Tokyo, Japan). A burr hole was made at an appropriate location (1 mm posterior to bregma and 3 mm right to midline). A 26-gauge needle was inserted at a position 4 mm ventral from the dura, and 5 µl of a PBS suspension of 9L tumor cells was inoculated thereto using a 10-µl microsyringe (Hamilton Company, Reno, Nev., USA). Then, $4 \times 10^4$ 9L cells were mixed with 5 µL of a PBS suspension of $4 \times 10^5$ MSCs or IL-2-transfected MSCs (MSC-IL2s) (infected with 1000 pu/cell AxCAhIL2-F/RGD). The resulting cell suspensions were intracranially injected as described above (FIG. 35a). Injection of the 9L cells either with unmodified MSCs or EGFP-modified MSCs (MSC-EGFPs) was also evaluated in the same manner.

Rats injected with both the 9L glioma cells and MSC-IL2s showed a significantly prolonged survival (26.3±2.2 days, P=0.0003 vs. 9L alone, P=0.0008 vs. MSC, P=0.0007 vs. MSC-EGFP) compared to the control rats, which were injected with 9L alone or with 9L cells together with unmodified MSCs or MSC-EGFPs (17.1±1.1, 22.0±0.8, 21.3±1.5 days). The rat groups injected with 9L cells together with unmodified MSCs (22.0±0.8 days, P=0.0003) or MSC-EGFPs (21.3±1.5 days, P=0.0003) survived for significantly longer than the controls, but no significant difference was found between survival of the MSC group and that of the MSC-EGFP group (P=0.5881).

IL-2 gene modification of the MSCs conferred additional therapeutic advantages to the survival of rats injected with both MSCs and 9L glioma cells, but genetic modification itself did not affect their survival.

The therapeutic benefits of MSC-IL2s were also confirmed in a therapeutic model of glioma-bearing rats. The rats were transplanted with $4 \times 10^4$ 9L glioma cells. On Day 3 after tumor inoculation, 5 µl of a PBS suspension containing $4 \times 10^5$ MSCs or MSC-IL2s was transplanted into the tumor (FIG. 36b).

The intratumoral inoculation of MSC-IL2s significantly prolonged survival of 9L glioma-bearing rats (27.7±1.1 days, P=0.0002 vs. 9L alone) as compared to the control (17.1±1.1 days). The average survival time of the MSC-EGFP-injected glioma-bearing rats (23.2±0.8 days) was significantly less than that of the MSC-IL2-injected rats (P=0.0024), but significantly more than the untreated control (P=0.0006).

Example 42

Effects of Genetically Modified MSCs on in vivo Tumor Growth Evaluated by MRI

The present inventors evaluated whether or not the prolonged survival observed after injecting MSC-IL2s or MSCs was related to tumor growth inhibition. The present inventors conducted magnetic resonance imaging (MRI) on all animals every seven days to estimate intracerebral tumor volume.

The animals were anaesthetized by an intraperitoneal injection of ketamine (2.7 to 3 mg/100-g) and xylazine (0.36 to 0.4 mg/100-g). Next, 0.2 ml of Gd-DTPA (0.8 to 1.0 mg/kg, Magnevist, Schering Japan, Tokyo, Japan) was injected to the animals, and coronal T1-weighted spin echo images (TR 500 msec, TE 10 msec, field of view 50×50 mm, slice thickness 1.5 mm, gapless) were obtained using a superconductive magnet of 7 T and 18 cm in diameter, connected via an interface to UNITYINOVA console (Oxford Instruments KK, Tokyo, Japan). The tumor volume ($mm^3$) was calculated as a sum of the Gd-DTPA enhanced portion of each MRI imaged area, times the image thickness. The estimated tumor volume based on MRI has a linear correlation with the actual tumor weight obtained immediately after the imaging test (Namba H et al. Evaluation of the bystander effect in experimental brain tumors bearing herpes simplex virus-thymidine kinase gene by serial magnetic resonance imaging. Hum Gene Ther 1996; 7: 1847-1852.).

In T1-weighted imaging, 9L gliomas were clearly recognized as enhanced regions in coronal cross sections (FIG. 37). As shown in Table 1 and FIG. 37, 9L gliomas showed progressive growth in the brains of untreated rats, and reached a fatal volume on Day 14 after tumor inoculation. Table 1 shows the 9L glioma volumes ($mm^3$) measured by MRI.

TABLE 1

|  | Day 7[b] | Day 14 | Day 21 | Day 28 |
|---|---|---|---|---|
| 9L alone (n = 4) | 17.6 ± 5.8 | 150.0 ± 10.6 | ND[c] | ND |
| MSCs (n = 4) | 5.4 ± 1.1* | 17.6 ± 5.6* | 151.3 ± 4.8 | ND |
| MSC-IL2s (n = 4) | 3.3 ± 0.9* | 5.3 ± 0.9* | 16.1 ± 0.9** | 143.7 ± 7.7 |

In Table 1, the symbol "b" represents the number of days after tumor inoculation; the symbol "c" indicates that the test was not done; the symbol "*" represents p<0.01 vs. 9L alone; and the symbol "**" represents p<0.01 vs. MSCs.

In contrast, the brain tumor volume of MSC-IL2- or MSC-treated animals was significantly smaller (P<0.01 compared to the untreated control on Day 14 after tumor inoculation). On Day 14, the unmodified MSC-treated group and the MSC-IL2-treated group showed no significant difference in tumor volume. However, the IL-2 gene modification showed a clear therapeutic effect 21 days after tumor inoculation according to MRI. At this time, the gliomas in unmodified MSC-treated animals had virtually reached fatal volume, but the tumors remained small when the animals were treated with MSC-IL2s. These findings on changes in tumor volume agree with the survival duration in different treatment groups.

Example 43

Induction of Lymphocyte Invasion into Gliomas by MSC-IL2 Transplant

The present inventors investigated whether transplantation of MSC-IL2s to 9L gliomas induces in vivo immunoreaction.

To detect the infiltration of CD4 or CD8-positive cells into gliomas after MSC-IL2 treatment, $4 \times 10^4$ 9L-DsR cells were transplanted, and $4 \times 10^5$ cells of MSC-EGFPs or MSC-IL2s were injected into the tumor three days after tumor inoculation. The rats were sacrificed seven days after tumor inoculation, and the excised brains were embedded in paraffin. Brain preparations 6 μm thick were immunohistochemically stained with an anti-rat CD4 (Clone W3/25, Serotec Inc., Oxford, UK) or an anti-rat CD8 (Clone OX-8, Serotec Inc.) monoclonal antibody, and visualized using a Vectastain ABC Kit (Vector Laboratories Ltd.).

Histological analyses of MSC-treated 9L glioma using HE staining revealed that the IL2 gene-modified MSC-treated 9L gliomas showed a large amount of mononuclear leukocyte infiltration (FIGS. 38c and d). In contrast, unmodified MSC-transplanted gliomas showed minimal inflammatory cell infiltration (FIGS. 38a and b). Samples of the unmodified MSC-transplanted tumors showed virtually no infiltration of CD4 and CD8 cells (FIGS. 38e and g). In clear contrast to this, tumors inoculated with IL-2 genetically modified MSCs showed infiltration of CD4- and CD8-positive lymphocytes (FIGS. 38f and h).

Example 44

Statistical Analyses

Statistical analysis of the cell proliferation assays and migration assays in Examples 32 to 43 were performed using Student's t-tests. Scheffe's tests were conducted for tumor volume assessments on Day 7 and Day 14, and Student's t-tests were performed on Day 21. P values less than 0.05 in the Student's t-tests and Scheffe's tests were considered significant. Statistical analyses of survival were conducted using log-rank tests.

Example 45

MSCs Introduced with Cytokine Genes Other than BDNF (1) Cytokine Productivity

Genes other than the BDNF (brain-derived neurotrophic factor) gene, such as GDNF (glial cell line-derived neurotrophic factor), CNTF (ciliary neurotrophic factor), or NT3 (neurotrophin-3) gene, were introduced into MSCs, and production of BDNF, GDNF, CNTF and NT3 by cultivated cells was examined.

The results are shown in FIG. 39. MSCs transfected with AxCAhBDNF-F/RGD (MSC-BDNFs) at MOIs of 100, 300, 1000, or 3000 pu/cell secreted BDNF at rates of 0.230±0.110, 0.434±0.122, 0.931±0.101, and 1.860±0.41 ng/$10^5$ cell/48-hr, respectively. The untransfected MSCs also produced BDNF (0.0407±0.0059 ng/$10^5$ cell/48-hr).

For GDNF, those MSCs transfected with AxCAhGDNF-F/RGD (MSC-GDNFs) at MOIs of 300, 1000, or 3000 pu/cell secreted GDNF at rates of 1.05±0.20, 2.26±0.41, and 4.15±0.54 ng/$10^5$ cell/48-hr, respectively. Untransfected MSCs also produced GDNF protein (0.044±0.034 ng/$10^5$ cell/48-hr). For CNTF, MSCs transfected with AxCAhCNTF-F/RGD (MSC-CNTFs) at MOIs of 3000, 1000, or 300 pu/cell secreted CNTF at rates of 0.136±0.028, 0.854±0.145, and 3.58±0.43 ng/$10^5$ cell/48-hr, respectively. Untransfected MSCs also produced CNTF protein (0.0520±0.0150 ng/$10^5$ cell/48-hr).

For NT3, MSCs transfected with AxCAhNT3-F/RGD (MSC-NT3s) at MOIs of 300, 1000, or 3000 pu/cell secreted NT3 at rates of 2.67±0.09, 4.24±0.16, and 6.88±0.07 ng/$10^5$ cell/48-hr, respectively. Untransfected MSCs also produced NT3 protein (0.12±0.001 ng/$10^5$ cell/48-hr).

(2) Evaluation of Neurological Disorders Induced by Cerebral Ischemia

MSC cells introduced with the GDNF, CNTF, or NT3 gene were transplanted to cerebral infarction regions as in the above Examples, and limb placement tests were conducted. The limb placement tests were performed according to the procedure in Example 27 (1). Limb placement disorder was evaluated according to the following parameters: 0: severe neurological disorder, 16: no neurological disorder. Limb placement tests were conducted one eight, and 15 days after MCAO.

The results are shown in FIG. 40. The four ischemic groups showed no statistical difference in limb placement score one day after MCAO (which was prior to intracranial injection of MSCs). Eight days after MCAO, the limb placement scores of rats administered with MSC-BDNF and MSC-GDNF were significantly greater than those of the DMEM rats (each P<0.05). Fifteen days after MCAO, the rats administered with MSC-BDNF and MSC-GDNF also showed significantly higher scores than those in the DMEM group (each P<0.05).

In contrast, on both Day 8 and Day 15 the rats administered with MSC-CNTF and MSC-NT3 did not score higher than the DMEM-administered control rats.

(3) Reduction in Infarct Volume after MSC-BDNF and MSC-GDNF Treatment as Determined by MRI MRI was conducted on all animals two, seven, and 14 days after MCAO. The procedures and evaluations are as in Example 27 (3).

Compared to the control DMEM group rats, MSC-BDNF group and MSC-GDNF group rats showed significant reductions in HLV seven days after MCAO (each P<0.05). Likewise, 14 days after, the MSC-BDNF group and MSC-GDNF group rats showed significant reductions in HLV compared to the control DMEM group rats. Both seven and 14 days after, rats administered with MSC-CNTF or MSC-NT3 showed no significant recovery in HLV, as compared to the control DMEM group and the MSC-EGFP group (each P<0.05). The results are shown in FIG. 41.

FIG. 42 shows representative T2-weighted (T2W) images of rats administered with DMEM, MSC-BDNF, MSC-GDNF, MSC-CNTF, or MSC-NT3, where the images were obtained two and seven days after MCAO. The MSC-BDNF group and MSC-GDNF group showed a reduction in ischemic injury volume on Day 7, as compared to other groups.

Example 46

Intravenous Administration of MSC-BDNF Cells

MSC cells ($10^7$ cells) introduced with the BDNF gene were prepared according to the above Examples. In the rats with severe cerebral infarction (permanent middle cerebral artery occlusion model), described in Example 16, cerebral infarction was produced and the above cells were administered into the left cava twelve hours later.

MRI was used to chronologically examine the therapeutic effects on living animals. The cerebral infarction lesions of the untreated group (control), MSC-administered group, and MSC-BDNF-administered group were observed 24 hours, 72 hours, and seven days after MCAO (FIG. 43).

In addition, the cerebral infarct volumes of the untreated group (control), MSC-administered group, and MSC-BDNF-administered group were calculated and examined six hours, 24 hours, 72 hours, and seven days after MCAO (FIG. 44).

A treadmill test was conducted on the untreated group (control), MSC-administered group, and MSC-BDNF-administered group 24 hours, 72 hours, and seven days after MCAO to examine motion recovery (FIG. 45).

All data demonstrate that MSCs introduced with the BDNF gene show higher therapeutic effects than MSCs alone.

Example 47

Intravenous Administration of MSC-PLGF Cells

Instead of the BDNF gene, PLGF (placental growth factor) was introduced into MSCs. Three hours after producing a cerebral infarction in rats with severe cerebral infarction (permanent middle cerebral artery occlusion model), described in Example 16, MSC-PLGF cells ($10^7$ cells) were administered into the left cava of the rats.

The cerebral infarction lesions in the untreated group (control) and in the MSC-PLGF-administered group were observed using MRI three hours, 24 hours, three days, and seven days after MCAO (FIG. 46). The results were compared in DW2 (b=1000) images and $T_2$WI images.

The volumes of areas showing abnormal signals which arose after MCAO were sequentially quantified using MRI analysis. The results show that reduction began 24 hours after MCAO in the DWI images, and three days after MCAO in the $T_2$WI images (FIG. 47).

To compare cerebral infarct volumes, the brain tissues of the untreated group (control) and MSC-PLGF-administered group were stained with TTC seven days after MCAO (FIG. 48).

All data demonstrate that MSCs introduced with the PLGF gene show higher therapeutic effects.

Example 48

Angiogenetic Effects of Injecting Angiopoietin Gene into a Cerebral Infarction Model The angiopoietin gene was directly injected into the cerebral infarction lesions of a rat cerebral infarction model (transient middle cerebral artery occlusion model: 45 minutes).

An adenovirus was used as a vector for introducing the angiopoietin gene. Capillary vessels were visualized using FITC dextran or Evans Blue to evaluate angiogenesis.

Images of the blood vascular system of a normal rat visualized with Evans Blue and FITC dextran are shown in FIG. 49.

FITC was used to visually compare angiogenesis induction in MCAO-model rats with or without gene injection (FIG. 50). The ipsilateral/contralateral ratio was also quantified (FIG. 51).

Evans Blue was also used to visually compare angiogenesis induction in MCAO-model rats with or without gene injection (FIG. 52).

As a result, remarkable angiogenesis was observed. Cerebral infarction is a disease in which blood vessels are occluded. Thus incorporating angiogenesis is expected to exhibit remarkable therapeutic effects.

Example 49

Local Administration of MSCs in Chronic Stages after Cerebral Infarction

MSCs were locally administered to rats with severe cerebral infarction (permanent middle cerebral artery occlusion model), described in Example 16, in chronic stages after cerebral infarction, and the therapeutic effect of this was studied. Specifically, two weeks after MCAO, $1 \times 10^4$ MSCs were transplanted into the cerebral infarction region. Treadmill tests were conducted one day, 14 days, 28 days, and 42 days after MSC administration, and motor function recovery was compared with an MSC-untreated group (the control). As a result, improvements in motor function could be seen. The results are shown in FIG. 53. Therapeutic effects were fairly low compared to transplantation in acute stages; however, some therapeutic effects were still observed. It is preferable to conduct treatment in an acute stage, since treatment in an acute stage shows greater therapeutic effect. However, in actual clinics the requirements from patients already with cerebral infarction are large, and thus the treatment is also thought to be effective for patients in chronic stages. Accordingly, the agents of the present invention are preferably used for patients with cranial nerve diseases in an acute stage, but they are not restricted to acute stages, and are also effective for patients in chronic stages, for example.

Example 51

Cell Preparation

The use of animals in this study was approved by the animal care and use committee of Sapporo Medical University and all procedures were carried out in accordance with institutional guidelines.

BMSCs

Bone marrow was obtained from femoral bone in adult female Sprague-Dawley rats weighing 200-250 g. Rats were anesthetized with ketamine (50 mg/kg) and xylazine (10 mg/kg) i.p. A small hole (2×3 mm) in the femoral bone was made with an air drill following skin incision (1 cm). Bone marrow (0.5 ml) was aspirated, diluted to 25 ml with Dulbecco's modified Eagle's medium (DMEM) (SIGMA, St Louis, Mo.) supplemented with 10% heat-inactivated fetal bovine serum (FBS) (GibcoBRL, Grand Island, N.Y.), 2 mM L-glutamine (Gibco BRL), 100 U/ml penicillin, 0.1 mg/ml streptomycin (Gibco BRL), was plated on 50-cm$^2$ Tissue Culture Dish (IWAKI, Tokyo, Japan), and incubated in a humidified atmosphere of 5% $CO_2$ at 37° C. for three days. BMSCs, when selected by plastic adhesion, it is preferred to eliminate the nonadherent cells by replacing the medium about 48 hours after cell seeding.

When cultures almost reached confluence, the adherent cells were detached with trypsin-EDTA solution (SIGMA) and subcultured at $1 \times 10^4$ cells/ml.

PMSCs

Peripheral blood was obtained from adult Sprague-Dawley rats weighting 200-250 g. Rats were deeply anesthetized with ketamine (50 mg/kg) and xylazine (10 mg/kg) i.p. Peripheral blood (about 8 ml) was aspirated from vena cava superior with a 18 gauge needle. Peripheral blood was diluted 1:3 in Puregene RBC Lysis Solution (Gentra systems, Minneapolis, Minn.) and was incubated in a 50-ml conical centrifuge tube for 5 min at room temperature. The tube was centrifuged at 3500 rpm for 2 minutes and the supernatant was discarded. The cell pellet was suspended in DMEM supplemented with 10% FBS, 2 mM L-glutamine, 100 U/ml penicillin, 0.1 mg/ml streptomycin and was plated on 50-cm$^2$ plastic tissue culture dishes and incubated in a humidified atmosphere of 5% $CO_2$ at 37° C. PMSCs, when selected by plastic adhesion, it is preferred to eliminate the nonadherent cells by replacing the medium about 48 hours after cell seeding. When cultures almost reached confluence, the adherent cells were detached with trypsin-EDTA solution and subcultured at $1\times10^4$ cells/ml. The cell numbers of both BMSC and PMSC were counted in a cytometer every a week.

Some of cultured cells were rinsed in PBS for three times and fixed for 10 minutes with a fixative solution containing 4% paraformaldehyde in 0.14 M Sorensen's phosphate buffer, pH 7.4, at room temperature. The cells were counterstained with May-Giemsa, and phase-contrast microphotographs were obtained using a Zeiss microscope.

Example 52

Phenotypic Characterization

Flow cytometric analysis of BMSCs and PMSCs were performed. Briefly, cell suspensions were washed twice with phosphate-buffered saline (PBS) containing 0.1% bovine serum albumin (BSA). For direct assays fifty thousand cells were incubated with FITC-conjugated CD 45 (Leukocyte Common Antigen) (BD Bioscience pharmingen, San Jose, Calif.), PE-conjugated CD 73 (Ecto-5'-nucleotidase) (BD Bioscience pharmingen), PE-conjugated CD 90 (Thy-1) (eBioscience, San Diego, Calif.) and PE-conjugated CD 106 (VCAM-1) (BD Bioscience pharmingen) at 4° C. for 30 minutes, and then washed twice with PBS containing 0.1% BSA. The cells were analyzed by cytometric analysis using a FACSCalibur flow cytometer (Becton Dickinson, San Jose, Calif.) with the use of CellQuest software.

Example 53

Induction of MSCs to Floating Spheric Cells

When inducing MSCs to floating spheric cells like neurospheres, MSCs were detached with trypsin-EDTA solution and were collected in a 50-ml tube in DMEM+10% FBS. After rinsing with DMEM, cells ($5\times10^4$ cells/ml) were suspended in Neural Progenitor basal medium (NPBM) (Cambrex, One Meadowlands Plaza, N.J.) supplemented with 2 mM L-glutamine, 10 ng/ml epidermal growth factor (EGF), 10 ng/ml basic fibroblast growth factor (bFGF), 100 U/ml penicillin, 0.1 mg/ml streptomycin, and were plated on Non-treated dish (IWAKI). Growth factors (EGF and bFGF) were added every day.

Example 54

Differentiation of Neurospheres to Neural Cells

When inducing the floating spheric cells (neurospheres) to neural cells, floating spheric cells were collected by centrifuging at 1500 rpm for 5 min, suspended in NPBM supplemented with 2 mM L-glutamine, 100 U/ml penicillin, and 0.1 mg/ml streptomycin, mechanically dissociated, and were plated on plastic tissue culture dish.

Example 55

RT-PCR

Total RNA was extracted from each cell culture using RNeasy Mini Kit (QIAGEN, Hilden, Germany). Reverse transcription with 100 ng RNA was performed using the SuperScript II RNase H— reverse transcriptase (Invitrogen, Carlsbad, Calif.). A final volume of 20 µl containing 100 ng RNA, 4 µl First Strand Buffer, 10 mM dNTPs, 100 mM DTT, 0.5 µg Oligo(dt)12-18 and 100 U of SuperScript II RNase H— reverse transcriptase was used. Then a PCR reaction was carried out using the Hot Star Taq Master Mix Kit (QIAGEN) in a final volume of 50 µl containing 25 µl Hot Star Taq Master Mix, and 10 mM upstream sense and downstream sense primers. Cyclical parameters were denatured at 94° C. for 30 sec, annealed at 60° C. for 30 sec, and finally elongated at 72° C. for 30 sec. Thirty five cycles were performed for each primer set. PCR products were resolved on 2% gel agarose. Primer sequence of amplified products were: mouse β-Actin sense (5'-TGGAATCCTGTGGCATCCATGAAAC-3') (SEQ ID NO: 3), mouse β-Actin antisense (5'-TAAAACGCAGCT-CAGTAACAGTCCG-3') (SEQ ID NO: 4), rat Nestin sense (5'-CTTAGTCTGGAGGTGGCTACATACA-3') (SEQ ID NO: 5), rat Nestin antisense (5'-GAGGATAGCAGAA-GAACTAGGCACT-3') (SEQ ID NO: 6), rat neurofilament M (NF-M) sense (5'-GGTCACTTCACATGCCATAGTCAA-3') (SEQ ID NO: 7), rat NF-M antisense (5'-GGCTCAGT-TGGTACTTTGCGTAA-3') (SEQ ID NO: 8), rat glial fibrillary acid protein (GFAP) sense (5'-ATTCCGCGCCTCTCCCTGTCTC-3') (SEQ ID NO: 9), and rat GFAP antisense (5'-GCTTCATCCGCCTCCT-GTCTGT-3') (SEQ ID NO: 10).

Example 56

Immunocytochemical Analysis

To identify the cell type derived from the BMSCs and PMSCs, immunocytochemical studies were performed with the use of antibodies to neurons (monoclonal mouse NF-M, SIGMA), and astrocytes (monoclonal mouse anti-GFAP, SIGMA). Cultured cells were rinsed in PBS for three times and fixed for 10 minutes with a fixative solution containing 4% paraformaldehyde in 0.14 M Sorensen's phosphate buffer, pH 7.4, at room temperature. After washing twice in PBS and incubating in PBS containing 0.1% Triton X-100 for 10 minutes at room temperature, fixed cells were incubated for 30 minutes in a blocking solution containing 0.1% Triton X-100, and 3% BSA before incubation with the primary antibody. Primary antibodies are labeled with Alexa Fluor 488 or Alexa Fluor 594 using Zenon mouse IgG Labeling Kits (Molecular Probes Inc., Eugene, Oreg.) according to the manufacturer's instruction. After immunostaining, coverslips were mounted cell-side down on microscope slides using mounting medium (DAKO Corp., Carpinteria, Calif.). Confocal images were obtained using a Zeiss laser scanning confocal microscope with the use of Zeiss software.

All data are presented as mean values ±S.D. Differences among groups were assessed by ANOVA with Scheffe's post hoc test to identify individual group differences. Differences were deemed statistically significant at $P<0.05$.

Example 57

Characteristics of BMSCs and PMSCs

After removing non-adherent cells by replacing the medium (day 2 in culture), a small portion of attached nucleated cells was visualized in the BMSC culture dish. By day 14 in culture, the attached BMSCs had developed into an adherent layer containing abundant dispersed fibroblast-like cells, and each colony was predominantly formed by several fibroblast-like cells (FIG. 54A). By day 28 in culture, the BMSCs had proliferated and tended to form a near continuous layer comprising mainly fibroblast-like cells (FIG. 54B).

In the cultures of PMSCs derived from peripheral blood, fibroblast-like cells with thin elongated processes around a central nucleus made their appearance at two weeks after culture initiation (FIG. 54C). By day 28 in culture, the cells also continued proliferating and formed a layer of flattened cells (FIG. 54D), with morphological features resembling those of BMSCs.

FIGS. 54E and 54F are flow cytometric data of the expression of surface antigens on BMSCs and PMSCs, respectively. These results show that both BMSCs and PMSCs express a similar pattern of surface antigens: $CD45^-$, $CD73^+$, $CD90^+$, and $CD106^-$.

Example 58

Growth Rate

The number of BMSCs and PMSCs were counted at weekly intervals in order to characterize the proliferation rate (FIG. 55). BMSCs slowly proliferated in the initial two weeks, and entered a rapid growth phase for the next four weeks. Proliferation of BMSCs became slower after 6 weeks, but cell number was maintained for the next two weeks. The number of BMSCs increased more than 4 logs for cultures maintained for eight weeks. In contrast, PMSCs displayed slow but constant growth over 8 weeks in culture, and expanded over 6-fold.

Example 59

Transformation of MCSs to Neurospheres

BMSCs transformed to nestin-positive neurospheres using an induction protocol (FIG. 56A) described in Methods. BMSCs began forming floating cell masses and nestin-positivity when they were inhibited from adhering to the culture dishes (non-treated dishes) and maintained in the appropriate medium and growth factors (see Methods). RT-PCR analysis for nestin mRNA expression in cDNA samples of cultured adherent BMSCs (FIG. 56E-*a*) and floating spheric cells (neurospheres) (FIG. 56E-*b*) are shown in FIG. 3E. The floating spheric cells displayed an amplification of a PCR fragment of the expected size for nestin (420-430 bp), but the cultured non-transformed BMSCs did not (FIG. 56F-*a*). PMSCs also showed similar transformation to nestin-positive neurospheres after induction (FIG. 56B), which was confirmed by RT-PCR (FIG. 56F-*b*).

Example 60

Differentiation from MSC-derived Neurosphere to Neural Cells

MSC-derived neurospheres differentiated into neuron- and glia-like cells in the appropriate culture condition. BMSC-derived neurospheres differentiated into adherent neural cells when they were mechanically dissociated, plated on plastic culture dish, and maintained in NPBM without growth factors. Adherent single layers contained abundant neuron- and glial-like cells. Immunocytochemical analysis indicated that the neuronal cells showed NF-M positivity (FIG. 57A), which was confirmed by RT-PCR. A sample of adherent cells displayed an amplification of a PCR fragment of the expected size for NF-M (330-340 bp) (FIG. 57E-*b*).

In addition, GFAP-positive cell differentiation was also demonstrated with immunostaining (FIG. 58A) and RT-PCR analysis (FIG. 5E-*b*). The expected size for an amplified PCR fragment of GFAP is 430-440 bp. PMSC-derived neurosphere showed similar differentiating potential to NF-M-positive neurons (FIG. 57B) and GFAP-positive glia (FIG. 58B), which were confirmed by RT-PCR in FIGS. 57F-*b* and 58F-b, respectively.

Example 61

Preparation of Mesenchymal Stem Cell Prepared from Rat Bone Marrow

The use of animals in this study were approved by the animal care and use committee of Sapporo Medical University and all procedures were carried out in accordance with institutional guidelines. Bone marrow was obtained from the femoral bones of the adult Sprague-Dawley rats weighting 200-250 g. Rats were anesthetized with ketamine (50 mg/kg) and xylazine (10 mg/kg) i.p. A small hole (2×3 mm) in the femoral bone was made with an air drill following skin incision (1 cm), and 0.5 ml bone marrow was aspirated with an 18 gauge needle. Bone marrow (0.5 ml) was mixed with 10 ml of Dulbecco's Modified Eagle Medium (DMEM, Sigma, USA)+10% FBS (Gibco, USA)+0.2 mM L-glutamine (Sigma, USA)+Penicillin/Streptomycin (Sigma, USA) solution, were plated in 100-$cm^2$ plastic tissue culture flasks and incubated for three days. After washing away the free cells, the adherent cells were cultured in the same medium in a humidified atmosphere of 5% $CO_2$ at 37° C. After reaching confluence, they were harvested and cryopreserved as primary BMSCs.

Example 62

Preparation of Mesenchymal Stem Cells Derived from Rat Peripheral Blood

Peripheral blood was obtained from the adult Sprague-Dawley rats weighting 200-250 g. Rats were anesthetized with ketamine (50 mg/kg) and xylazine (10 mg/kg) i.p. Peripheral blood (7-10 ml) was aspirated from vena cava superior with an 18 gauge needle. The peripheral blood was mixed with 30 ml of RBC lysis solution (Gentra systems, Minneapolis, USA), was reacted for 5 minutes at room temparature, and was centrifuged at 3500 rpm for 2 minutes. The RBC lysate supernatant was poured off, and the mononuclear cell fraction was resuspended with DMEM+10% FBS+0.2 mM L-glutamine+Penicillin/Streptomycin solution. Cells were plated in 100-$cm^2$ plastic tissue culture flasks and the adherent cells were cultured in the same medium in a humidified atmosphere of 5% $CO_2$ at 37° C. After reaching confluence, they were harvested and cryopreserved as PMSCs.

Example 63

Phenotypic Characterization of the Primary BMSCs and PMSCs

Flow cytometric analysis of BMSCs and PMSCs was performed. Briefly, cell suspensions were washed twice with PBS containing 0.1% bovine serum albumin (BSA). For direct assays one million cells were incubated with FITC-conjugated CD45 (Leukocyte Common Antigen) (BD Bioscience pharmingen, San Jose, Calif.), and PE-conjugated CD73 (Ecto-5'-nucleotidase) (BD Bioscience pharmingen, San Jose, Calif.), PE-CD90 (Thy-1) (eBioscience, San Diego, Calif.) and PE-CD106 (VCAM-1) (BD Bioscience pharmingen, San Jose, Calif.) at 4° C. for 30 minutes, and then washed twice with PBS containing 0.1% BSA. The cells were analyzed by cytometric analysis using a FACSCalibur flow cytometer (Becton Dickinson) with the use of CellQuest software.

Example 64

Cerebral Ischemic Model

The rat MCAO model was used as a stroke model. Permanent MCAO was by using method of intraluminal vascular occlusion as described by Longa E Z, Weinstein P R, Carlson S, Cummins R. Reversible middle cerebral artery occlusion without craniectomy in rats. Stroke 1989; 20:84-91. Adult female Sprague-Dawley rats weighing 250-300 g were initially anesthetized with ketamine (50 mg/kg) and xylazine (10 mg/kg) i.p. A length of 20.0-22.0 mm 4-0 surgical suture (Dermalon, Sherwood Davis and Geck, UK) with the tip rounded by heating near a flame was advanced from the external carotid artery into the lumen of the internal carotid artery until it blocked the origin of the MCA.

Example 65

Transplantation Procedures

Experiments consisted of three groups (n=85). In group 1 (control), rats were given medium alone (without donor cell administration) injected i.v. at 6 h after MCAO (just after the initial MRI measurement) (n=15). In group 2, rats were given rat BMSCs ($1.0 \times 10^6$P) in 1 ml total fluid volume (DMEM) injected i.v. at 6 h after MCAO (n=15). In group 3, rats were given rat PMSCs ($1.0 \times 10^6$) injected i.v. at 6 h after MCAO (n=15). All rats were daily injected with cyclosporine (10 mg/kg) i.p. Five rats in each group were used to calculate the infarct lesion volume, and the remaining rats were used for the additional histological, behavior and other analysis.

In some experiments, Adex1CAlacZ adenovirus was used to transduce the LacZ gene into the MSCs. Details of the construction procedures are described in the cited references to Iihoshi (Brain Res 2004; 1007:1-9), Nomura (Nueorscience 2005; 136:161-169), Nakamura (Cancer Res 1994; 54:5757-5760), Nakagawa (Hum Gene Ther 1998; 9:1739-1745), and Takiguchi (Life Sci 2000; 6:991-1001). This adenoviral vector carries an adenovirus serotype-5 genome lacking the E1A, E1B and E3 regions to prevent virus replication, and contains the *Escherichia coli* h-galactosidase gene, lacZ gene, between the CAG promoter, composed of the cytomegalovirus enhancer plus the chicken β-actin promoter, and the rabbit β-globin polyadenylation signal in the place of the E1A and E1B regions. The recombinant adenovirus was propagated and isolated in 293 cells. Viral solutions were stored at $-80°$ C. until use. For in vitro adenoviral infection, $1.0 \times 10^6$ rat MSCs were placed with Adex1CAlacZ at 50 MOI for 1 h and incubated at $37°$ C. in DMEM containing 10% fetal calf serum.

Example 66

MR Imaging

Rats were anesthetized with ketamine (50 mg/kg) and xylazine (10 mg/kg) i.p. The femoral vein of rats was cannulated for contrast agent injection. Each rat was placed in an animal holder/MRI probe apparatus and positioned inside the magnet. The animal's head was held in place inside the imaging coil. All MRI measurements were performed using a 7-T, 18-cm-bore superconducting magnet (Oxford Magnet Technologies) interfaced to a UNITYINOVA console (Oxford Instruments, UK and Varian, Inc., Palo Alto, Calif., USA). $T_2$ weighted images ($T_2$WI) were obtained from a 1.0-mm-thick coronal section with a 0.5 mm gap using a 30 mm×30 mm field of view, TR=3000 ms, TE=37 ms, and reconstructed using a 256×128 image matrix. Diffusion weighted images (DWI) were obtained at the same condition as $T_2$ WI except b value (b value=966) and image matrix (128×128). Accurate positioning of the brain was performed to center the image slice 5 mm posterior to the rhinal fissure with the head of the rat held in a flat skull position. MRI measurements were obtained 6 hours, 1 day, 3 days and 7 days after MCAO.

The ischemic lesion area was calculated from both $T_2$WI and DWI using imaging software (Scion Image, Version Beta 4.0.2, Scion Corporation), based on the method described by Nomura (Neuorscience 2005; 136:161-169) and Neumann-Haefelin (Stroke 2000; 31:1965-1972). For each slice, the higher intensity lesions in both $T_2$WI and DWI where the signal intensity were 1.25 times higher than the counterpart in the contra-lateral brain lesion were marked as the ischemic lesion area, and infarct volume was calculated taking slice thickness (1 mm/slice) into account.

Example 67

Dynamic Susceptibility Contrast-enhanced Perfusion Weighted Imaging (PWI)

PWI was acquired using $T_2$ weighted (TR=13 msec, TE=6.0 msec) gradient echo sequence. A dynamic image series of 30 measurements resulted in a total scan time of 26 seconds, with a FOV of 30 mm, and image acquisition matrix of 128×64 which was interpolated by zero-filling to 512×512. During the dynamic series, a triple dose (0.6 ml/kg) bolus injection of Magnevist (Schering A G, Deutschland) was started after the $5^{th}$ acquired volume to ensure a sufficient pre-contrast baseline. Images were reconstructed by an Inova Vision. PWI measurements were obtained 6 hrs, 1, 3 and 7 days after MCAO. For the PWI and PWI-derived parameter maps, only one representative slice (involving cortex and stria terminalis) with the maximum lesion involving both cortex and striatum was chosen for CBF quantification. The readout of abnormal rCBF from the regions of perfusion deficiency as a percentage of that measured in the contralateral brain was generated using Perfusion Solver software. Regions of interest (ROI) consist of four groups, based on the results of DWI, $TB_{2B}$WI and PWI. ROI-1 is defined as abnormal in all images, ROI-2 as normal in only $TB_{2B}$WI and abnormal in others, ROI-3 as abnormal in only PWI and normal in others, ROI-4 as normal in all images (FIG. 63).

Example 68

Histological Analysis

TTC Staining and Quantitative Analysis of Infarct Volume

One week after transplantation, the rats were anesthetized with ketamine (50 mg/kg) and xylazine (10 mg/kg) i.p. The brains were removed carefully and dissected into coronal 1 mm sections using a vibratome. The fresh brain slices were immersed in a 2% solution of 2,3,5-triphenyl tetrazolium chloride (TTC) in normal saline at $37°$ C. for 30 min. The cross-sectional area of infarction in each brain slice was examined with a dissection microscope and was measured using an image analysis software (Adobe Photoshop). The total infarct volume for each brain was calculated by summation of the infarcted area of all brain slices.

H-E Staining

The rats were anesthetized with ketamine (50 mg/kg) and xylazine (10 mg/kg) i.p. and perfused through the heart, first with PBS, and then with a fixative solution containing 10% paraformaldehyde in 0.14 M Sorensen's phosphate buffer, pH 7.4. Brains were removed and placed in 10% paraformaldehyde in phosphate-buffer overnight, dehydrated, and embedded in paraffin. Transverse sections (1.5 µm) were cut, and were counterstained with hematoxylin and eosin.

Example 69

Detection of Donor MSCs and Phenotypic Analysis in vivo X-gal Staining

One week after transplantation, brains of the deeply anesthetized rats were removed and fixed in 0.5% glutaraldehyde in phosphate buffer for 1 h. Brains were removed and brain slices (1000 µm) were cut with a vibratome and β-galactosidase expressing cells were detected by incubating the sections at 37° C. overnight with X-gal to a final concentration of 1 mg/ml in X-Gal developer (35 mM $K_3Fe(CN)_6$/35 mM $K_4Fe(CN)_6 3H_2O$/2 mM $MgCl_2$ in phosphate-buffered saline) to form a blue reaction product within the cell.

Example 70

Immunohistochemistry

One week after transplantation, analysis of the transplanted cells in vivo was carried out using laser scanning confocal microscopy. Brains of the deeply anesthetized rats were removed, fixed in 4% paraformaldehyde in phosphate-buffer, dehydrated with 30% sucrose in 0.1 M PBS for overnight, and frozen in powdered dry ice. Coronal cryostat sections (10 µm) were processed for immunohistochemistry. To identify the cells derived from the donor peripheral blood, immuno-labeling studies were performed with the use of antibodies to beta-galactosidase (rhodamine-labeled polyclonal rabbit anti-beta-galactosidase antibody, DAKO). To excite the rhodamine fluorochrome (red), a 543-nm laser line from a HeNe laser was used. Confocal images were obtained using a Zeiss laser scanning confocal microscope with the use of Zeiss software.

Example 71

Capillary Vessels in Ischemic Brain

To examine capillary vessels in ischemic brain, fluorescein isothiocyanate (FITC) dextran ($2 \times 10^P$ molecular weight, Sigma; 0.1 mL of 50 mg/mL) was administered intravenously to the ischemic rats subjected to 7 days of MCAO. Brains were removed and brain slices (100 µm) were cut with a vibratome. To excite the FITC (green), a 488-nm laserline generated by an argon laser was used. Confocal images were obtained using a Zeiss laser scanning confocal microscope with the use of Zeiss software, and vessel volumes were measured in the three dimensions using the software of Zeiss LSM.

Example 72

Treadmill Stress Test

Rats were trained 20 min per day for 2 days a week to run on a motor driven treadmill at a speed of 20 m/min. Rats were placed on a moving belt facing away from the electrified grid and induced to run in the direction opposite of the movement of the belt. Thus, to avoid foot-shocks (with intensity in 1.0 mA), the rats had to move forward. Only the rats that had leaned to avoid the mild electrical shock were included in this study (n=15). The maximum speed at which the rats could run on a motor driven treadmill was recorded.

The lesion volume, the rCBF ratio, the capillary vascular volume, and the behavior scores (treadmill stress test) recorded were statistically analyzed. Data are presented as mean values ±S.D. Differences among groups were assessed by ANOVA with Scheffe's post hoc test or Kruskal-Wallis test to identify individual group differences. Differences were deemed statistically significant at $P<0.05$.

Example 73

Characteristics of BMSCs and PMSCs

BMSCs and PMSCs cultured as plastic adherent cells could be maintained in vitro. The morphological features of the BMSCs are shown in FIG. 59A. Characteristic flattened and spindle-shaped cells can be recognized. An antigenic characteristic feature of BMSCs is a CD45 (−), CD73 (+), CD90 (+), CD106 (−) cell surface phenotype (FIG. 59C). The morphological (FIG. 59B) and antigenic (FIG. 59D) characteristics of PMSCs are very similar to those of BMSCs.

Example 74

Characterization of Ischemic Lesion Size by Magnetic Resonance Image Analysis

An estimate of lesion size was obtained using in vivo MRI (see Experimental Procedures). Brain images (DWI and $T_2WI$) were collected from all experimental animals 6 hrs, 1, 3 and 7 days after MCAO. The cells were intravenously delivered immediately after the 6 hrs MRI. The upper row in FIG. 60A corresponds to 6 hrs DWI post-MCAO for control (A1), BMSCs (B1) and PMSCs (C1) injected rats. Respective images are shown at 1, 3 and 7 days for each group. These coronal forebrain sections were obtained at the level of caudato-putamen complex. Note the reduction in density in lesions on the right side of the brains that were subjected to ischemic injury. Lesion volume ($mm^3$) was determined by analysis of high intensity areas on serial images collected through the cerebrum (see Experimental Procedures).

At 6 hrs post-MCAO, lesion volume of DWI was similar for the three groups (FIG. 60D). Lesion volume increased at 1 day, but was less for both the BMSC and PMSC groups. The control lesion group showed a reduced lesion volume at 3 and 7 days, but the MSC groups showed greater reduction in lesion volume (FIG. 60D).

Using $T_2WI$ (FIG. 61), infarction volume was similar in the three groups at 6 hrs post-MCAO (FIG. 61D). Both the BMSC and PMSC injected groups showed reduced lesion volume at 1, 3, and 7 days post MCAO.

A difference between DWI and $TB_{2B}WI$ was observed. Lesion volume decreased after 1 day in the three groups in the DWI analysis. Using $T_2WI$, lesion volume increased from 1 to 3 days. However, the BMSC and PMSC groups showed reduced volumes in both DWI and $T_2WI$ analysis.

Example 75

Histological Determination of Infarction Volume

After completion of the MRI analysis to estimate lesion volume, before and after cell delivery, the animals were perfused and stained with TTC to obtain a second independent measure of infarction volume. Normal brain (gray matter) tissue typically stains with TTC, but infarcted lesions show no or reduced staining. TTC-staining that was obtained one week after MCAO without cell transplantation is shown in FIG. 63A-1. Note the reduced staining on the lesion side. Lesion volume was calculated by measuring the area of reduced TTC-staining in the forebrain (see Experimental Procedures). As with MRI analysis, there was a progressive reduction in infarction size with both BMSCs and PMSCs treatment (FIG. 62A-2, 62A-3, respectively). Lesion volume was $263.0\pm35.26$ mm$P^{3P}$ (control group; n=5), $180.0\pm5.89$ mm$P^{3P}$, (BMSCs transplantation; n=5), and $185.86\pm19.12$ mm$P^{3P}$ (PMSCs; n=5, p<0.05).

HE stained sections from the sham lesion cortex (FIG. 62B-1), and cortex from BMSCs (FIG. 624B-2) and PMSCs (FIG. 62B-3) groups indicated more neuron preservation and fewer inflammation cells were present in the cell infusion groups.

Example 76

Identification and Characterization of Donor Cells in vivo

LacZ-transfected BMSCs and PMSCs that had been i.v. administered ($1.0\times10^6$ cells) 6 hours after MCAO were identified in vivo. The LacZ-expressing MSCs were found primarily in the lesion. The transmitted light images in the LacZ-transfected BMSCs and PMSCs are shown in FIG. 62C-2 and FIG. 62C-3, respectively. Note the abundance of LacZ-positive blue-cellular-like elements in and around the lesion, indicating that systemic deliver of both types of cells reached the lesion site. There was a paucity of blue staining in the non-treated group (FIG. 62C-1). Immunohistochemical studies were carried out to identify LacZ-positive cells in and around the lesion zone in animals transplanted with LacZ-transfected MSCs. The micro photographs of BMSCs (FIG. 62D-2) and PMSCs (FIG. 62D-3) demonstrated a large number of LacZ-positive cells in and around the lesion ($300\pm30$ cells/mm$^2$, n=5), although there was virtually no LacZ-positive cells in the non-damaged hemisphere.

Example 77

Dynamic Susceptibility Contrast-enhanced PWI

The PWI-derived parameter maps to assess regional cerebral blood flow allowed further quantitative analysis for the hemodynamic changes of the lesions (see Methods). FIG. 64A-C shows images obtained at 6 hrs (row 1), 1 day (row 2), 3 days (row 3), and 7 days (row 4). Control, BMSC- and PMSC-injected groups are in columns A, B and C, respectively.

The four regions of interest (ROI) for the analysis are defined in Methods and shown in FIG. 63. The severity of the lesion was greatest in ROI-1 and progressively less in ROI-2 through ROI-4. A rCBF ratio was calculated at each ROI from PWI obtained in the infarction hemisphere divided by that of the non-infarcted hemisphere. In ROI-1, the rCBF ratio of control, BMSC-treated, and PMSC-treated groups were similar and decreased to less than 20% at 6 hours post-MCAO, and remained low at 3 and 7 days (FIG. 64D). The rCBF ratio in ROI-2 of the three groups was similar at 6 hrs, 1 and 3 days post MCAO. However, the rCBF ratio of both BMSC-treated and PMSC-treated groups was increased at 7 days after MCAO as compared to control (FIG. 64E). The rCBF ratio in ROI-3 was similar for the three groups at 6 hrs, 1, and 3 days, but again the MSC groups had a greater rCBF ratio at 7 days (FIG. 64F). In ROI-4, the rCBF ratio slightly decreased in all groups at all time points, but not more than 20% (FIG. 64G).

Example 78

Analysis of Capillary in Confocal Images

To examine whether the administration of BMSCs and PMSCs induces angiogenesis, three-dimensional analysis of capillary vessels in the lesion was performed using Zeiss LSM5 PASCAL software. FIG. 7A shows the three dimensional capillary image in the normal rat brain. The capillary vascular volume in ROI-3 seven days after MCAO was increased in both BMSC-treated (FIG. 65C) and PMSC-treated groups (FIG. 65D) compared to the medium-treated group (FIG. 65B). The capillary vascular volume was expressed as a ratio by dividing that obtained from the ischemic hemisphere by that of the contralateral control hemisphere. The ratio was significantly higher in both the BMSC-treated ($0.62\pm0.05$, n=5; p<0.05) and the PMSC-treated ($0.61\pm0.05$, n=5; p<0.05) groups as compared to the medium-treated group ($0.30\pm0.02$, n=5).

Example 79

Functional Analysis

To access behavioral performance in the lesioned and transplanted animals, the treadmill stress test was used (FIG. 66). Behavioral testing began 24 hours after lesion induction alone or with cell transplantation. In the treadmill stress test control animals (no lesion) reach a maximum treadmill velocity of about 70 m/min.$^2$ Twenty-four hours after MCAO without transplantation, maximum velocity on the treadmill test was $10.0\pm6.54$ m/min (n=5). Non-treated animals showed increased treadmill velocity with slow improvement up to 7 days ($20.8\pm10.9$ m/min, n=5). In both BMSCs and PMSCs transplantation groups, the improvement in velocity was greater over the time course up to 7 days.

INDUSTRIAL APPLICABILITY

The present inventors found that regenerative medicines with the excellent features outlined below can be performed using mesenchymal cells (mesenchymal stem cells), specifically bone marrow cells, cord blood cells, or peripheral blood cells. Specifically, regenerative treatments using bone marrow cells, cord blood cells, or peripheral blood cells, using simple in vivo administration (e.g., intravenous administration) of patient-derived bone marrow cells by injection or drip infusion, enable the regeneration of sites damaged by nervous system injuries, and therapies for disorders. Such nervous system injuries cannot in fact be treated by conventional techniques. The efficacy of the present treatments on cerebral infarction has been rigorously verified. Additionally, these treatments are considered effective for all neurological diseases, such as injuries of the nervous system due to cerebral infarction, intracerebral bleeding, spinal cord injury, myocardial infarction, cerebral stroke including subarachnoidal hemorrhage, central and peripheral demyelination diseases, central and peripheral degenerative diseases, brain tumor, higher-function disorders including dementia, mental disorders, epilepsy, traumatic neurological diseases including head injuries, cerebral contusion, spinal cord injuries, inflammatory diseases, and brain cell-damaging infective diseases including Creutzfeldt-Jakob disease. The treatments can be conducted in both specialized therapy facilities and in general therapy sites (such as general hospitals, during ambulance transportation, or at the site of incidents). These are revolutionary treatments, since they enable therapies of disorders that cannot be treated by conventional treatments, and further, these treatments can be achieved using a simple procedure, such as intravenous administration. In addition, since neurological injuries cause severe disorders in patients, patients can benefit tremendously from therapies for these disorders, which is of tremendous social significance.

The medical action mechanisms of the regenerative medicines of the present invention are as follows: Transplanted bone marrow cells or mesenchymal stem cells migrate to and fixate in an affected area (an in vivo injury site), recovering the functions of the affected area by secreting appropriate substances, accelerating inherent autotherapy, or differentiating into appropriate cells. Accordingly, the regenerative medicines of the present invention can exert effects on all types of diseases and events accompanied by neurological injury.

The invention claimed is:

1. A method of treating stroke, an ischemic lesion, brain tumor or cerebral infarction in a patient in need thereof, comprising: (a) culturing mesenchymal stem cells prepared from peripheral blood to produce peripheral blood-derived mesenchymal stem cells (PMSCs) having the marker profile of CD45(−), CD73(+), CD90(+) and CD106(−); and (b) after culturing, injecting into the patient a therapeutically effective amount of the PMSCs from (a), wherein the PMSCs migrate to the area of cerebral stroke, ischemic lesion, brain tumor or cerebral infarction.

2. The method of claim 1, wherein the injection is intravenous.

3. The method of claim 1, wherein the PMSCs are autologous.

* * * * *